(12) United States Patent
Mazzaferro et al.

(10) Patent No.: US 10,577,336 B2
(45) Date of Patent: Mar. 3, 2020

(54) MORPHOLINE AND 1,4-OXAZEPANE AMIDES AS SOMATOSTATIN RECEPTOR SUBTYPE 4 (SSTR4) AGONISTS

(71) Applicant: Boehringer Ingelheim International GmbH, Ingelheim am Rhein (DE)

(72) Inventors: Rocco Mazzaferro, San Giuliano Milanese (IT); Marco Ferrara, San Donato Milanese (IT); Riccardo Giovannini, Biberach an der Riss (DE); Iain Lingard, Monza (IT); Klaus Rudolf, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/048,665

(22) Filed: Jul. 30, 2018

(65) Prior Publication Data
US 2018/0339971 A1 Nov. 29, 2018

Related U.S. Application Data

(63) Continuation of application No. 15/526,361, filed as application No. PCT/EP2015/076440 on Nov. 12, 2015, now Pat. No. 10,071,974.

(30) Foreign Application Priority Data

Nov. 14, 2014 (EP) .................................. 14193185

(51) Int. Cl.
| | | |
|---|---|---|
| *A61K 31/55* | (2006.01) | |
| *A61K 31/5377* | (2006.01) | |
| *C07D 267/10* | (2006.01) | |
| *C07D 413/12* | (2006.01) | |
| *C07D 471/04* | (2006.01) | |
| *C07D 265/30* | (2006.01) | |

(52) U.S. Cl.
CPC ........ *C07D 267/10* (2013.01); *A61K 31/5377* (2013.01); *A61K 31/55* (2013.01); *C07D 265/30* (2013.01); *C07D 413/12* (2013.01); *C07D 471/04* (2013.01)

(58) Field of Classification Search
None
See application file for complete search history.

(56) References Cited

FOREIGN PATENT DOCUMENTS

| WO | 2006053120 A1 | 5/2006 |
| WO | 2010059922 A1 | 5/2010 |
| WO | 2012120476 A1 | 9/2012 |

OTHER PUBLICATIONS

Database Registry Chemical Abstracts Service, Columbus, Ohio, Accession No. RN 1576099-10-9, Entered STN: Mar. 30, 2014.*
Crinder et al., "Somatostatin sst4 Ligands: Chemistry and Pharmacology", Mini-Reviews in Medicinal Chemistry, 2007, 7, pp. 213-220.
International Search Report and Written Opinion for corresponding application PCT/EP2015/076440, dated Jan. 8, 2016.
Database Registry Chemical Abstracts Service, Ohio, Accession No. RN 1284035-76-2, Entered STN: Apr. 22, 2011.
Database Registry Chemical Abstracts Service, Ohio, Accession No. RN 1291668-72-8, Entered STN:May 8, 2011.
Database Registry Chemical Abstracts Service, Ohio, Accession No. RN 1304059-21-9, Entered STN: Jun. 1, 2011.
Ito, A medium term rat liver bioassay for rapid in vivo detection of carcinogenic potential of chemicals, Cancer Science, 94(1), 2003.
Database Registry Chemical Abstracts Service, Ohio, Acession No. 1291898, Entered STN: May 9, 2011.
Database registry Chemical Abstracts Services, Ohio, Acession No. 1304059, Entered STN: Jun. 1, 2011.
Database Registry Chemical Abstracts Service, Ohio, Acession No. 1304060, Entered STN Jun. 1, 2011.
Database Registry Chemical Abstracts Service, Ohio, Accession No. 1306877, Entered STN Jun. 7, 2011.
Database Registry Chemical Abstracts Service, Ohio, Acession No. 1306879, Entered STN Jun. 7, 2011.
Database Registry Chemical Abstracts Service, Ohio, Acccession No. 1307877 Entered STN Jun. 8, 2011.
Database Registry Chem Abstracts Service, No. 1607563, May 2014.
Database Chemical Abstracts Registry Service, No. 1607530, May 2014.
Database Registry Chem Abstracts Service, No. 1606354, May 2014.
Database Registry Chem Abstracts Service, No. 1606218, May 2014.
Database Registry Chem Abstracts Service, No. 16066046, May 2014.
Database Registry Chem Abstracts Service, No. 1583704, Apr. 2014.
Database Registry Chem Abstracts Service, No. 1583077, Apr. 2014.
Database Registry Chem Abstracts Service, No. 1585349 Apr. 2019.
Database Chem Abstracts Service, Ohio, RN 1580683, Apr. 2014.
Database Registry Chem Abstracts Service, No. 1580526, Apr. 2014.

* cited by examiner

*Primary Examiner* — Samantha L Shterengarts
(74) *Attorney, Agent, or Firm* — David L. Kershner

(57) ABSTRACT

The invention relates to morpholine and 1,4-oxazepane amide derivatives of general formula (I), which are agonists of somatostatin receptor subtype 4 (SSTR4), useful for preventing or treating medical disorders related to SSTR4. In addition, the invention relates to processes for preparing pharmaceutical compositions as well as processes for manufacture of the compounds according to the invention.

12 Claims, No Drawings

MORPHOLINE AND 1,4-OXAZEPANE AMIDES AS SOMATOSTATIN RECEPTOR SUBTYPE 4 (SSTR4) AGONISTS

FIELD OF THE INVENTION

The invention relates to morpholine and 1,4-oxazepane amide derivatives of general formula (I), which are agonists of somatostatin receptor subtype 4 (SSTR4), useful for preventing or treating medical disorders related to SSTR4. In addition, the invention relates to processes for manufacture of the compounds according to the invention.

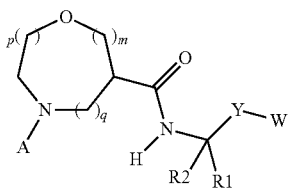

(I)

BACKGROUND OF THE INVENTION

Somatostatin, or somatotropin-release inhibitory factor (SRIF), is a cyclic peptide found in humans. It is produced widely in the human body and acts both systemically and locally to inhibit the secretion of various hormones, growth factors and neurotransmitters. The effects of somatostatin are mediated by a family of G protein-coupled receptors, of which five subtypes are known. These subtypes are divided into two subfamilies, the first comprising SSTR2, SSTR3 and SSTR5 and the second SSTR1 and SSTR4.

Somatostatin is involved in the regulation of processes such as for example cellular proliferation, glucose homeostasis, inflammation and pain.

In this aspect somatostatin or other members of the somatostatin peptide family are believed to inhibit nociceptive and inflammatory processes via the SSTR4 pathway.

A number of further therapeutic areas for SSTR4 agonists have been discussed (see e.g. Crider, A; *Mini Rev. Med. Chem.* 2002, 7, 213 (and references therein); WO 2010/059922 (and references therein).

Selective SSTR4 agonists have been disclosed, for instance, in *J. Am. Chem. Soc.* 1998, 120, 1368-1373.

WO 2010/059922 provides pyrrolidine carboxamide agonists of SSTR4.

U.S. Ser. No. 14/275,879 relates to 3-aza-bicyclo[3.1.0] hexane-6-carboxylic acid amide derivatives as SSTR4 agonists.

However, there is further need for selective SSTR4 agonists, especially for non-peptidic agonists, which show high stability, permeability and other advantageous properties, such as oral efficacy and metabolic stability.

AIM OF THE INVENTION

It has now been found that compounds of the present invention according to general formula (I) are effective agonists of somatostatin receptor 4 (SSTR4).

Besides the agonistic property toward somatostatin receptor 4, the compounds of the present invention provide advantageous pharmacokinetic properties. For example the compounds of the present invention show high metabolic stability.

Furthermore, the compounds according to the present invention show high selectivity for the SSTR4 receptor with respect to the other subtypes of the same subfamily including the SSTR1 receptor. As a consequence the probability of side effects is reduced.

Accordingly, one aspect of the invention refers to compounds according to formula (I) and salts, hydrates or solvates thereof as agonists of somatostatin receptor 4.

Another aspect of the invention refers to compounds according to formula (I) and salts, hydrates or solvates thereof as selective agonists of SSTR4 over other subtypes of the same family, including selectivity over the other subtype of the same subfamily (SSTR1).

A further aspect of the invention relates to the physiologically acceptable salts of the compounds of general formula (I) according to this invention with inorganic or organic acids.

In a further aspect this invention relates to pharmaceutical compositions, containing at least one compound according to formula (I) or a physiologically acceptable salt, hydrate or solvate thereof, optionally together with one or more inert carriers and/or diluents.

A further aspect of the present invention relates to compounds according to formula (I) or a physiologically acceptable salt thereof or pharmaceutical compositions comprising compounds according to formula (I) or physiologically acceptable salts thereof for the use in the prevention and/or treatment of disorders related to SSTR4.

Another aspect of the invention relates to processes of manufacture of the compounds of the present invention.

A further aspect of the present invention relates to compounds according to formula (I) or a physiologically acceptable salt thereof or pharmaceutical compositions comprising compounds according to formula (I) or physiologically acceptable salts thereof for the use in the prevention and/or treatment of diseases or conditions which can be influenced by activation of SSTR4. In this aspect the present invention relates to compounds according to formula (I) or a physiologically acceptable salt thereof for the treatment of pain of various origins and/or inflammation.

Other aims of the present invention will become apparent to the skilled man directly from the foregoing and following remarks.

DETAILED DESCRIPTION

In a first aspect the present invention relates to compounds of general formula (I)

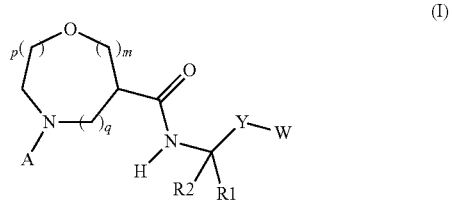

(I)

wherein
m=0, p=1, q=1 or;
m=1, p=1, q=1 or;
m=0, p=2, q=1 or;
m=0, p=1, q=2.
A is selected from the group $A^1$ consisting of H and $C_{1-6}$-alkyl;

$R^1$ and $R^2$ are independently selected from the group $R^{1.1}$, $R^{2.1}$ consisting of H, $C_{1-6}$-alkyl and $C_{3-6}$-cycloalkyl, wherein at least one of $R^1$ or $R^2$ is $C_{1-6}$-alkyl or $C_{3-6}$-cycloalkyl, or wherein $R^1$ and $R^2$ together form a 2- to 5-membered alkylene-bridge incorporating 0 to 2 heteroatoms independently selected from the group consisting of N, O or S wherein the $C_{1-6}$-alkyl, the $C_{3-6}$-cycloalkyl or the alkylene-bridge is optionally substituted with halogens;

W is selected from the group $W^1$ consisting of a mono- or bicyclic aryl, mono- or bicyclic heteroaryl, mono- or bicyclic heterocyclyl and mono- or bicyclic cycloalkyl, wherein each of these ring systems are optionally substituted with one or more $R^3$, and wherein the heteroaryl comprises up to 4 heteroatoms and one or two 5- or 6-membered ring(s);

$R^3$ is independently selected from the group $R^{31}$ consisting of $C_{1-6}$-alkyl, $C_{3-8}$-cycloalkyl, $C_{1-6}$-alkyl-O—, benzyl, halogen, HO—, NC—, mono- or bicyclic heteroaryl, and 5- or 6-membered monocyclic heterocyclyl containing one heteroatom selected from the group consisting of N, O or $S(O)_r$, wherein the heteroaryl contains up to 4 heteroatoms and one or two 5- or 6-membered ring(s), and r is 0, 1 or 2, wherein the $C_{1-6}$-alkyl, $C_{3-6}$-cycloalkyl, $C_{1-6}$-alkyl-O—, benzyl, heteroaryl and the heterocyclyl are optionally substituted with halogens, HO—, acetyl, $C_{1-6}$-alkyl-O—, oxo, $R^4$—$S(O)_2$—, with $R^4$ being aryl, $C_{3-6}$-cycloalkyl and/or $C_{1-6}$-alkyl;

Y is selected from the group $Y^1$ consisting of a bond, and —$CH_2O$—;

or a salt of any of the above compounds, with the provisio that

N-[1-(3-methoxyphenyl)ethyl]morpholine-2-carboxamide and

N-[1-(naphthalen-1-yl)ethyl]morpholine-2-carboxamide, and optionally

N-[2-[4-(1,1-dimethylethyl)phenoxy]-1-methylethyl]-2-morpholinecarboxamide,

N-[2-(3-fluorophenoxy)-1-methylethyl]-2-morpholinecarboxamide,

N-[1-(phenoxymethyl)propyl]-2-morpholinecarboxamide,

N-[2-(3-methoxyphenoxy)propyl]-2-morpholinecarboxamide,

N-[1-methyl-2-(4-methylphenoxy)ethyl]-2-morpholinecarboxamide,

N-[2-(4-fluorophenoxy)-1-methylethyl]-2-morpholinecarboxamide,

N-[1-[(2-fluorophenoxy)methyl]-2,2-dimethylpropyl]-2-morpholinecarboxamide and

N-[1-methyl-2-(4-methylphenoxy)ethyl]-2-morpholinecarboxamide are excluded.

The compounds

N-[1-(3-Methoxyphenyl)ethyl]morpholine-2-carboxamide and

N-[1-(Naphthalen-1-yl)ethyl]morpholine-2-carboxamide are described in WO2012/120476 as intermediates for the preparation of modulators for the calcium sensing receptor.

The other optionally excluded compounds may be entries of chemical libraries or chemical catalogues. However, they seem not to be published or described elsewhere.

Unless otherwise stated, the groups, residues, and substituents, particularly $R^1$, $R^2$, $R^3$, $R^4$, A, W and Y are defined as above and hereinafter. If residues, substituents, or groups occur several times in a compound they may have the same or different meanings. Some preferred meanings of groups and substituents of the compounds according to the invention will be given hereinafter.

In preferred embodiments m is 0, p is 1 and q is 1 or m is 1, p is 1 and q is 1.

In further preferred embodiments m is 1, p is 1 and q is 1.

In a further embodiment of the present invention

A is selected from the group $A^2$ consisting of H or $C_{1-3}$-alkyl.

In a further embodiment of the present invention

A is selected from the group $A^3$ consisting of H or $H_3C$—.

In a further embodiment of the present invention

A is selected from the group $A^4$ consisting of H.

$R^1$ and $R^2$ are independently selected from the group $R^{1.2}$, $R^{2.2}$ consisting of $C_{1-6}$-alkyl and $C_{3-6}$-cycloalkyl, or wherein $R^1$ and $R^2$ together form a 2- to 5-membered alkylene-bridge incorporating 0 to 2 heteroatoms independently selected from the group consisting of N, O or S, wherein the $C_{1-6}$-alkyl, the $C_{3-6}$-cycloalkyl or the alkylene-bridge is optionally substituted with halogens.

In a further embodiment of the present invention $R^1$ and $R^2$ are independently selected from the group $R^{1.3}$, $R^{2.3}$ consisting of H, $C_{1-3}$-alkyl and $C_{3-4}$-cycloalkyl or wherein $R^1$ and $R^2$ together form a 2- to 5-membered alkylene-bridge incorporating 0 to 2 heteroatoms independently selected from the group consisting of N, O or S, wherein the $C_{1-3}$-alkyl, the $C_{3-4}$-cycloalkyl or the alkylene-bridge is optionally substituted with halogens.

In a further embodiment of the present invention $R^1$ and $R^2$ are selected from the group $R^{1.4}$ and $R^{2.4}$ consisting of $C_{1-3}$-alkyl or, wherein $R^1$ and $R^2$ together form a 2- to 5-membered alkylene-bridge incorporating 0 to 2 heteroatoms independently selected from the group consisting of N, O and S.

In a further embodiment of the present invention $R^1$ and $R^2$ are selected from the group $R^{1.5}$ and $R^{2.5}$ consisting of $H_3C$— or wherein $R^1$ and $R^2$ together form a 2- or 3-membered alkylene-bridge.

In a further embodiment of the present invention $R^1$ and $R^2$ are selected from the group $R^{1.6}$ and $R^{2.6}$ consisting of $H_3C$—.

In a further embodiment of the present invention

W is selected from the group $W^2$ consisting of a mono- or bicyclic aryl, a mono- or bicyclic heteroaryl and a mono- or bicyclic heterocyclyl, wherein each of these ring systems are optionally substituted with one or more $R^3$, and wherein the heteroaryl comprises up to 4 heteroatoms and one or two 5- or 6-membered ring(s).

In a further embodiment of the present invention

W is selected from the group $W^3$ consisting of a monocyclic aryl, a monocyclic heteroaryl and a monocyclic heterocyclyl, wherein each of these ring systems are optionally substituted with one or more $R^3$, and wherein the heteroaryl comprises up to 4 heteroatoms and one 5- or 6-membered ring.

In a further embodiment of the present invention

W is selected from the group $W^4$ consisting of a bicyclic aryl, a bicyclic heteroaryl and a bicyclic heterocyclyl, wherein each of these ring systems are optionally substituted with one or more $R^3$, and wherein the heteroaryl comprises up to 4 heteroatoms and two 5- or 6-membered rings.

In a further embodiment of the present invention

W is a selected from the group $W^5$ consisting of

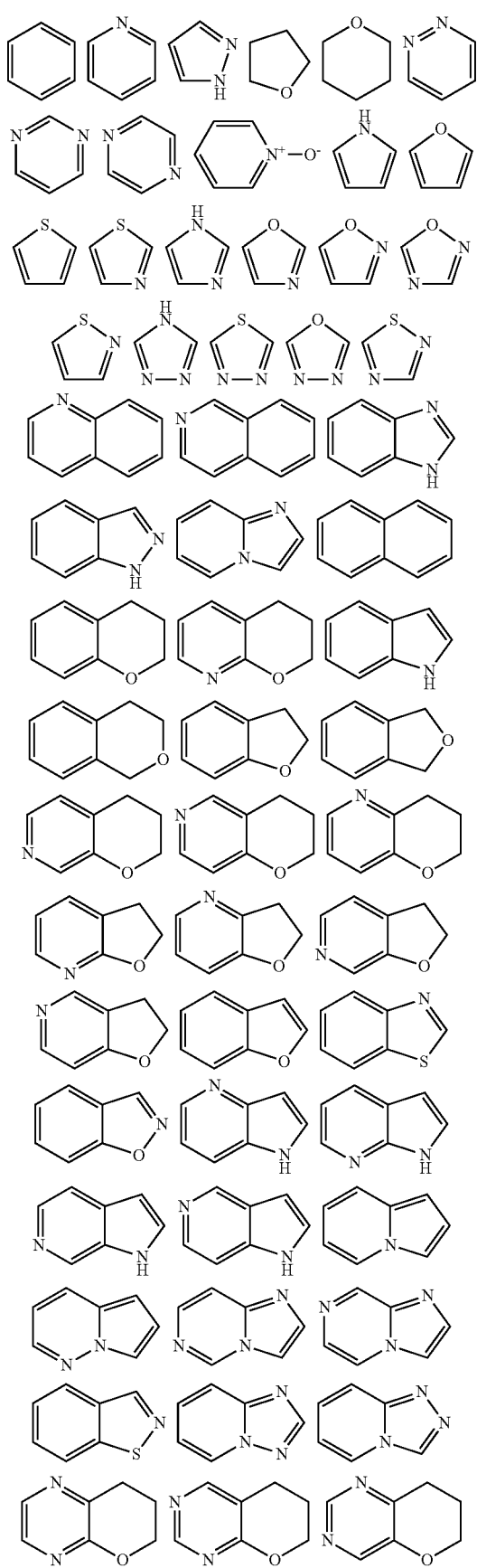
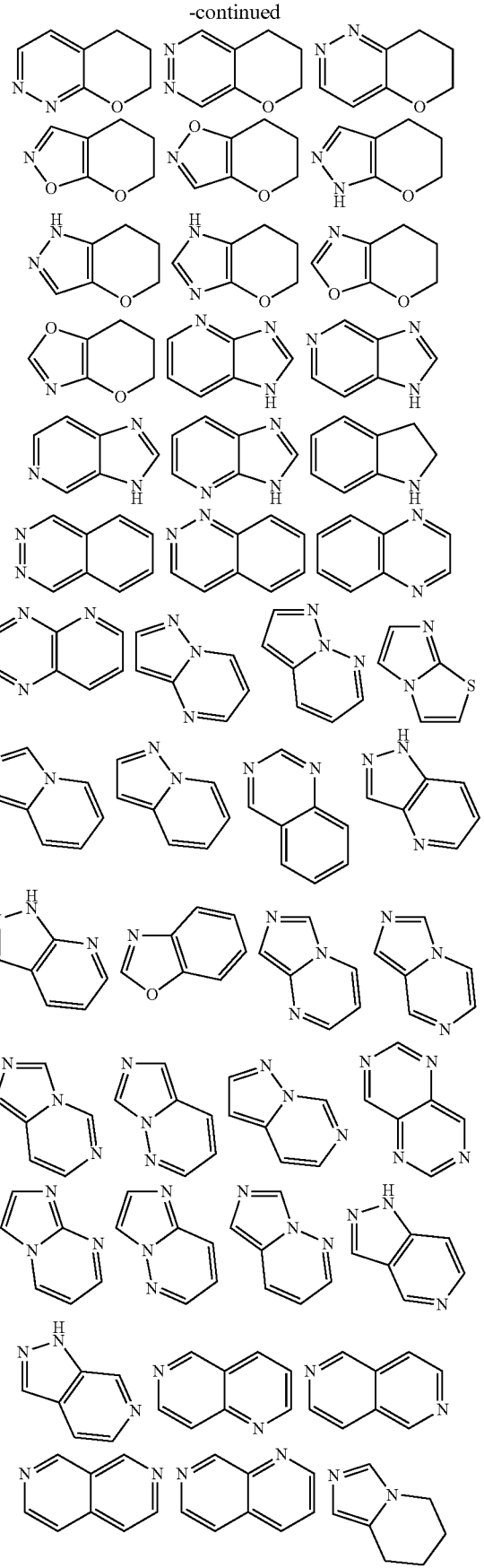
-continued

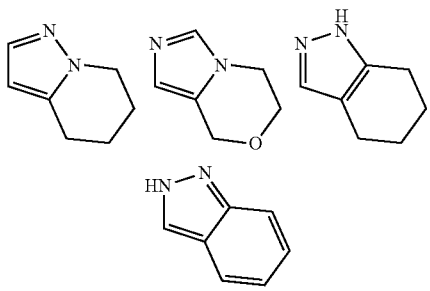

wherein each of these ring systems are optionally substituted with one or more $R^3$.

In a further embodiment of the present invention W is a selected from the group $W^6$ consisting of

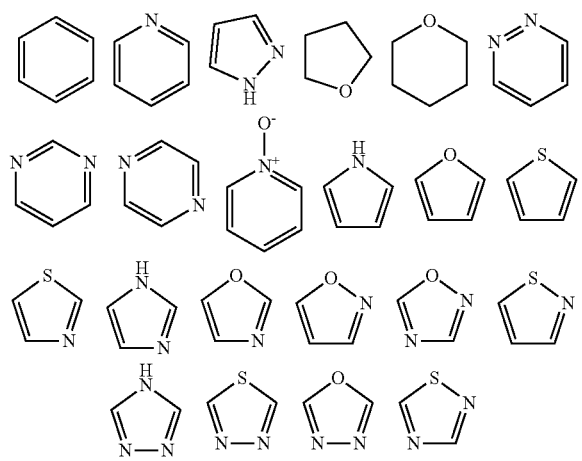

wherein each of these ring systems are optionally substituted with one or more $R^3$.

In a further embodiment of the present invention W is a selected from the group $W^7$ consisting of

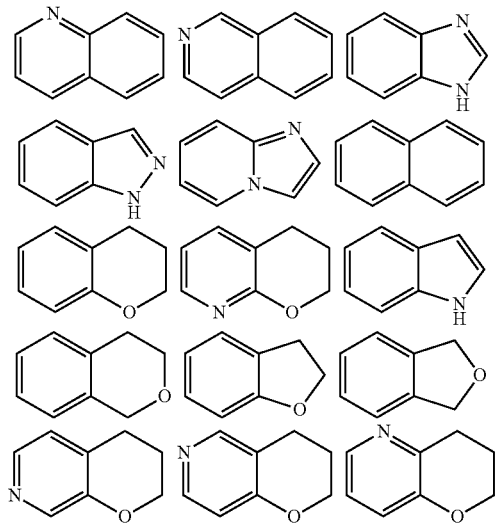

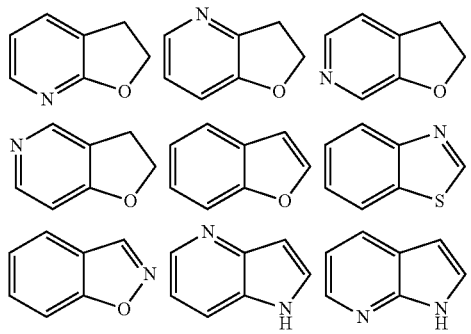

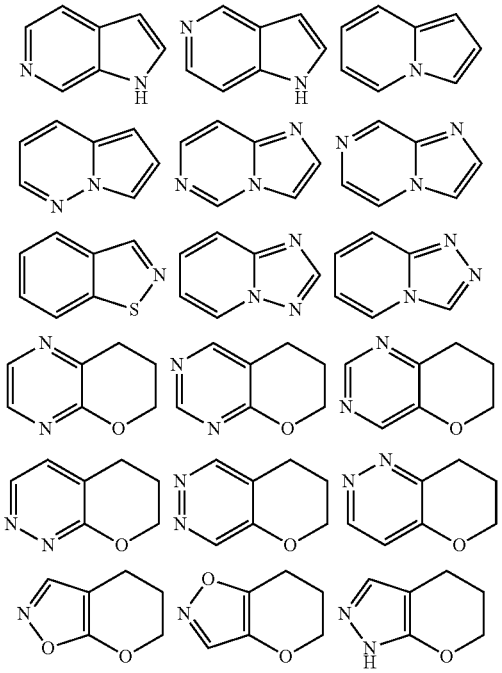

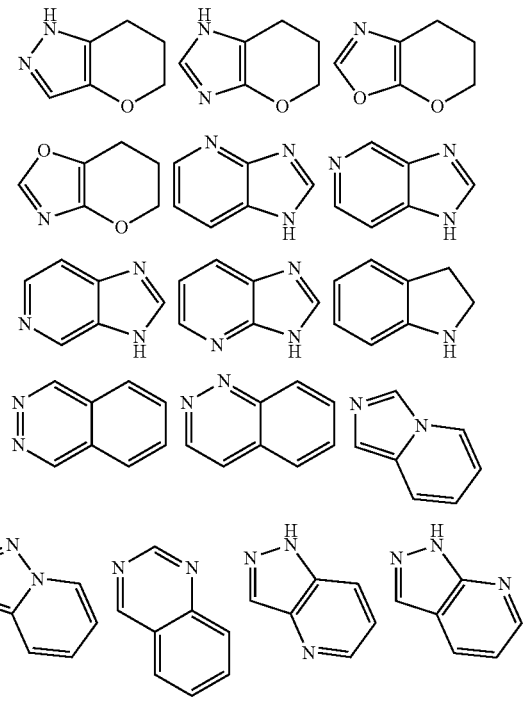

-continued

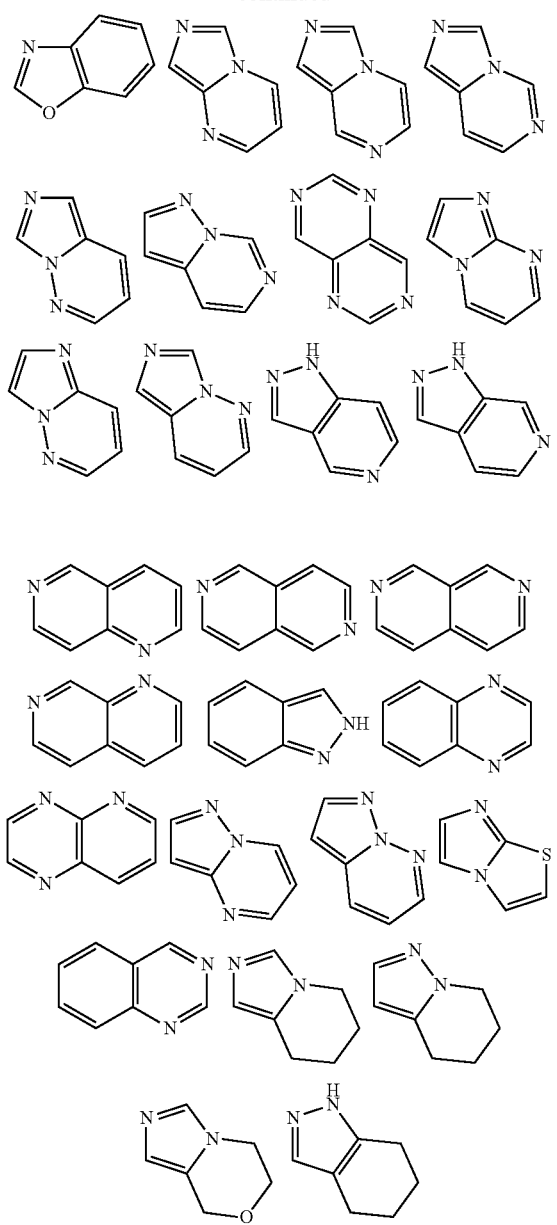

wherein each of these ring systems are optionally substituted with one or more R³.

In a further embodiment of the present invention
W is selected from the group W⁸ consisting of

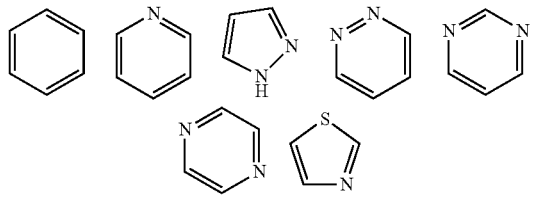

wherein each of these ring systems are optionally substituted with one to three R³.

In a further embodiment of the present invention
W is selected from the group W⁹ consisting of

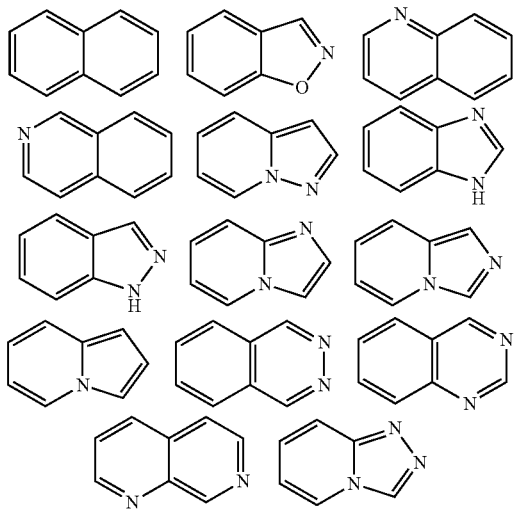

wherein each of these ring systems are optionally substituted with one to three R³.

In a further embodiment of the present invention
W is selected from the group W¹⁰ consisting of

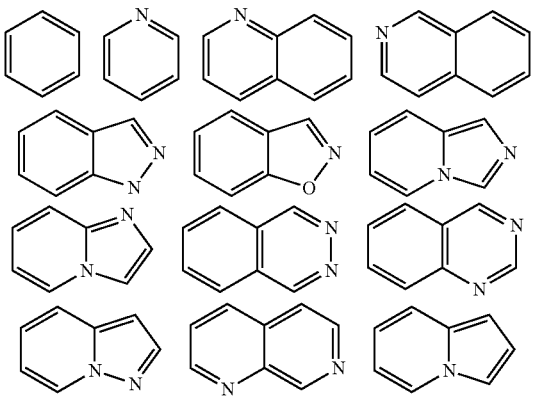

wherein each of these ring systems are optionally substituted with one to three R³.

In a further embodiment of the present invention
W is selected from the group W¹¹ consisting of

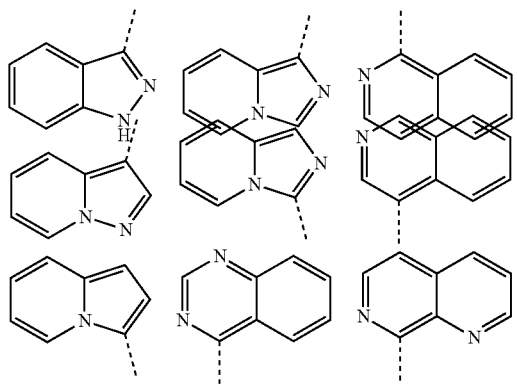

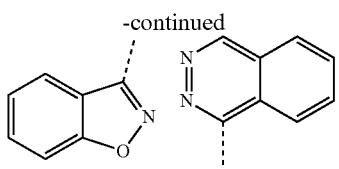

wherein each of these ring systems is preferentially attached to Y as indicated by a dotted line and optionally substituted with one to three $R^3$.

In a further embodiment of the present invention $R^3$ is independently selected from the group $R^{3.2}$ consisting of $C_{1-6}$-alkyl, $C_{3-8}$-cycloalkyl, $C_{1-6}$-alkyl-O—, benzyl, halogen, HO—, and NC—, wherein the $C_{1-6}$-alkyl, $C_{3-8}$-cycloalkyl, $C_{1-6}$-alkyl-O—, and the benzyl-substituents are optionally substituted with halogens and/or HO—;

In a further embodiment of the present invention $R^3$ is independently selected from the group $R^{3.3}$ consisting of $C_{1-3}$-alkyl, $C_{3-6}$-cycloalkyl, $C_{1-3}$-alkyl-O—, halogen, NC—, wherein, in case $R^3$ is connected to N-atoms of W, $R^3$ is selected from the group consisting of $C_{1-3}$-alkyl and $C_{3-6}$-cycloalkyl, wherein the $C_{1-3}$-alkyl, $C_{3-6}$-cycloalkyl and $C_{1-3}$-alkyl-O-substituents are optionally substituted with halogens.

In a further embodiment of the present invention $R^3$ is independently selected from the group $R^{3.4}$ consisting of $H_3C$—, cyclopropyl, $H_3CO$—, F—, Cl—, NC— and $F_3C$—, wherein, in case $R^3$ is connected to N-atoms of W, $R^3$ is selected from $H_3C$— and cyclopropyl.

In a further embodiment of the present invention $R^3$ is independently selected from the group $R^{3.5}$ consisting of $H_3C$—, cyclopropyl, $F_3C$—, Cl and F—, wherein, in case $R^3$ is connected to N-atoms of W, $R^3$ is $H_3C$—.

In a further embodiment of the present invention $R^3$ is selected from the group $R^{3.6}$ consisting of $H_3C$—, Cl and F.

In a further embodiment of the present invention Y is selected from the group $Y^2$ consisting of —$CH_2O$—.

In a further embodiment of the present invention Y is selected from the group $Y^3$ consisting of a bond.

In a further embodiment, if W is a monocyclic ring, at least one of $R^3$ is preferably attached at the ortho-position or neighbouring position with respect to the attachment point of W to Y.

In a further embodiment, if W is a monocyclic ring, Y is preferably selected from $Y^2$. In a further embodiment, if W is a bicyclic ring, Y is preferably selected from $Y^3$.

In a further aspect the present invention relates to pharmaceutically acceptable salts, hydrates or solvates, more specifically to pharmaceutically acceptable salts, hydrates or solvates for use as a medicament.

In a further aspect, the present invention relates to pharmaceutical compositions containing at least one compound according to the specifications above or a pharmaceutically acceptable salt, hydrate or solvate thereof together with one or more pharmaceutically acceptable carrier.

In a further aspect, the present invention relates compounds according to the specifications above for use in the treatment or prevention of diseases or conditions which can be influenced by modulation of SSTR4, for example for the treatment of pain, e.g. of acute pain, neuropathic peripheral pain, chronic pain or osteoarthritis.

In a further aspect, the present invention relates a pharmaceutically acceptable salt, hydrate or solvate of the compounds according to the specifications above for use in the treatment or prevention of diseases or conditions which can be influenced by modulation of SSTR4, for example for the treatment of pain, e.g. of acute pain, neuropathic peripheral pain, chronic pain or osteoarthritis.

In a further aspect, the present invention relates to a pharmaceutical composition containing at least one compound according to the specifications above or a pharmaceutically acceptable salt, hydrate or solvate thereof together with one or more pharmaceutically acceptable carrier for use in the treatment or prevention of diseases or conditions which can be influenced by modulation of SSTR4, for example for the treatment of pain, e.g. of acute pain, neuropathic peripheral pain, chronic pain or osteoarthritis.

Each $R^{1.x}$, $R^{2.x}$, $R^{3.x}$, $A^x$, $W^x$, and $Y^x$ represents a characterized, individual embodiment for the corresponding substituent as described above. Thus given the above definitions, substituents $R^1$, $R^2$, $R^3$, A, W, and Y are fully characterized by the term ($R^{1.x}$, $R^{2.x}$, $R^{3.x}$, $A^x$, $W^x$, and $Y^x$), wherein for each index x an individual figure is given that ranges from "1" to the highest number given above. All individual embodiments described by the term in parentheses with full permutation of the indices x, referring to the definitions above, shall be comprised by the present invention.

The following Table 1 shows, exemplarily and generally in the order of increasing preference from the first line to the last line, such embodiments E-1 to E-21 of the invention that are considered preferred. This means that, for example, embodiments E-15 to E-21 are preferred over earlier entries, such as E-1 to E-7.

TABLE 1

Preferred embodiments E-1 to E-21 of the invention.

| | A | W | $R^1/R^2$ | $R^3$ | Y |
|---|---|---|---|---|---|
| E-1 | $A^1$ | $W^1$ | $R^{1.1}/R^{2.1}$ | $R^{3.1}$ | $Y^1$ |
| E-2 | $A^1$ | $W^2$ | $R^{1.1}/R^{2.1}$ | $R^{3.1}$ | $Y^1$ |
| E-3 | $A^1$ | $W^3$ | $R^{1.1}/R^{2.1}$ | $R^{3.1}$ | $Y^2$ |
| E-4 | $A^1$ | $W^4$ | $R^{1.1}/R^{2.1}$ | $R^{3.1}$ | $Y^3$ |
| E-5 | $A^1$ | $W^2$ | $R^{1.2}/R^{2.2}$ | $R^{3.2}$ | $Y^1$ |
| E-6 | $A^2$ | $W^2$ | $R^{1.2}/R^{2.2}$ | $R^{3.1}$ | $Y^1$ |
| E-7 | $A^3$ | $W^2$ | $R^{1.2}/R^{2.2}$ | $R^{3.2}$ | $Y^1$ |
| E-8 | $A^4$ | $W^2$ | $R^{1.2}/R^{2.2}$ | $R^{3.2}$ | $Y^1$ |
| E-9 | $A^4$ | $W^5$ | $R^{1.3}/R^{2.3}$ | $R^{3.2}$ | $Y^1$ |
| E-10 | $A^4$ | $W^5$ | $R^{1.4}/R^{2.4}$ | $R^{3.2}$ | $Y^1$ |
| E-11 | $A^4$ | $W^5$ | $R^{1.4}/R^{2.4}$ | $R^{3.2}$ | $Y^1$ |
| E-12 | $A^4$ | $W^6$ | $R^{1.3}/R^{2.3}$ | $R^{3.2}$ | $Y^2$ |
| E-13 | $A^4$ | $W^7$ | $R^{1.3}/R^{2.3}$ | $R^{3.2}$ | $Y^3$ |
| E-14 | $A^4$ | $W^8$ | $R^{1.3}/R^{2.3}$ | $R^{3.2}$ | $Y^2$ |
| E-15 | $A^4$ | $W^9$ | $R^{1.3}/R^{2.3}$ | $R^{3.2}$ | $Y^3$ |
| E-16 | $A^4$ | $W^8$ | $R^{1.5}/R^{2.5}$ | $R^{3.3}$ | $Y^2$ |
| E-17 | $A^4$ | $W^9$ | $R^{1.5}/R^{2.5}$ | $R^{3.3}$ | $Y^3$ |
| E-18 | $A^4$ | $W^{10}$ | $R^{1.5}/R^{2.5}$ | $R^{3.3}$ | $Y^1$ |
| E-19 | $A^4$ | $W^{10}$ | $R^{1.5}/R^{2.5}$ | $R^{3.4}$ | $Y^1$ |
| E-20 | $A^4$ | $W^{10}$ | $R^{1.6}/R^{2.6}$ | $R^{3.5}$ | $Y^3$ |
| E-21 | $A^4$ | $W^{11}$ | $R^{1.6}/R^{2.6}$ | $R^{3.6}$ | $Y^3$ | the tautomers thereof, the stereoisomers thereof, the mixtures thereof, the salts thereof, the hydrates thereof and the solvates thereof.

The combination of substituents of Table 1 is applicable to the following combinations of m, p and q:
m=0, p=1, q=1 or
m=1, p=1, q=1 or
m=0, p=2, q=1 or
m=0, p=1, q=2.

Preferred combinations of m, p and q are:
m=0, p=1, q=1 and m=1, p=1, q=1.

The most preferred combination of m, p and q is:
m=1, p=1, q=1

Accordingly, for example E-5 covers compounds of formula (I), wherein
A is selected from the group consisting of H and $C_{1-6}$-alkyl;
W is selected from the group consisting of a mono- or bicyclic aryl, a mono- or bicyclic heteroaryl and a mono- or bicyclic heterocyclyl, wherein each of these ring systems are optionally substituted with one or more $R^3$, and wherein the heteroaryl comprises up to 4 heteroatoms and one or two 5- or 6-membered ring(s);
$R^1$ and $R^2$ are independently selected from the group consisting of $C_{1-6}$-alkyl and $C_{3-6}$-cycloalkyl, or wherein $R^1$ and $R^2$ together form a 2- to 5-membered alkylene-bridge incorporating 0 to 2 heteroatoms independently selected from the group consisting of N, O or S, wherein the $C_{1-6}$-alkyl, the $C_{3-6}$-cycloalkyl or the alkylene-bridge is optionally substituted with halogens or MeO—;
$R^3$ is independently selected from the group consisting of $C_{1-6}$-alkyl, $C_{3-8}$-cycloalkyl, $C_{1-6}$-alkyl-O—, benzyl, halogen, HO—, and NC—, wherein the $C_{1-6}$-alkyl, $C_{3-8}$-cycloalkyl, $C_{1-6}$-alkyl-O—, and the benzyl-substituents are optionally substituted with halogens and/or HO—;
Y is selected from the group consisting of a bond and —CH$_2$O—;
m is 0, p is 1 and q is 1 or
m is 1, p is 1 and q is 1 or
m is 0, p is 2 and q is 1 or
m is 0, p is 1 and q is 2;
the tautomers thereof, the stereoisomers thereof, the mixtures thereof, the salts thereof, the hydrates thereof and the solvates thereof.

Accordingly, for example E-18 covers compounds of formula (I), wherein
A is H,
W is selected from the group consisting of wherein each of these ring systems are optionally substituted with one to three $R^3$;
$R^1$ and $R^2$ are selected from the group consisting of $H_3C$— or wherein $R^1$ and $R^2$ together form a 2- or 3-membered alkylene-bridge;
$R^3$ is independently selected from the group consisting of $C_{1-3}$-alkyl, $C_{3-6}$-cycloalkyl, $C_{1-3}$-alkyl-O—, halogen, NC—, wherein, in case $R^3$ is connected to N-atoms of W, $R^3$ is selected from the group consisting of $C_{1-3}$-alkyl and $C_{3-6}$-cycloalkyl, wherein the $C_{1-3}$-alkyl, $C_{3-6}$-cycloalkyl and $C_{1-3}$-alkyl-O-substituents are optionally substituted with halogens;
Y is selected from the group consisting of a bond and —CH$_2$O—;
m is 0, p is 1 and q is 1 or
m is 1, p is 1 and q is 1 or
m is 0, p is 2 and q is 1 or
m is 0, p is 1 and q is 2;
the tautomers thereof, the stereoisomers thereof, the mixtures thereof, the salts thereof, the hydrates thereof and the solvates thereof.

In a further aspect the invention relates to compounds according to E-1 for the use as a medicament.

The present invention preferrably relates to the following compounds:

| Comp. | Structure |
|---|---|
| I | 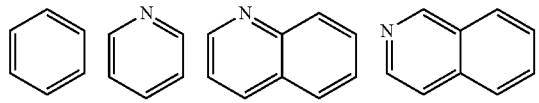 |
| II | 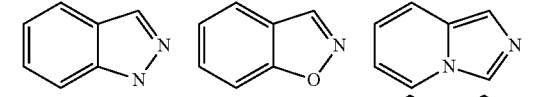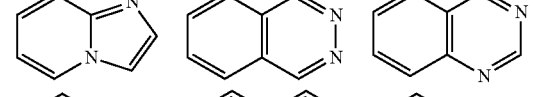 |
| III | 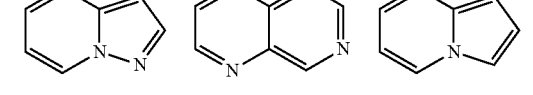 |

-continued
| Comp. | Structure |
|---|---|
| IV | 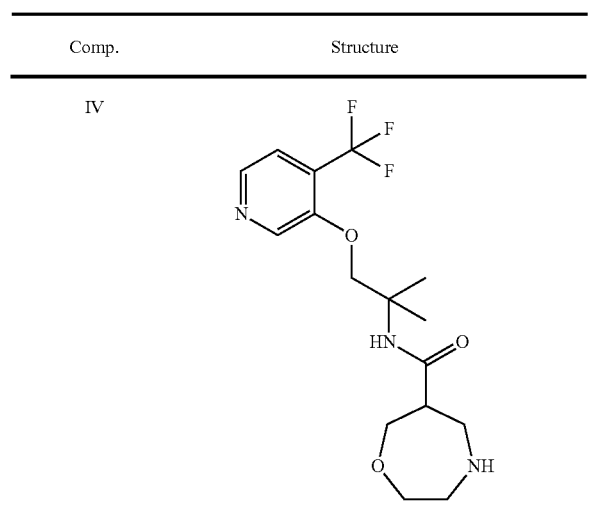 |
| V | 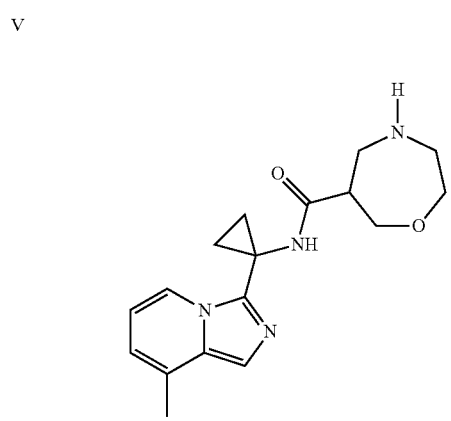 |
| VI | 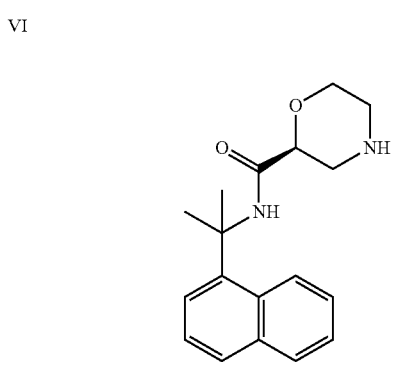 |
| VII | 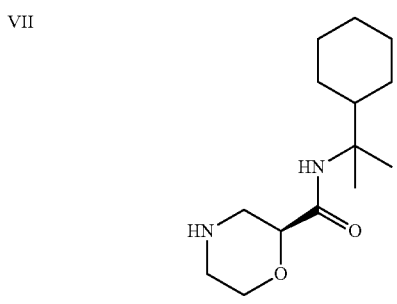 |
-continued
| Comp. | Structure |
|---|---|
| VIII | 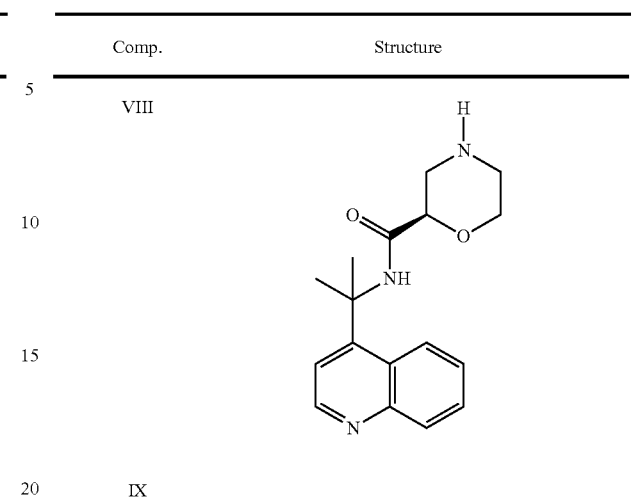 |
| IX | 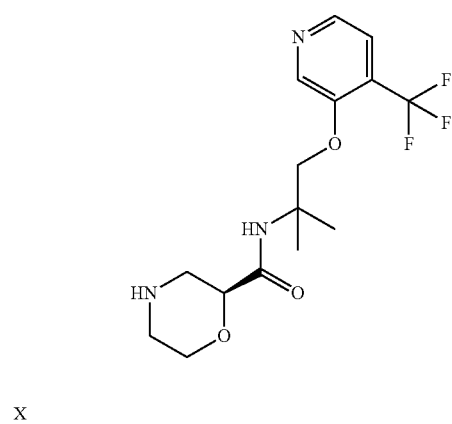 |
| X | 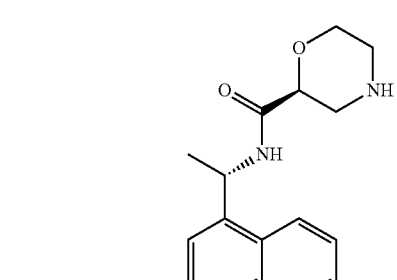 |
| XI | 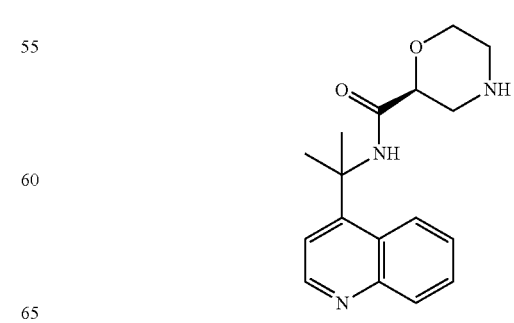 |

| Comp. | Structure |
|---|---|
| XII | |
| XIII | |
| XIV | |
| XV | |
| XVI | 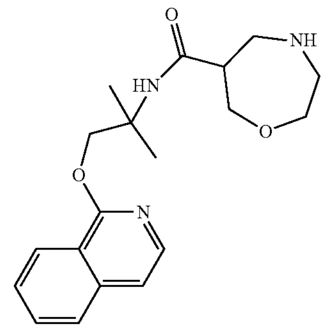 [SMILES: CC(C)(COc1nccc2ccccc12)NC(=O)C1CNCCOC1] |
| XVII | 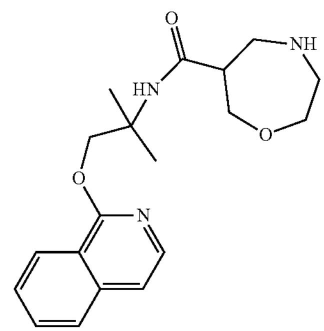 [SMILES: CC(C)(COc1nccc2ccccc12)NC(=O)C1CNCCOC1] |
| XVIII | 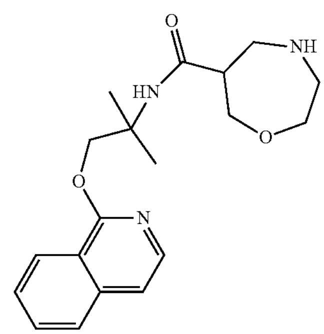 [SMILES: CC(C)(COc1nccc2ccccc12)NC(=O)C1CNCCOC1] |
| XIX | 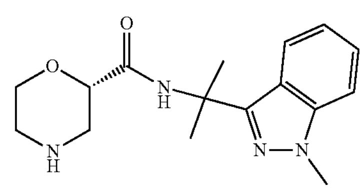 [SMILES: Cn1nc(C(C)(C)NC(=O)[C@@H]2CNCCO2)c2ccccc21] |
| XX | 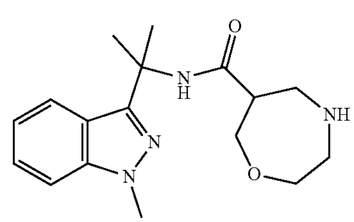 [SMILES: Cn1nc(C(C)(C)NC(=O)C2CNCCOC2)c2ccccc21] |
| XXI | 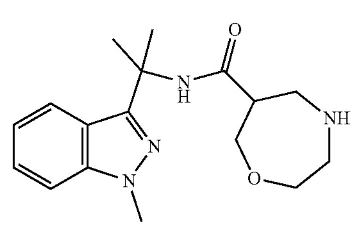 [SMILES: Cn1nc(C(C)(C)NC(=O)C2CNCCOC2)c2ccccc21] |

| Comp. | Structure |
|---|---|
| XXII | 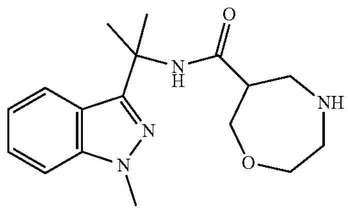 [SMILES: Cn1nc(C(C)(C)NC(=O)C2CNCCOC2)c2ccccc21] |
| XXIII | 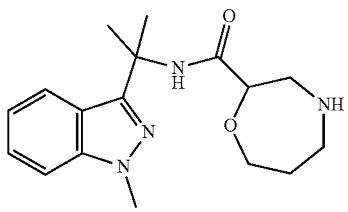 [SMILES: Cn1nc(C(C)(C)NC(=O)C2CNCCCO2)c2ccccc21] |
| XXIV | 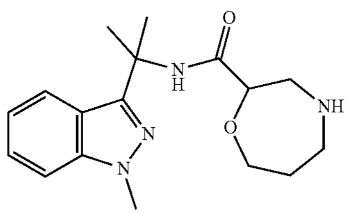 [SMILES: Cn1nc(C(C)(C)NC(=O)C2CNCCCO2)c2ccccc21] |
| XXV | 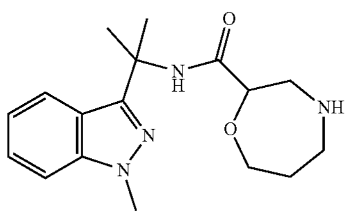 [SMILES: Cn1nc(C(C)(C)NC(=O)C2CNCCCO2)c2ccccc21] |
| XXVI | 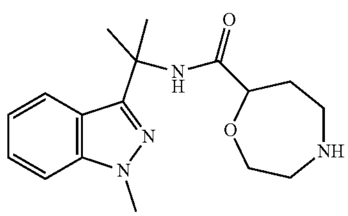 [SMILES: Cn1nc(C(C)(C)NC(=O)C2CCNCCO2)c2ccccc21] |
| XXVII | 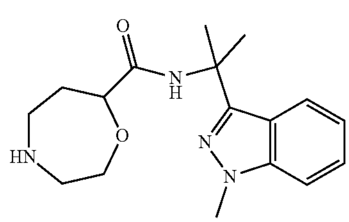 [SMILES: Cn1nc(C(C)(C)NC(=O)C2CCNCCO2)c2ccccc21] |
| XXVIII | 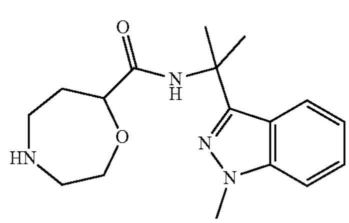 [SMILES: Cn1nc(C(C)(C)NC(=O)C2CCNCCO2)c2ccccc21] |
| XXIX | |
| XXX | |
| XXXI | |
| XXXII | |
| XXXIII | |
| XXXIV | |

-continued

| Comp. | Structure |
|---|---|
| XXXV | 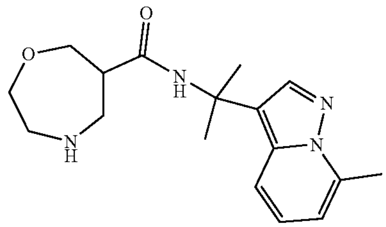 [SMILES: Cc1cccc2c(C(C)(C)NC(=O)C3CNCCOC3)cnn12] |
| XXXVI | 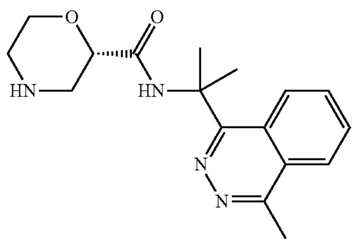 [SMILES: Cc1nnc(C(C)(C)NC(=O)[C@@H]2CNCCO2)c2ccccc12] |
| XXXVII | 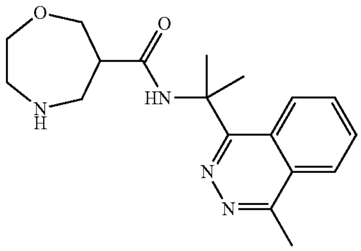 [SMILES: Cc1nnc(C(C)(C)NC(=O)C2CNCCOC2)c2ccccc12] |
| XXXVIII | 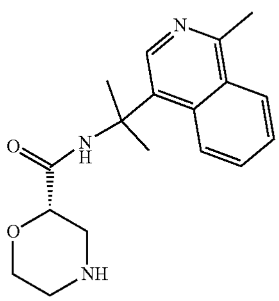 [SMILES: Cc1ncc(C(C)(C)NC(=O)[C@@H]2CNCCO2)c2ccccc12] |
| XXXIX | 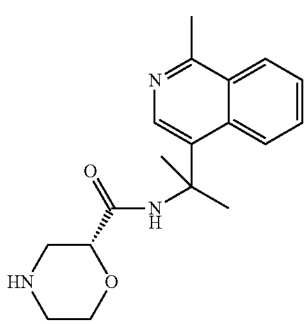 [SMILES: Cc1ncc(C(C)(C)NC(=O)[C@H]2CNCCO2)c2ccccc12] |
| XL | 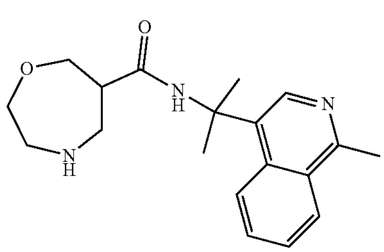 [SMILES: Cc1ncc(C(C)(C)NC(=O)C2CNCCOC2)c2ccccc12] |

-continued

| Comp. | Structure |
|---|---|
| XLI | 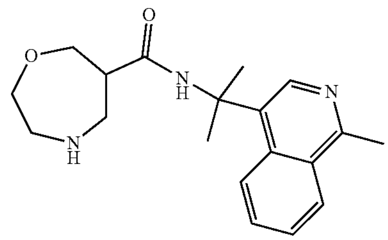 [SMILES: Cc1ncc(C(C)(C)NC(=O)C2CNCCOC2)c2ccccc12] |
| XLII | 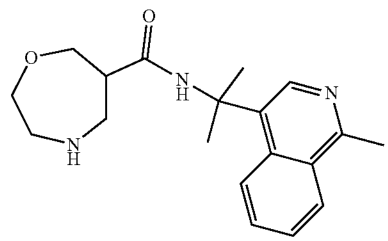 [SMILES: Cc1ncc(C(C)(C)NC(=O)C2CNCCOC2)c2ccccc12] |
| XLIII | 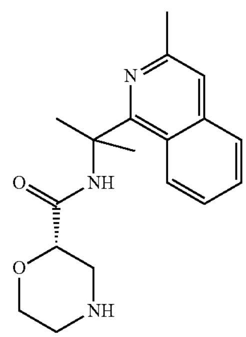 [SMILES: Cc1cc2ccccc2c(C(C)(C)NC(=O)[C@@H]2CNCCO2)n1] |
| XLIV | 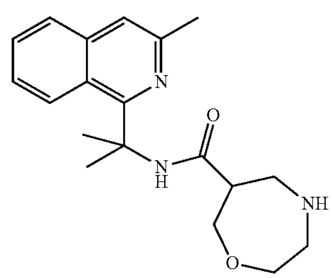 [SMILES: Cc1cc2ccccc2c(C(C)(C)NC(=O)C2CNCCOC2)n1] |
| XLV | 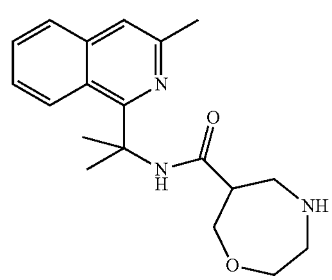 [SMILES: Cc1cc2ccccc2c(C(C)(C)NC(=O)C2CNCCOC2)n1] |

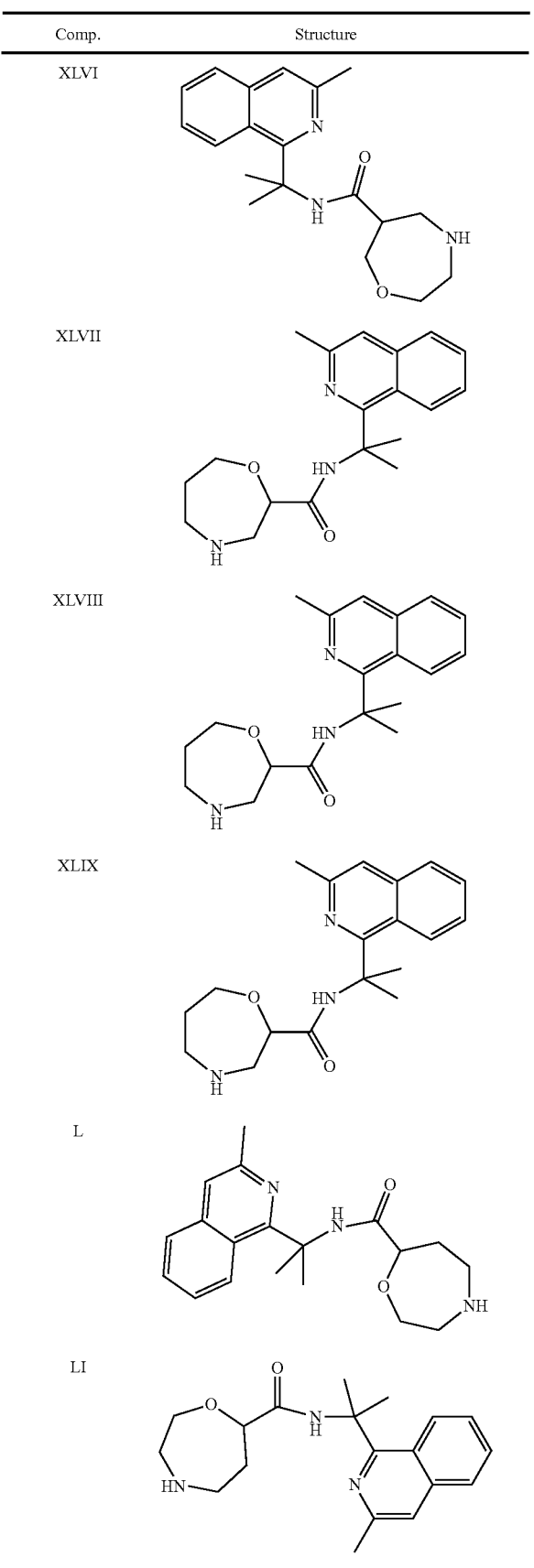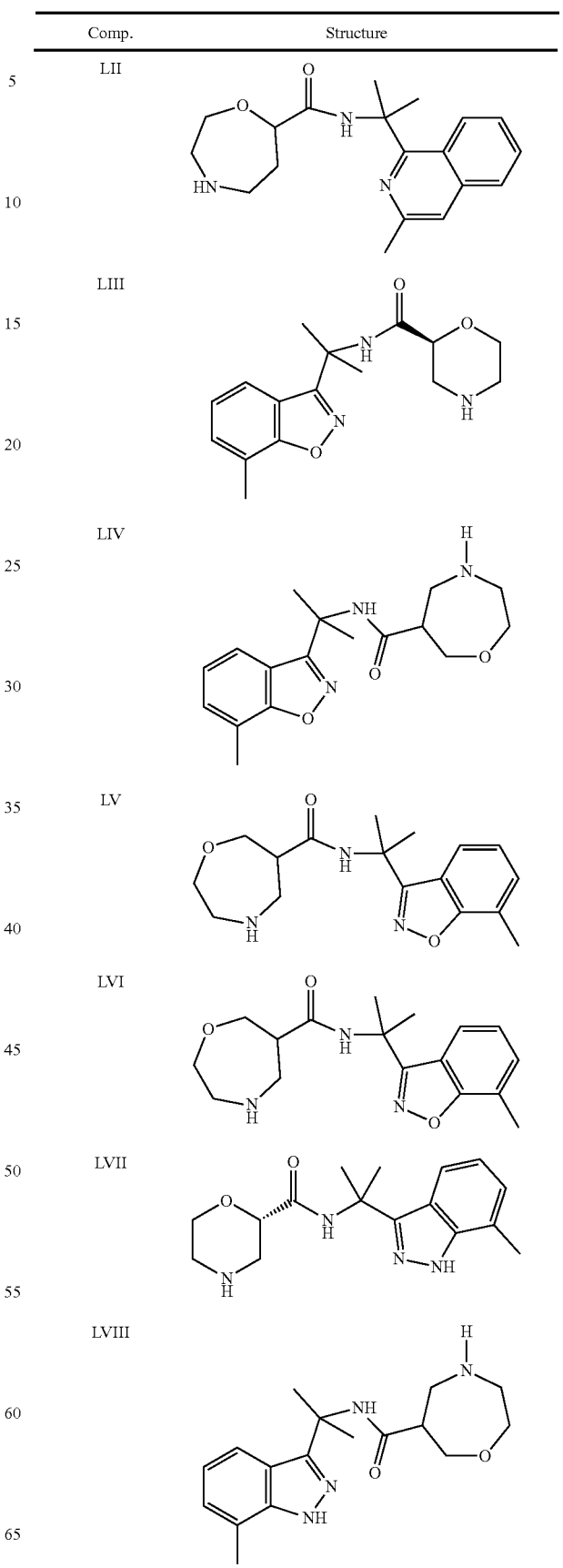

| Comp. | Structure |
|---|---|
| LIX | 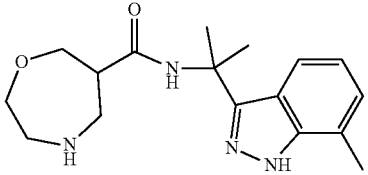 [SMILES: Cc1cccc2c(C(C)(C)NC(=O)C3CNCCOC3)n[nH]c12] |
| LX | 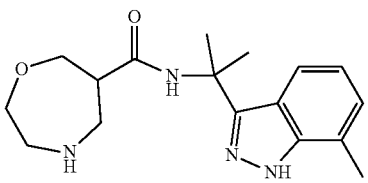 [SMILES: Cc1cccc2c(C(C)(C)NC(=O)C3CNCCOC3)n[nH]c12] |
| LXI | 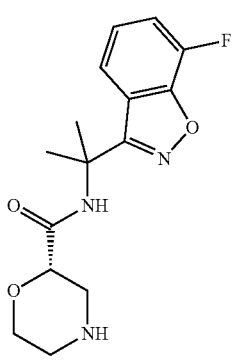 [SMILES: CC(C)(NC(=O)[C@@H]1CNCCO1)c1noc2c(F)cccc12] |
| LXII | 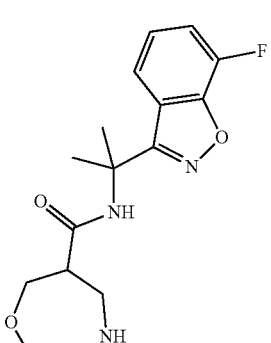 |
| LXIII | 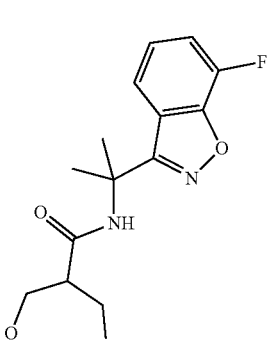 |
| LXIV | 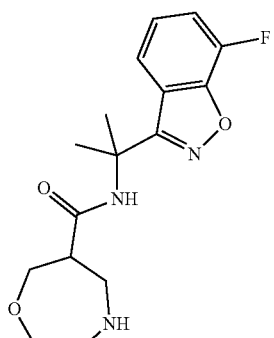 |
| LXV | 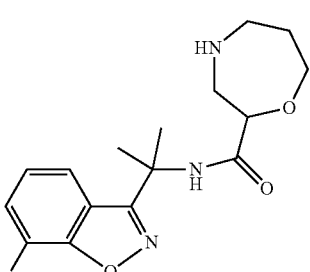 |
| LXVI | 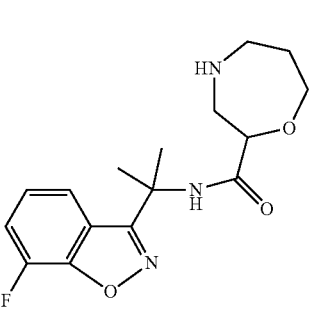 [SMILES: CC(C)(NC(=O)C1CNCCCO1)c1noc2c(F)cccc12] |
| LXVII | 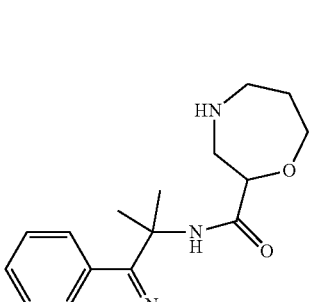 |
| LXVIII | 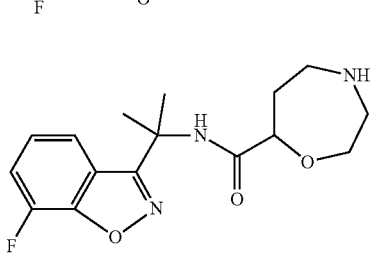 |

| Comp. | Structure |
|---|---|
| LXIX | 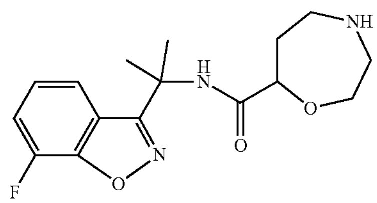 [SMILES: CC(C)(NC(=O)C1CCNCCO1)c1noc2c(F)cccc12] |
| LXX | 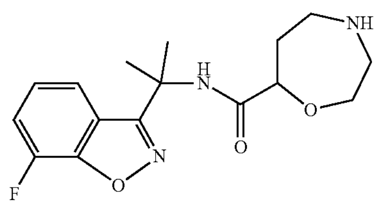 [SMILES: CC(C)(NC(=O)C1CCNCCO1)c1noc2c(F)cccc12] |
| LXXI | 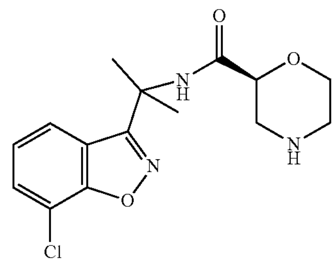 [SMILES: CC(C)(NC(=O)[C@@H]1CNCCO1)c1noc2c(Cl)cccc12] |
| LXXII | 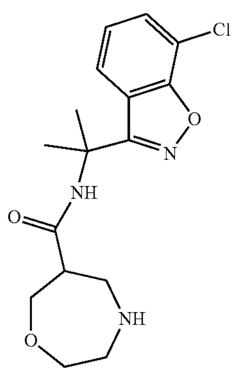 [SMILES: CC(C)(NC(=O)C1CNCCOC1)c1noc2c(Cl)cccc12] |
| LXXIII | 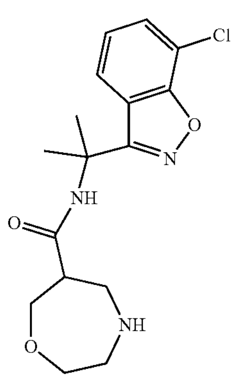 [SMILES: CC(C)(NC(=O)C1CNCCOC1)c1noc2c(Cl)cccc12] |

| Comp. | Structure |
|---|---|
| LXXIV | 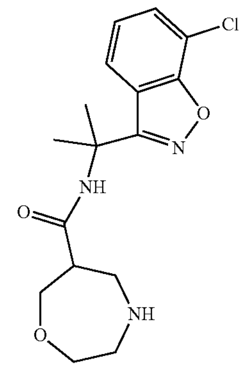 [SMILES: CC(C)(NC(=O)C1CNCCOC1)c1noc2c(Cl)cccc12] |
| LXXV | 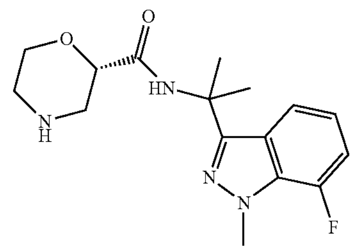 [SMILES: Cn1nc(C(C)(C)NC(=O)[C@@H]2CNCCO2)c2cccc(F)c21] |
| LXXVI | 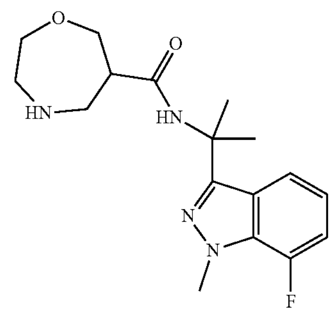 [SMILES: Cn1nc(C(C)(C)NC(=O)C2CNCCOC2)c2cccc(F)c21] |
| LXXVII | 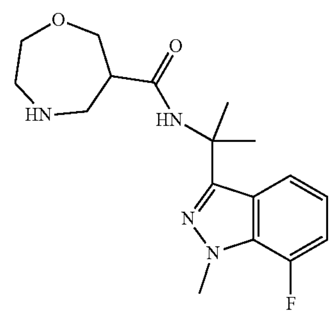 [SMILES: Cn1nc(C(C)(C)NC(=O)C2CNCCOC2)c2cccc(F)c21] |
| LXXVIII | 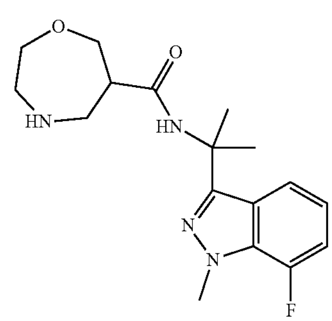 [SMILES: Cn1nc(C(C)(C)NC(=O)C2CNCCOC2)c2cccc(F)c21] |

| Comp. | Structure |
|---|---|
| LXXIX | |
| LXXX | |
| LXXXI | |
| LXXXII | |
| LXXXIII | |
| LXXXIV | 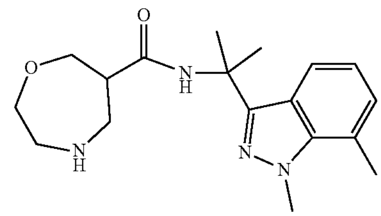 [SMILES: Cc1cccc2c(C(C)(C)NC(=O)C3CNCCOC3)nn(C)c12] |
| LXXXV | 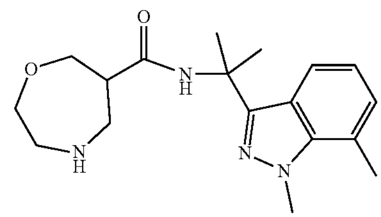 [SMILES: Cc1cccc2c(C(C)(C)NC(=O)C3CNCCOC3)nn(C)c12] |
| LXXXVI | 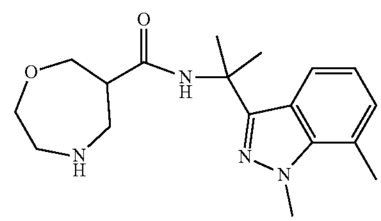 [SMILES: Cc1cccc2c(C(C)(C)NC(=O)C3CNCCOC3)nn(C)c12] |
| LXXXVII | 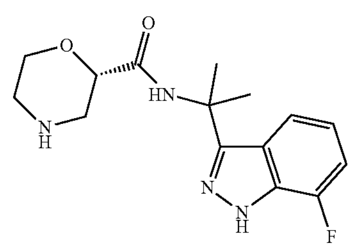 [SMILES: CC(C)(NC(=O)[C@@H]1CNCCO1)c1n[nH]c2c(F)cccc12] |
| LXXXVIII | 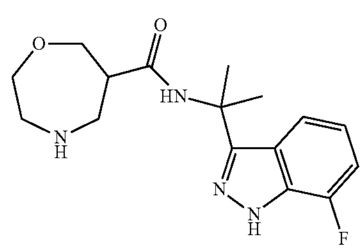 [SMILES: CC(C)(NC(=O)C1CNCCOC1)c1n[nH]c2c(F)cccc12] |
| LXXXIX | 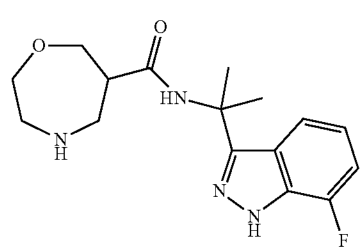 [SMILES: CC(C)(NC(=O)C1CNCCOC1)c1n[nH]c2c(F)cccc12] |

| Comp. | Structure |
|---|---|
| XC | 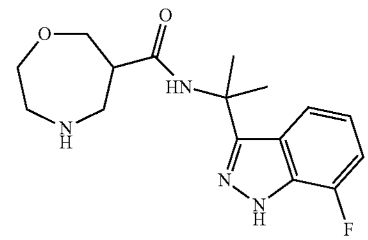 [SMILES: CC(C)(NC(=O)C1CNCCOC1)c1n[nH]c2c(F)cccc12] |
| XCI | 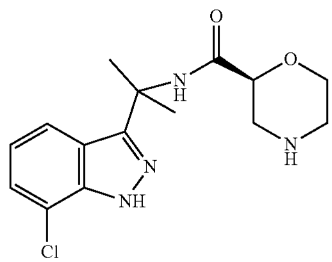 [SMILES: CC(C)(NC(=O)[C@@H]1CNCCO1)c1n[nH]c2c(Cl)cccc12] |
| XCII | 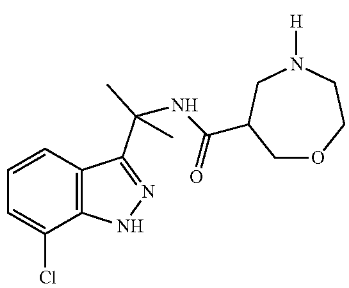 [SMILES: CC(C)(NC(=O)C1CNCCOC1)c1n[nH]c2c(Cl)cccc12] |
| XCIII | 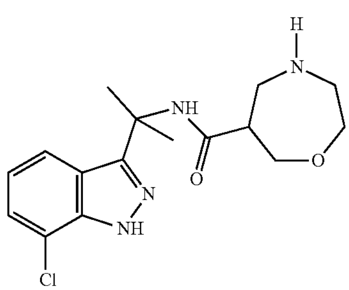 [SMILES: CC(C)(NC(=O)C1CNCCOC1)c1n[nH]c2c(Cl)cccc12] |
| XCIV | 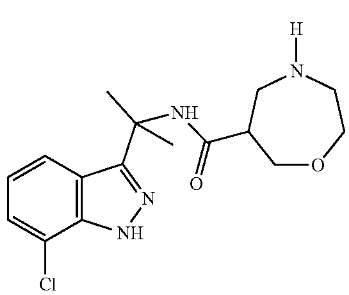 [SMILES: CC(C)(NC(=O)C1CNCCOC1)c1n[nH]c2c(Cl)cccc12] |

| Comp. | Structure |
|---|---|
| XCV | 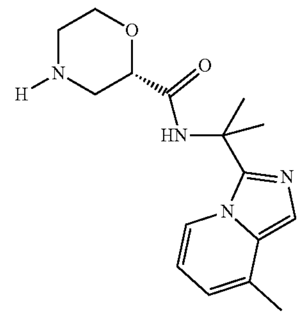 [SMILES: Cc1cccn2c(C(C)(C)NC(=O)[C@@H]3CNCCO3)ncc12] |
| XCVI | 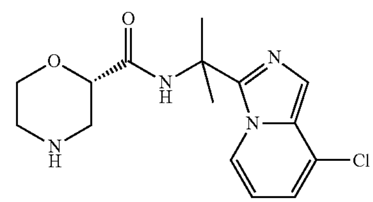 [SMILES: CC(C)(NC(=O)[C@@H]1CNCCO1)c1ncc2c(Cl)cccn12] |
| XCVII | 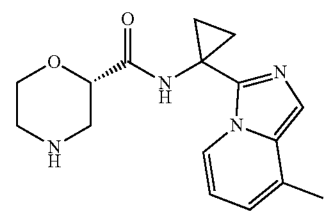 [SMILES: Cc1cccn2c(C3(NC(=O)[C@@H]4CNCCO4)CC3)ncc12] |
| XCVIII | 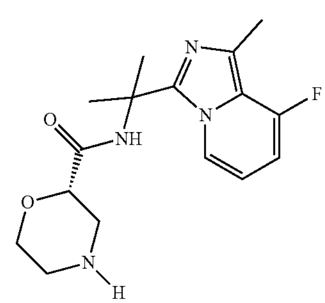 [SMILES: Cc1nc(C(C)(C)NC(=O)[C@@H]2CNCCO2)n2cccc(F)c12] |
| XCIX | 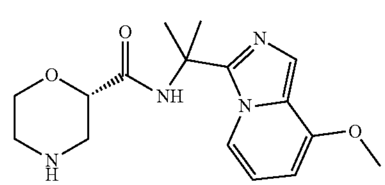 [SMILES: COc1cccn2c(C(C)(C)NC(=O)[C@@H]3CNCCO3)ncc12] |
| C | 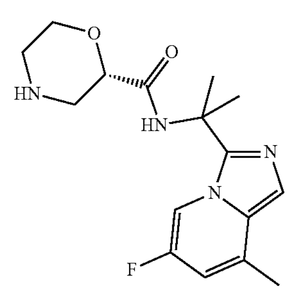 [SMILES: Cc1cc(F)cn2c(C(C)(C)NC(=O)[C@@H]3CNCCO3)ncc12] |

-continued
| Comp. | Structure |
|---|---|
| CI | 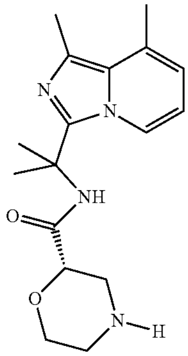 [SMILES: Cc1cccn2c(C(C)(C)NC(=O)[C@@H]3CNCCO3)nc(C)c12] |
| CII | 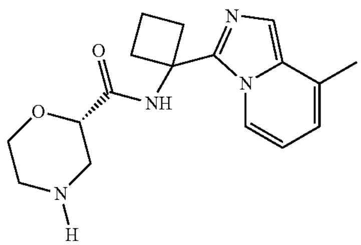 [SMILES: Cc1cccn2c(C3(NC(=O)[C@@H]4CNCCO4)CCC3)ncc12] |
| CIII | 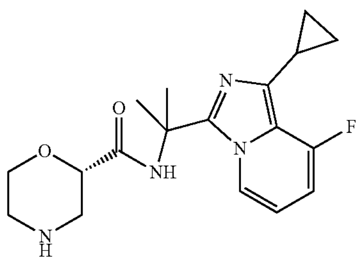 [SMILES: CC(C)(NC(=O)[C@@H]1CNCCO1)c1nc(C2CC2)c2c(F)cccn12] |
| CIV | 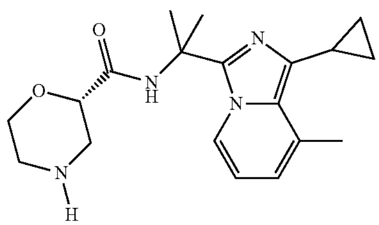 [SMILES: Cc1cccn2c(C(C)(C)NC(=O)[C@@H]3CNCCO3)nc(C3CC3)c12] |
| CV | 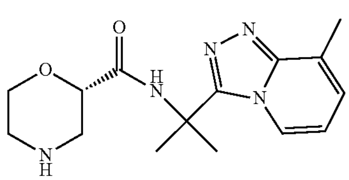 [SMILES: Cc1cccn2c(C(C)(C)NC(=O)[C@@H]3CNCCO3)nnc12] |
| CVI | 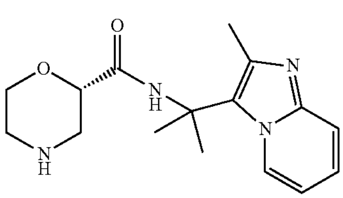 [SMILES: Cc1nc2ccccn2c1C(C)(C)NC(=O)[C@@H]1CNCCO1] |
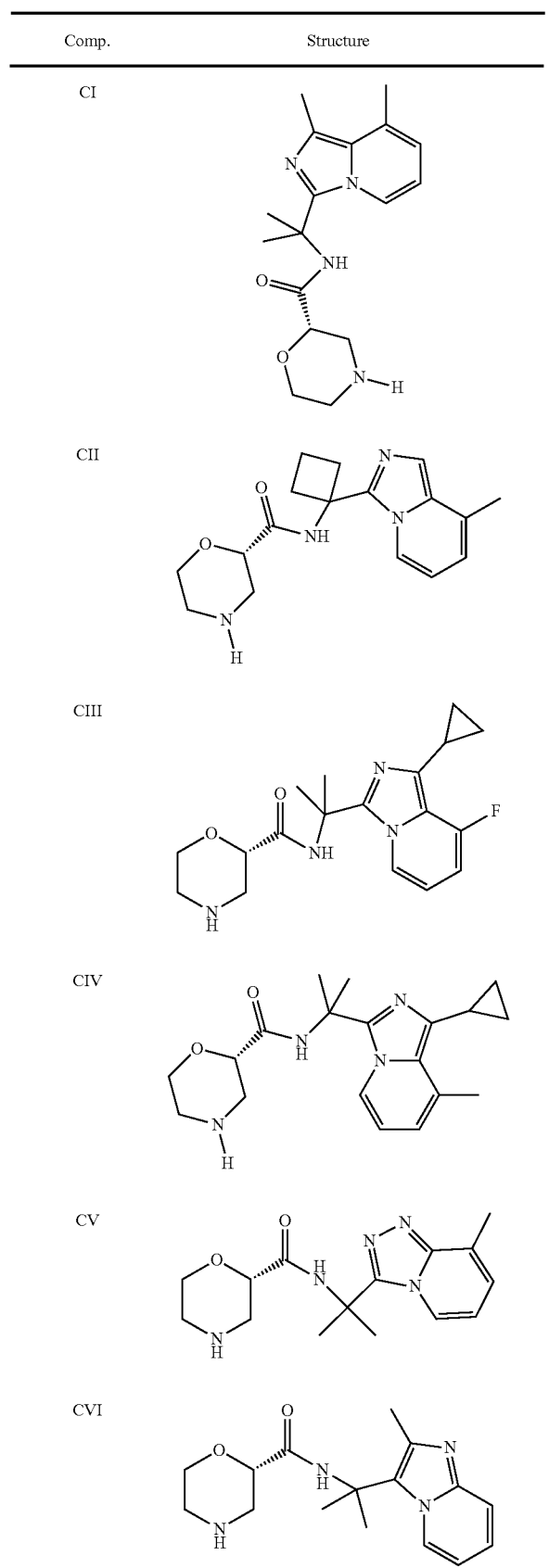
-continued
| Comp. | Structure |
|---|---|
| CVII | 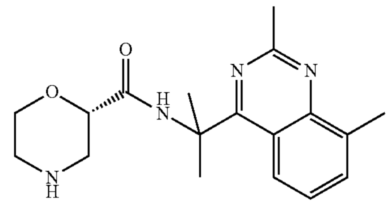 [SMILES: Cc1nc(C(C)(C)NC(=O)[C@@H]2CNCCO2)c2cccc(C)c2n1] |
| CVIII | 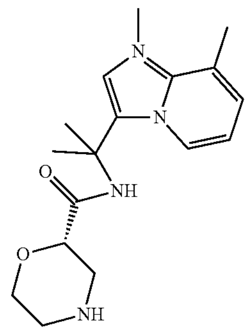 |
| CIX | 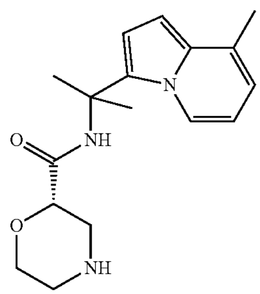 [SMILES: Cc1cccn2c(C(C)(C)NC(=O)[C@@H]3CNCCO3)ccc12] |
| CX | 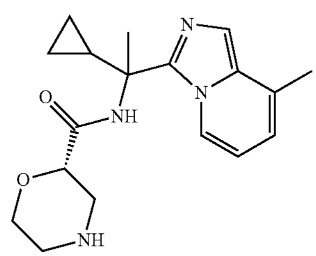 [SMILES: Cc1cccn2c(C(C)(NC(=O)[C@@H]3CNCCO3)C3CC3)ncc12] |
| CXI | 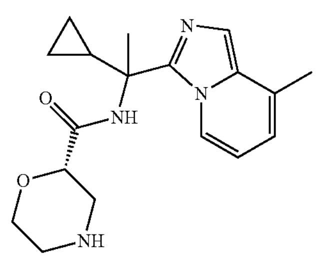 [SMILES: Cc1cccn2c(C(C)(NC(=O)[C@@H]3CNCCO3)C3CC3)ncc12] |
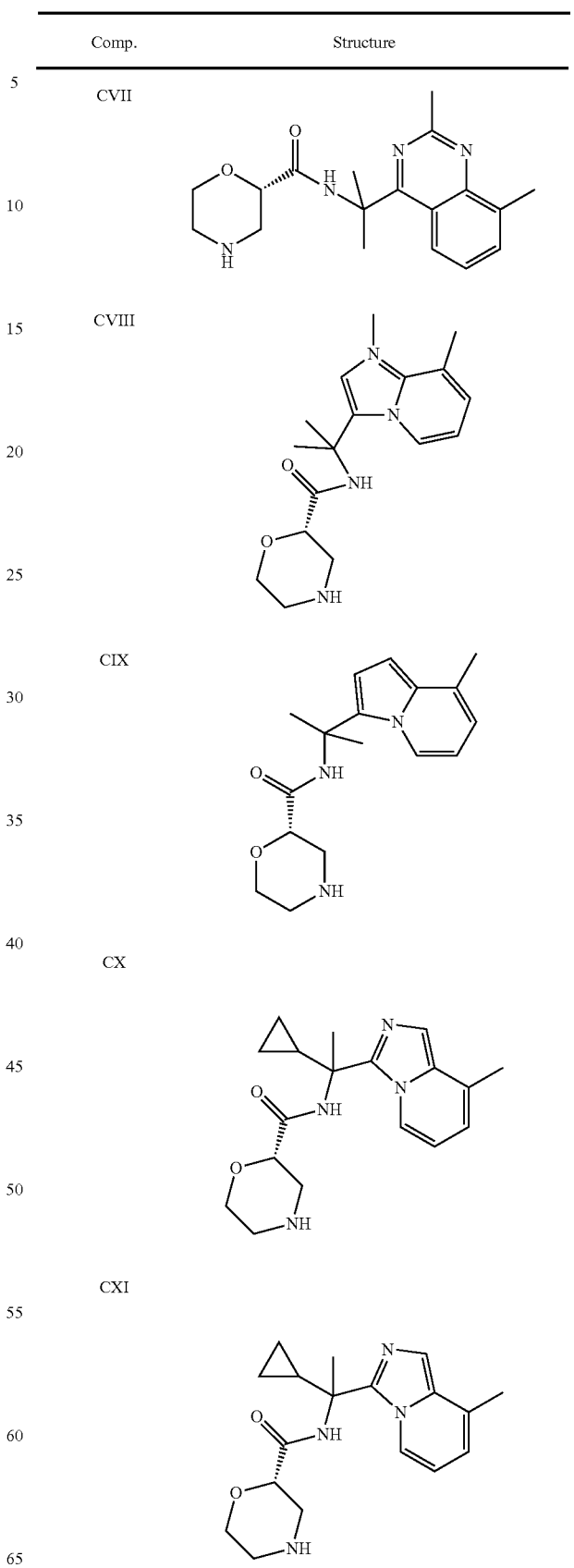

| Comp. | Structure |
|---|---|
| CXII | 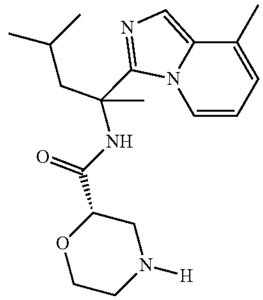 [SMILES: Cc1cccn2c(C(C)(CC(C)C)NC(=O)[C@@H]3CNCCO3)ncc12] |
| CXIII | 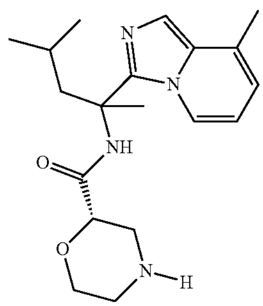 [SMILES: Cc1cccn2c(C(C)(CC(C)C)NC(=O)[C@@H]3CNCCO3)ncc12] |
| CXIV | 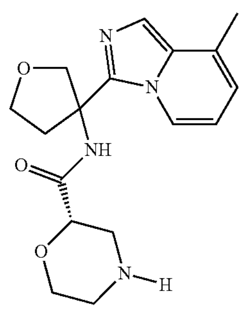 [SMILES: Cc1cccn2c(C3(NC(=O)[C@@H]4CNCCO4)CCOC3)ncc12] |
| CXV | 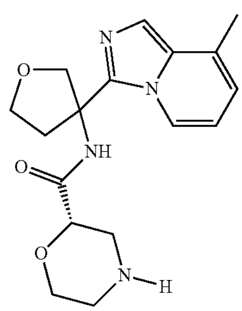 [SMILES: Cc1cccn2c(C3(NC(=O)[C@@H]4CNCCO4)CCOC3)ncc12] |
| CXVI | 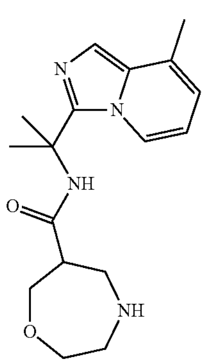 [SMILES: Cc1cccn2c(C(C)(C)NC(=O)C3CNCCOC3)ncc12] |
| CXVII | |
| CXVIII | |
| CXIX | |
| CXX | |
| CXXI | |

| Comp. | Structure |
|---|---|
| CXXII | 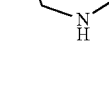 |
| CXXIII | 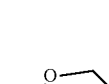 |
| CXXIV | 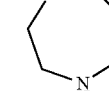 |
| CXXV |  |
| Comp. | Structure |
|---|---|
| CXXVI |  |
| CXXVII | |
| CXXVIII | |
| CXXIX | |
| CXXX | |

| Comp. | Structure |
|---|---|
| CXXXI | |
| CXXXII | |
| CXXXIII | |
| CXXXIV | |
| CXXXV | 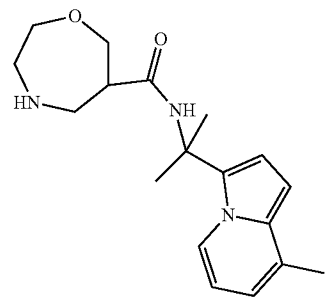 [SMILES: Cc1cccn2c(C(C)(C)NC(=O)C3CNCCOC3)ccc12] |
| CXXXVI | 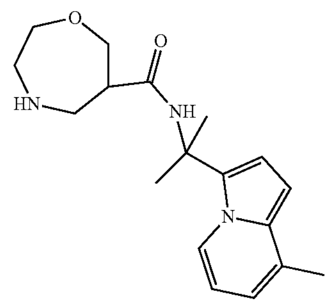 [SMILES: Cc1cccn2c(C(C)(C)NC(=O)C3CNCCOC3)ccc12] |
| CXXXVII | 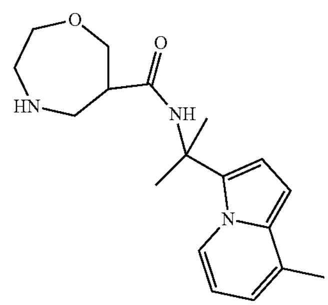 [SMILES: Cc1cccn2c(C(C)(C)NC(=O)C3CNCCOC3)ccc12] |
| CXXXVIII | 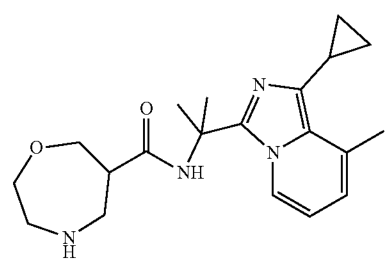 [SMILES: Cc1cccn2c(C(C)(C)NC(=O)C3CNCCOC3)nc(C3CC3)c12] |
| CXXXIX | 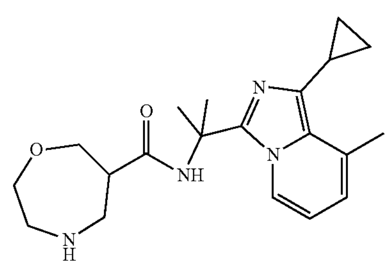 [SMILES: Cc1cccn2c(C(C)(C)NC(=O)C3CNCCOC3)nc(C3CC3)c12] |

| Comp. | Structure |
|---|---|
| CXL | 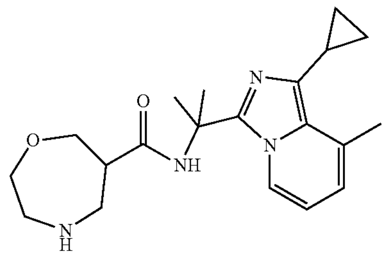 [SMILES: Cc1cccn2c(C(C)(C)NC(=O)C3CNCCOC3)nc(C3CC3)c12] |
| CXLI | 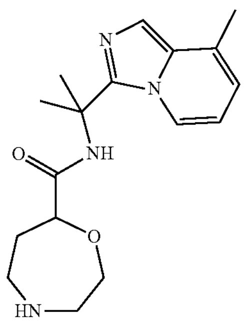 [SMILES: Cc1cccn2c(C(C)(C)NC(=O)C3CCNCCO3)ncc12] |
| CXLII | 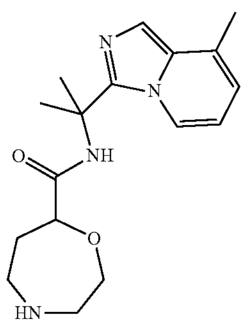 [SMILES: Cc1cccn2c(C(C)(C)NC(=O)C3CCNCCO3)ncc12] |
| CXLIII | 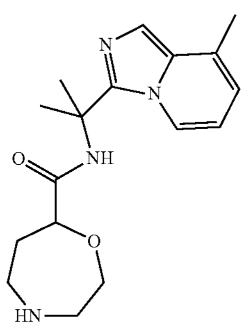 [SMILES: Cc1cccn2c(C(C)(C)NC(=O)C3CCNCCO3)ncc12] |
| CXLIV | 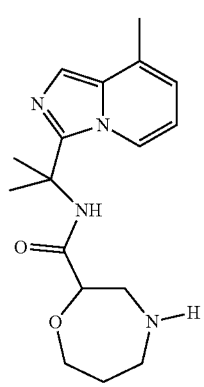 [SMILES: Cc1cccn2c(C(C)(C)NC(=O)C3CNCCCO3)ncc12] |
| CXLV | |
| CXLVI | |
| CXLVII | |
| CXLVIII | |

| Comp. | Structure |
|---|---|
| CXLIX | (structure depicted) |

TERMS AND DEFINITIONS USED

General Definitions:

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

The number of substituents $R^3$ of W is preferably from 0 to 3, more preferably from 0 to 2, most preferably 1 or 2.

For the instances where Y is —$CH_2O$— this to be interpreted such that the oxygen atom of —$CH_2O$— is connected to W.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The prefix "meso" indicates the presence of a symmetry element of the second kind (mirror plane, centre of inversion, rotation-reflection axis) in a chemical species.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term "halogen" generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH$ (CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Alkylene:

The term "C$_{1-n}$-alkylene" wherein n is an integer 2 to n, either alone or in combination with another radical, denotes an acyclic, straight or branched chain divalent alkyl radical containing from 1 to n carbon atoms. For example the term C$_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(CH$_2$CH$_3$)—, —CH(CH$_2$CH$_3$)—CH$_2$—, —CH(CH$_2$CH$_2$CH$_3$)—, —CH(CH(CH$_3$))$_2$— and —C(CH$_3$)(CH$_2$CH$_3$)—.

Alkenyl:

The term "C$_{2-n}$-alkenyl" is used for a group as defined in the definition for "C$_{1-n}$-alkyl" with at least two carbon atoms, if at least two of those carbon atoms of said group are bonded to each other by a double bond.

Alkynyl:

The term "C$_{2-n}$-alkynyl" is used for a group as defined in the definition for "C$_{1-n}$-alkyl" with at least two carbon atoms, if at least two of those carbon atoms of said group are bonded to each other by a triple bond.

Cycloalkyl:

The term "C$_{3-n}$-cycloalkyl" wherein n is an integer from 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

Heterocyclyl:

The term "heterocyclyl" means a saturated or unsaturated mono- or polycyclic-ring systems including aromatic ring system containing one or more heteroatoms selected from N, O or S(O)r, wherein r=0, 1 or 2, consisting of 5 to 11 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

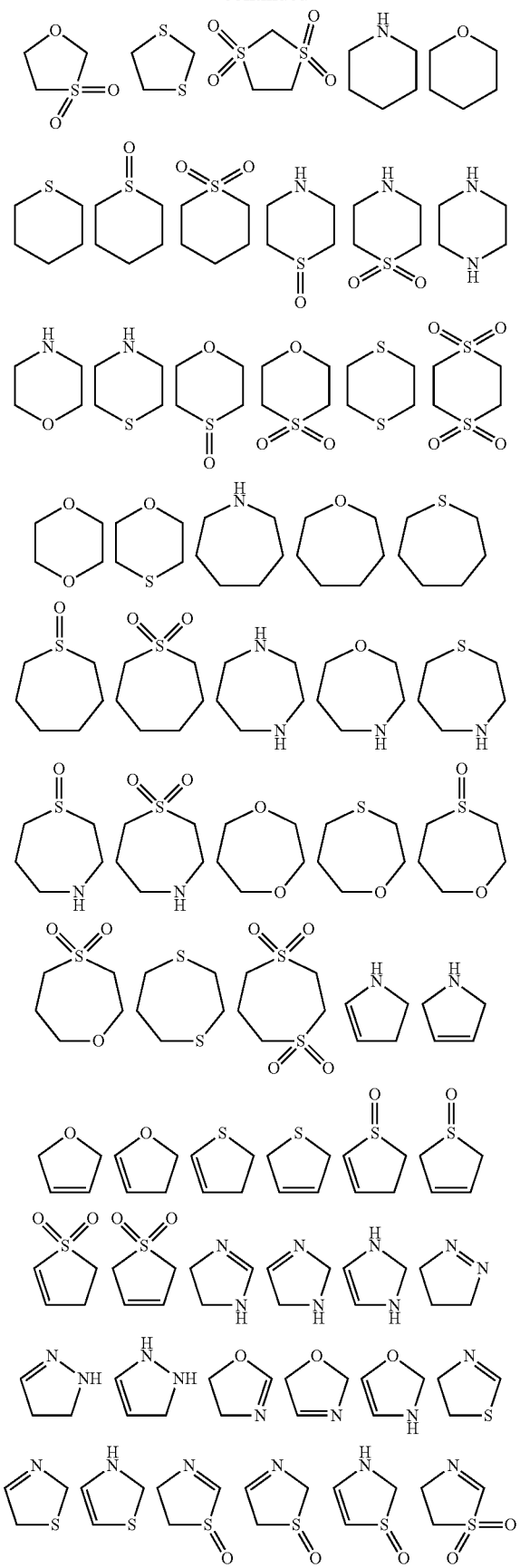

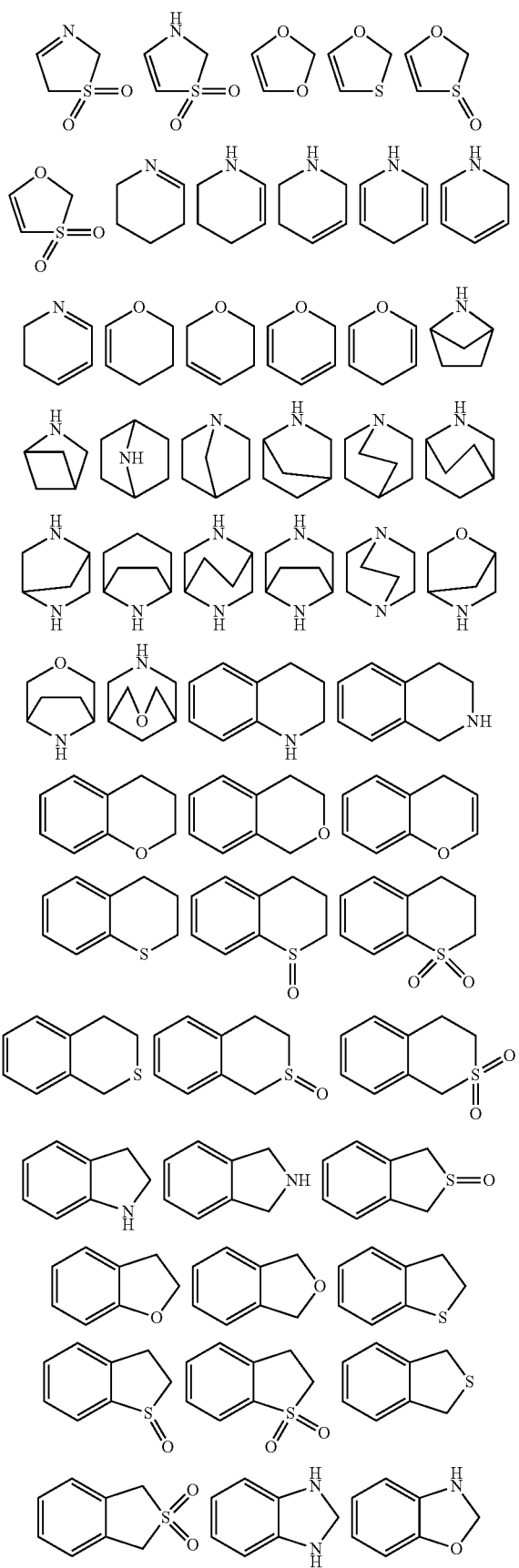
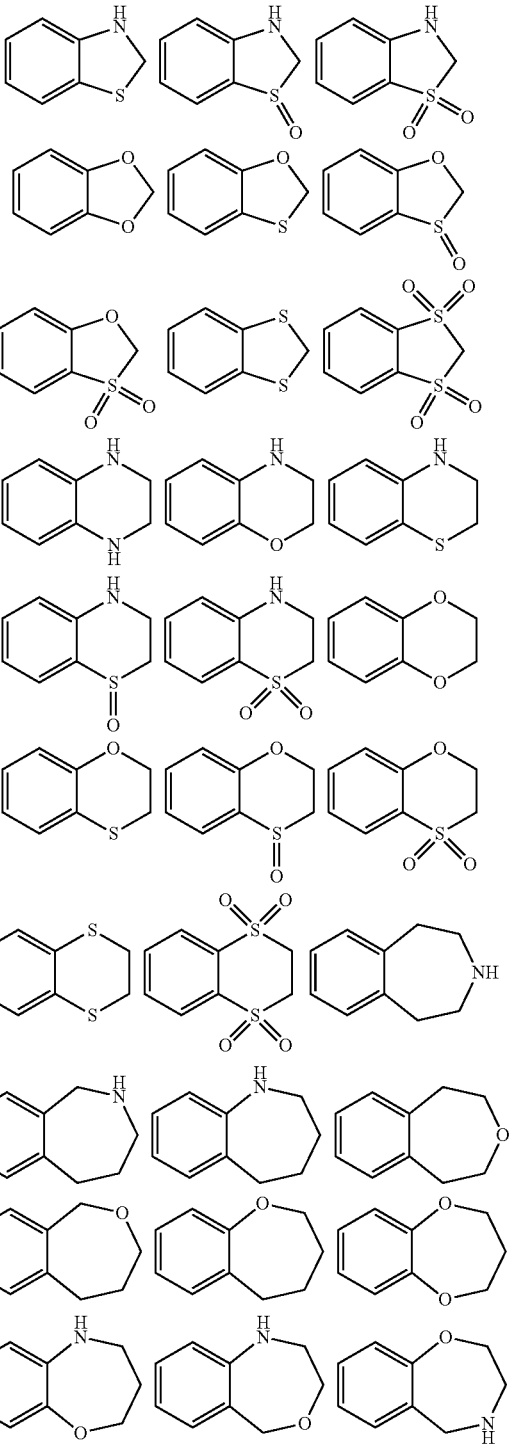

Aryl:

The term "aryl" as used herein, either alone or in combination with another radical, denotes a carbocyclic aromatic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heteroaryl:

The term "heteroaryl" means a mono- or bicyclic-ring systems containing one or more heteroatoms selected from N, O or $S(O)_r$, wherein r=0, 1 or 2, consisting of 5 to 10 ring atoms, wherein at least one of the heteroatoms is part of an aromatic ring. The term "heteroaryl" is intended to include all the possible isomeric forms. Preferred heteroaryls for the present invention comprise up to 4 heteroatoms and at least one 5- or 6-membered ring, more preferably at least one 6-membered ring.

Thus, the term "heteroaryl" includes the following exemplary structures which are not depicted as radicals as each form may be attached through a covalent bond to any atom so long as appropriate valences are maintained:

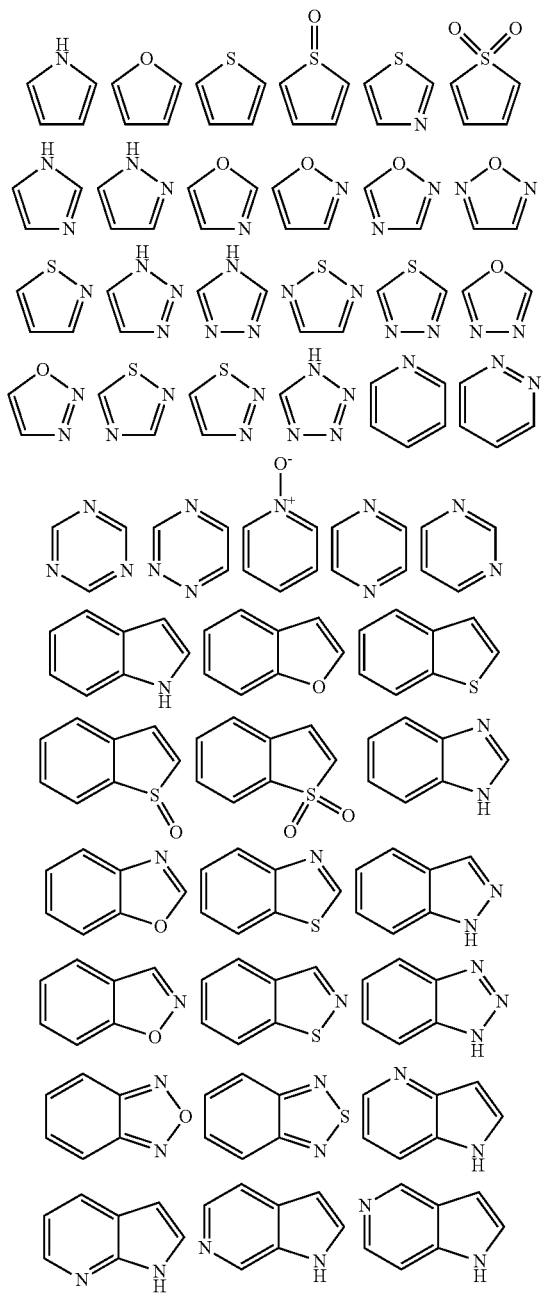
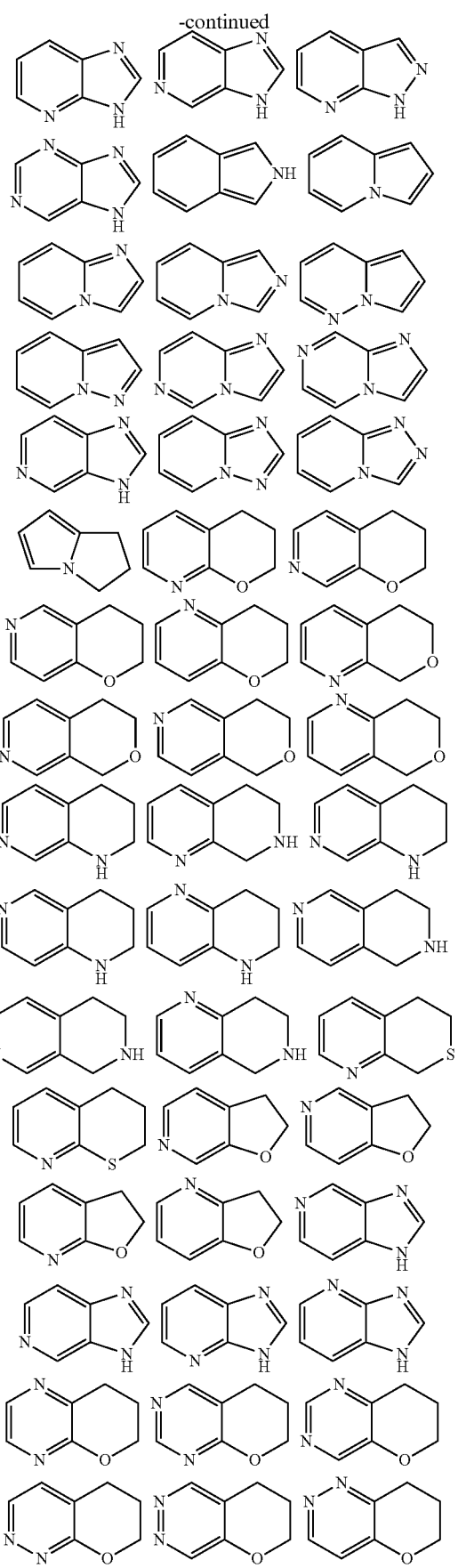

-continued

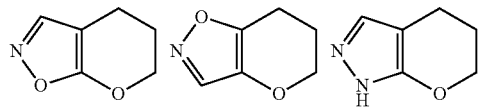

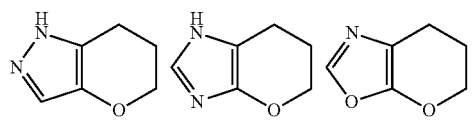

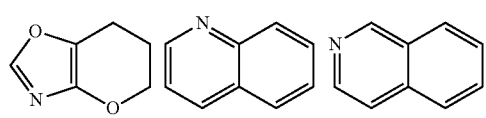

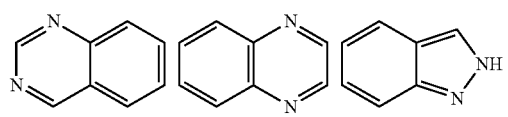

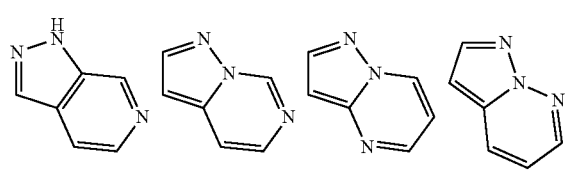

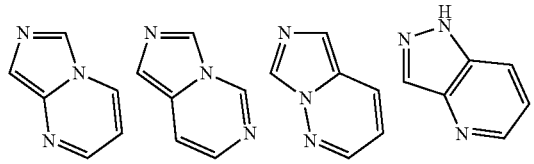

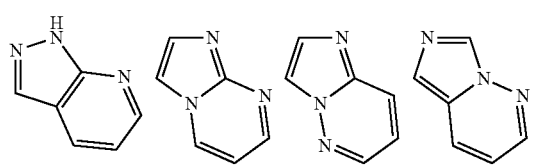

Many of the terms given above may be used repeatedly in the definition of a formula or group and in each case have one of the meanings given above, independently of one another.

METHODS OF PREPARATION

The compounds according to the invention may be obtained using methods of synthesis known in principle. Preferably, the compounds are obtained by the following methods according to the invention which are described in more detail hereinafter.

The following schemes shall illustrate generally how to manufacture the compounds according to general formula (I) and the corresponding intermediate compounds by way of example. The abbreviated substituents may be as defined above if not defined otherwise within the context of the schemes. For a list of abbreviations, see below.

Scheme 1

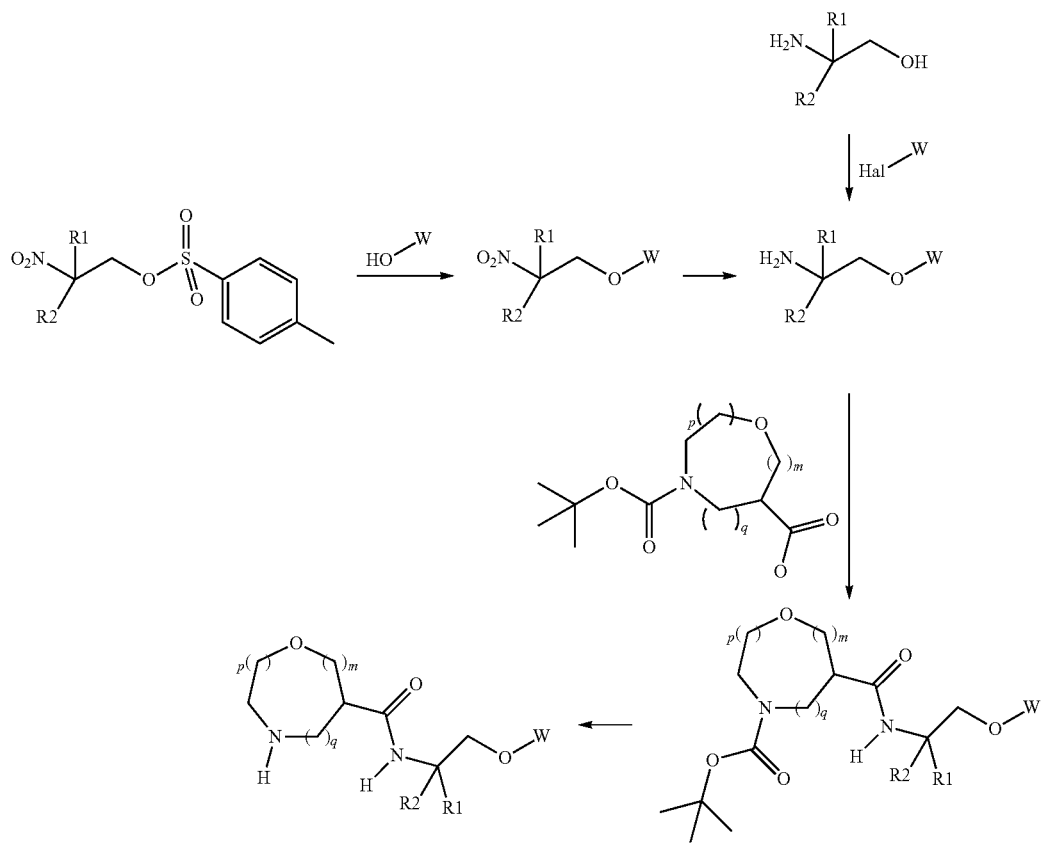

In scheme 1, Hal=halogen.

Scheme 1: In a first step a derivative of toluene-4-sulfonic acid 2-nitro-ethyl ester is reacted with an alcohol in the presence of an appropriate base such as Cesium carbonate in an appropriate solvent such as N,N-dimethylacetamide at elevated temperatures. The nitro group of the resulting product is converted in the corresponding primary amine by hydrogenation in the presence of an appropriate catalyst such as Raney Nickel in an appropriate solvent such as methanol. Alternatively, the amino ether is prepared by reacting an amino alcohol with a halide in the presence of an appropriate base such as sodium hydride in an appropriate solvent such as dioxane. The amino ether is coupled with an appropriate carboxylic acid in an appropriate solvent such as DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Scheme 2

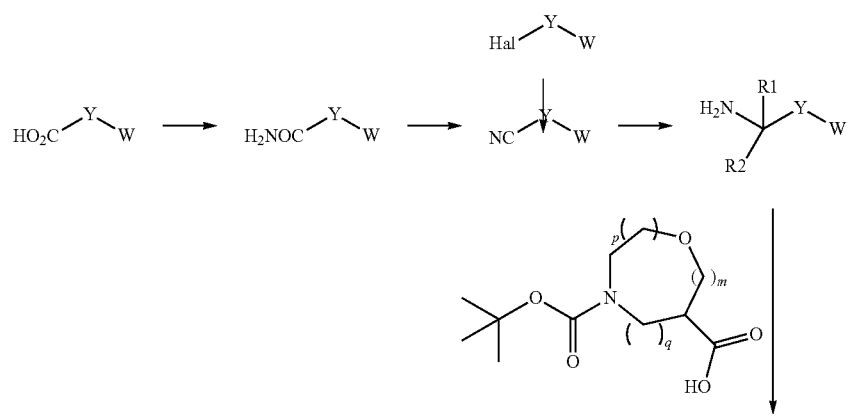

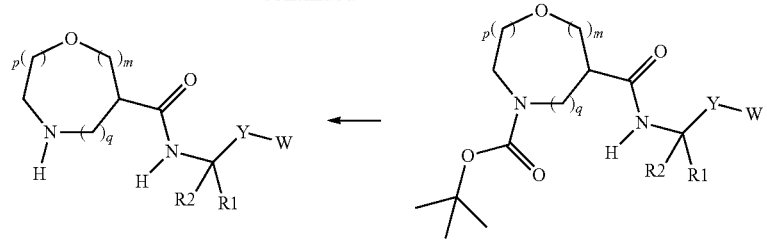

In scheme 2, Hal=halogen.

Scheme 2: In a first step a carboxylic acid is coupled with ammonium hydroxide in the presence of 1,1'-carbonyldiimidazole in an appropriate solvent such as THF. The primary amide functional group is converted into a nitrile functional group using Burgess reagent in an appropriate solvent such as DCM or using trifluoroacetic anhydride and pyridine in an appropriate solvent such as DCM. Alternatively, a halogen-substituted derivative is converted into a nitrile upon treatment with Zinc cyanide in the presence of a Palladium source (e.g. tris(dibenzylideneacetone)dipalladium(0) or 1,1-bis(diphenylphosphino) ferrocenedichloro palladium (II)), a phosphine (e.g. 1,1'-bis(diphenylphosphino)ferrocene), optionally Zinc, in appropriate solvents such as DMF or N,N-dimethyl-acetamide at elevated temperatures. Nitriles are reacted with Cerium (III) chloride and alkyl-lithiums (see *J. Org. Chem.* 1992, 57, 4521-452) in an appropriate solvent such as THF or alternatively with Grignard reagents in an appropriate solvent such as toluene at elevated temperatures. The resulting amine is coupled with an appropriate carboxylic acid in an appropriate solvent such as DCM or DMF and in the presence of a coupling agent (e.g. HATU or TBTU) and a base (e.g. TEA or DIPEA). In case W is substituted with $R^3$=halogen, such group can be substituted upon treatment with a stannane or a boronic acid or a trifluoroborate or a boroxine in the presence of a Palladium source (e.g 1,1'-Bis(diphenylphosphino)ferrocene-palladium(II)dichloride dichloromethane complex), in appropriate solvents such as DMF at elevated temperatures.

The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol. Alternatively, Boc removal is accomplished by treatment with a silylating agent (e.g. tert-butyldimethylsilyl trifluoromethanesulfonate) in the presence of a base (e.g. 2,6-lutidine) in appropriate solvents such as DCM followed by reaction with a fluoride source (e.g. tetrabutylammonium fluoride) in appropriate solvents such as THF.

Scheme 3

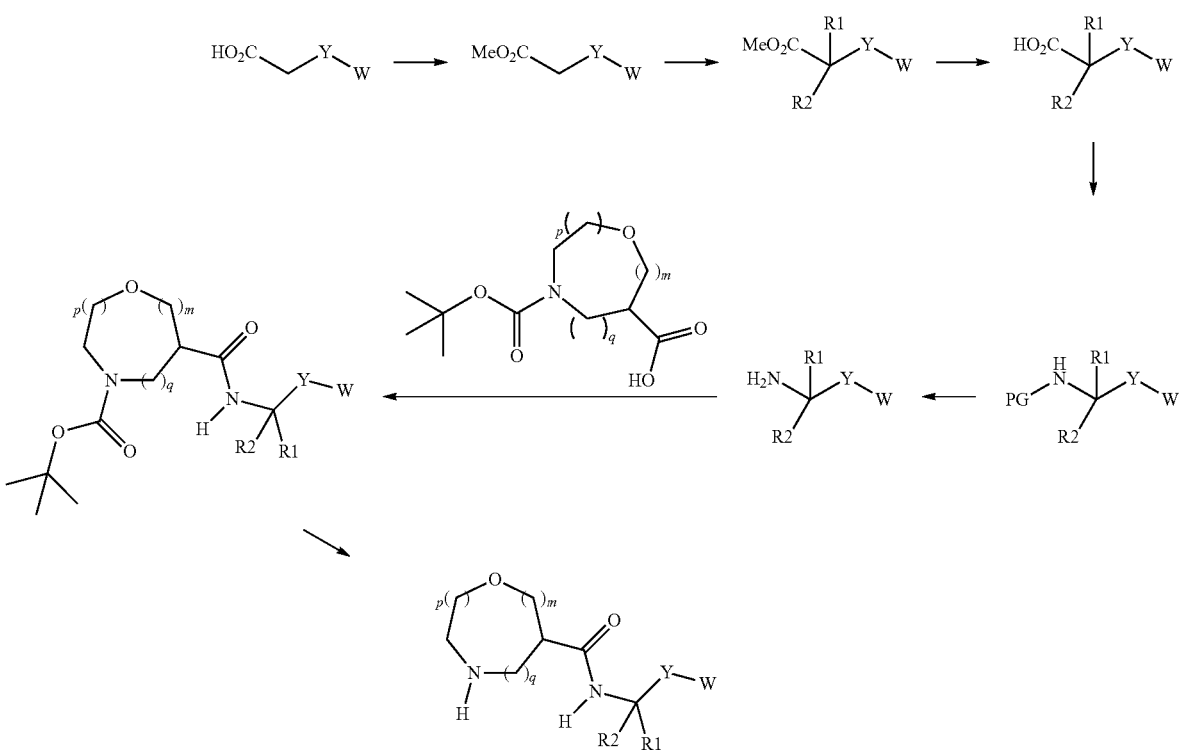

In scheme 3, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting group is 4-methoxy-benzyloxycarbonyl-.

Scheme 3: In a first step a carboxylic is converted into the corresponding ester (e.g. with trimethylsilyldiazomethane in DCM/MeOH). The ester is bis-alkylated by treatment with a base (e.g. Lithium bis(trimethylsilyl)amide) in an appropriate solvent such as THF followed by treatment with alkyalating agent(s) (e.g. iodomethane). The bis-alkylated ester is hydrolysed to the carboxylic acid with a base (e.g. lithium hydroxyde) in appropriate solvent such as THF and water. The carboxylic acid is treated with diphenylphosphoryl azide, a base (e.g. TEA) and an alcohol (e.g. 4-methoxybenzyl alcohol) in an appropriate solvent such as toluene at high temperatures. The 4-methoxy-benzyloxycarbonyl protecting group is deprotected with TFA in an appropriate solvent such as DCM. The amine is coupled with an appropriate carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 4

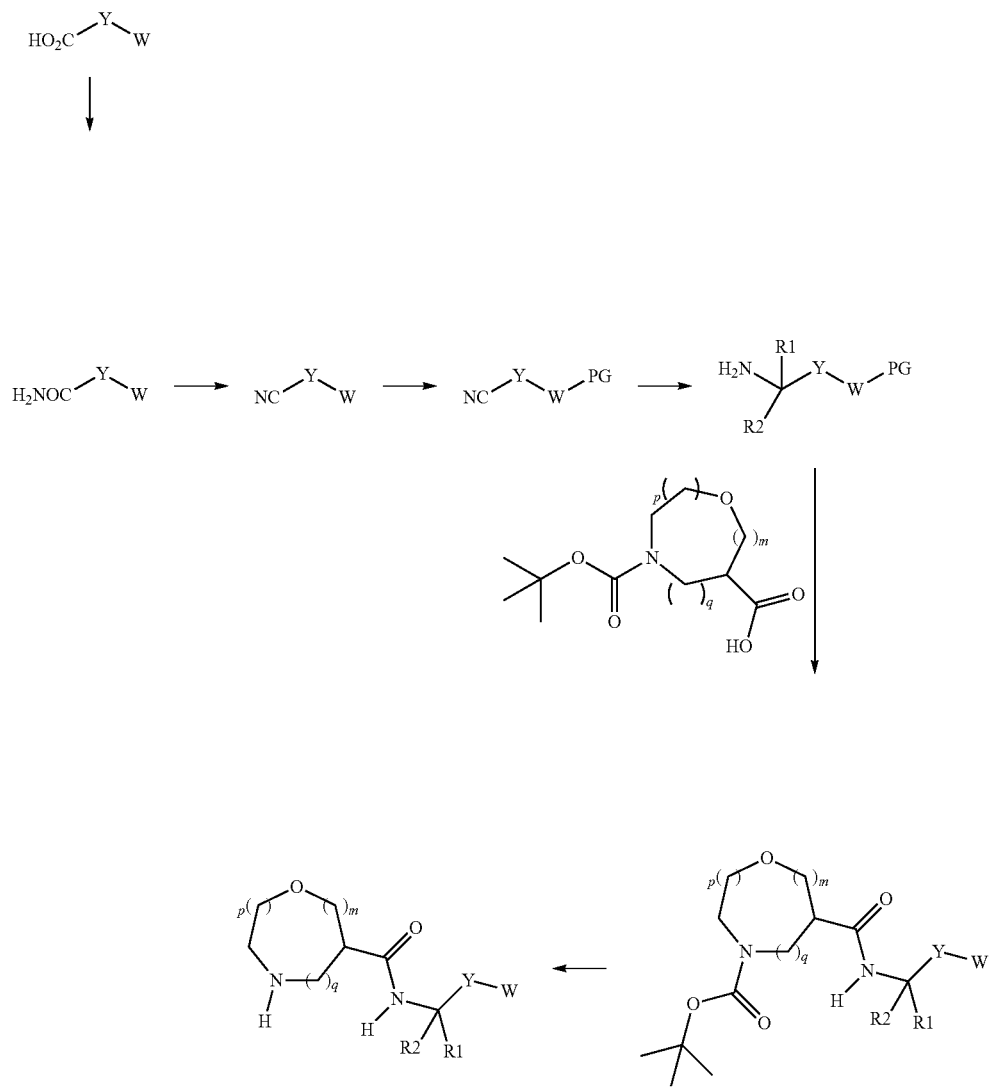

In scheme 4, PG=protecting group for a heteroaryl or heterocyclyl Nitrogen such as outlined in: Peter G. M. Wuts, Theodora W. Greene, Greene's Protective Groups in Organic Synthesis, Wiley-Interscience; 4 edition (Oct. 30, 2006).

Preferred protecting group is trimethylsilylethoxymethyl-.

Scheme 4: in a first step a carboxylic acid is coupled with ammonium hydroxide in the presence of 1,1'-carbonyldiimidazole in an appropriate solvent such as THF. The primary amide functional group is converted into a nitrile functional group using Burgess reagent in an appropriate solvent such as DCM. The trimethylsilylethoxymethyl-protecting group is installed by reaction with 2-(trimethylsilyl)ethoxymethyl chloride, a base (e.g. Sodium hydride) in an appropriate solvent such as DMF. Protected nitriles compounds are reacted with Cerium (III) chloride and alkyllithiums (see *J. Org. Chem.* 1992, 57, 4521-452) in an appropriate solvent such as THF or alternatively with Grignard reagents in an appropriate solvent such as toluene at elevated temperatures. The resulting amine is coupled with an appropriate acid in an appropriate solvent such as DCM or DMF and in the presence of a coupling agent (e.g. HATU or TBTU) and a base (e.g. TEA or DIPEA). The trimethylsilylethoxymethyl-protecting group is removed with tetrabutylammonium fluoride and ethylenediamine. The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 5

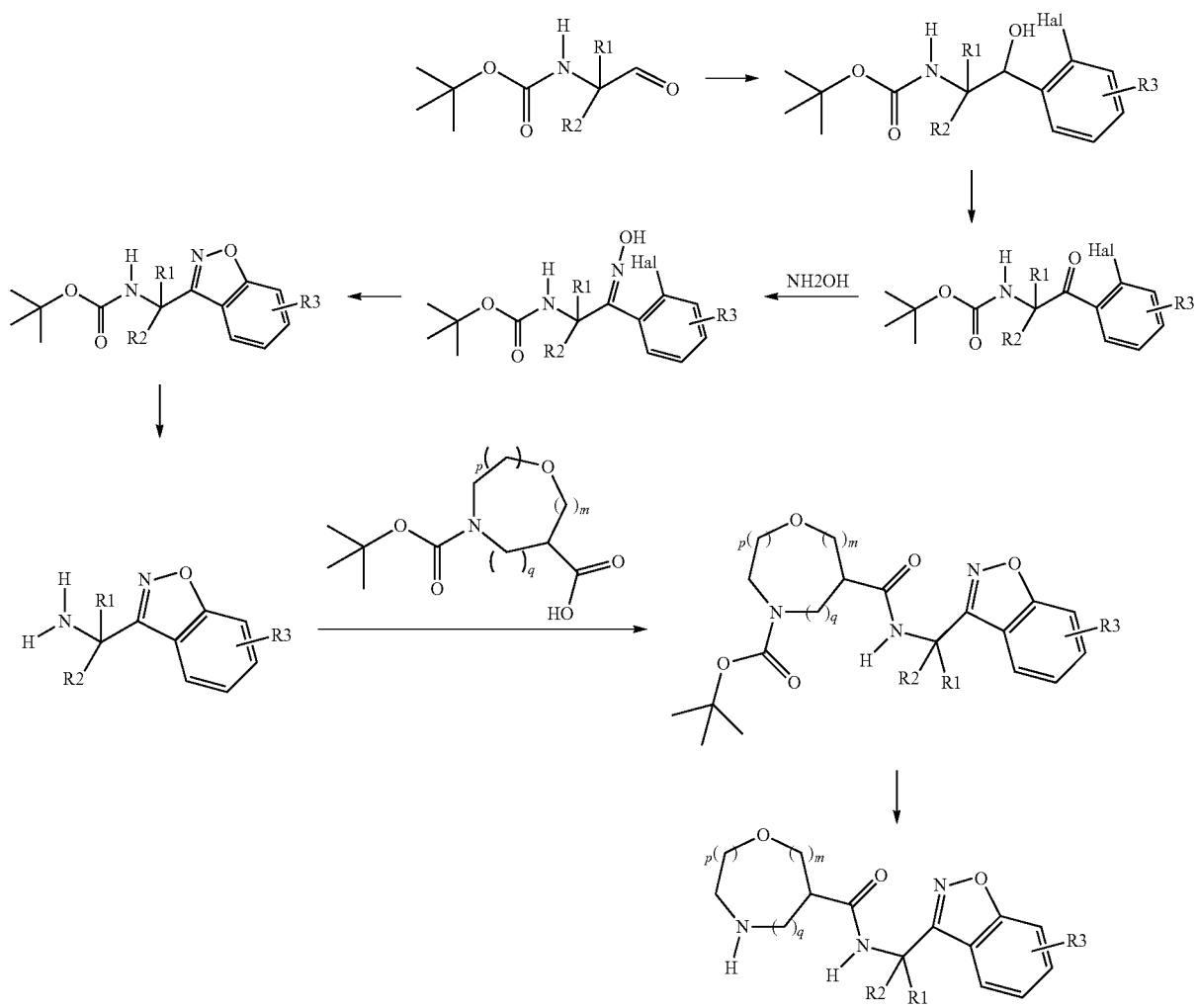

In scheme 5, Hal=halogen.

Scheme 5: in a first step an aldehyde is reacted with an ortho-metallated halide in an appropriate solvent such as THF at low temperatures to afford an alcohol, which in turn is oxidized to the ketone with Dess-Martin periodinane in DCM. The ketone is converted to the oxime upon treatment with hydroxylamine hydrochloride in an appropriate solvent such as pyridine. Reaction with a base (e.g. potassium tert-butoxide) in an appropriate solvent such as THF gives rise to a benzoisoxazole optionally substituted with one or more $R^3$. The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol. The resulting amine is coupled with an acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 6

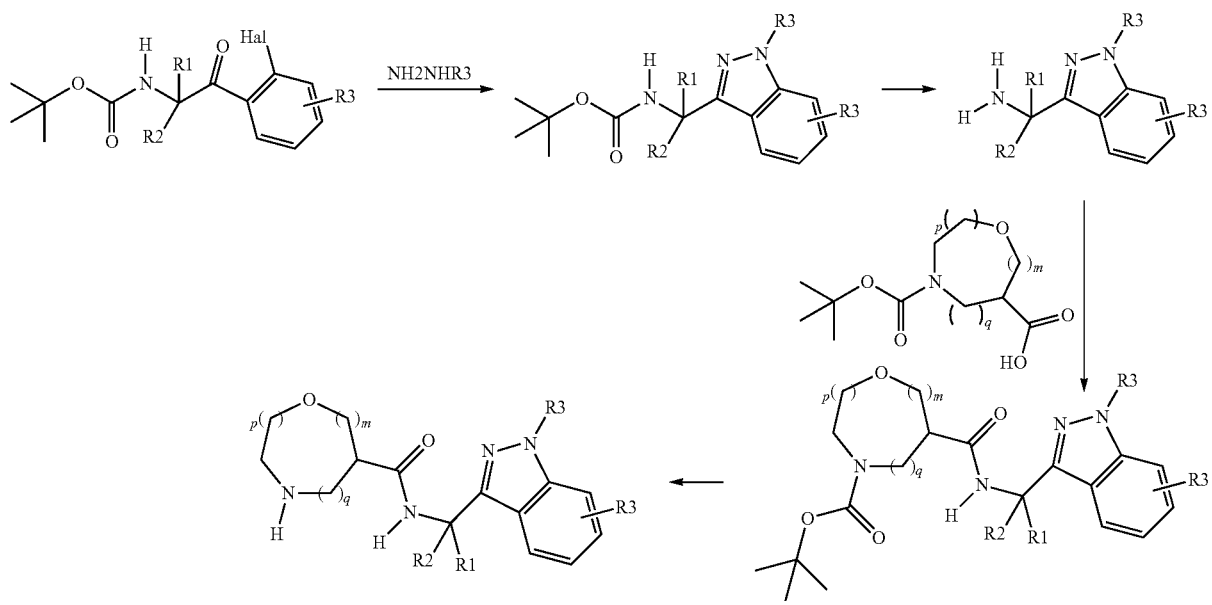

In scheme 6, Hal=halogen.

Scheme 6: the previously described ketone is converted to the 1H-indazole optionally substituted with one or more $R^3$ upon treatment with optionally substituted hydrazine in an appropriate solvent such as ethanol at high temperatures. In case $R^3$=halogen, such group can be substituted upon treatment with a boronic acid in the presence of a Palladium source (e.g. 1,1'-Bis(diphenylphosphino)ferrocenepalladium (ii) dichloride), a base (e.g. potassium carbonate) in appropriate solvents such as DMF at elevated temperatures. The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol. The resulting amine is coupled with an acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 7

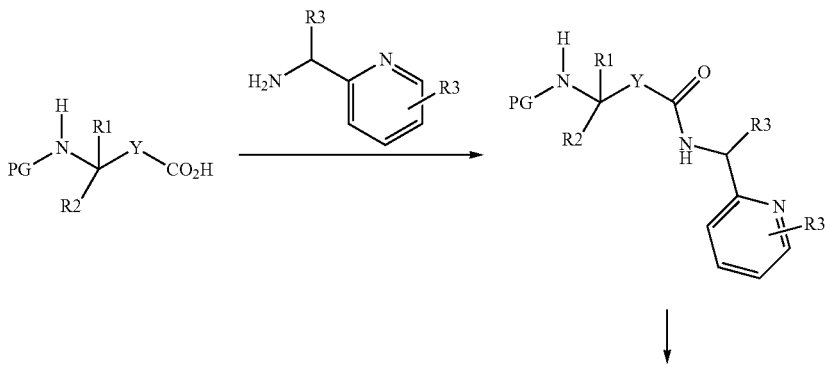

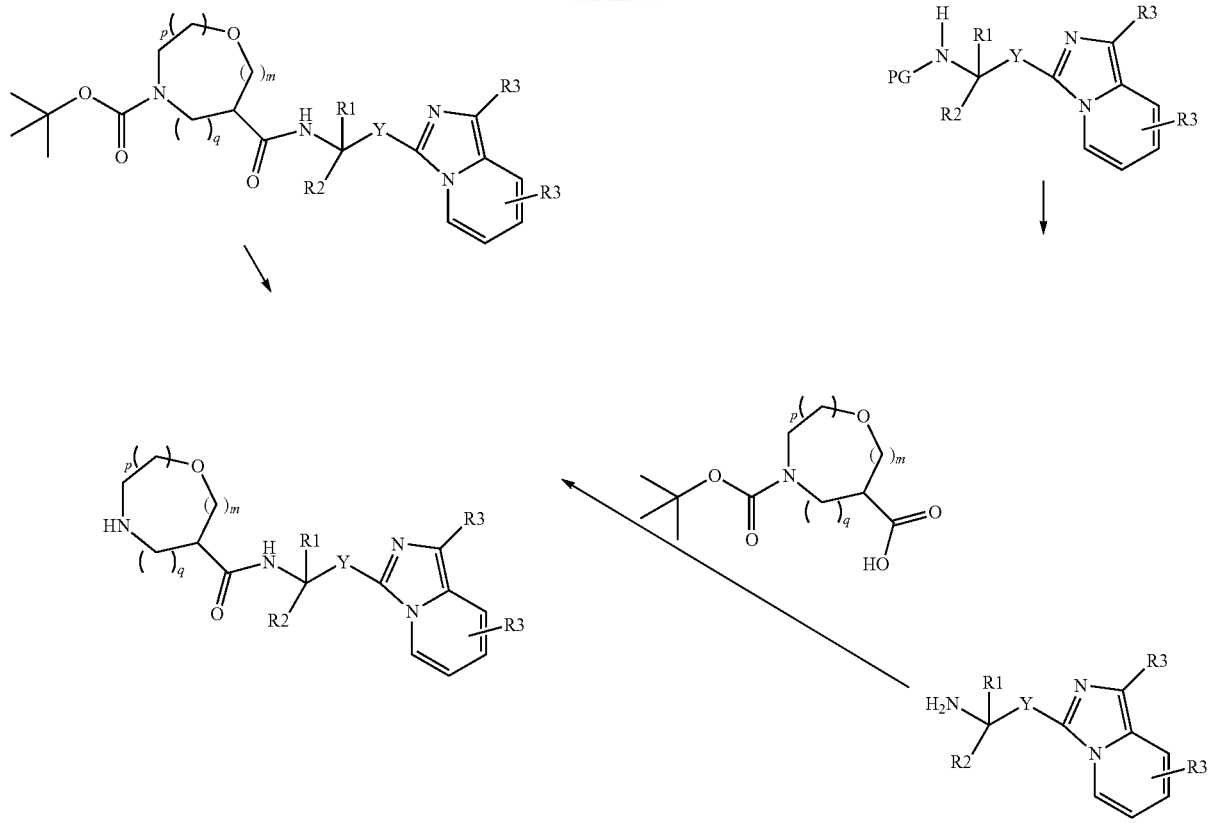

In scheme 7, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting groups are tert-butoxycarbonyl-, benzyloxycarbonyl- and 9-fluorenylmethoxycarbonyl-. $R^3$=substituents as defined for W.

Scheme 7: In a first step a carboxylic acid is coupled with 2-(aminomethyl)-substituted pyridine in an appropriate solvent such as THF or DCM and in the presence of a coupling agent (e.g. TBTU or HATU) and a base (e.g. TEA). Condensation is achieved using Burgess reagent in an appropriate solvent such as DCM or using phosphorus oxychloride and DMF at elevated temperatures. The tert-butoxycarbonyl-protecting group is removed with hydrochloric acid in an appropriate solvent such as ethyl ether while the benzyloxycarbonyl- is removed by hydrogenation in the presence of a catalyst (e.g. palladium on carbon) in appropriate solvents such as MeOH and water. The resulting amine is coupled with a suitable carboxylic acid in an appropriate solvent such as THF or DCM and in the presence of a coupling agent (e.g. HATU) and a base (e.g. TEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 8

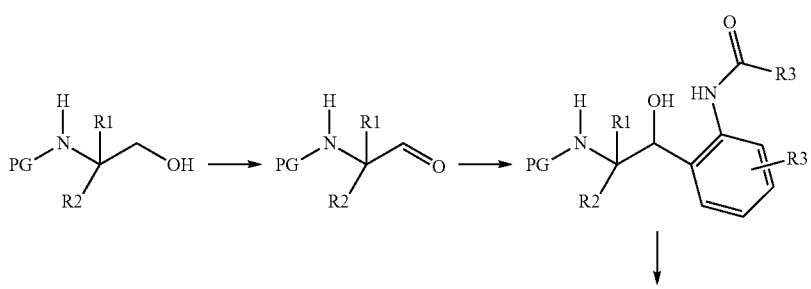

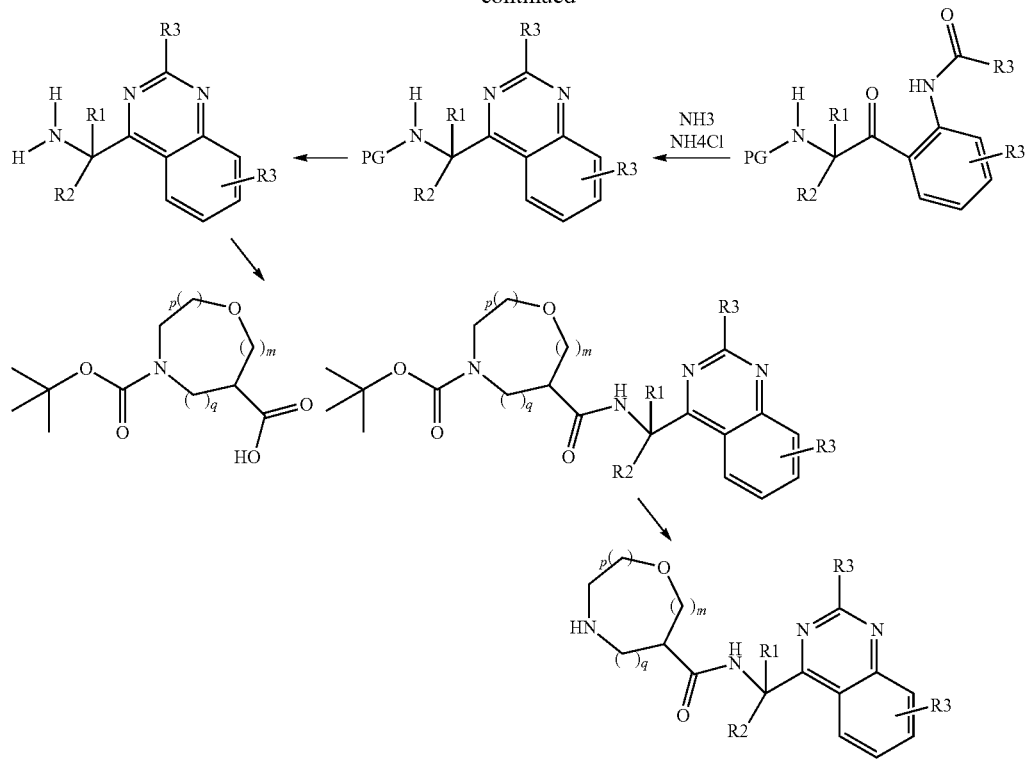

In scheme 8, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting group is tert-butoxycarbonyl-.

R3=substituents as defined for W.

Scheme 8: in a first step an alcohol is oxidized to the aldehyde with Dess-Martin periodinane in DCM. The aldehyde is reacted with an ortho-metallated acetanilide prepared from a corresponding 2-halo acetanilide by halogen-metal exchange in an appropriate solvent such as THF at low temperatures to afford an alcohol, which in turn is oxidized to the ketone with Dess-Martin periodinane in DCM. The ketone is converted to the quinazoline optionally substituted with one or more R3 upon treatment with ammonia and ammonium chloride in an appropriate solvent such as methanol at high temperatures. When the resulting product is Boc-protected, deprotection is accomplished with hydrochloric acid in an appropriate solvent such as dioxane, methanol or ethyl ether. Alternatively, Boc cleavage is carried out upon heating at elevated temperatures in appropriate solvents such as water and methanol. The resulting amine is coupled with a suitable carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

METHOD OF TREATMENT

Indications

The present invention relates to the use of a compound of formula (I) for the treatment and/or prevention of a disease or medical condition.

The present invention relates to compounds of formula (I) or pharmaceutically acceptable salts thereof, which are useful in the prevention and/or treatment of a disease and/or condition in which the activation of SSTR4 receptors is of therapeutic benefit, including improvement of symptoms, including but not limited to the treatment and/or prevention of pain of any kind and/or inflammatory diseases and/or associated conditions.

In a further aspect the present invention encompasses the compounds of the above-mentioned general formula (I) or pharmaceutically acceptable salts thereof, according to the invention for use as medicaments.

In view of their pharmacological effect the substances are suitable for the treatment of (1) acute pain such as for example toothache, peri- and post-operative pain, traumatic pain, muscle pain, the pain caused by burns, sunburn, trigeminal neuralgia, pain caused by colic, as well as spasms of the gastro-intestinal tract or uterus; sprains (2) visceral pain such as for example chronic pelvic pain, gynaecological pain, pain before and during menstruation, pain caused by pancreatitis, peptic ulcers, interstitial cystitis, renal colic, cholecystitis, prostatitis, angina pectoris, pain caused by irritable bowel, non-ulcerative dyspepsia and gastritis, prostatitis, non-cardiac thoracic pain and pain caused by myocardial ischaemia and cardiac infarct;

(3) neuropathic pain such as lumbosacral radiculopathy, low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;

(4) inflammatory pain/receptor-mediated pain in connection with diseases such as for example osteoarthritis, rheumatoid arthritis, inflammatory arthropathy, rheumatic fever, tendo-synovitis, bursitis, tendonitis, gout and gout-arthritis, traumatic arthritis, vulvodynia, damage to and diseases of the muscles and fascia, juvenile arthritis, spondylitis, psoriasis-arthritis, myositides, dental disease, influenza and other viral infections such as colds, systemic lupus erythematodes or pain caused by burns;

(5) tumour pain associated with cancers such as for example lymphatic or myeloid leukaemia, Hodgkin's disease, non-Hodgkin's lymphomas, lymphogranulomatosis, lymphosarcomas, solid malignant tumours and extensive metastases;

(6) headache diseases of various origins, such as for example cluster headaches, migraine (with or without aura) and tension headaches;

(7) sympathetically maintained pain like complex regional pain syndrome Type I and II;

(8) painful conditions of mixed origin, such as for example chronic back pain including lumbago, or fibromyalgia, sciatica, endometriosis, kidney stones.

The compounds are also suitable for treating
(9) inflammatory and/or oedematous diseases of the skin and mucous membranes, such as for example allergic and non-allergic dermatitis, atopic dermatitis, psoriasis, burns, sunburn, bacterial inflammations, irritations and inflammations triggered by chemical or natural substances (plants, insects, insect bites), itching; inflammation of the gums, oedema following trauma caused by burns, angiooedema or uveitis;

(10) Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepatic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;

(11) inflammatory changes connected with diseases of the airways and lungs such as bronchial asthma, including allergic asthma (atopic and non-atopic) as well as bronchospasm on exertion, occupationally induced asthma, viral or bacterial exacerbation of an existing asthma and other non-allergically induced asthmatic diseases; chronic bronchitis and chronic obstructive pulmonary disease (COPD) including pulmonary emphysema, viral or bacterial exacerbation of chronic bronchitis or chronic obstructive bronchitis, acute adult respiratory distress syndrome (ARDS), bronchitis, lung inflammation, allergic rhinitis (seasonal and all year round) vasomotor rhinitis and diseases caused by dust in the lungs such as aluminosis, anthracosis, asbestosis, chalicosis, siderosis, silicosis, tabacosis and byssinosis, exogenous allergic alveolitis, pulmonary fibrosis, bronchiectasis, pulmonary diseases in alpha1-antitrypsin deficiency and cough;

(12) inflammatory diseases of the gastrointestinal tract including Crohn's disease and ulcerative colitis, irritable bowel syndrome, pancreatitis;

(13) inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;

(14) diabetes mellitus and its effects (such as e.g. diabetic vasculopathy, diabetic neuropathy, diabetic retinopathy, diabetic nephropathy) and diabetic symptoms in insulitis (for example hyperglycaemia, diuresis, proteinuria and increased renal excretion of nitrite and kallikrein); Doan syndrome and orthostatic hypotension;

(15) sepsis and septic shock after bacterial infections or after trauma;

(16) inflammatory diseases of the joints and connective tissue such as vascular diseases of the connective tissue, sprains and fractures, and musculoskeletal diseases with inflammatory symptoms such as acute rheumatic fever, polymyalgia rheumatica, reactive arthritis, rheumatoid arthritis, spondylarthritis, and also osteoarthritis, and inflammation of the connective tissue of other origins, and collagenoses of all origins such as systemic lupus erythematodes, scleroderma, polymyositis, dermatomyositis, Sjögren syndrome, Still's disease or Felty syndrome; as well as vascular diseases such as panarteriitis nodosa, polyarthritis nodosa, periarteriitis nodosa, arteriitis temporalis, Wegner's granulomatosis, giant cell arteriitis, arteriosclerosis and erythema nodosum;

(17) diseases of and damage to the central nervous system such as for example cerebral oedema and the treatment and prevention of psychiatric diseases such as depression, for example, and for the treatment and prevention of epilepsy;

(18) disorders of the motility or spasms of respiratory, genito-urinary, gastro-intestinal including biliary or vascular structures and organs;

(19) post-operative fever;

(20) for the treatment and prevention of arteriosclerosis and related complaints;

(21) for the treatment and prevention of diseases of the genito-urinary tract such as for example urinary incontinence and related complaints, benign prostatic hyperplasia and hyperactive bladder, nephritis, cystitis (interstitial cystitis);

(22) for the treatment and prevention of morbid obesity and related complaints;

(23) neurological diseases such as cerebral oedema and angioedema, cerebral dementia like e.g. Parkinson's and Alzheimers disease, senile dementia; multiple sclerosis, epilepsy, temporal lobe epilepsy, drug resistant epilepsy, stroke, myasthenia gravis, brain and meningeal infections like encephalomyelitis, meningitis, HIV as well as schizophrenia, delusional disorders, autism, affective disorders and tic disorders;

(24) cognitive impairments associated with schizophrenia, Alzheimer's Disease and other neurological and psychiatric disorders. With respect to Alzheimer's disease, the compounds of general formula (I) may also be useful as disease modifying agent;

(25) work-related diseases like pneumoconiosis, including aluminosis, anthracosis, asbestosis, chalicosis, ptilosis, siderosis, silicosis, tabacosis and byssinosis;

(26) benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, large bowel cancer, small bowel cancer, stomach cancer, colon cancer, gastroenteropancreatic tumours, gastric carcinomas, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; the proliferation of adenoma cells, thyroid cancer, GI tumours, cholan-giocarcinoma, hepatic cancer, vesical cancer, chondrosarcoma, malignant pheochromocytoma, neuroblastoma, thymoma, paragangliomas, phaeochromocytomas, ependymomas, leukemia e.g., leukemia of basophilic leukemia, chronic lymphocytic leukemia, chronic myeloid leukemia, Hodgkin disease and non-Hodgkin lymphoma; adenomatous polyps, including familial adenomatous polyposis (FAP) as well preventing polyps from forming in patients at risk of FAP. Suitable uses may include use in the treatment of acromegaly, cancer, arthritis, carcinoid tumours, and vasoactive intestinal peptide tumours;

(27) various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching;

(28) anxiety, depression, schizophrenia, epilepsy, attention deficit and hyperactive disorders and neurodegenerative diseases such as dementia, Alzheimer's disease and Parkinson's disease. The treatment of affective disorders includes bipolar disorders, e.g. manic-depressive psychoses, extreme psychotic states, e.g. mania and excessive mood swings for which a behavioural stabilization is being sought. The treatment of anxiety states includes generalized anxiety as well as social anxiety, agoraphobia and those behavioural states characterized by social withdrawal, e.g. negative symptoms;

(29) diseases involving pathological vascular proliferation, e.g. angiogenesis, restenosis, smooth muscle proliferation, endothelial cell proliferation and new blood vessel sprouting or conditions requiring the activation of neovascularization. The angiogenic disease may for example be age-related macular degeneration or vascular proliferation associated with surgical procedures, e.g. angioplasty and AV shunts. Other possible uses are the treatments of arteriosclerosis, plaque neovascularization, hypertrophic cardiomyopathy, myocardial angiogenesis, valvular disease, myo-cardiac infarction, coronary collaterals, cerebral collaterals and ischemic limb angiogenesis;

(30) pathological condition in the retina and/or iris-ciliary body of mammals. Such conditions may be high intraocular pressure (IOP) and/or deep ocular infections. Treatable diseases may e.g. be glaucoma, stromal keratitis, iritis, retinitis, cataract and conjunctivitis. Other diseases connected to the eye may be ocular and corneal angiogenic conditions, for example, corneal graft rejection, retrolental fibroplasia, Osier-Webber Syndrome or rubeosis.

(31) compounds of the invention, after incorporation of a label (e.g. 35-S, 123-I, 125-I, 111-In, 11-C, etc.) either directly in the compound or via a suitable spacer, can also be used for the imaging of healthy or diseased tissues and/or organs, such as prostate, lung, brain, blood vessels or tumours possessing ssti and/or SSTR4 receptors.

Preferred according to the present invention is the use of a compound of formula (I) for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula (I) to a human being.

Dosage:

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions:

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

A further aspect of the invention is a pharmaceutical formulation including a compound of formula (I) in admixture with a pharmaceutically acceptable adjuvant, diluent or carrier.

COMBINATION THERAPY

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
- non-steroidal antiinflammatory drugs (NSAIDs) including COX-2 inhibitors;
- opiate receptor agonists;
- Cannabionoid agonists or inhibitors of the endocannabinoid pathway
- Sodium channel blockers;
- N-type calcium channel blockers;
- serotonergic and noradrenergic modulators;
- corticosteroids;
- histamine H1, H2, H3 and H4 receptor antagonists;
- proton pump inhibitors;
- leukotriene antagonists and 5-lipoxygenase inhibitors;
- local anesthetics;
- VR1 agonists and antagonists;
- Nicotinic acetylcholine receptor agonists;
- P2X3 receptor antagonists;
- NGF agonists and antagonists or anti-NGF antibodies;
- NK1 and NK2 antagonists;
- Bradykinin B1 antagonists
- CCR2 antagonists
- iNOS or nNOS or eNOS inhibitors
- NMDA antagonist;
- potassium channel modulators;
- GABA modulators;
- serotonergic and noradrenergic modulators;
- anti-migraine drugs;
- neuropathic pain drugs such as pregabaline or duloxetine.

Said list is not considered to have a limiting character.

In the following representative examples of such treatment options shall be given:
- Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;
- Antiviral drugs like acyclovir, tenovir, pleconaril, peramivir, pocosanol and the like.
- Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;
- Opiate receptor agonists: morphine, propoxyphene (Darvon), tramadol, buprenorphin and the like;
- Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs inlcuding but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;
- anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;
- IL-1 receptor antagonists such as but not limited to Kineret;
- Sodium channel blockers: carbamazepine, mexiletine, lamotrigine, tectin, lacosamide and the like.
- N-type calcium channel blockers: Ziconotide and the like;
- Serotonergic and noradrenergic modulators: paroxetine, duloxetine, clonidine, amitriptyline, citalopram;
- Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;
- Histamine H2 receptor antagonists: cimetidine, famotidine and ranitidine and the like;
- Histamine H3 receptor antagonists: ciproxifan and the like
- Histamine H4 receptor antagonists: thioperamide and the like
- Proton pump inhibitors: omeprazole, pantoprazole and esomeprazole and the like;
- Leukotriene antagonists and 5-lipoxygenase inhibitors: zafirlukast, montelukast, pranlukast and zileuton and the like;
- Local anesthetics such as ambroxol, lidocaine and the like;
- Potassium channel modulators, like retigabine;
- GABA modulators: lacosamide, pregabalin, gabapentin and the like;
- Anti-migraine drugs: sumatriptan, zolmitriptan, naratriptan, eletriptan, telcegepant and the like;
- NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

CHEMICAL MANUFACTURE

Abbreviations

Ac Acetyl
ACN acetonitrile

APCI Atmospheric pressure chemical ionization
Boc tert-butyloxycarbony
Burgess reagent: methoxycarbonylsulfamoyl-triethyl ammonium hydroxide inner salt
CDI 1,1'-carbonyldiimidazole
d day
dba dibenzylideneacetone
DCM dichloromethane
DIPEA diisopropylethylamine
DME 1,2-dimethoxyethane
DMF dimethylformamide
DMSO dimethyl sulfoxide
ESI electrospray ionization (in MS)
EtOAc ethylacetate
EtOH ethanol
Exp. example
GC gas chromathography
GC-MS coupled gas chromatography-mass spectrometry
h hour(s)
HATU O-(7-azabenzotriazol-1-yl)-N,N,N',N'-tetramethyl-uronium-hexafluorophosphate
HPLC high performance liquid chromatography
HPLC-MS coupled high performance liquid chromatography-mass spectrometry
LC liquid chromatography
LC-MS coupled liquid chromatography-mass spectrometry
M molar (mol/L)
MeOH methanol
min minute(s)
MS mass spectrometry
NMP 1-methyl-2-pyrrolidinone
RP reverse phase
rt room temperature
Rt retention time (in HPLC/LC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography-mass spectrometry Methods:
UPLC-MS and HPLC-MS Methods:
Method 1
Instrument: LC/MS Waters Acquity UPLC System DAD, SQD single quadrupole; column: HSS C18 1.8 µm 2.1×50 mm, Temp 35° C.; mobile phase: A=H$_2$O 90%+10% CH$_3$CN+CF$_3$COOH 0.1%, B=CH$_3$CN 90%+H$_2$O 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ESI+; scan range: 90-900 amu Method 2
Instrument: LC/MS Waters Acquity UPLC System DAD, SQD single quadrupole; column: BEH C18 1.7 µm 2.1×50 mm, Temp 35° C.; mobile phase: A=H$_2$O 90%+10% CH$_3$CN+NH$_4$COOH 5 mmol, B=CH$_3$CN 90%+H$_2$O 10%; gradient: 0.0 min 0% B→1.20 min 100% B→1.45 min 100% B→1.55 min 0% B→1.75 min 0% B; flow rate: 0.70 ml/min; detection: UV 254 nm; detection: SQD, single quadrupole; ion source: ESI+/ESI−; scan range: 90-900 amu Method 3
Instrument: LC/MS Waters Acquity UPLC System DAD, ELSD detector, SQD single quadrupole; column: HSS C18 1.8 µm 2.1×50 mm, Temp 35° C.; mobile phase: A=H$_2$O 90%+10% CH$_3$CN+CF$_3$COOH 0.1%, B=CH$_3$CN 90%+H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ESI+/ESI−; scan range: 90-900 amu Method 4
Instrument: LC/MS Waters Acquity UPLC System DAD, ELSD detector, SQD single quadrupole; column: BEH C18 1.7 µm 2.1×50 mm; mobile phase: A=H$_2$O 90%+CH$_3$CN 10%+NH$_4$COOH 5 mM, B=CH$_3$CN 90%+H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ESI+/ESI−; scan range: 90-900 amu Method 4a
Instrument: LC/MS Waters Acquity UPLC System DAD, ELSD detector, SQD single quadrupole; column: BEH C18 1.7 µm 2.1×50 mm, Temp 35° C.; mobile phase: A=H$_2$O 90%+CH$_3$CN 10%+NH$_4$HCO$_3$ 5 mM, B=CH$_3$CN 90%+H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ESI+/ESI−; scan range: 90-900 amu Method 5
Instrument: LC/MS Waters Acquity UPLC System DAD, ELSD detector, SQD single quadrupole; column: HSS C18 1.8 µm 2.1×50 mm, Temp 35° C.; mobile phase: A=H$_2$O 90%+CH$_3$CN 10%+CF$_3$COOH 0.1%, B=CH$_3$CN 90%+H$_2$O 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ES+/ES−; scan range: 90-900 amu Method 6
Instrument: LC/MS ThermoFinnigan HPLC Surveyor DAD, LCQ Fleet Ion Trap; column: Simmetry Shield RPB, 5 µm, 4.6×150 mm; eluent A: 90% water+10% ACN+HCOOH 0.1%; eluent B=ACN 90%+10% H$_2$O+HCOOH 0.1%; gradient: 0.0 min 5% B→1.5 min 5% B→11.5 min 95% B→13.0 min 95% B→13.3 min 5% B→15.0 min 5% B; flow rate: 1.0 mL/min; UV Detection: 254 nm; Detection: Finnigan Fleet, Ion Trap; ion source: ESI+; scan range: 100-900 amu Method 7
Instrument: LC/MS ThermoFinnigan. HPLC Surveyor DAD, MSQ Quadrupole; column: Synergi Hydro RP100 A, 2.5 um, 3×50 mm; eluent A: 90% water+10% ACN+ammonium formate 10 mM; eluent B=ACN 90%+10% H$_2$O+NH$_4$COOH 10 mM; gradient: 0.0 min 0% B→1.50 min 0% B→8.00 min 100% B→10.00 min 100% B→11.00 min 0% B→12.00 min 0% B; flow rate: 0.7 mL/min; UV Detection: 254 nm; Ion source: APCI+/APCI−.

Method 7a
Instrument: LC/MS ThermoFinnigan. HPLC Surveyor DAD, MSQ Quadrupole; column: Synergi Hydro RP100 A, 2.5 um, 3×50 mm; eluent A: 90% water+10% ACN+ammonium formate 10 mM; eluent B=ACN 90%+10% H$_2$O+NH$_4$COOH 10 mM; gradient: 0.0 min 0% B→0.50 min 0% B→6.50 min 100% B→7.50 min 100% B→8.00 min 0% B→9.00 min 0% B; flow rate: 1.2 mL/min; UV Detection: 254 nm; Ion source: APCI+/APCI−.

Method 7b
Instrument: LC/MS ThermoFinnigan. HPLC Surveyor DAD, MSQ Quadrupole; column: Synergi Hydro RP100 A, 2.5 um, 3×50 mm; eluent A: 90% water+10% ACN+ammonium formate 5 mM; eluent B=ACN 90%+10% $H_2O$; gradient: 0.0 min 0% B→4.00 min 100% B→5.30 min 100% B→5.50 min 0% B→6.00 min 0% B; flow rate: 1.2 mL/min; UV Detection: 254 nm; Ion source: APCI+/APCI−.
Method 8
Instrument: LC/MS ThermoFinnigan. HPLC Surveyor DAD, MSQ Quadrupole; column: Synergi Hydro RP100 A, 2.5 um, 3×50 mm; eluent A: 90% water+10% ACN+ammonium formate 10 mM; eluent B=ACN 90%+10% $H_2O$+ $NH_4COOH$ 10 mM; gradient: 0.0 min 0% B→4.00 min 100% B→5.30 min 100% B→5.50 min 0% B→6.00 min 0% B; flow rate: 1.2 mL/min; UV Detection: 254 nm; Ion source: APCI+/APCI−.
Method 9
Instrument: LC/MS Waters Alliance 2695 HPLC System DAD, Quattro Micro Triple quadrupole; column: SunFire C18 3.5 μm 4.6×50 mm; eluent A: $H_2O$ 90%+10% $CH_3CN$+ $CF_3COOH$ 0.05%; eluent B=$CH_3CN$ 90%+10% $H_2O$; gradient: 0.0 min 0% B→4.50 min 100% B→5.80 min 100% B→6.00 min 0% B; flow rate: 1.3 mL/min; UV Detection: 254 nm; Ion source: ESI+.
Method 10
Instrument: LC/MS Waters Alliance 2695 HPLC System DAD, Quattro Micro Triple quadrupole; column: Atlantis dC18 5 μm 4.6×50 mm; eluent A: $H_2O$ 90%+10% $CH_3CN$+ $CF_3COOH$ 0.05%; eluent B=$CH_3CN$ 90%+10% $H_2O$; gradient: 0.0 min 0% B→0.70 min 0% B→4.50 min 100% B→5.80 min 100% B→6.00 min 0% B; flow rate: 1.3 mL/min; UV Detection: 254 nm; Ion source: ESI+.
Method 11
Instrument: LC/MS Waters Alliance 2695 HPLC System DAD, Quattro Micro Triple quadrupole; column: Xbridge Phenyl 3.5 μm 3×30 mm; eluent A: $H_2O$ 90%+10% $CH_3CN$+$NH_4HCO_3$ 5 mM; eluent B=$CH_3CN$ 90%+10% $H_2O$; gradient: 0.0 min 0% B→4.50 min 100% B→5.80 min 100% B→6.00 min 0% B; flow rate: 1.3 mL/min; UV Detection: 254 nm; Ion source: ESI+/ESI−
Method 12
Instrument: LC/MS ThermoFinnigan HPLC Surveyor DAD, LCQFleet Ion Trap; column: Xselect CSH, 2.5 μm, 4.6×50 mm; eluent A: $H_2O$ 90%+10% $CH_3CN$+HCOOH 0.1%; eluent B=$CH_3CN$ 90%+$H_2O$ 10%+HCOOH 0.1%; gradient: 0.0 min 0% B→4.00 min 100% B→5.30 min 100% B→5.50 min 0% B→6.00 min 0% B; flow rate: 1.4 mL/min; UV Detection: 254 nm; Ion source: ESI+/ESI−
Method 12a
Instrument: LC/MS Waters Alliance 2695 HPLC System DAD, Quattro Micro Triple quadrupole; column: Zorbax Eclipse XDB-C18 3.5 μm 4.6×50 mm, Temp 35° C.; eluent A: $H_2O$ 90%+10% $CH_3CN$+$NH_4COOH$ 5 mM; eluent B=$CH_3CN$ 90%+10% $H_2O$; gradient: 0.0 min 0% B→4.50 min 100% B→5.80 min 100% B→6.00 min 0% B; flow rate: 1.3 mL/min; UV Detection: 254 nm; Ion source: ESI+/ESI−
GC-MS Methods:
Method 13
Instrument: GC/MS Thermo Scientific TRACE GC ULTRA, DSQ II MS single quadrupole; column: Agilent DB-5MS, 25 m×0.2 5 mmol×0.25 μm; carrier gas: Helium, 1 mL/min constant flow; oven program: 50° C., to 100° C. in 10° C./min, to 200° C. in 20° C./min, to 320° C. in 30° C./min (hold 10 min); detection: DSQ II MS single quadrupole; ion source: EI; scan range: 50-450 amu
Chiral HPLC Methods:
Method 14
HPLC apparatus type: Agilent 1100; column: Daicel Chiralcel OJ-H, 5.0 μm, 250 mm×4.6 mm; method: eluent hexane/ethanol 90:10; flow rate: 1 mL/min, Temperature: 25° C.; UV Detection: 230 nm
Method 15
HPLC apparatus type: Agilent 1100; column: Daicel Chiralpack AD-H, 5.0 μm, 250 mm×4.6 mm; method: eluent hexane/IPA 95:5; flow rate: 1 mL/min, Temperature: 25° C.; UV Detection: 230 nm
Method 16
HPLC apparatus type: Agilent 1100; column: Daicel Chiralpack AD-H, 5.0 μm, 250 mm×4.6 mm; method: eluent hexane/IPA 75:25; flow rate: 1 mL/min, Temperature: 25° C.; UV Detection: 230 nm
Method 17
HPLC apparatus type: Agilent 1100; column: Daicel Chiralpack AD-H, 5.0 μm, 250 mm×4.6 mm; method: eluent hexane/IPA 85:15; flow rate: 1 mL/min, Temperature: 25° C.; UV Detection: 230 nm
Method 18
HPLC apparatus type: Agilent 1100; column: Daicel Chiralpack AD-H, 5.0 μm, 250 mm×4.6 mm; method: eluent hexane/IPA 90:10; flow rate: 1 mL/min, Temperature: 25° C.; UV Detection: 230 nm
Method 19
HPLC apparatus type: Agilent 1100; column: Daicel Chiralpack AS-H, 5.0 μm, 250 mm×4.6 mm; method: eluent hexane/ethanol 96:4; flow rate: 1 mL/min, Temperature: 25° C.; UV Detection: 230 nm
Method 20
HPLC apparatus type: Agilent 1100; column: Daicel Chiralcel OJ-H, 5.0 μm, 250 mm×4.6 mm; method: eluent hexane/ethanol 85:15; flow rate: 1 mL/min, Temperature: 25° C.; UV Detection: 230 nm
Method 21
HPLC apparatus type: Agilent 1100; column: Daicel Chiralpack AD-H, 5.0 μm, 250 mm×4.6 mm; method: eluent hexane/IPA 98:2; flow rate: 1 mL/min, Temperature: 25° C.; UV Detection: 230 nm
Method 22
HPLC apparatus type: Agilent 1100; column: Daicel Chiralpack AD-H, 5.0 μm, 250 mm×4.6 mm; method: eluent hexane/IPA 80:20; flow rate: 1 mL/min, Temperature: 25° C.; UV Detection: 230 nm
Microwave Heating:
Discover® CEM instruments, equipped with 10 and 35 mL vessels
NMR Equipment:
The $^1$H NMR spectra were recorded on a Bruker Avance III (500 MHz) or a Varian 400 (400 MHz) or Varian Mercury (300 MHz) instrument using deuterated dimethylsulfoxide (DMSO-d6) as the solvent with tetramethylsilane (TMS) and residual solvent peak as an internal standard. Chemical shifts are reported in δ values (ppm) relative to TMS.

EXPERIMENTAL

Example 1a

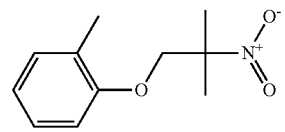

2-Methyl-2-nitropropyl-p-toluenesulfonate (3.0 g, 11 mmol), 2-methyl-phenol (1.3 g, 12 mmol) and cesium carbonate (4.3 g, 13 mmol) are heated in N,N-dimethylacetamide (50 mL) at 150° C. for 3 h. The reaction mixture is treated with water and 4M HCl and extracted with ethyl acetate. The organic layer is washed with brine, dried over $Na_2SO_4$ and evaporated under reduced pressure to furnish a residue that is purified by flash chromatography (eluent 0-20% EtOAc/cyclohexane) to furnish the title compound (2.1 g, 96% content, 88%).

UPLC-MS (Method 2): $R_t$=1.31 min

MS (ESI+): m/z=210 (M+H)+ luoromethyl)-pyridine (8 g, 48.46 mmol) is added. The resulting mixture is heated at 100° C. for 1 h. The reaction is diluted with DCM and washed with water. The organic layer is separated, dried and evaporated under reduced pressure to furnish a residue that dissolved in MeOH and washed with n-heptane. Volatiles are removed under reduced pressure to give the title compound (9.5 g, 84%).

HPLC-MS (Method 11): $R_t$=1.97 min

MS (ESI+): m/z=235 (M+H)+

The following example is synthesized in analogy to the preparation of example 2b:

| Example | Structure | Reactant | $^1$H-NMR |
|---|---|---|---|
| 2c | 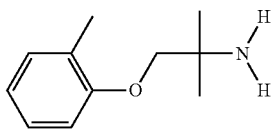 | 1-chloroisoquinoline (1.5 g, 9.2 mmol) | (400 MHz, DMSO-d$_6$): δ 1.18 ppm (s, 6H), 1.65 ppm (br, 2H), 4.15 ppm (s, 2H), 7.36 (d, J = 6.0, 1H), 7.64 (ddd, J = 1.2, 6.8, 8.2 Hz, 1H), 7.77 (ddd, J = 1.2, 7.0, 8.2 Hz, 1H), 7.88 (d, J = 8.0, 1H), 7.96 (d, J = 5.9, 1H), 8.29 (dd, J = 1.1, 8.2 Hz, 1H) |

Example 2a

Example 3a

Raney Nickel (300 mg, 3.50 mmol) is added to example 1a (2.1 g, 96% content, 9.64 mmol) dissolved in MeOH (50 mL) and the mixture is hydrogenated at 3 bar overnight. The catalyst is removed by filtration and the reaction evaporated under reduced pressure to furnish the title compound (1.6 g, 91% content, 84%) that is used as such.

UPLC-MS (Method 2): $R_t$=0.73 min

MS (ESI+): m/z=180 (M+H)+

Example 2b

2-Amino-2-methyl-propan-1-ol (19 mL, 194 mmol) is dissolved in dioxane (50 mL) and sodium hydride (60% suspension in mineral oil, 8.1 g, 204 mmol) is added portionwise at 0° C. and after 15 minutes 3-fluoro-4-(trif- TBTU (153 mg, 0.477 mmol) is added to (2S)-4-tert-butoxycarbonylmorpholine-2-carboxylic acid (100 mg, 0,432 mmol), example 2a (76 mg, 0,432 mmol) and TEA (180 µl, 1,297 mmol) in DMF (1 mL) and stirring is continued overnight. Water and ethyl ether are added and the organic layer is washed with NaHCO$_3$ saturated solution and brine. The organic layer is dried and evaporated to furnish a residue that is purified by flash chromatography (eluent 10-50% EtOAc/cyclohexane) to furnish the title compound (80 mg, 47%).

UPLC-MS (Method 2): $R_t$=1.43 min

MS (ESI+): m/z=393 (M+H)+

The following example is synthesized in analogy to the preparation of example 3a using HATU instead of TBTU and DIPEA instead of TEA:

| Example | Structure | Reactant(s) | UPLC-MS R$_t$ [min], method | MS (ESI+, m/z) (M + H)$^+$ |
|---|---|---|---|---|
| 3b (racemic mixture) | 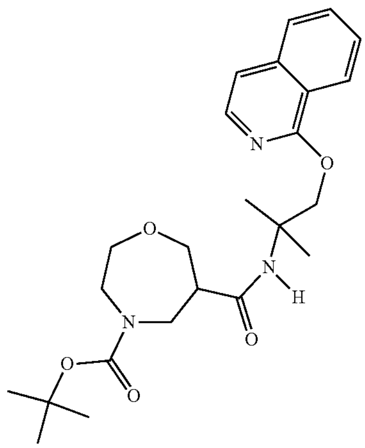 [SMILES: CC(C)(COc1nccc2ccccc12)NC(=O)C1COCCN(C(=O)OC(C)(C)C)C1] | Example 2c (200 mg, 0.925 mmol); 4-(tert-butoxycarbonyl)-1,4-oxazepane-6-carboxylic acid (250 mg, 1.017 mmol) | 1.31 2 | 444 |

The enantiomers of the example 3b are separated by HPLC using a chiral stationary phase.

Method for Separation:

HPLC apparatus type: Waters 600 Pump, 2767 Autosampler, UV Detector 2489; column: Daicel Chiralcel OJ-H, 5.0 µm, 250 mm×20 mm; method: eluent hexane/EtOH 90:10; flow rate: 15 mL/min, temperature: 25° C.; UV Detection: 230 nm Example 3c: stereoisomer 1, unknown absolute stereochemistry Example 3d: stereoisomer 2 unknown absolute stereochemistry Chiral HPLC (Method 14)

| Example | R$_t$ [min] |
|---|---|
| 3c | 5.60 |
| 3d | 6.66 |

Example 4a

To a solution of 1-methylindazole-3-carboxylic acid (1 g, 5.67 mmol) in dry THF (15 mL), CU (1 g, 6.24 mmol) is added. The mixture is stirred at rt for 1.5 h, then ammonium hydroxide (13 mL of a 30% solution in water) is added and the mixture stirred for additional 15 min. Solvents are evaporated, the crude dissolved in EtOAc, washed with 0.1 N hydrochloric acid, sat. NaHCO$_3$ and brine. The organic layer is separated, dried and evaporated under vacuum to obtain the title compound (840 mg, 83%) used in the next step without any further purification.

$^1$H NMR (300 MHz, DMSO-d$_6$): δ 4.12 (s, 3H), 7.26 (ddd, J=1.0, 6.7, 7.6 Hz, 1H), 7.33 (br, s, 1H), 7.46 (ddd, J=1.0, 6.8, 8.0 Hz, 1H), 7.65 (br, s, 1H), 7.71 (dd, J=8.2 Hz, 1H), 8.16 (dd, J=8.2 Hz, 1H)

The following examples are synthesized in analogy to the preparation of example 4a:

| Example | Structure | Reactant(s) | UPLC-MS $R_t$ [min], method, MS (ESI+, m/z) (M + H)+ |
|---|---|---|---|
| 4b | 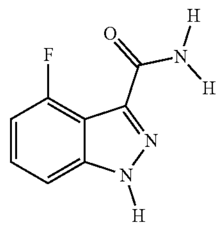 [SMILES: NC(=O)c1n[nH]c2cccc(F)c12] | 4-fluoro-1H-indazole-3-carboxylic acid (1.1 g, 5.80 mmol) | 0.62 2 180 |
| 4c | 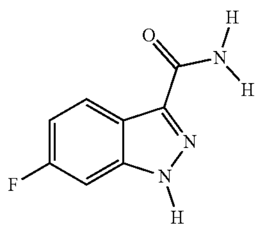 [SMILES: NC(=O)c1n[nH]c2cc(F)ccc12] | 6-fluoro-1H-indazole-3-carboxylic acid (3.0 g, 16.65 mmol) | 0.69 1 180 |
| 4d | 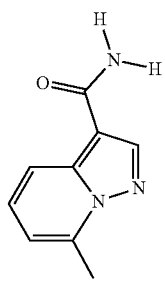 | 7-Methyl-pyrazolo[1,5-a]pyridine-3-carboxylic acid (synthesised as described in *J. Comb. Chem.*, 2005, 7, 309-316; 160 mg, 0.91 mmol) | 0.59 2 176 |
| 4e | 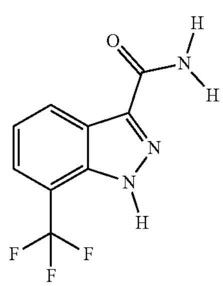 [SMILES: NC(=O)c1n[nH]c2c(C(F)(F)F)cccc12] | 7-(trifluoromethyl)-1H-indazole-3-carboxylic acid (2.0 g, 6.08 mmol) | 0.77 2 230 |

Example 4f

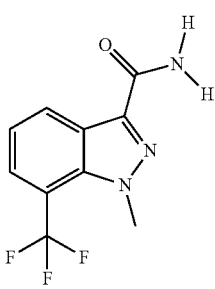 [SMILES: Cn1nc(C(N)=O)c2cccc(C(F)(F)F)c21]

Cesium carbonate (1.37 g, 4.19 mmol) is added to a solution of 4e (800 mg, 3.49 mmol) in DMF (10 mL). After 15 min, Iodomethane (215 μl, 3.49 mmol) is added dropwise to the reaction mixture. After 5 min the reaction is diluted with EtOAc, washed with saturated ammonium chloride and water. The organic layer is separated and dried with a Phase separator cartridge and evaporated under vacuum to obtain a the title compound (800 mg, 85% content, 80%), that is used as such.

UPLC-MS (Method 2): $R_t$=0.93

MS (ESI+): m/z=244 (M+H)+

Example 5a

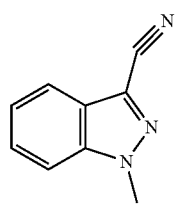

Burgess reagent (1.7 g, 7.19 mmol) is added to a solution of 4a (840 mg, 4.79 mmol) in DCM (15 mL), and the mixture is heated for 3 h at 35° C. The reaction is diluted with DCM, washed with 0.2N hydrochloric acid and brine. The organic layer is separated and dried with a Phase separator cartridge and evaporated under vacuum to obtain a crude that is purified by flash chromatography (eluent 0-20% EtOAc/cyclohexane) to furnish the title compound (680 mg, 90%).

GC-MS (Method 13): $R_t$=9.74 min

MS (EI+): m/z=157 [M]+

Example 5b

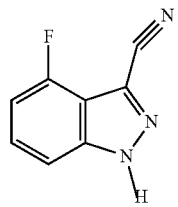

Trifluoroacetic anhydride (1.16 mL, 8.37 mmol) is added to a solution of 4b (600 mg, 3,35 mmol) in pyridine (6 mL) and DCM (15 mL). After 30 min the reaction is diluted with EtOAc, washed with saturated NaHCO₃, saturated NH₄Cl, water and brine. The organic layer is separated and dried with a Phase separator cartridge and evaporated under vacuum to furnish the title compound (500 mg, 93%), that is used as such.

UPLC-MS (Method 2): $R_t$=0,91

MS (ESI+): m/z=162 (M+H)+

The following examples are synthesized in analogy to the preparation of example 5b:

| Example | Structure | Reactant(s) | UPLC-MS R$_t$ [min], method | MS (ESI+, m/z) (M + H)⁺ |
|---|---|---|---|---|
| 5c | 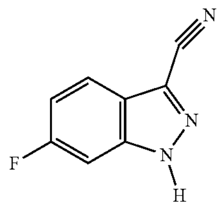 [SMILES: N#Cc1n[nH]c2cc(F)ccc12] | Example 4c (1.20 g, 6.70 mmol) | 0.85 2 | 162 |
| 5d | 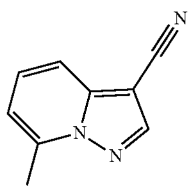 | Example 4d (109 mg, 0.62 mmol) | 0.89 2 | 158 |

| Example | Structure | Reactant(s) | ¹H NMR |
|---|---|---|---|
| 5e | 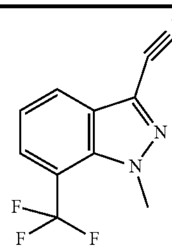 | Example 4f (800 mg, 90% content, 2.96 mmol) | ¹H NMR (500 MHz, DMSO-d₆): δ 4.26-4.28 (3H, m), 7.59 (1H, dd, J = 7.8, 7.8 Hz), 8.08 (1H, d, J = 7.5 Hz), 8.28 (1H, d, J = 8.2 Hz) |

Example 5f

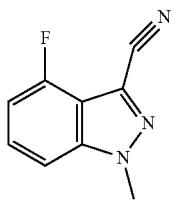

Cesium carbonate (1.31 g, 4,03 mmol) is added to a solution of 5b (500 mg, 3.10 mmol) in DMF (10 mL). After 15 min, iodomethane (192 μl, 3,10 mmol) is added dropwise to the reaction mixture. After stirring overnight the reaction is diluted with EtOAc, washed with saturated ammonium chloride and water. The organic layer is separated and dried with a Phase separator cartridge and evaporated under vacuum to obtain a crude that is purified by flash chromatography (eluent 0-20% EtOAc/cyclohexane) to furnish the title compound (340 mg, 63%).

UPLC-MS (Method 2): R$_t$=0,99

MS (ESI+): m/z=176 (M+H)⁺

The following example is synthesized in analogy to the preparation of example 5f:

| Example | Structure | Reactant(s) | UPLC-MS R$_t$ [min], method | MS (ESI+, m/z) (M + H)⁺ |
|---|---|---|---|---|
| 5g | 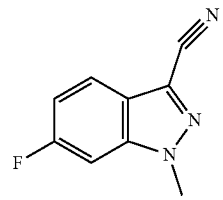 | Example 5c (600 mg, 3.72 mmol) | 1.09 1 | 176 |

Example 5h

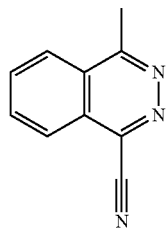

1-Chloro-4-methylphthalazine (5.00 g, 28.00 mmol), Zinc cyanide (3.62 g, 30,79 mmol), 1,1'-Bis(diphenylphosphino)ferrocene (1.40 g, 2,52 mmol), Tris(dibenzylideneacetone)dipalladium(0) (1.03 g, 1,12 mmol) in DMF (50 mL) were heated at 100° C. for 3 h. The reaction is diluted with EtOAc/water. The organic layer is separated, washed with brine, dried and evaporated under reduced pressure to give a residue that is purified by flash chromatography (eluent 0-60% EtOAc/cyclohexane) to furnish the title compound (4.17 g, 88%).

GC-MS (Method 13): R$_t$=10.85 min

MS (EI+): m/z=169 [M]⁺

The following example is synthesized in analogy to the preparation of example 5h:

| Example | Structure | Reactant(s) | HPLC-MS R$_t$ [min], method | MS (ESI+, m/z) (M + H)⁺ |
|---|---|---|---|---|
| 5i | 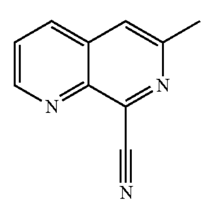 | 8-Chloro-6-methyl-1,7-naphthyridine (700 mg, 3.92 mmol) | 3.26 10 | 170 |

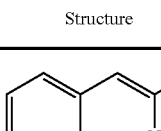

Example 6a

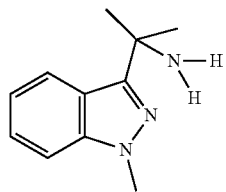

Under nitrogen atmosphere, dry THF (22 mL) is added to anhydrous Cerium (III) chloride (3.2 g, 13 mmol) at 0° C. The reaction is allowed to reach rt and stirred for 2 h. At −78° C. methyllithium as a complex with Lithium Iodide (1.6M in ethyl ether, 8.1 mL, 13.1 mmol) is added and stirring is continued for 30 minutes at −78° C. A solution of 5a (680 mg, 4.32 mmol) in THF dry (3 mL) is added to the mixture and stirring is continued for 30 minutes at −78° C. and then overnight at rt. Saturated $NH_4Cl$ and NaOH (50% in water) are added to the mixture until a precipitate forms. Undissolved material is filtered away on a celite pad. The filtrate is washed with water, separated and dried with a phase separator cartridge. The solvent is evaporated under reduced pressure to obtain a crude (350 mg, 30%) used in the next step without any further purification.

GC-MS (Method 13): $R_t$=9,85 min

MS (EI+): m/z=189 $[M]^+$

The following examples are synthesized in analogy to the preparation of example 6a:

| Example | Structure | Reactant(s) | UPLC-MS $R_t$ [min], method | MS (ESI+, m/z) $(M + H)^+$ |
|---|---|---|---|---|
| 6b | 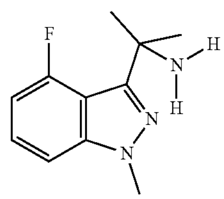 | Example 5f (300 mg, 1.71 mmol) | 0.64 2 | 191 $(M − NH_2)^+$ |
| 6c | 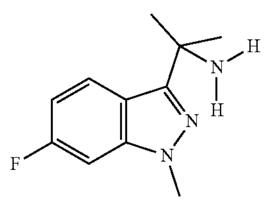 | Example 5g (300 mg, 1.71 mmol) | 0.68 1 | 191 $(M − NH_2)^+$ |
| 6d | 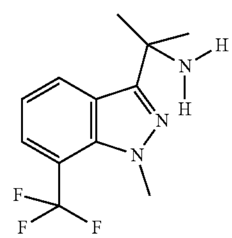 [SMILES: Cn1nc(C(C)(C)N)c2cccc(C(F)(F)F)c21] | Example 5e (400 mg, 1.78 mmol) | 0.77 2 | 241 $(M − NH_2)^+$ |
| 6e | 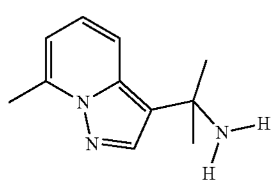 | Example 5d (97 mg, 0.62 mmol) | 0.61 2 | 173 $(M − NH_2)^+$ |
| 6f | 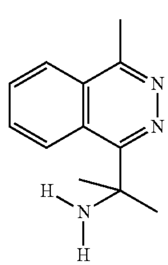 | Example 5h (2.80 g, 16.6 mmol) | 0.57 2 | 202 |

| Example | Structure | Reactant(s) | UPLC-MS $R_t$ [min], method | MS (ESI+, m/z) $(M + H)^+$ |
|---|---|---|---|---|
| 6g | 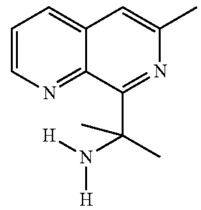 | Example 5i (300 mg, 1.77 mmol) | 0.62 2 | 202 |
| 6h | 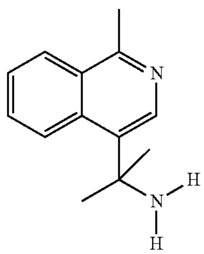 | 1-Methyl-4-Isoquinolinecarbonitrile (500 mg, 2.97 mmol) | 0.60 2 | 201 |
| 6i | 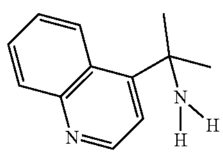 | 4-cyanoquinoline (400 mg, 2.595 mmol) | 0.62 2 | 187 |

Example 6j

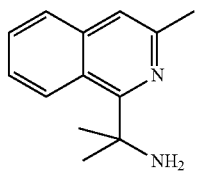

Example 6j is prepared as described for example 6a using 3-methylisoquinoline-1-carbonitrile (350 mg, 2.08 mmol) as starting material. Following work-up, the resulting residue is purified by flash chromatography (eluent 100% DCM to 95:5:0.5 DCM/MeOH/NH$_4$OH) to furnish the title compound (162 mg, 39%).

GC-MS (Method 13): $R_t$=10.28
MS (EI+): m/z=200 [M]$^+$

Example 7a

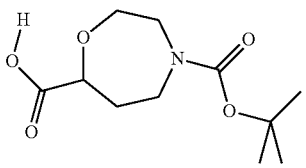 [SMILES: CC(C)(C)OC(=O)N1CCOC(C(=O)O)CC1]

To a solution of 2-benzyloxymethyl-oxirane (20,0 g; 121 mmol) in DMF (250 mL) and water (50 mL) is added KCN (15,8 g; 241 mmol) and the mixture is stirred at room temperature overnight. The mixture was extracted with EtOAc, and the organic was separated, dried with Na$_2$SO$_4$ and concentrated under reduced pressure to give a residue that is purified by flash chromatography (eluent 10% EtOAc/petroleum ether) to furnish 4-benzyloxy-3-hydroxy-butyronitrile (14.6 g, 54%). 4-Benzyloxy-3-hydroxy-butyronitrile (5.0 g, 26,147 mmol) is dissolved in ethyl ether and at 0° C. Lithium aluminum hydride (2M in THF, 20 mL, 40 mmol) is added. After 10 min saturated sodium sulfate is slowly added. After stirring 0° C. for 30 min, the reaction mixture is dried over magnesium sulfate, filtered over Celite and evaporated under reduced pressure to give 4-amino-1-benzyloxy-butan-2-ol (4.35 g, 80% content, 68%) that is used as such.

UPLC-MS (Method 2): $R_t$=0.60 min
MS (ESI+): m/z=196 (M+H)$^+$

Chloroacetyl chloride (58 µl, 0,728 mmol) is added to TEA (125 µl, 0,899 mmol) and 4-amino-1-benzyloxy-butan-2-ol (147 mg, 80% content, 0,601 mmol) in DCM (3 mL) at 0° C. After 1 h at rt, water is added. The organic layer is separated, washed with brine, dried on a phase separator cartridge and evaporated under reduced pressure to give a residue that is purified by flash chromatography (eluent DCM/MeOH/NH$_4$OH 100/0/0 to 90/10/0.1) to furnish N-(4-benzyloxy-3-hydroxy-butyl)-2-chloro-acetamide (168 mg, 87% content, 89%).

UPLC-MS (Method 2): $R_t$=0.81 min
MS (ESI+): m/z=272 (M+H)$^+$

Powdered NaOH (2.9 g, 71,167 mmol) is added to N-(4-benzyloxy-3-hydroxy-butyl)-2-chloro-acetamide (4.1 g, 92%, 14,233 mmol) in DCM (400 mL) and the mixture is stirred overnight at rt. The solid residue is filtered off and the organic layer is washed with sat. NH$_4$Cl, then with H$_2$O. The organic layer is dried on a phase separator cartridge and evaporated under reduced pressure to give a residue that is purified by flash chromatography (eluent DCM/MeOH/NH₄OH 100/0/0 to 90/10/0.1) to furnish 7-benzyloxymethyl-[1,4]oxazepan-3-one (2.3 g, 89% content, 60%).

UPLC-MS (Method 2): $R_t$=0.81 min

MS (ESI+): m/z=236 (M+H)⁺

Lithium aluminum hydride (2M in THF, 1.5 mL, 3,020 mmol) is added dropwise to 7-benzyloxymethyl-[1,4]oxazepan-3-one (418 mg, 85% content, 1,510 mmol) in THF (10 mL) at 0° C. After 2 h at rt sodium sulfate is slowly added, the reaction mixture is filtered over Celite and evaporated under reduced pressure to give a residue that is purified on a SCX cartridge, which is washed with MeOH and DCM, and then eluted with NH₃ in MeOH to give 7-benzyloxymethyl-[1,4]oxazepane (318 mg, 95%).

UPLC-MS (Method 2): $R_t$=0.64 min

MS (ESI+): m/z=222 (M+H)⁺

Di-t-butyl dicarbonate (370 mg, 1,695 mmol) is added to 7-benzyloxymethyl-[1,4]oxazepane (366 mg, 85% content, 1,406 mmol) in THF (7 mL). After stirring overnight the reaction mixture is evaporated under reduced pressure to give a residue that is purified by flash chromatography (eluent 35% EtOAc/cyclohexane) to furnish 7-Benzyloxymethyl-[1,4]oxazepane-4-carboxylic acid tert-butyl ester (265 mg, 59%).

UPLC-MS (Method 2): $R_t$=1.29 min

MS (ESI+): m/z=322 (M+H)⁺

7-Benzyloxymethyl-[1,4]oxazepane-4-carboxylic acid tert-butyl ester (263 mg, 0.818 mmol) is dissolved in MeOH (5 mL) and palladium (50 mg, 10% content) is added.

The mixture is hydrogenated at 3 bar for 4 h and overnight at 4 bar. The catalyst is removed by filtration and washed with MeOH. The resulting solution is evaporated under reduced pressure to furnish 7-Hydroxymethyl-[1,4]oxazepane-4-carboxylic acid tert-butyl ester (180 mg, 95%), that is used as such.

UPLC-MS (Method 2): $R_t$=0.77 min

MS (ESI+): m/z=232 (M+H)⁺

Dess-Martin periodinane (360 mg, 0.849 mmol) is added portionwise to 7-Hydroxymethyl-[1,4]oxazepane-4-carboxylic acid tert-butyl ester (178 mg, 0.770 mmol) in DCM (3 mL) cooled to 0° C. and stirring is continued at rt overnight. 10% sodium thiosulfate solution is added and stirring is continued for 30 min. The organic layers is separated, washed with saturated NaHCO₃ solution, dried on a Phase separator cartridge and evaporated under reduced pressure to furnish a residue that is dissolved in tert-butanol (2 mL). Sodium dihydrogen phosphate (90 mg, 0.750 mmol) and Sodium chlorite (68 mg, 0.752 mmol) in water (0.4 mL). After stirring overnight, ethyl acetate is added. The organic layers is separated, dried on a Phase separator cartridge and evaporated under reduced pressure to give a residue that is partitioned between 1M NaOH and DCM. The aqueous layer is separated, acidified with 4M HCl and ethyl acetate is added. The organic layers is separated, dried on a Phase separator cartridge and evaporated under reduced pressure to furnish the title compound (102 mg).

HPLC-MS (Method 7a): $R_t$=0.30 min

MS (APCI+): m/z=244 (M−H)⁻

Example 8a

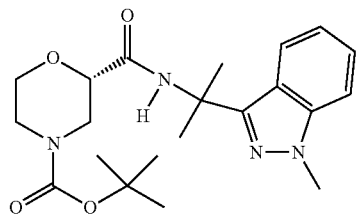 [SMILES: Cn1nc(C(C)(C)NC(=O)[C@@H]2CN(C(=O)OC(C)(C)C)CCO2)c2ccccc21]

HATU (157 mg, 0,412 mmol) is added to (2S)-4-tert-butoxycarbonylmorpholine-2-carboxylic acid (73 mg, 0,317 mmol), example 6a (100 mg, 60% content, 0.317 mmol) and DIPEA (166 µl, 0,951 mmol) in dry DMF (2 mL) and stirring is continued overnight. Volatiles are evaporated under reduced pressure to furnish a residue that is diluted with ethyl acetate and washed with saturated NaHCO₃ and brine. The organic layers is separated, dried on a Phase separator cartridge and evaporated under reduced pressure to give a residue purified by flash chromatography (eluent 10-40% EtOAc/cyclohexane) to furnish the title compound (79 mg, 98% content, 61%).

UPLC-MS (Method 2): $R_t$=1.17

MS (ESI+): m/z=403 (M+H)⁺

The following example is synthesized in analogy to the preparation of example 8a:

| Example | Structure | Reactant(s) | UPLC-MS $R_t$ [min], method | MS (ESI+, m/z) (M + H)⁺ |
|---|---|---|---|---|
| 8b (racemic mixture) | ![structure] | Example 6a (100 mg, 30% content, 0.159 mmol), 4-(tert-butoxycarbonyl)-1,4-oxazepane-6-carboxylic acid (250 mg, 1.017 mmol) | 1.14 2 | 417 |

The enantiomers of the example 8b are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/EtOH 95:5; flow rate: 15 mL/min, temperature: 25° C.; UV Detection: 230 nm

| Example 8c: stereoisomer 1, unknown absolute stereochemistry | Example 8d: stereoisomer 2 unknown absolute stereochemistry | Example 8f: stereoisomer 1, unknown absolute stereochemistry | Example 8g: stereoisomer 2 unknown absolute stereochemistry |
|---|---|---|---|
| 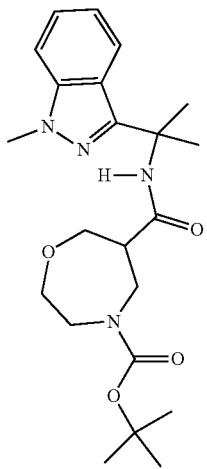 [SMILES: Cn1nc(C(C)(C)NC(=O)C2COCCN(C(=O)OC(C)(C)C)C2)c2ccccc21] | 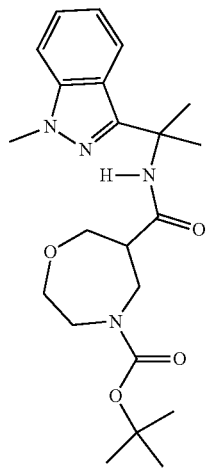 [SMILES: Cn1nc(C(C)(C)NC(=O)C2COCCN(C(=O)OC(C)(C)C)C2)c2ccccc21] | 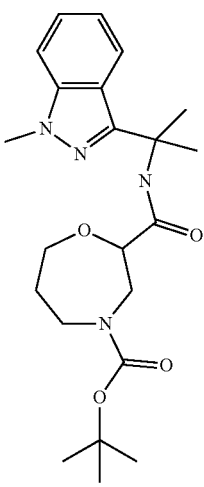 [SMILES: Cn1nc(C(C)(C)NC(=O)C2CN(C(=O)OC(C)(C)C)CCCO2)c2ccccc21] | 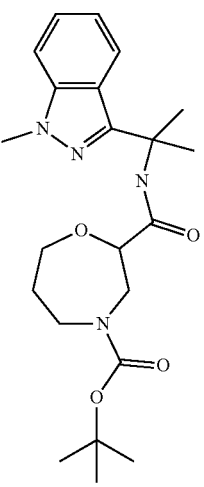 [SMILES: Cn1nc(C(C)(C)NC(=O)C2CN(C(=O)OC(C)(C)C)CCCO2)c2ccccc21] |

| Example | Chiral HPLC (Method 15) $R_t$ [min] | HPLC-MS (Method 7a): $R_t$ [min] | MS (APCI+): m/z |
|---|---|---|---|
| 8c | 15.45 | 4.40 | 417 |
| 8d | 16.63 | 4.40 | 417 |

The following example is synthesized in analogy to the preparation of example 8a:

| Example | Structure | Reactant(s) | UPLC-MS $R_t$ [min], method | MS (ESI+, m/z) (M + H)+ |
|---|---|---|---|---|
| 8e (racemic mixture) | 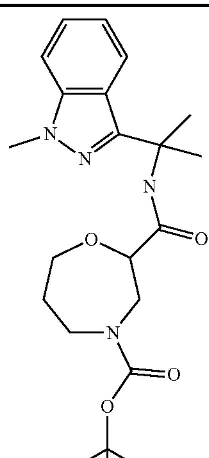 | Example 6a (707 mg, 30% content, 1.121 mmol), 4-Boc-2-homo-morpholine-carboxylic acid (250 mg, 1.019 mmol) | 1.25 2 | 417 |

The enantiomers of the example 8e are separated by HPLC using a chiral stationary phase.
Method for Separation:
HPLC apparatus type: Waters 600 Pump, 2767 Autosampler, UV Detector 2489; column: Daicel Chiralpak AD-H, 5.0 µm, 250 mm×20 mm; method: eluent hexane/IPA 75:25; flow rate: 15 mL/min, temperature: 25° C.; UV Detection: 230 nm

| Example | Chiral HPLC (Method 16) $R_t$ [min] | $^1$H NMR (500 MHz, DMSO-$d_6$) δ |
|---|---|---|
| 8f | 5.30 | 1.39 (d, br, 9H), 1.73 ppm (d, br, 6H), 1.79 (m, 2H), 3.09-3.24 (m, 2H), 3.51-3.65 (m, 2H), 3.76-3.86 (m, 1H), 3.97 (s, 3H), 4.00 (dd, J = 4.1, 9.9 Hz, 1H), 4.06 (m, 1H), 7.07 (t, J = 7.4 Hz, 1H), 7.36 (ddd, J = 1.0, 6.8, 8.2 Hz, 1H), 7.56 (d, J = 8.5 Hz, 1H), 7.83 (d, J = 8.1 Hz, 1H), 8.13 (d, br, 1H) |
| 8g | 6.40 | 1.39 (d, br, 9H), 1.73 ppm (d, br, 6H), 1.79 (m, 2H), 3.09-3.24 (m, 2H), 3.51-3.65 (m, 2H), 3.76-3.86 (m, 1H), 3.97 (s, 3H), 4.00 (dd, J = 4.1, 9.9 Hz, 1H), 4.06 (m, 1H), 7.07 (t, J = 7.4 Hz, 1H), 7.36 (ddd, J = 1.0, 6.8, 8.2 Hz, 1H), 7.56 (d, J = 8.5 Hz, 1H), 7.83 (d, J = 8.1 Hz, 1H), 8.13 (d, br, 1H) |

The following example is synthesized in analogy to the preparation of example 8a:

| Example | Structure | Reactant(s) | UPLC-MS $R_t$ [min], method | MS (ESI+, m/z) (M + H)+ |
|---|---|---|---|---|
| 8h (racemic mixture) | 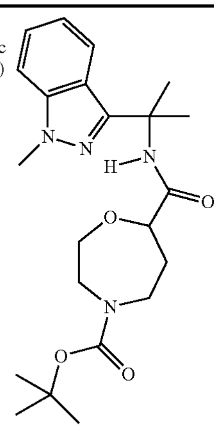 | Example 6a (122 mg, 80% content, 0.516 mmol), example 7a (115 mg, 0.469 mmol) | 1.19 2 | 417 |

The enantiomers of the example 8h are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/IPA 80:20; flow rate: 15 mL/min, temperature: 25° C.; UV Detection: 230 nm

| Example 8i: stereoisomer 1, unknown absolute stereochemisstry | Example 8j: stereoisomer 2 unknown absolute stereochemistry |
|---|---|

| Example | Chiral HPLC (Method 17) $R_t$ [min] | HPLC-MS (Method 7a): $R_t$ [min] | MS (APCI+): mz |
|---|---|---|---|
| 8i | 7.21 | 4.65 | 417 |
| 8j | 9.33 | 4.63 | 417 |

The following examples are synthesized in analogy to the preparation of example 8a:

| Example | Structure | Reactant(s) | UPLC-MS $R_t$ [min], method | MS (ESI+, m/z) (M + H)+ |
|---|---|---|---|---|
| 8k | 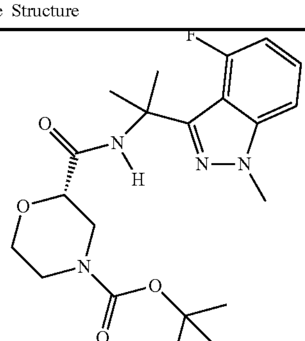 | Example 6b (70 mg, 40% content, 0.135 mmol) | 1.21 2 | 421 |
| 8l | 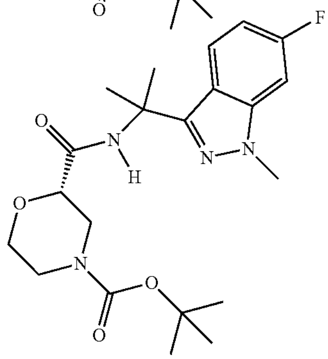 | Example 6c (90 mg, 40% content, 0.174 mmol) | 1.18 2 | 421 |

-continued

| Example | Structure | Reactant(s) | UPLC-MS $R_t$ [min], method | MS (ESI+, m/z) $(M + H)^+$ |
|---|---|---|---|---|
| 8m | 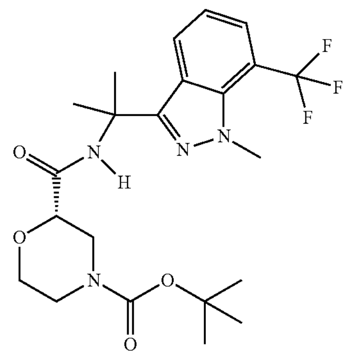 [SMILES: Cn1nc(C(C)(C)NC(=O)[C@@H]2CN(C(=O)OC(C)(C)C)CCO2)c2cccc(C(F)(F)F)c21] | Example 6d (100 mg, 72% content, 0.280 mmol) | 1.35 2 | 471 |
| 8n | 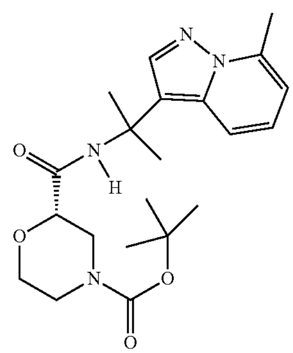 [SMILES: Cc1cccc2c(C(C)(C)NC(=O)[C@@H]3CN(C(=O)OC(C)(C)C)CCO3)cnn12] | Example 6e (180 mg, 55% content, 0.523 mmol) | 1.13 2 | 403 |
| 8o (racemic mixture) | 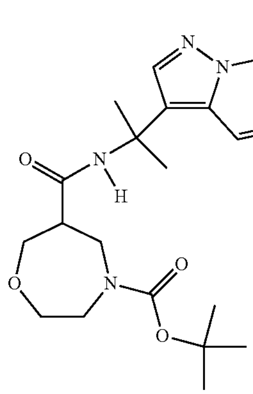 | Example 6e (180 mg, 55% content, 0.523 mmol), 4-(tert-butoxycarbonyl)-1,4-oxazepane-6-carboxylic acid (128 mg, 0.523 mmol) | 1.07 2 | 417 |

The enantiomers of the example 8o are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/IPA 80:20; flow rate: 15 mL/min, temperature: 25° C.; UV Detection: 230 nm

| Example 8p: stereoisomer 1, unknown absolute stereochemistry | Example 8q: stereoisomer 2 unknown absolute stereochemistry |
|---|---|

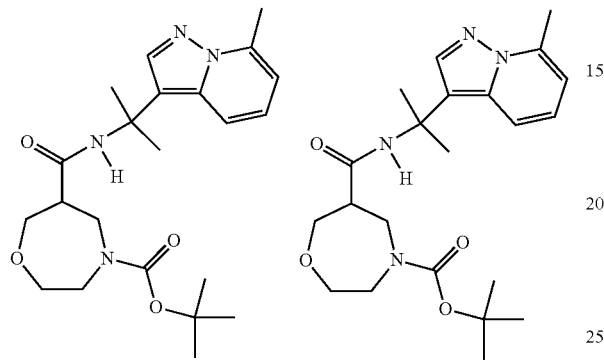

| Example | Chiral HPLC (Method 16) R$_t$ [min] |
|---|---|
| 8p | 4.64 |
| 8q | 8.51 |

The following examples are synthesized in analogy to the preparation of example 8a:

| Example | Structure | Reactant(s) | HPLC-MS or UPLC-MS R$_t$ [min] method | MS (ESI+ or APCI+, m/z) (M + H)$^+$ |
|---|---|---|---|---|
| 8r | 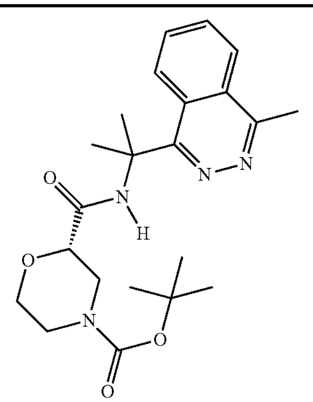 | Example 6f (225 mg, 18% content, 0.201 mmol) | 0.99<br>2 | 415 |
| 8s (racemic mixture) | 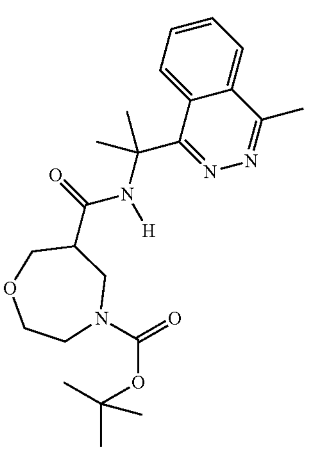 [SMILES: Cc1nnc(C(C)(C)NC(=O)C2COCCN(C(=O)OC(C)(C)C)C2)c2ccccc12] | Example 6f (675 mg, 18% content, 0.604 mmol), 4-(tert-butoxycarbonyl)-1,4-oxazepane-6-carboxylic acid (148 mg, 0.604 mmol) | 3.97<br>7a | 429 |

-continued

| Example | Structure | Reactant(s) | HPLC-MS or UPLC-MS R$_t$ [min] method | MS (ESI+ or APCI+, m/z) (M + H)$^+$ |
|---|---|---|---|---|
| 8t | 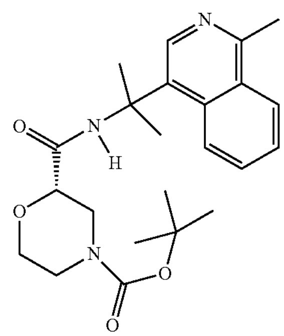 [SMILES: Cc1ncc(C(C)(C)NC(=O)[C@@H]2CN(C(=O)OC(C)(C)C)CCO2)c2ccccc12] | Example 6h (210 mg, 58% content, 0.608 mmol) | 1.06 2 | 414 |
| 8u | 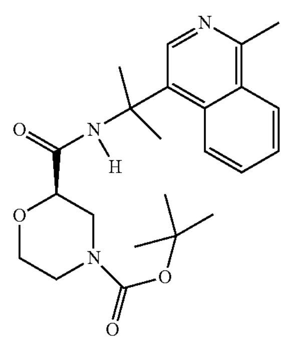 [SMILES: Cc1ncc(C(C)(C)NC(=O)[C@H]2CN(C(=O)OC(C)(C)C)CCO2)c2ccccc12] | Example 6h (30 mg, 60% content, 0.090 mmol), (2R)-4-tert-butoxycarbonyl morpholine-2-carboxylic acid (73 mg, 0.317 mmol) | 1.07 2 | 414 |
| 8v (racemic mixture) | 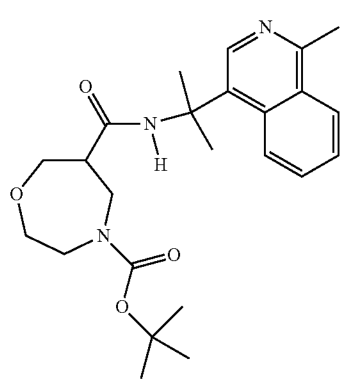 [SMILES: Cc1ncc(C(C)(C)NC(=O)C2COCCN(C(=O)OC(C)(C)C)C2)c2ccccc12] | Example 6h (420 mg, 58% content, 1.216 mmol), 4-(tert-butoxycarbonyl)-1,4-oxazepane-6-carboxylic acid (298 mg, 1.216 mmol) | 1.04 2 | 428 |

The enantiomers of the example 8v are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/IPA 75:25; flow rate: 15 mL/min, temperature: 25° C.; UV Detection: 230 nm

| Example 8w: stereoisomer 1, unknown absolute stereochemistry | Example 8y: stereoisomer 2 unknown absolute stereochemistry | |
|---|---|---|
| Example | Chiral HPLC (Method 17) $R_t$ [min] | HPLC-MS (Method 7a): $R_t$ [min] | MS (APCI+): mz |
| 8w | 4.75 | 4.33 | 428 |
| 8y | 6.36 | 4.33 | 428 |

The following examples are synthesized in analogy to the preparation of example 8a:

| Example | Structure | Reactant(s) | UPLC-MS $R_t$ [min], method | MS (ESI+, m/z) (M + H)+ |
|---|---|---|---|---|
| 8z | 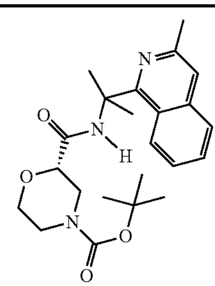 | Example 6j (80 mg, 90% content, 0.359 mmol) | 1.37 2 | 414 |
| 8aa (racemic mixture) | 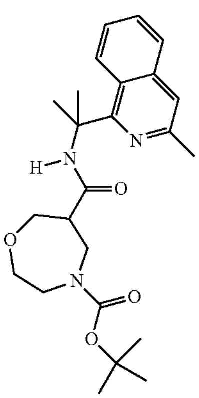 [SMILES: Cc1cc2ccccc2c(C(C)(C)NC(=O)C2COCCN(C(=O)OC(C)(C)C)C2)n1] | Example 6j (250 mg, 76% content, 0.949 mmol), 4-(tert-butoxy-carbonyl)-1,4-oxazepane-6-carboxylic acid (233 mg, 0.949 mmol) | 1.31 2 | 428 |

The enantiomers of the example 8aa are separated by HPLC using a chiral stationary phase.

Method for Separation:

HPLC apparatus type: Waters 600 Pump, 2767 Autosampler, UV Detector 2489; column: Daicel chiralpack OJ-H, 5.0 μm, 250 mm×20 mm; method: eluent hexane/ethanol 95:5; flow rate: 15 mL/min, temperature: 25° C.; UV Detection: 230 nm

| Example 8ab: stereoisomer 1, unknown absolute stereochemistry | Example 8ac: stereoisomer 2 unknown absolute stereochemistry |
|---|---|

| Example | Chiral HPLC (Method 15) $R_t$ [min] |
|---|---|
| 8ab | 9.80 |
| 8ac | 11.84 |

The following example is synthesized in analogy to the preparation of example 8a:

| Example | Structure | Reactant(s) | UPLC-MS $R_t$ [min], method | MS (ESI+, m/z) (M + H)+ |
|---|---|---|---|---|
| 8ad (racemic mixture) | 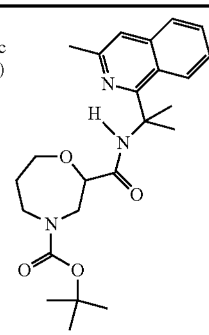 | Example 6j (200 mg, 76% content, 0.759 mmol), 4-Boc-2-homomorpho-linecarboxylic acid (186 mg, 0.759 mmol) | 1.43 2 | 428 |

The enantiomers of the example 8ad are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/IPA 85:15; flow rate: 15 mL/min, temperature: 25° C.; UV Detection: 230 nm

| Example 8ae: stereoisomer 1, unknown absolute stereochemistry | Example 8af: stereoisomer 2 unknown absolute stereochemistry |
|---|---|

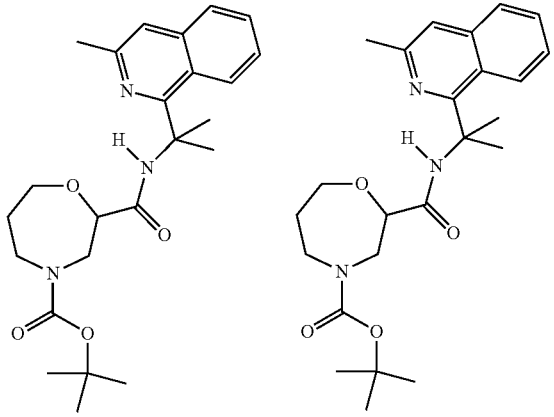

| Example | Chiral (Method 17) R$_t$ [min] | HPLC-MS (Method 7a): R$_t$ [min] | MS (APCI+): m/z |
|---|---|---|---|
| 8ae | 4.63 | 5.60 | 428 |
| 8af | 5.50 | 5.58 | 428 |

The following example is synthesized in analogy to the preparation of example 8a:

| Example | Structure | Reactant(s) | UPLC R$_t$ [min], method | MS (ESI+, m/z) (M + H)$^+$ |
|---|---|---|---|---|
| 8ag (racemic mixture) | 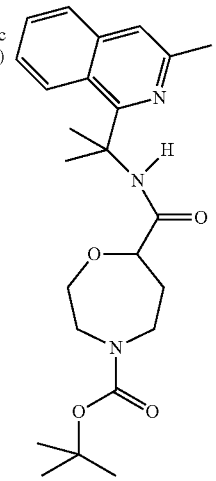 | Example 6j (100 mg, 85% content, 0.424 mmol), example 7a (105 mg, 0.424 mmol) | 1.39 2 | 428 |

The enantiomers of the example 8ag are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/IPA 80:20; flow rate: 15 mL/min, temperature: 25° C.; UV Detection: 230 nm

| Example 8ah: stereoisomer 1, unknown absolute stereochemistry | Example 8ai: stereoisomer 2 unknown absolute stereochemistry |
|---|---|

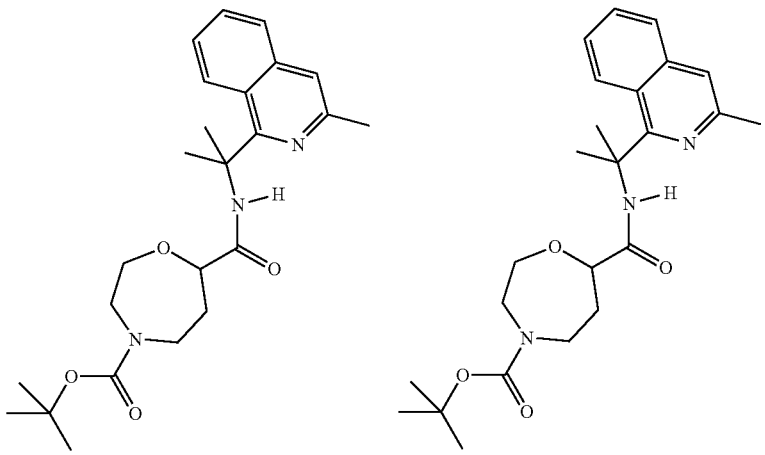

| Example | Chiral HPLC (Method 16) R$_t$ [min] | HPLC-MS (Method 7a): R$_t$ [min] | MS (APCI+): m/z |
|---|---|---|---|
| 8ah | 4.17 | 5.40 | 428 |
| 8ai | 5.38 | 5.40 | 428 |

Example 9a

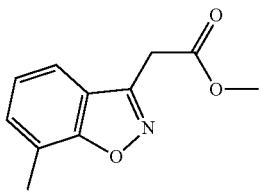

Hydroxylamine hydrochloride (4.4 g, 62,582 mmol) is added to a solution of 4-hydroxy-8-methyl-2H-1-benzopyran-2-one (3.15 g, 17.88 mmol) in MeOH (30 mL) at rt. Sodium acetate (5.1 g, 62,582 mmol) is added portionwise in 1.5 h. The reaction is stirred for 1.5 h at rt and then is heated at reflux overnight. Hydroxylamine hydrochloride (1.9 g, 26,821 mmol) and sodium acetate (2.2 g, 26,821 mmol) are added. The reaction is stirred for 3 h at reflux. Volatiles are evaporated, water is added and the mixture is cooled with ice-water bath. The aqueous layer is acidified to pH=3 with 4N HCl. A precipitate is filtered out and washed several times with water.

The precipitate is dried under reduced pressure at 50° C. to (7-methyl-benzo[d]isoxazol-3-yl)-acetic acid (1.4 g, 42%).

HPLC-MS (Method 11): $R_t$=3.49 min
MS (ESI+): m/z=146 (M-$CO_2$H)$^+$

Trimethylsilydiazomethane (3.8 mL, 7,517 mmol) is added dropwise to (7-methyl-benzo[d]isoxazol-3-yl)-acetic acid (1.42 g, 6,833 mmol) in DCM/MeOH 10:1 (8.5 mL/0.85 mL) at 0° C. and stirring is continued for 1 h at 0° C. Volatiles are evaporated to give the title compound (1.39 g, 95% content, 94%).

UPLC-MS (Method 2): $R_t$=1.02 min
MS (ESI+): m/z=206 (M+H)$^+$

Example 10a

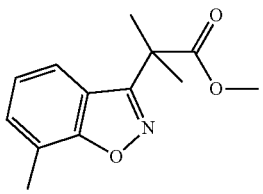 [SMILES: COC(=O)C(C)(C)c1noc2c(C)cccc12]

Sodium hydride (60% suspension in mineral oil, 973 mg, 24.32 mmol) is added portionwise to example 30b (1.42 g, 95% content, 6.57 mmol) in DMF (12 mL) at 0° C. The reaction is allowed to reach rt and stirred for 30 min. Iodomethane (2.1 mL, 33.20 mmol) is added dropwise to the reaction mixture cooled at 0° C. and the reaction is stirred at rt overnight.

Water is added and the reaction is extracted with EtOAc. Organic phase is washed with brine, dried and evaporated to give a residue that is purified by flash chromatography (eluent 0-40% EtOAc/Cyclohexane) to furnish the title compound (1.47 g, 96%).

GC-MS (Method 13): $R_t$=10.32 min
MS (EI+): m/z=233 [M]$^+$

Example 11a

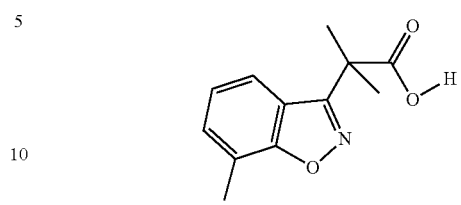

Lithium hydroxide monohydrate (793 mg, 18.91 mmol) is added to example 10a (1.47 g, 6.30 mmol) in water/THF 1:1 (28 mL) and the reaction is stirred at rt overnight. THF is evaporated, the mixture is cooled with ice-water bath. The aqueous layer is acidified to pH=4-5 with 1N HCl and extracted with DCM. Organic layer is dried on a phase separator cartridge and evaporated to give the title compound (1.28 g, 93%)

HPLC-MS (Method 7a): $R_t$=2.22 min
MS (APCI+): m/z=220 (M+H)$^+$

Example 12a

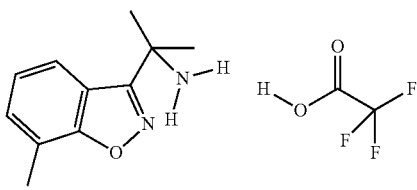

Diphenylphosphoryl azide (0.596 mL, 2,773 mmol) is added to example 11a (640 mg, 2,919 mmol) and TEA (0.386 mL, 2,773 mmol) in toluene (5.4 mL) and the mixture is stirred at rt for 1 h and at 80° C. for 2 h. 4-Methoxybenzyl alcohol (0.364 mL, 2,919 mmol) and TEA (0.386 mL, 2,773 mmol) are added and stirring is continued overnight at 80° C. The mixture is diluted with EtOAc, washed with 10% citric acid, washed with brine, dried and evaporated to give a residue that is purified by flash chromatography (eluent 0-20% EtOAc/cyclohexane) to furnish [1-methyl-1-(7-methyl-benzo[d]isoxazol-3-yl)-ethyl]carbamic acid 4-methoxy-benzyl ester (794 mg, 77%).

HPLC-MS (Method 12): $R_t$=3.73 min
MS (ESI+): m/z=377 (M+Na)$^+$

TFA (4.3 mL) is added to [1-methyl-1-(7-methyl-benzo[d]isoxazol-3-yl)-ethyl]-carbamic acid 4-methoxy-benzyl ester (350 mg, 0,988 mmol) in DCM (4.4 mL) at 0° C. After stirring for 30 min at rt, volatiles are evaporated under reduced pressure to afford the title compound (300 mg, 98% content, 98%) that is used as such.

UPLC-MS (Method 2): $R_t$=0.66 min
MS (ESI+): m/z=191 (M+H)$^+$

Example 13a

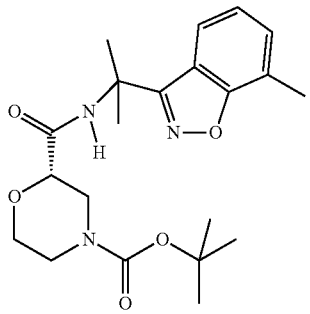 [SMILES: Cc1cccc2c(C(C)(C)NC(=O)[C@@H]3CN(C(=O)OC(C)(C)C)CCO3)noc12]

HATU (133 mg, 0,350 mmol) is added to (2S)-4-tert-butoxycarbonylmorpholine-2-carboxylic acid (63 mg, 0,270 mmol), example 12a (82 mg, 90% content, 0,243 mmol) and DIPEA (140 µl, 0,804 mmol) in dry DMF (2 mL) and stirring is continued for overnight. The reaction mixture is diluted with DCM and water. The organic layers is separated, dried on a Phase separator cartridge and evaporated under reduced pressure to give a residue that is purified by flash chromatography (eluent 20-50% EtOAc/cyclohexane) to furnish the title compound (99 mg, 95% content, 98%).

UPLC-MS (Method 2): $R_t$=1.27 min

MS (ESI+): m/z=404 (M+H)$^+$

The following example is synthesized in analogy to the preparation of example 13a:

| Example | Structure | Reactant(s) | UPLC-MS $R_t$ [min], method | MS (ESI+, m/z) (M + H)$^+$ |
|---|---|---|---|---|
| 13b (racemic mixture) | 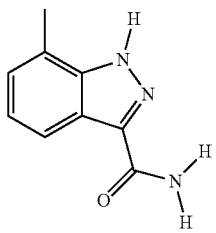 | Example 12a (200 mg, 90% content, 0.592 mmol), 4-tert-butoxy-carbonyl)-1,4-oxazepane-6-carboxylic acid (162 mg, 0.660 mmol) | 1.21 2 | 418 |

The enantiomers of the example 13b are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 90:10; flow rate: 15 mL/min, temperature: 25° C.; UV Detection: 230 nm

| | Example 8w: stereoisomer 1, unknown absolute stereochemistry | Example 8y: stereoisomer 2, unknown absolute stereochemistry |
|---|---|---|

| Example | Chiral HPLC (Method 17) $R_t$ [min] | HPLC-MS (Method 11): $R_t$ [min] | MS (APCI+): m/z |
|---|---|---|---|
| 13c | 4.17 | 2.92 | 418 |
| 13d | 4.53 | 2.91 | 418 |

Example 14a

Example 14a is prepared from 7-methyl-1H-indazole-3-carboxylic acid (13.1 mmol) in analogy to example 4a to give the title compound (730 mg, 77% content, 25%)

UPLC-MS (Method 2): $R_t$=0.69 min

MS (ESI+): m/z=176 (M+H)$^+$

Example 15a

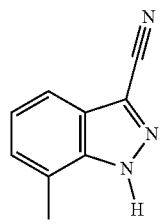

Example 15a is prepared from example 14a (650 mg, 77% content, 2.86 mmol) in analogy to example 5b to give the title compound (109 mg, 91% content, 22%)

UPLC-MS (Method 2): $R_t$=0.96 min

MS (ESI+): m/z=158 (M+H)$^+$

Example 16a

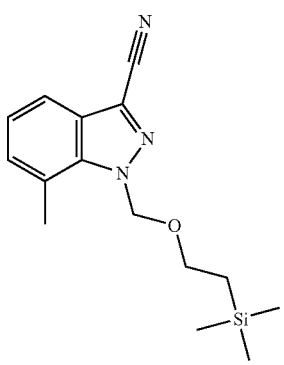 [SMILES: Cc1cccc2c(C#N)nn(COCC[Si](C)(C)C)c12]

Sodium hydride (60% suspension in mineral oil, 31 mg, 0.76 mmol) is added to a solution of 15a (109 mg, 91% content, 0.63 mmol) in DMF (1 mL) at 0° C. After 20 min, 2-(trimethylsilyl)ethoxymethyl chloride (157 µl, 0.88 mmol) is added dropwise to the reaction mixture. After stirring for 1 h at rt, the reaction is diluted with EtOAc, washed with NaHCO$_3$ saturated solution and brine. The organic layer is separated and dried with a Phase separator cartridge and evaporated under vacuum to give a residue that is purified by flash chromatography (eluent 0-10% EtOAc/cyclohexane) to furnish the title compound (182 mg).

UPLC-MS (Method 2): R$_t$=1.61
MS (ESI+): m/z=288 (M+H)$^+$

The following example is synthesized in analogy to the preparation of example 6a:

| Example | Structure | Reactant(s) | UPLC-MS R$_t$ [min], method | MS (ESI+, m/z) (M + H)$^+$ |
|---|---|---|---|---|
| 17a | 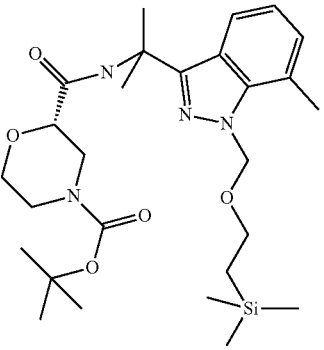 [SMILES: Cc1cccc2c(C(C)(C)NC(=O)[C@@H]3CN(C(=O)OC(C)(C)C)CCO3)nn(COCC[Si](C)(C)C)c12] | Example 16a (500 mg, 80% content, 1.392 mmol) | 1.13 2 | 303 (M—NH$_2$)$^+$ |

The following examples are synthesized in analogy to the preparation of example 8a:

| Example | Structure | Reactant(s) | UPLC-MS R$_t$ [min], method | MS (ESI+, m/z) (M + H)$^+$ |
|---|---|---|---|---|
| 18a | 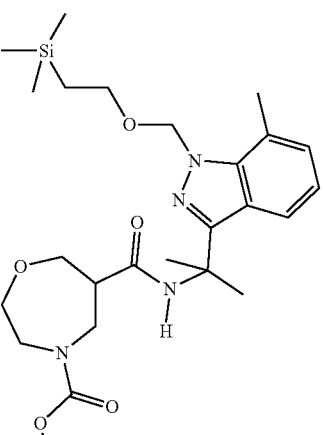 | Example 17a (150 mg, 64% content, 0.300 mmol) | 1.732 | 533 |
| 18b (racemic mixture) | 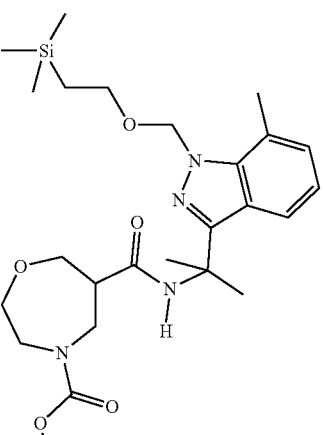 | Example 17a (313 mg, 75% content, 0.735 mmol), 4-(tert-butoxycarbonyl)-1,4-oxazepane-6-carboxylic acid (180 mg, 0.734 mmol) | 1.612 | 547 |

Example 19a

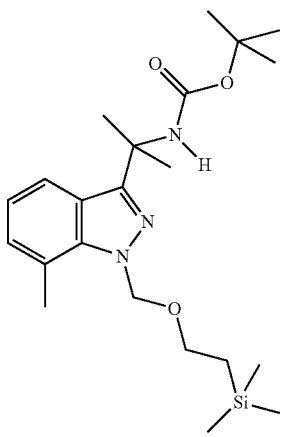 [SMILES: Cc1cccc2c(C(C)(C)NC(=O)OC(C)(C)C)nn(COCC[Si](C)(C)C)c12]

Di-t-butyl dicarbonate (145 mg, 0.664 mmol) is added to example 17a (300 mg, 64% content, 0.601 mmol) and TEA (0.127 mL, 0.901 mmol) in THF (3 mL). After stirring overnight the reaction mixture is evaporated under reduced pressure to give a residue that is purified by flash chromatography (eluent 0-20% EtOAc/cyclohexane) to furnish the title compound (146 mg, 58%).

UPLC-MS (Method 2): $R_t$=1.73 min

MS (ESI+): m/z=420 (M+H)$^+$

Example 20a

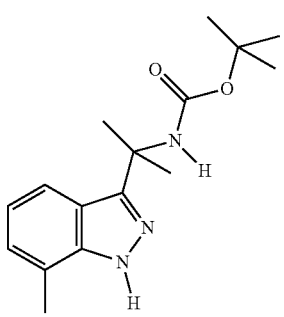 [SMILES: Cc1cccc2c(C(C)(C)NC(=O)OC(C)(C)C)n[nH]c12]

Example 19a (145 mg, 0.346 mmol), tetrabutylammonium fluoride (1.0 M in THF, 5.0 mL, 5.0 mmol) and ethylenediamine (140 µl, 2.094 mmol) are heated at 65° C. overnight. The reaction mixture is diluted with ethyl acetate and washed with DCM and water. The organic layers is separated, dried on a Phase separator cartridge and evaporated under reduced pressure to give a residue purified by flash chromatography (eluent 10-50% EtOAc/cyclohexane) to furnish the title compound (73 mg, 73%).

UPLC-MS (Method 2): $R_t$=1.11 min

MS (ESI+): m/z=290 (M+H)$^+$

Example 22a

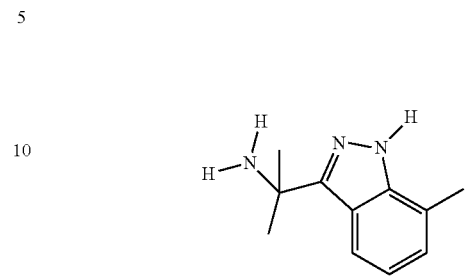

Example 20a (84 mg, 0.19 mmol) is dissolved in dioxane (2 mL), cooled to 0° C. and then hydrogen chloride 4M in dioxane (0.628 mL, 2,512 mmol) is added dropwise. Stirring is continued overnight at rt. Solvents are removed and the residue is loaded on an SCX cartridge. Fractions obtained upon eluting with metabolic ammonia are evaporated under reduced pressure to give the title compound (47 mg, 99%)

UPLC-MS (Method 2): $R_t$=0.66 min

MS (ESI+): m/z=190 (M+H)$^+$

The following examples are synthesized in analogy to the preparation of example 8a:

| Example | Structure | Reactant(s) | UPLC-MS $R_t$ [min], method | MS (APCl+, M/Z) (M + H)$^+$ |
|---|---|---|---|---|
| 23a (racemic mixture) | 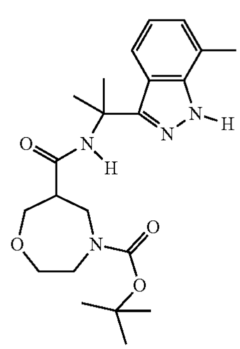 [SMILES: Cc1cccc2c(C(C)(C)NC(=O)C3COCCN(C(=O)OC(C)(C)C)C3)n[nH]c12] | Example 22a (47 mg, 0.248 mmol), 4-(tert-butoxycarbonyl)-1,4-oxazepane-6-carboxylic acid (61 mg, 0.248 mmol) | 4.227a | 417 |

The enantiomers of the example 23a are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 85:15; flow rate: 15 mL/min, temperature: 25° C.; UV Detection: 230 nm Example 23b:
stereoisomer 1, unknown
absolute stereochemistry Example 23c:
stereoisomer 2
unknown absolute stereochemistry

| Example | Chiral HPLC (Method 17) R$_t$ [min] | HPLC-MS (Method 7a): R$_t$ [min] | MS (APCI$_+$): m/z |
|---|---|---|---|
| 23b | 8.45 | 4.20 | 417 |
| 23c | 10.06 | 4.18 | 417 |

Example 24a (Racemic Mixture)

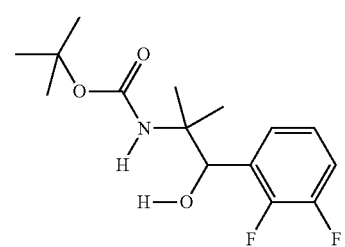 [SMILES: CC(C)(C)OC(=O)NC(C)(C)C(O)c1cccc(F)c1F]

n-Butyllithium (2.5 M in hexanes, 150 mL, 374 mmol) is added to 1,2-difluorobenzene (32 mL, 321 mmol) in THF (301 mL) at −78° C. Stirring is continued for 2 h. Tert-butyl 2-formylpropan-2-ylcarbamate (20.0 g, 107 mmol) in THF (50 mL) is added to the reaction mixture at −78° C. and stirring is continued for 1 h at that temperature. Saturated NH$_4$C$_1$ is added to the reaction mixture at −78° C. The reaction mixture is warmed to rt. The organic layer is separated, washed with brine, dried with a Phase separator cartridge and evaporated under vacuum to give a residue that is washed several times with pentane to furnish the title compound (16.2 g, 50%).

HPLC-MS (Method 11): R$_t$=2.92 min

MS (ESI+): m/z=302 (M+H)$^+$

The following example is synthesized in analogy to the preparation of example 24a:

| Example | Structure | Reactant(s) | UPLC-MS R$_t$ [min], method | MS (ESI$_+$, m/z) (M + H)$^+$ |
|---|---|---|---|---|
| 24b (racemic mixture) | 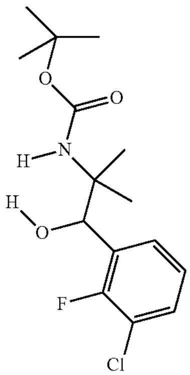 [SMILES: CC(C)(C)OC(=O)NC(C)(C)C(O)c1cccc(Cl)c1F] | Tert-butyl 2-formylpropan-2-ylcarbamate (12.0 g, 64.1 mmol); 1-chloro-2-fluorobenzene (20 mL, 190 mmol) | 1.312 | 318 |

Example 25a

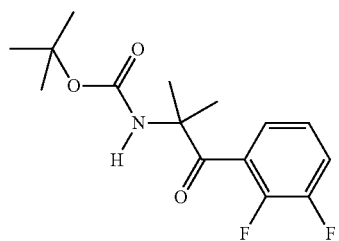 [SMILES: CC(C)(C)OC(=O)NC(C)(C)C(=O)c1cccc(F)c1F]

Dess-Martin periodinane (25.0 g, 59.1 mmol) is added portionwise to example 24a (16.2 g, 53.8 mmol) in DCM (159 mL) cooled to 0° C. and stirring is continued at rt overnight. 10% sodium thiosulfate solution is added and stirring is continued for 30 min. The organic layers is separated, washed with saturated NaHCO$_3$ solution, dried on a Phase separator cartridge and evaporated under reduced pressure to furnish the title compound (16.0 g, 99%), that is used as such.

HPLC-MS (Method 7a): R$_t$=4.82 min

MS (APCI+): m/z=200 (M+H-Boc)$^+$

The following example is synthesized in analogy to the preparation of example 25a:

| Example | Structure | Reactant(s) | UPLC-MS $R_t$ [min], method | MS (ESI+, m/z) (M + H)+ |
|---|---|---|---|---|
| 25b | 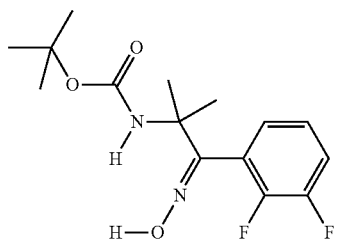 [SMILES: CC(C)(C)OC(=O)NC(C)(C)C(=NO)c1cccc(F)c1F] | Example 24b (12.6 g, 39.6 mmol) | 1.312 | 316 |

Example 26a

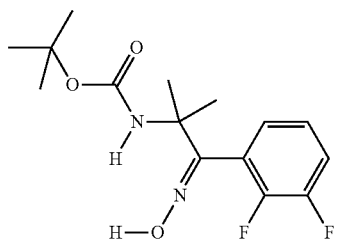 [SMILES: CC(C)(C)OC(=O)NC(C)(C)C(=NO)c1cccc(F)c1F]

Hydroxylamine hydrochloride (4.64 g, 66.8 mmol) is added to example 25a (8.00 g, 26.7 mmol) in pyridine (35 mL) and stirring is continued at 50° C. overnight. Volatiles are evaporated under reduced pressure, DCM and water are added. The organic layers is separated, washed with brine, dried on a Phase separator cartridge and evaporated under reduced pressure to furnish the title compound (8.20 g, 98%), that is used as such.

$^1$H NMR (500 MHz, DMSO-$d_6$): δ 1.27 ppm (s, br, 3H), 1.37 ppm (s, 9H), 1.53 ppm (s, br, 3H), 6.87 (s, br, 1H), 6.91 (m, 1H), 7.21 (m, 1H), 7.39 (m, 1H), 10.95 (s, 1H).

The following examples is synthesized in analogy to the preparation of example 26a:

| Example | Structure | Reactant(s) | UPLC-MS $R_t$ [min], method | MS (ESI+, m/z) (M + H)+ |
|---|---|---|---|---|
| 26b | 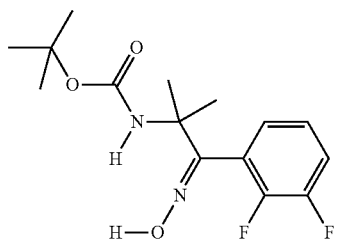 [SMILES: CC(C)(C)OC(=O)NC(C)(C)C(=NO)c1cccc(F)c1F] | Example 25b (5.00 g, 15.8 mmol) | 1.212 | 331 |

Example 27a

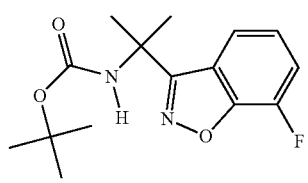 [SMILES: CC(C)(C)OC(=O)NC(C)(C)c1noc2c(F)cccc12]

Potassium tert-butoxide (3.51 g, 31.3 mmol) is added to example 26a (8.20 g, 26.1 mmol) in THF (80 mL) and the reaction mixture is stirred at rt for 3 h. The reaction is diluted with EtOAc, washed with water and brine. The organic layer is separated and dried with a Phase separator cartridge and evaporated under vacuum to furnish the title compound (340 mg, 60%), that is used as such.

UPLC-MS (Method 2): $R_t$=1.23 min

MS (ESI+): m/z=295 (M+H)+

The following example is synthesized in analogy to the preparation of example 27a:

| Example | Structure | Reactant(s) | UPLC-MS $R_t$ [min], method | MS (ESI+, m/z) (M + H)+ |
|---|---|---|---|---|
| 27b | 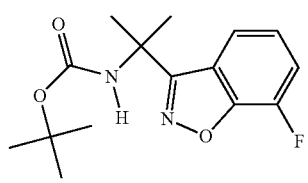 [SMILES: CC(C)(C)OC(=O)NC(C)(C)c1noc2c(F)cccc12] | Example 26b (5.79 g, 80% content, 14.0 mmol) | 1.302 | 311 |

Example 28a

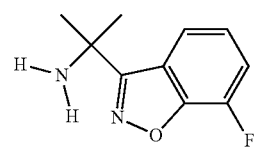

Example 27a (1.00 g, 3.40 mmol) is dissolved in MeOH (3 mL) and then hydrogen chloride 4M in dioxane (6.0 mL, 24 mmol) is added dropwise. Stirring is continued overnight at rt. The reaction mixture is basified with metabolic ammonia and water and DCM are added. The organic layer is separated, dried and evaporated under reduced pressure to afford the title compound (0.58 g, 88%), that is used as such.

UPLC-MS (Method 2): $R_t$=0.67 min

MS (ESI+): m/z=195 (M+H)+

Example 28b

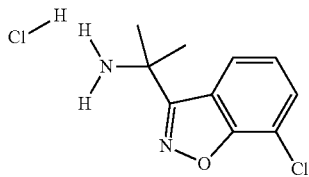

Example 27b (500 mg, 1,609 mmol) is dissolved in dioxane and then hydrogen chloride 4M in dioxane (4.0 mL, 16 mmol) is added dropwise. Stirring is continued overnight at rt. Volatiles are evaporated under reduced pressure to give a residue that is washed several times with ethyl ether afford the title compound (374 mg, 94%), that is used as such.

UPLC-MS (Method 2): $R_t$=0.70 min

MS (ESI+): m/z=211 (M+H)$^+$

The following examples are synthesized in analogy to the preparation of example 8a:

| Example | Structure | Reactant(s) | UPLC-MS $R_t$ [min], method | MS (ESI+, m/z) (M + H)$^+$ |
|---|---|---|---|---|
| 29a | 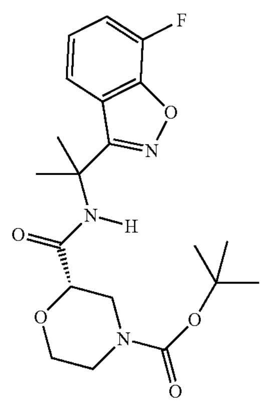 [SMILES: CC(C)(C)OC(=O)N1CCO[C@H](C(=O)NC(C)(C)c2noc3c(F)cccc23)C1] | Example 28a (150 g, 80% content, 0.618 mmol) | 1.212 | 408 |
| 29b (racemic mixture) | 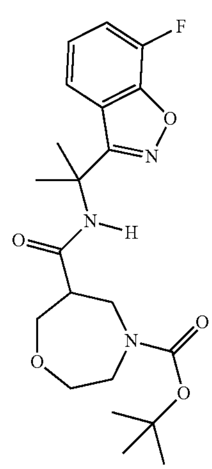 [SMILES: CC(C)(C)OC(=O)N1CCOCC(C(=O)NC(C)(C)c2noc3c(F)cccc23)C1] | Example 28a (150 mg, 80% content, 0.618 mmol), 4-tert-butoxycarbonyl)-1,4-oxazepane-6-carboxylic acid (152 mg, 0.618 mmol) | 1.172 | 422 |

The enantiomers of the example 29b are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 92:8; flow rate: 15 mL/min, temperature: 25° C.; UV Detection: 230 nm

| Example 29c: stereoisomer 1, unknown absolute stereochemistry | Example 29d: stereoisomer 2, unknown absolute stereochemistry |
|---|---|

| Example | Chiral HPLC (Method 18) $R_t$ [min] |
|---|---|
| 29c | 5.28 |
| 29d | 5.86 |

The following example is synthesized in analogy to the preparation of example 8a:

| Example | Structure | Reactant(s) | UPLC-MS $R_t$ [min], method | MS (ESI+, m/z) (M + H)+ |
|---|---|---|---|---|
| 29e (racemic mixture) | 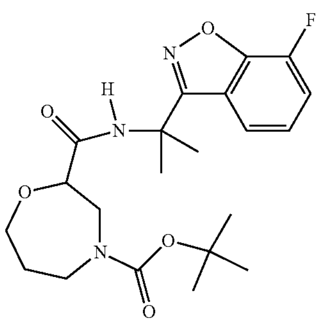 [SMILES: CC(C)(C)OC(=O)N1CCCOC(C(=O)NC(C)(C)c2noc3c(F)cccc23)C1] | Example 28a (143 mg, 0.734 mmol), 4-Boc-2-homomorpholine-carboxylic acid (150 mg, 0.612 mmol) | 1.282 | 422 |

The enantiomers of the example 29e are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 85:15; flow rate: 15 mL/min, temperature: 25° C.; UV Detection: 230 nm

| Example 29f: stereoisomer 1, unknown absolute stereochemistry | Example 29g: stereoisomer 2 unknown absolute stereochemistry |
|---|---|

| Example | Chiral HPLC (Method 17) R$_t$ [min] |
|---|---|
| 29f | 6.30 |
| 29g | 7.14 |

The following example is synthesized in analogy to the preparation of example 8a:

| Example | Structure | Reactant(s) | UPLC-MS R$_t$ [min], method | MS (ESI$_+$, m/z) (M + H)$^+$ |
|---|---|---|---|---|
| 29h (racemic mixture) | 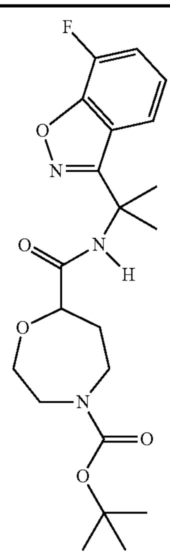 | Example 28a (105 mg, 0.538 mmol), example 7a (110 mg, 0.448 mmol) | 1.222 | 422 |

The enantiomers of the example 29h are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 90:10; flow rate: 15 mL/min, temperature: 25° C.; UV Detection: 230 nm

| Example 29i: stereoisomer 1, unknown absolute stereochemistry | Example 29j: stereoisomer 2 unknown absolute stereochemistry |
|---|---|

| Example | Chiral HPLC (Method 17) R$_t$ [min] |
|---|---|
| 29i | 6.01 |
| 29j | 6.76 |

The following examples are synthesized in analogy to the preparation of example 8a:
| Example | Structure | Reactant(s) | UPLC-MS $R_t$ [min], method | MS (ESI+, m/z) (M + H)+ |
|---|---|---|---|---|
| 29k | 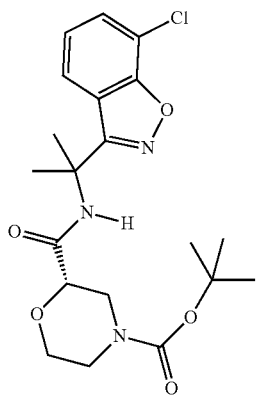 [SMILES: CC(C)(C)OC(=O)N1CCO[C@H](C(=O)NC(C)(C)c2noc3c(Cl)cccc23)C1] | Example 28b (81 mg, 95% content, 0.313 mmol) | 1.282 | 424 |
| 29l (racemic mixture) | 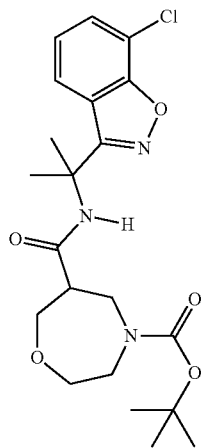 [SMILES: CC(C)(C)OC(=O)N1CCOCC(C(=O)NC(C)(C)c2noc3c(Cl)cccc23)C1] | Example 28b (210 mg, 0.850 mmol), 4-tert-butoxycarbonyl)-1,4-oxazepane-6-carboxylic acid (209 mg, 0.852 mmol) | 1.232 | 438 |

The enantiomers of the example 291 are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/IPA 92:8; flow rate: 15 mL/min, temperature: 25° C.; UV Detection: 230 nm

| Example 29m: stereoisomer 1, unknown absolute stereochemistry | Example 29n: stereoisomer 2 unknown absolute stereochemistry |
|---|---|

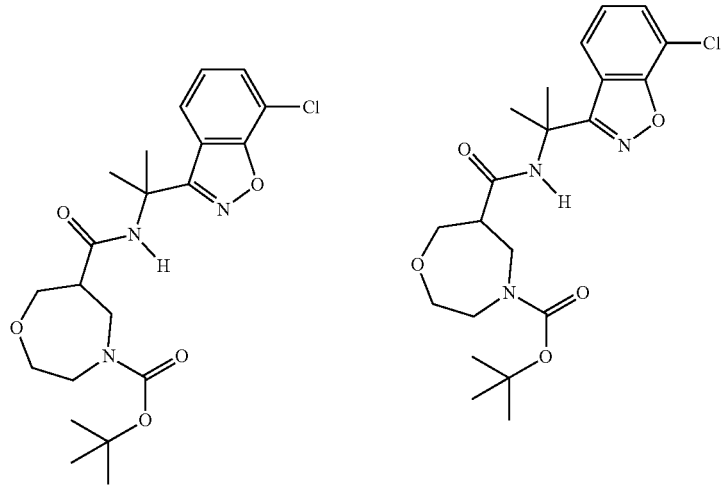

| Example | Chiral HPLC (Method 15) $R_t$ [min] | HPLC-MS (Method 7a): $R_t$ [min] | MS (APCl$_+$): m/z |
|---|---|---|---|
| 29m | 9.59 | 4.80 | 438 |
| 29n | 11.51 | 4.80 | 438 |

Example 30a

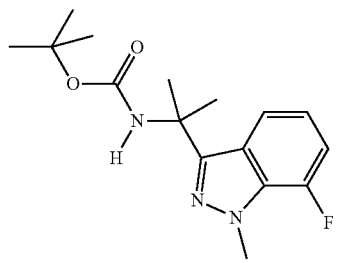 [SMILES: Cn1nc(C(C)(C)NC(=O)OC(C)(C)C)c2cccc(F)c21]

Example 25a (3.50 g, 11.7 mmol) and methylhydrazine (7.4 mL, 140 mmol) in EtOH (14 mL) are heated at 80° C. for 6 h and at rt over weekend. Volatiles are evaporated under reduced pressure to give a residue that is purified by flash chromatography (eluent 5% EtOAc/cyclohexane) to furnish the title compound (2.60 g, 72%).

$^1$H NMR (500 MHz, DMSO-d$_6$): δ 0.86 (s, br, 2H), 1.25 (s, br, 7H), 1.59 (s, 6H), 4.09 (d, J=1.0 Hz, 3H), 7.00 (ddd, J=4.3, 7.9, 12.3 Hz, 1H), 7.13 (dd, J=7.6, 12.4 Hz, 1H), 7.44 (s, br, 1H), 7.13 (d, J=8.1 Hz, 1H)

The following examples are synthesized in analogy to the preparation of example 30a:

| Example | Structure | Reactant | UPLC-MS $R_t$ [min], method | MS (ESI$_+$, m/z) (M + H)$^+$ |
|---|---|---|---|---|
| 30b | 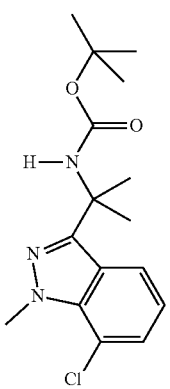 [SMILES: Cn1nc(C(C)(C)NC(=O)OC(C)(C)C)c2cccc(Cl)c21] | Example 25b (1.86 g, 6.18 mmol) | 1.372 | 324 |

Example 30c

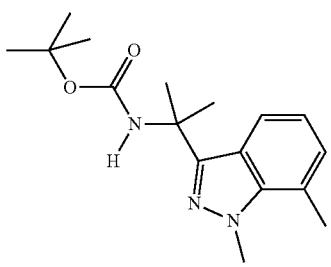 [SMILES: Cc1cccc2c(C(C)(C)NC(=O)OC(C)(C)C)nn(C)c12]

Trimethylboroxine (1.2 mL, 8.5 mmol) is added to example 30b (1.00 g, 92% content, 2,841 mmol), potassium carbonate 1.96 g, 14,206 mmol) and 1,1'-bis(diphenylphosphino)ferrocene-palladium(II)dichloride dichloromethane complex (232 mg, 0,284 mmol) in DMF (14 mL) and the reaction mixture is heated at 100° C. overnight. Trimethylboroxine (542 µl, 3.87 mmol), potassium carbonate (892 mg, 6.46 mmol) and 1,1'-bis(diphenylphosphino)ferrocene-palladium(II)dichloride dichloromethane complex (105 mg, 0.129 mmol) are added to the reaction mixture cooled to rt and the reaction mixture is heated at 100° C. overnight. Volatiles are evaporated under reduced pressure and the residue dissolved with EtOAc/water. The organic layer is separated, dried and evaporated under reduced pressure to give a residue that is purified by flash chromatography (eluent 0-20% EtOAc/cyclohexane) to furnish the title compound (700 mg, 81%).

UPLC-MS (Method 2): $R_t$=1.23 min
MS (ESI+): m/z=304 (M+H)$^+$

Example 30d

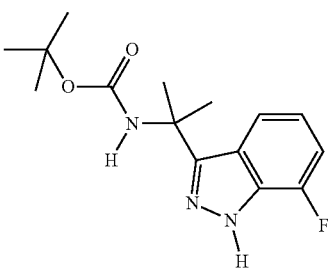 [SMILES: CC(C)(C)OC(=O)NC(C)(C)c1n[nH]c2c(F)cccc12]

Example 25a (1.86 g, 6.18 mmol) and hydrazine hydrate (65% content, 1.6 mL, 21,633 mmol) in EtOH (20 mL) are split in two equal batches and heated under microwaves irradiation (140° C.) for 35 min. EtOAc and water are added to the reaction mixture. The organic layer is separated, washed with brine, dried and evaporated under reduced pressure to give a residue that is purified by flash chromatography (eluent 0-10% EtOAc/DCM) to furnish the title compound (1.72 g, 95%).

UPLC-MS (Method 2): $R_t$=1.06 min
MS (ESI+): m/z=294 (M+H)$^+$

The following examples are synthesized in analogy to the preparation of example 30d:

| Example | Structure | Reactant | UPLC-MS $R_t$ [min], method | MS (ESI+, m/z) (M + H)$^+$ |
|---|---|---|---|---|
| 30e | 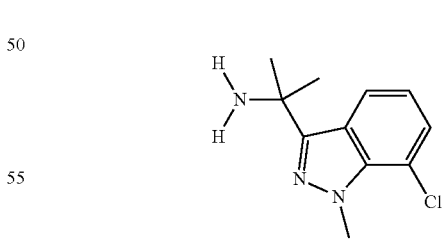 | Example 30a (1.00 g, 3.17 mmol) | 1.132 | 310 |

The following examples are synthesized in analogy to the preparation of example 28b:

| Example | Structure | Reactant | UPLC-MS $R_t$ [min], method | MS (ESI+, m/z) (M + H)$^+$ |
|---|---|---|---|---|
| 31a | (structure) | Example 30a (600 mg, 1.952 mmol) | 0.672 | 191 (M − NH$_2$)$^+$ |

Example 31b

Example 30b (150 mg, 0,463 mmol) is suspended in MeOH/Water 1:1 (1 mL/1 mL) and heated under microwaves irradiation (140° C.) for 70 min. The reaction mixture is purified on a SCX cartridge, which is washed with MeOH and DCM, and then eluted with NH$_3$ in MeOH to give the title compound (50 mg, 48%).

TLC Rf=0.18 (eluent 90:10:1 DCM/MeOH/NH$_4$OH)

The following examples are synthesized in analogy to the preparation of example 31 b:

| Example | Structure | Reactant | UPLC-MS R$_t$ [min], method | MS (ESI+, m/z) (M + H)+ |
|---|---|---|---|---|
| 31c | 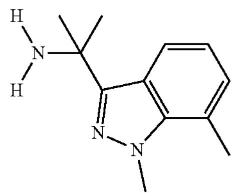 | Example 30c (150 mg, 0.494 mmol) | 0.702 | 187 (M − NH$_2$)+ |
| 31d | 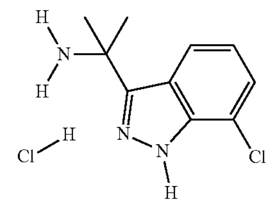 | Example 30d (608 mg, 2.073 mmol) | 0.632 | 177 (M − NH$_2$)+ |
| 31e | 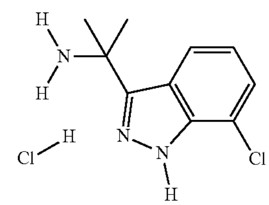 | Example 30e (555 mg, 1.792 mmol) | 0.662 | 193 (M − NH$_2$)+ |

The following examples are synthesized in analogy to the preparation of example 28b:

The following examples are synthesized in analogy to the preparation of example 8a:

| Example | Structure | Reactant(s) | HPLC-MS or UPLC-MS R$_t$ [min], method | MS (ESI+ or APCI+, m/z) (M + H)+ |
|---|---|---|---|---|
| 32a | 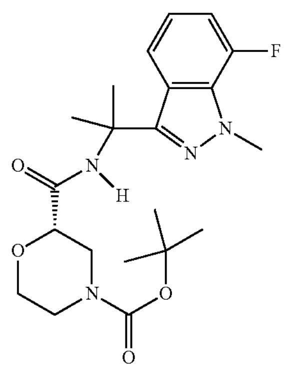 | Example 31a (92 mg, 0.375 mmol) | 1.272 | 421 |
| 32b (racemic mixture) | 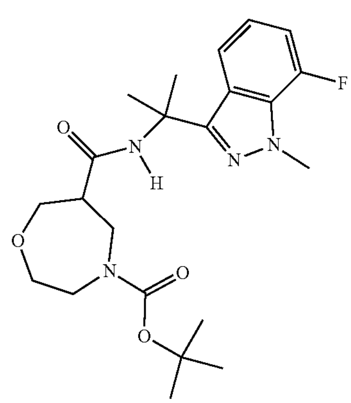 [SMILES: Cn1nc(C(C)(C)NC(=O)C2COCCN(C(=O)OC(C)(C)C)C2)c2cccc(F)c21] | Example 31a (183 mg, 0.751 mmol), 4-(tert-butoxycarbonyl)-1,4-oxazepane-6-carboxylic acid (184 mg, 0.751 mmol) | 2.911 | 435 |

| Example | Structure | Reactant(s) | HPLC-MS or UPLC-MS $R_t$ [min], method | MS (ESI+ or APCI+, m/z) (M + H)+ |
|---|---|---|---|---|
| 32c | 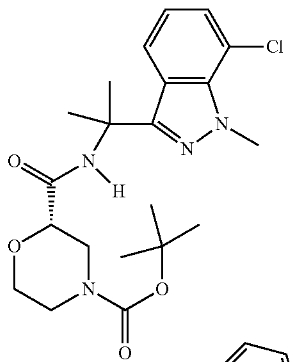 | Example 31b (50 mg, 0.224 mmol) | 5.30 7a | 437 |
| 32d (racemic mixture) | 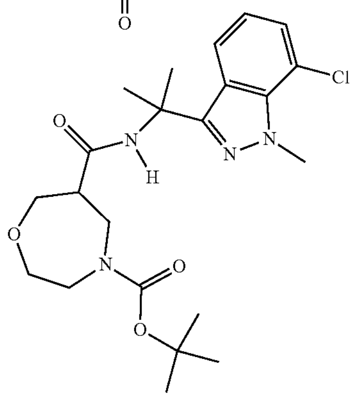 | Example 31b (150 mg, 0.577 mmol), 4-(tert-butoxycarbonyl)-1,4-oxazepane-6-carboxylic acid (141 mg, 0.577 mmol) | 3.04 11 | 451 |

The enantiomers of the example 32d are separated by HPLC using a chiral stationary phase.
Method for Separation:
HPLC apparatus type: Waters 600 Pump, 2767 Autosampler, UV Detector 2489; column: Daicel Chiralpak AS-H, 5.0 μm, 250 mm×20 mm; method: eluent hexane/EtOH 95:5; flow rate: 15 mL/min, temperature: 25° C.; UV Detection: 230 nm

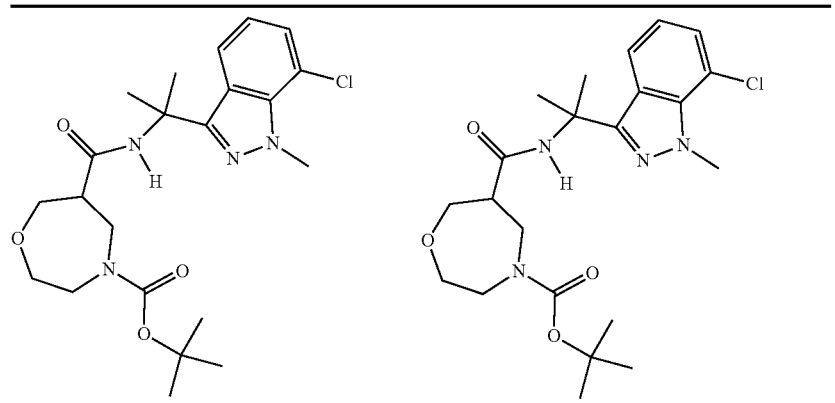

Example 32e: stereoisomer 1, unknown absolute stereochemistry

Example 32f: stereoisomer 2 unknown absolute stereochemistry

| Example | Chiral HPLC (Method 19) $R_t$ [min] | HPLC-MS (Method 7a): $R_t$ [min] | MS (APCI+): m/z |
|---|---|---|---|
| 32e | 6.47 | 4.93 | 451 |
| 32f | 7.43 | 4.92 | 451 |

The following examples are synthesized in analogy to the preparation of example 8a:

| Example | Structure | Reactant(s) | HPLC-MS or UPLC-MS $R_t$ [min], method | MS (ESI pos or APCI, m/z) $(M + H)^+$ |
|---|---|---|---|---|
| 32g | 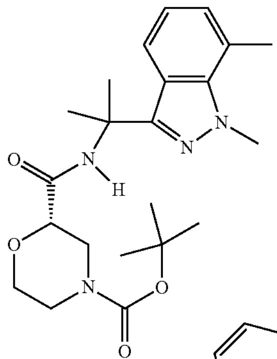 | Example 31c (65 mg, 0.320 mmol) | 5.01 7a | 417 |
| 32h (racemic mixture) | 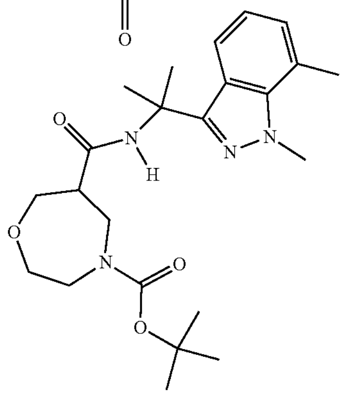 | Example 31c (230 mg, 0.959 mmol), 4-(tert-butoxycarbonyl)-1,4-oxazepane-6-carboxylic acid (235 mg, 0.959 mmol) | 4.67 7a | 431 |

The enantiomers of the example 32h are separated by HPLC using a chiral stationary phase.
Method for Separation:
HPLC apparatus type: Waters 600 Pump, 2767 Autosampler, UV Detector 2489; column: Daicel Chiralpak AS-H, 5.0 μm, 250 mm×20 mm; method: eluent hexane/EtOH 94:6; flow rate: 15 mL/min, temperature: 25° C.; UV Detection: 230 nm

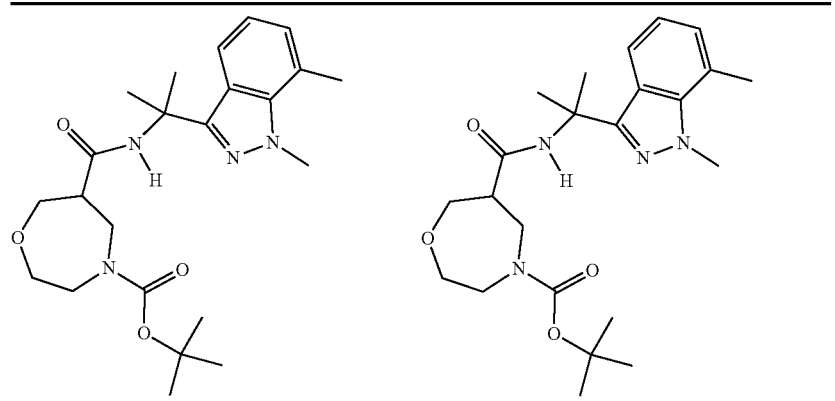

Example 32i: stereoisomer 1, unknown absolute stereochemistry

Example 32j: stereoisomer 2 unknown absolute stereochemistry

| Example | Chiral HPLC (Method 19) $R_t$ [min] | HPLC-MS (Method 7a): $R_t$ [min] | MS (APCI$_+$): m/z |
|---|---|---|---|
| 32i | 8.56 | 4.62 | 431 |
| 32j | 11.56 | 4.62 | 431 |

The following examples are synthesized in analogy to the preparation of example 8a:

| Example | Structure | Reactant(s) | UPLC-MS $R_t$ [min], method | MS (ESI$_+$, m/z) (M + H)$^+$ |
|---|---|---|---|---|
| 32k | 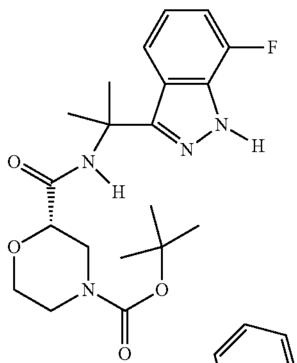 | Example 31d (80 mg, 0.348 mmol) | 1.122 | 407 |
| 32l (racemic mixture) | 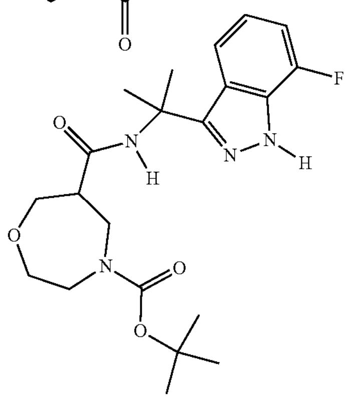 | Example 31d (200 mg, 0.871 mmol), 4-(tert-butoxycarbonyl)-1,4-oxazepane-6-carboxylic acid (214 mg, 0.871 mmol) | 1.052 | 421 |

The enantiomers of the example 32l are separated by HPLC using a chiral stationary phase.

Method for Separation:
HPLC apparatus type: Waters 600 Pump, 2767 Autosampler, UV Detector 2489; column: Daicel Chiralpak AD-H, 5.0 μm, 250 mm×20 mm; method: eluent hexane/IPA 80:20; flow rate: 15 mL/min, temperature: 25° C.; UV Detection: 230 nm

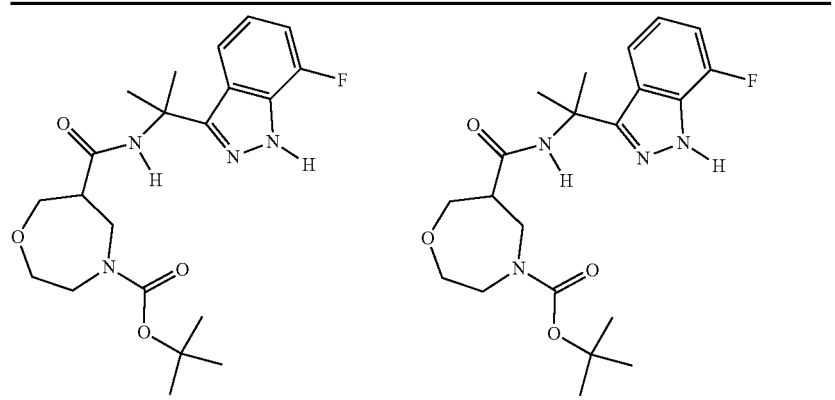

Example 32m: stereoisomer 1, unknown absolute stereochemistry

Example 32n: stereoisomer 2 unknown absolute stereochemistry

| Example | Chiral HPLC (Method 16) $R_t$ [min] | HPLC-MS (Method 7a): $R_t$ [min] | MS (APCl$_+$): m/z |
|---|---|---|---|
| 32m | 5.28 | 4.08 | 421 |
| 32n | 5.82 | 4.08 | 421 |

The following examples are synthesized in analogy to the preparation of example 8a:

| Example | Structure | Reactant(s) | UPLC-MS R$_t$ [min], method | MS (ESI$_+$, m/z) (M + H)$^+$ |
|---|---|---|---|---|
| 32o | 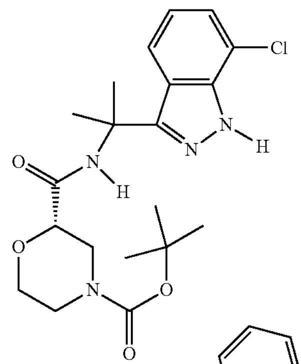 | Example 31e (50 mg, 0.203 mmol) | 1.172 | 423 |
| 32p (racemic mixture) | 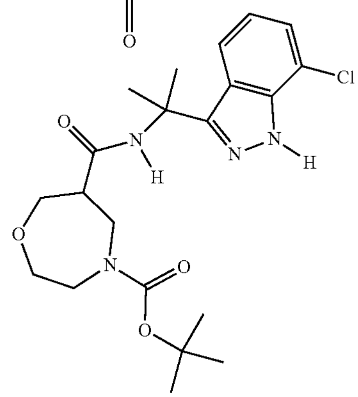 | Example 31e (118 mg, 0.479 mmol), 4-(tert-butoxycarbonyl)-1,4-oxazepane-6-carboxylic acid (118 mg, 0.481 mmol) | 1.102 | 437 |

The enantiomers of the example 32p are separated by HPLC using a chiral stationary phase.
Method for Separation:
HPLC apparatus type: Waters 600 Pump, 2767 Autosampler, UV Detector 2489; column: Daicel Chiralpak AS-H, 5.0 μm, 250 mm×20 mm; method: eluent hexane/EtOH 95:5; flow rate: 15 mL/min, temperature: 25° C.; UV Detection: 230 nm

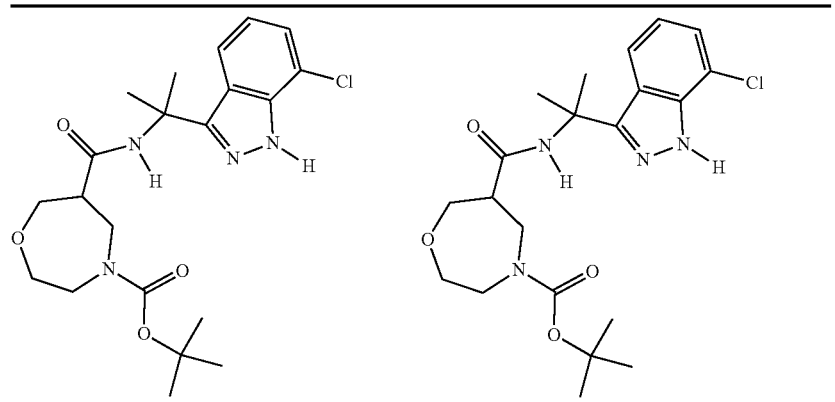

Example 32q: stereoisomer 1, unknown absolute stereochemistry

Example 32r: stereoisomer 2 unknown absolute stereochemistry

| Example | Chiral HPLC (Method 19) R$_t$ [min] | HPLC-MS (Method 7a): R$_t$ [min] | MS (APCl$_+$): m/z |
|---|---|---|---|
| 32q | 9.83 | 4.30 | 437 |
| 32r | 11.05 | 4.30 | 437 |

Example 33a

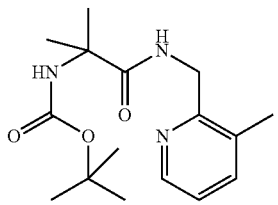 [SMILES: Cc1cccnc1CNC(=O)C(C)(C)NC(=O)OC(C)(C)C]

3-methyl-2-(aminomethyl)pyridine (13.5 g, 110 mmol), is suspended in dry THF and 2-tert-butoxycarbonylamino-2-methylpropionic acid (22.4 g, 110 mmol) is added followed by TEA (46.1 mL, 331 mmol) and TBTU (35.4 g, 110 mmol). The mixture is stirred overnight at room temperature then the solvent is evaporated, the residue is diluted with dichloromethane and washed with 1N NaOH solution and brine. The organic layer is dried, filtered and evaporated under reduced pressure to give a residue that is purified by flash chromatography (eluent 50-100% EtOAc/cyclohexane) to furnish the title compound (28.5 g, 84%).

UPLC-MS (Method 2): $R_t$=0.98 min

MS (ESI+): m/z=308 (M+H)$^+$

The following examples are synthesized in analogy to the preparation of example 33a (using HATU as the coupling agent where specified). Where appropriate products are purified by flash chromatography (eluent gradient of EtOAc in cyclohexane):

| Example | Structure | Reactant(s) Conditions | UPLC-MS $R_t$ [min], method | MS (ESI$_+$, m/z) (M + H)$^+$ |
|---|---|---|---|---|
| 33b | 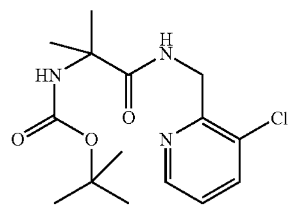 [SMILES: CC(C)(C)OC(=O)NC(C)(C)C(=O)NCc1ncccc1Cl] | (3-chloropyridin-2-yl)methanamine (1 g) HATU | 0.911 | 328 |
| 33c | 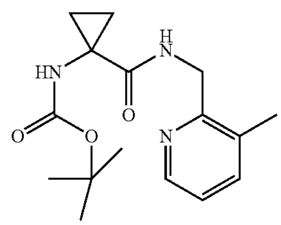 [SMILES: Cc1cccnc1CNC(=O)C1(NC(=O)OC(C)(C)C)CC1] | C-(3-Methyl-pyridin-2-yl)-methylamine (500 mg) Boc-1-amino-1-cyclopropyanecarboxylic acid (823 mg) | 0.661 | 306 |
| 33d | 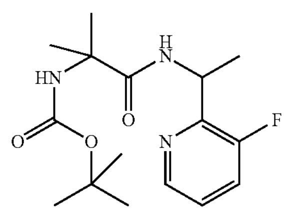 [SMILES: CC(NC(=O)C(C)(C)NC(=O)OC(C)(C)C)c1ncccc1F] | 1-(3-Fluoro-pyridin-2-yl)-ethylamine hydrochloride (5.8 g) HATU | 0.942 | 326 |
| 33e | 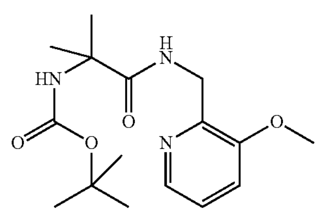 [SMILES: COc1cccnc1CNC(=O)C(C)(C)NC(=O)OC(C)(C)C] | C-(3-Methoxy-pyridin-2-yl)-methylamine dihydrochloride (1 g) HATU | 0.681 | 324 |
| 33f | 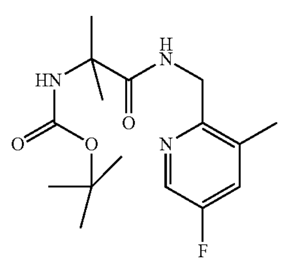 [SMILES: Cc1cc(F)cnc1CNC(=O)C(C)(C)NC(=O)OC(C)(C)C] | C-(5-fluoro-3-methyl-pyridin-2-yl)-methylamine (202 mg) HATU | 1.042 | 326 |

-continued

| Example | Structure | Reactant(s) Conditions | UPLC-MS R$_t$ [min], method | MS (ESI$_+$, m/z) (M + H)$^+$ |
|---------|-----------|------------------------|------------------------------|-------------------------------|
| 33g | 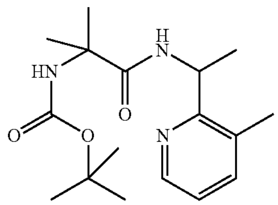 [SMILES: Cc1cccnc1C(C)NC(=O)C(C)(C)NC(=O)OC(C)(C)C] | 1-(3-methyl-2-pyridinyl)ethanamine (1 g) HATU 4 day reaction | 0.982 | 322 |
| 33h | 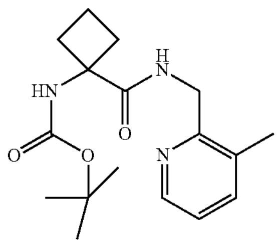 [SMILES: Cc1cccnc1CNC(=O)C1(NC(=O)OC(C)(C)C)CCC1] | C-(3-Methyl-pyridin-2-yl)-methylamine (500 mg) Boc-1-amino-1-cyclobutanecarboxylic acid (880 mg) overnight reaction | 0.902 | 320 |
| 33i | 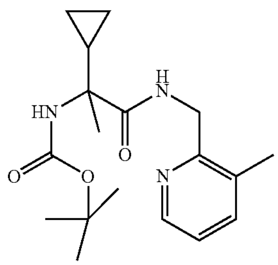 [SMILES: Cc1cccnc1CNC(=O)C(C)(NC(=O)OC(C)(C)C)C1CC1] | C-(3-Methyl-pyridin-2-yl)-methylamine (530 mg) 2-([(tert-butoxy)carbonyl]amino)-2-cyclopropylpropanoic acid (1.0 g) | 1.022 | 334 |
| 33j | 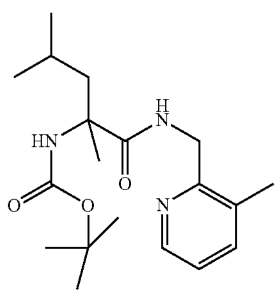 [SMILES: Cc1cccnc1CNC(=O)C(C)(CC(C)C)NC(=O)OC(C)(C)C] | C-(3-Methyl-pyridin-2-yl)-methylamine (483 mg) 2-tert-Butoxycarbonylamino-2,4-dimethyl-pentanoic acid (968 mg) | 1.202 | 350 |
| 33k | 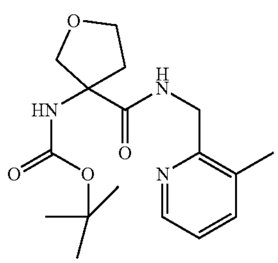 [SMILES: Cc1cccnc1CNC(=O)C1(NC(=O)OC(C)(C)C)CCOC1] | C-(3-Methyl-pyridin-2-yl)-methylamine (520 mg) 3-tert-Butoxycarbonylamino-tetrahydro-furan-3-carboxylic acid (990 mg) | 0.852 | 336 |
| 33l | 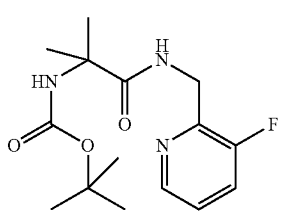 [SMILES: CC(C)(C)OC(=O)NC(C)(C)C(=O)NCc1ncccc1F] | 1-(3-fluoropyridin-2-yl)methanamine (1 g) | 0.822 | 312 |

Example 34a

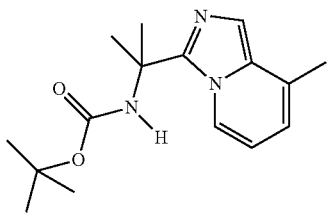 [SMILES: Cc1cccn2c(C(C)(C)NC(=O)OC(C)(C)C)ncc12]

Example 33a (28.5 g, 92.8 mmol) is dissolved in DCM (360 mL) and cooled to 0° C., then Burgess reagent (20.1 g, 84.5 mmol) is added. The mixture is allowed to reach rt and stirred for 3 days. The reaction mixture is washed with water and brine. The organic layer is dried, filtered and evaporated under reduced pressure to give a residue that is purified by flash chromatography (eluent EtOAc/cyclohexane 30:70) to furnish the title compound (13.8 g, 51%).

UPLC-MS (Method 2): $R_t$=1.01 min

MS (ESI+): m/z=290 (M+H)$^+$

The following examples are synthesized in analogy to the preparation of example 34a. Where appropriate products are purified by flash chromatography (eluent gradient of EtOAc in cyclohexane):

| Example | Structure | Reactant(s) Conditions | LC-MS $R_t$ [min], method | MS (ESI$_+$, m/z) (M + H)$^+$ |
|---|---|---|---|---|
| 34b | 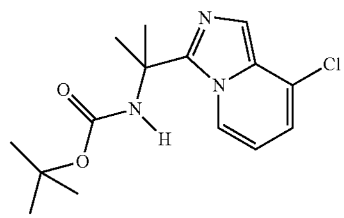 [SMILES: CC(C)(C)OC(=O)NC(C)(C)c1ncc2c(Cl)cccn12] | Example 33b (2.30 g, 7.02 mmol overnight reaction | 0.841 | 310 |
| 34c | 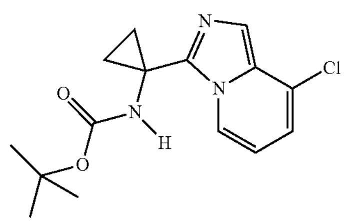 [SMILES: CC(C)(C)OC(=O)NC1(c2ncc3c(Cl)cccn23)CC1] | Example 33c (0.77 g, 2.52 mmol) overnight reaction | $^1$H NMR (500 MHz, DMSO-d$_6$): (rotamers) δ 1.18 (br, m, 2H), 1.23 (br, m, 2H), 1.30 (br, s, 9H), 2.34 (s, 3H), 6.56 (ddd, J = 1.1, 2.0, 6.5 Hz, 1H), 6.63 (dd, J = 6.7 Hz, 1H), 7.22 (d, J = 0.6 Hz, 1H), 7.90 (br, s, 1H), 8.48 (br, d, J = 4.7 Hz, 1H) | |
| 34d | 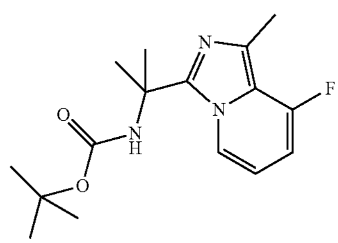 [SMILES: Cc1nc(C(C)(C)NC(=O)OC(C)(C)C)n2cccc(F)c12] | Example 33d (10 g, 30.73 mmol) overnight reaction | 1.542 | 308 |
| 34e | 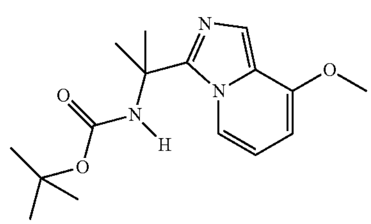 [SMILES: COc1cccn2c(C(C)(C)NC(=O)OC(C)(C)C)ncc12] | Example 33e (1.51 g, 4.67 mmol) overnight reaction | 0.771 | 306 |
| 34f | 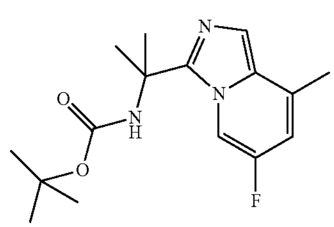 [SMILES: Cc1cc(F)cn2c(C(C)(C)NC(=O)OC(C)(C)C)ncc12] | Example 33f (102 mg, 0.31 mmol) overnight reaction | 1.112 | 308 |

-continued

| Example | Structure | Reactant(s) Conditions | LC-MS R$_t$ [min], method | MS (ESI$_+$, m/z) (M + H)$^+$ |
|---|---|---|---|---|
| 34g | 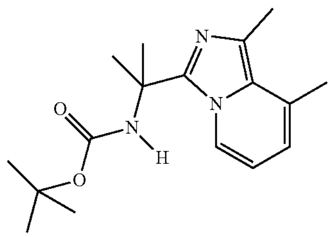 [SMILES: Cc1cccn2c(C(C)(C)NC(=O)OC(C)(C)C)nc(C)c12] | Example 33g (2.04 g, 6.33 mmol) overnight reaction | 1.052 | 304 |
| 34h | 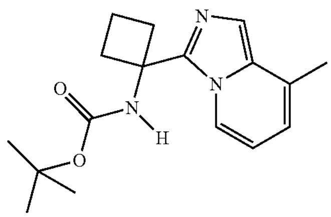 [SMILES: Cc1cccn2c(C3(NC(=O)OC(C)(C)C)CCC3)ncc12] | Example 33h (1.16 g, 3.63 mmol) overnight reaction | 1.122 | 302 |
| 34i | 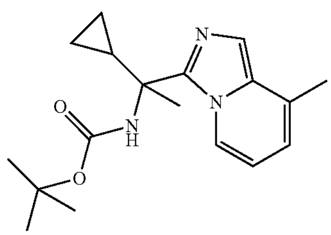 [SMILES: Cc1cccn2c(C(C)(NC(=O)OC(C)(C)C)C3CC3)ncc12] | Example 33i (1.40 g, 3.95 mmol) overnight reaction | 1.092 | 316 |
| 34j | 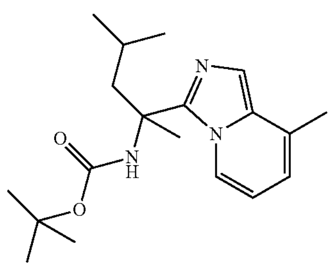 [SMILES: Cc1cccn2c(C(C)(CC(C)C)NC(=O)OC(C)(C)C)ncc12] | Example 33j (0.98 g, 2.80 mmol) overnight reaction | 1.252 | 332 |
| 34k | 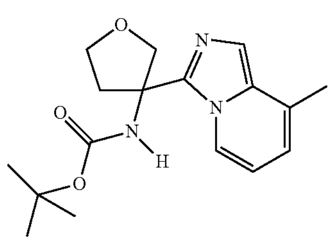 [SMILES: Cc1cccn2c(C3(NC(=O)OC(C)(C)C)CCOC3)ncc12] | Example 34k (0.92 g, 0.38 mmol) overnight reaction | 0.942 | 318 |
| 34l | 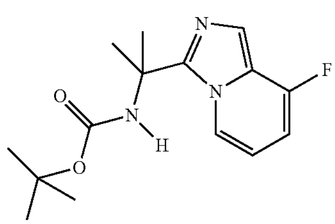 [SMILES: CC(C)(C)OC(=O)NC(C)(C)c1ncc2c(F)cccn12] | Example 33l (1.0 g, 3.21 mmol) | 0.972 | 294 |

Example 34m

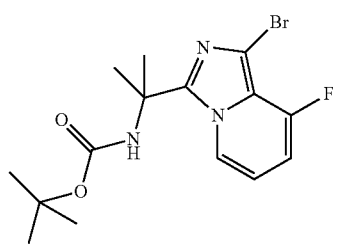 [SMILES: CC(C)(C)OC(=O)NC(C)(C)c1nc(Br)c2c(F)cccn12]

Example 33l (1.3 g, 4.43 mmol) is suspended in DCM (12 mL) and cooled to 0° C. N-bromosucciminide (0.83 g, 4.65 mmol) is added and the mixture stirred at 0° C. for 60 minutes. Saturated aqueous sodium thiosulfate solution is added, the mixture stirred for 30 minutes and the phases separated. The organic layer is evaporated under reduced pressure to give a residue that is purified by flash chromatography (eluent 0-50% ethyl acetate in cyclohexane) to furnish the title compound (600 mg, 36%).

UPLC-MS (Method 2): $R_t$=1.22 min

MS (ESI+): m/z=372/374 (M+H)$^+$

Example 34n

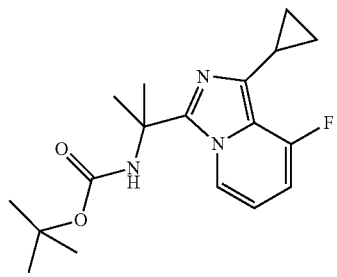 [SMILES: CC(C)(C)OC(=O)NC(C)(C)c1nc(C2CC2)c2c(F)cccn12]

Example 33m (600 mg, 1.61 mmol), potassium cyclopropyltrifluoroborate (477 mg, 3.22 mmol), Potassium triphosphate (1.20 g mg, 5.64 mmol), tricyclohexylphosphine (90 mg, 0.32 mmol) and palladium (II) acetate (36 mg, 0.16 mmol) are suspended in a mixture of toluene (17 mL) and water (0.2 mL) in a microwave vial and degassed for 5 minutes with a flow of nitrogen gas. The mixture is heated under microwave irradiation for 2×5 hours at 120° C. then allowed to cool and diluted with ethyl acetate and water. The phases are separated, the organic phase filtered through decalite and the solvent removed under vacuum. The residue is purified by flash chromatography (0-20% ethyl acetate in cyclohexane) to give the title compound (170 mg, 30%).

UPLC-MS (Method 2): $R_t$=1.34 min

MS (ESI+): m/z=334 (M+H)$^+$

Example 34o

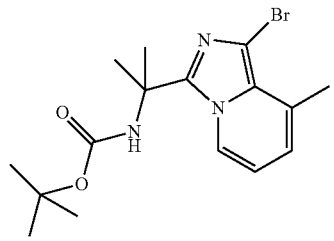 [SMILES: Cc1cccn2c(C(C)(C)NC(=O)OC(C)(C)C)nc(Br)c12]

Prepared in analogy to the method described for Example 34m using Example 34a (5.0 g, 17.3 mmol) as starting material.

HPLC-MS (Method 7a): $R_t$=4.73 min

MS (ESI+): m/z=368/370 (M+H)$^+$

Example 34p

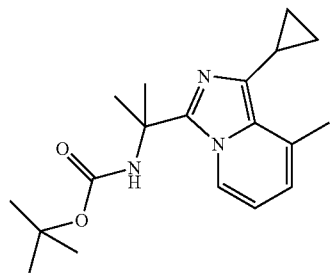 [SMILES: Cc1cccn2c(C(C)(C)NC(=O)OC(C)(C)C)nc(C3CC3)c12]

Prepared in analogy to the method described for Example 34n using Example 34o (250 mg, 0.68 mmol) as starting material.

UPLC-MS (Method 2): $R_t$=1.47 min

MS (ESI+): m/z=330 (M+H)$^+$

Example 35a

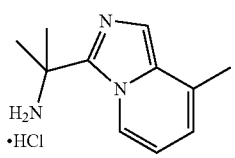

Example 34a (13.8 g, 47.7 mmol) is suspended in dry methanol (71 mL) and cooled to 0° C. 2M Hydrogen chloride in diethyl ether (236 mL, 472 mmol) is added and the mixture is stirred overnight. The solvent is evaporated and the residue is used without purification (10.7 g, 99%).

UPLC-MS (Method 2): $R_t$=0.81 min

MS (ESI+): m/z=174 (M-NH$_2$)$^+$

The following examples are synthesized in analogy to the preparation of example 34a:

| Example | Structure | Reactant(s) Conditions | UPLC-MS R$_t$ [min], method | MS (ESI+, m/z) (M + H)$^+$ |
|---|---|---|---|---|
| 35b | 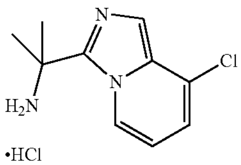 | Example 34b (448 mg, 1.45 mmol) 4M HCl in 1,4-dioxane, 1 hour | 0.671 | 210 |
| 35c | 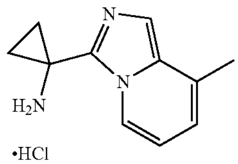 | Example 34c (570 mg, 1.98 mmol) 2M HCl in diethyl ether (9.75 mL), methanol (3 mL) Overnight reaction | 0.491 | 188 |
| 35d | 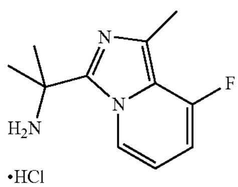 | Example 34d (110 mg, 0.30 mmol) 2M HCl in diethyl ether (10 mL), 1 hour | 0.932 | 192 (M − NH2)$^+$ |
| 35e | 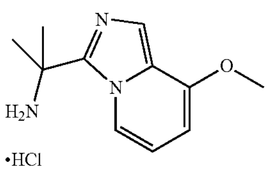 | Example 34e (150 mg, 0.49 mmol) 4M HCl in 1,4-dioxane, 1 hour | 0.621 | 189 (M − NH2)$^+$ |
| 35f | 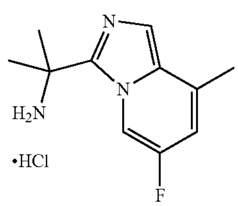 | Example 34f (24 mg, 0.08 mmol) 2M HCl in diethyl ether (2 mL), 4 hour reaction | 0.942 | 191 (M − NH2)$^+$ |
| 35g | 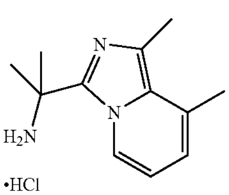 | Example 34g (300 mg, 0.99 mmol) 2M HCl in diethyl ether (5 mL), methanol (2 mL) Overnight reaction | 0.732 | 187 (M − NH2)$^+$ |
| 35h | 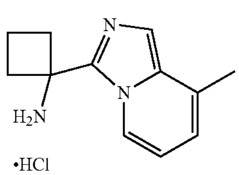 | Example 34h (588 mg, 1.95 mmol) 2M HCl in diethyl ether (9.75 mL), methanol (3 mL) Overnight reaction | 0.892 | 185 (M − NH2)$^+$ |
| 35i | 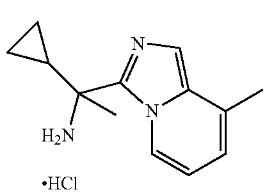 [SMILES: Cc1cccn2c(C(C)(N)C3CC3)ncc12 ; Cl] | Example 34i (1.0 g, 3.17 mmol) 4M HCl in 1,4-dioxane, 1 hour | 0.682 | 199 (M − NH2)$^+$ |

| Example | Structure | Reactant(s) Conditions | UPLC-MS $R_t$ [min], method | MS (ESI+, m/z) (M + H)+ |
|---|---|---|---|---|
| 35j | (structure) ·HCl | Example 34j (469 mg, 1.41 mmol) 2M HCl in diethyl ether (7 mL), methanol (2 mL) Overnight reaction | 1.042 | 216 (M − NH2)+ |
| 35k | (structure) ·HCl | Example 34k (233 mg, 0.73 mmol) 2M HCl in diethyl ether (3.6 mL), methanol (3 mL) Overnight reaction | 0.732 | 201 (M − NH2)+ |
| 35l | (structure) ·HCl | Example 34n (170 mg, 0.51 mmol) 2M HCl in diethyl ether (10 mL), 1 hour | 1.142 | 218 (M − NH2)+ |
| 35m | (structure) ·HCl | Example 34p (340 mg, 1.03 mmol) 2M HCl in diethyl ether (5 mL), methanol (5 mL) Overnight reaction | 1.072 | 230 |

Example 36a

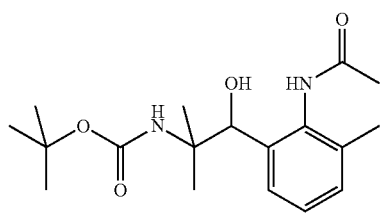 [SMILES: CC(=O)Nc1c(C)cccc1C(O)C(C)(C)NC(=O)OC(C)(C)C]

2-Bromo-6-methylacetanilide (3.70 g, 50% content, 8.11 mmol) is dissolved in dry THF (30 mL) and cooled to −78° C. under a nitrogen atmosphere. n-Butyllithium (2.5 M solution in hexane, 13.6 mL, 34 mmol) is added dropwise and the mixture stirred at −78° C. for 30 minutes. tert-Butyl 2-formylpropan-2-ylcarbamate (2.90 g, 15.5 mmol) in dry THF (20 mL) is added dropwise and the mixture stirred for 2 hours at −78° C. Saturated aqueous ammonium chloride solution is added, the mixture allowed to warm to room temperature and the phases separated. The organic phase is washed with brine, dried and the solvent removed. The residue is purified by flash chromatography (Eluent 0-100% EtOAc in cyclohexane) to give the title product (356 mg, 11%).

UPLC-MS (Method 1): $R_t$=0.96 min
MS (ESI+): m/z=337 (M+H)+

Example 37a

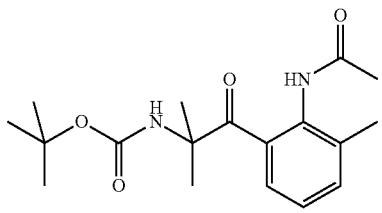 [SMILES: CC(=O)Nc1c(C)cccc1C(=O)C(C)(C)NC(=O)OC(C)(C)C]

Example 36a (356 mg, 85% content) is suspended in DCM and Dess Martin periodinane (420 mg, 0.99) is added. The mixture is stirred for 4 hours and then shaken with 10% aqueous sodium thiosulfate solution and the phases separated. The organic phase is washed with saturated aqueous sodium bicarbonate solution, dried and the solvent removed.

The residue is purified by flash chromatography (Eluent 0-50% EtOAc in cyclohexane) to give the title product (265 mg, 88%).

LC-MS (Method 1): R$_t$=1.05 min
MS (ESI+): m/z=335 (M+H)$^+$

Example 38a

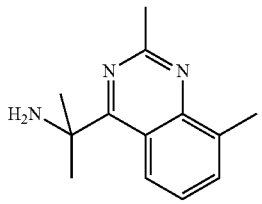 [SMILES: Cc1nc(C(C)(C)N)c2cccc(C)c2n1]

Example 37a (265 mg, 0.79 mmol) and ammonium chloride (383 mg, 7.13 mmol) are suspended in 7M ammonia in methanol (5 mL) and heated under microwave irradiation at 140° C. for 16 hours. The solvent is removed, the residue suspended in methanol and filtered to remove excess ammonium chloride then loaded onto a prewashed SCX cartridge, washed with water and methanol and eluted with 7M ammonia in methanol. The solvent is removed under vacuum to give the crude title product (140 mg).

LC-MS (Method 1): R$_t$=0.70 min
MS (ESI+): m/z=216 (M+H)$^+$

Example 39a

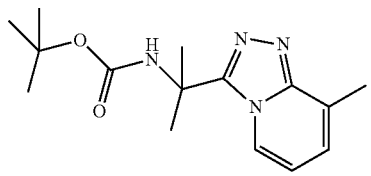 [SMILES: Cc1cccn2c(C(C)(C)NC(=O)OC(C)(C)C)nnc12]

Step 1:

Boc-AIB-OH (0.50 g, 2.44 mmol), 2-hydrazino-3-methylpyridine (1.0 g, 8.24 mmol), HATU (3.70 g, 9.73 mmol) and triethyl amine (2.48 mL, 17.8 mmol) are suspended in DCM and the mixture stirred overnight, The mixture is filtered, the solvent removed and the residue purified by flash chromatography (eluent 0-100% ethyl acetate in cyclohexane) to give impure hydrazide intermediate (800 mg) which is used directly in the following step.

Step 2:

The material from step 1 is suspended in dry DCM (20 ML) and polymer supported triphenylphosphine (3 mmol/g, 1.3 g. 3.9 mmol), trimethylsilylazide (520 μL, 3.9 mmol) and diethylazodicarboxylate (2.03 mL, 4.7 mmol) are added. The mixture is stirred overnight, filtered and the solvent removed. The residue is purified by flash chromatography (eluent 0-100% ethyl acetate in cyclohexane) to give the title product (Yield 180 mg).

UPLC-MS (Method 2): R$_t$=0.76 min
MS (ESI+): m/z=291 (M+H)$^+$

Example 40a

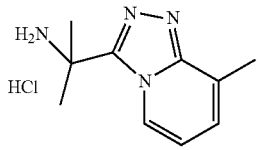

Example 39a (180 mg, 0.62 mmol) is suspended in 4M HCl in dioxane (4 ML) and stirred for 3 hours. The solvent is removed under vacuum to give the title product (150 mg, 90% content).

UPLC-MS (Method 2): R$_t$=0.49 min
MS (ESI+): m/z=191 (M+H)$^+$

Example 41a

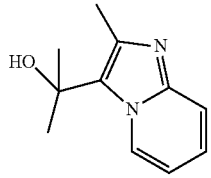

Ethyl 2-methylimidazo[1,2-a]pyridine-3-carboxylate (3.30 g, 16.1 mmol) is suspended in dry THF and cooled to −20° C. under nitrogen atmosphere. Methylmagnesium bromide (1.4 M in THF/toluene, 35 mL, 48.5 mmol) is added dropwise, the mixture allowed to warm to room temperature and stirred overnight. Saturated aqueous ammonium chloride solution is added and the mixture extracted with ethyl acetate. The organic extracts are dried and the solvent removed. The residue is purified by flash chromatography (eluent 0-100% EtOAc in cyclohexane) to give the title product (yield 1.20 g, 39%).

$^1$H NMR (500 MHz, DMSO-d$_6$): δ 1.64 (s, 6H), 2.44 (s, 3H), 5.40 (s, 1H), 6.82 (dd, 1H), 7.16 (dd, 1H), 7.43 (d, 1H), 8.84 (dd, 1H).

Example 42a

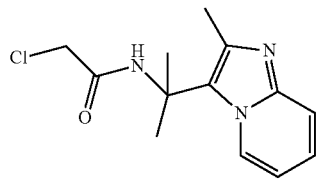 [SMILES: Cc1nc2ccccn2c1C(C)(C)NC(=O)CCl]

Example 41a (1.2 g, 6.31 mmol) is suspended in chloroacetonitrile (15 mL) and TFA (15 mL) and the mixture stirred overnight, The solvent is evaporated and the residue is purified by flash chromatography (eluent 0-10% MeOH in DCM) to give the title product (yield 0.5 g, 30%).

LC-MS (Method 1): R$_t$=0.60 min
MS (ESI+): m/z=266 (M+H)$^+$

Example 43a

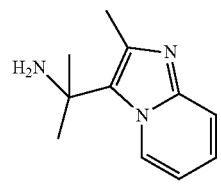

Example 42a (100 mg, 0.38 mmol) is suspended in 6M aqueous HCl (2 mL) and heated at 80° C. overnight, The mixture is loaded onto a prewashed SCX cartridge, washed with water and methanol and eluted with 7M $NH_3$ in methanol. The solvent is removed to give the title product (yield 70 mg, 98%).

$^1$H NMR (400 MHz, DMSO-$d_6$): δ 1.57 (s, 6H), 2.44 (s, 3H), 6.74 (dd, 1H), 7.08 (dd, 1H), 7.34 (d, 1H), 9.15 (dd, 1H). $NH_2$ not observed.

Example 44a

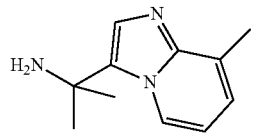

The title product is synthesised from ethyl 8-methylimidazo[1,2-a]pyridine-3-carboxylate (1.0 g, prepared in analogy to the procedure described in Bioorg. Med. Chem. Lett, 2012, 1870-1873), in analogy to the procedure described for the synthesis of Example 41a through to Example 43a (yield 37 mg).

UPLC-MS (Method 2): $R_t$=0.78 min

MS (ESI+): m/z=190 (M+H)$^+$

Example 45a

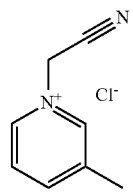

3-picoline (5.0 g, 53.7 mmol) is suspended in acetonitrile and chloroacetinitrile (6.76 mL, 107.4 mmol) is added. The mixture is stirred at room temperature for 4 hours and the precipitate is collected by filtration and dried under vacuum to give the title compound (7.0 g).

$^1$H NMR (500 MHz, DMSO-$d_6$): δ 2.53 (s, 3H), δ 6.04 (s, 2H), 8.16 (dd, J=6.0, 8.0 Hz, 1H), 8.58 (d, J=8.0, 1H), 9.09 (d, J=6.0 Hz, 1H), 9.17 (s, 1H).

Example 46a

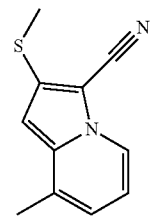

Example 45a (3.22 g, 19.1 mmol), 1-nitro-2,2-bis-metil-mercapto-etilene (3.16 g, 19.1 mmol) and triethylamine (3.30 mL, 38.2) are suspended in ethanol (40 mL) and refluxed overnight. The solvent is evaporated and the residue purified by flash chromatography (eluent 0-10% ethyl acetate in cyclohexane) to give the title compound (0.8 g)

UPLC-MS (Method 2): $R_t$=1.25 min

MS (ESI+): m/z=203 (M+H)$^+$

Example 47a

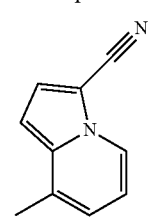

Example 46a (4.8 g, combined batches, 23.7 mmol) and excess raney nickel (approx. 20 g) are suspended in ethanol and stirred for 6 hours. The solvent is evaporated and the residue purified by flash chromatography (eluent 0-10% ethyl acetate in cyclohexane) to give the title compound (900 mg)

HPLC-MS (Method 7a): $R_t$=4.42 min

MS (APCI+): m/z=157 (M+H)$^+$

Example 48a

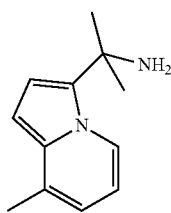

Cerium(III) chloride (7.89 g, 32 mmol) is heated under vacuum at 140° C. for 3 hours then cooled to room temperature under nitrogen atmosphere and dry THF (90 mL) are added. The mixture is stirred at room temperature overnight then cooled to −78° C. Methyl lithium LiCl complex (2 M in diethyl ether, 20 mL, 32 mmol) is added and the mixture stirred at −78° C. for 2 hours. Example 47a (500 mg, 3.2 mmol) in dry THF (5 mL) is added dropwise, the mixture stirred for 2 hours at −78° C. then saturated ammonium chloride solution is added followed by 32% aqueous ammonia. The mixture is warmed to room temperature, filtered through celite, washing with abundant DCM. The organic phase is washed with water, dried and the solvent removed to give a crude title compound (600 mg)

UPLC-MS (Method 2): $R_t$=1.12 min
MS (ESI+): m/z=172 (M-NH$_2$)$^+$

Example 49a

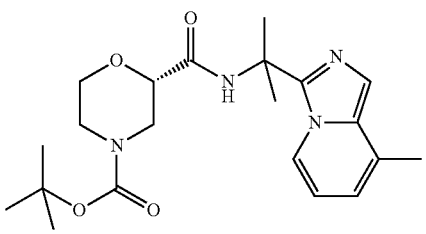 [SMILES: Cc1cccn2c(C(C)(C)NC(=O)[C@@H]3CN(C(=O)OC(C)(C)C)CCO3)ncc12]

Example 35a (156 mg, 0.69 mmol), (2S)-4-tert-butoxycarbonylmorpholine-2-carboxylic acid (160 mg, 0.69 mmol), TBTU (221 mg, 0.69 mmol) and triethylamine (480 uL, 3.45 mmol) are suspended in dichloromethane (10 mL) and stirred overnight at room temperature. The mixture is diluted with dichloromethane, washed with water and dilute aqueous sodium hydroxide solution, dried and the solvent evaporated. The residue was purified by flash chromatography (30% EtOAc in cyclohexane) to give the title compound (151 mg)

UPLC-MS (Method 2): $R_t$=1.10 min

MS (ESI+): m/z=403 (M+H)$^+$

The following examples are synthesized in analogy to the preparation of example 49a:

| Example | Structure | Reactant(s) Conditions | LC-MS $R_t$ [min], method | MS (ESI+, m/z) (M + H)$^+$ |
|---|---|---|---|---|
| 49b | 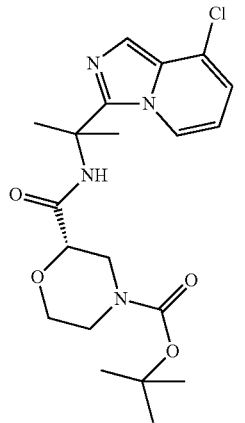 [SMILES: CC(C)(C)OC(=O)N1CCO[C@H](C(=O)NC(C)(C)c2ncc3c(Cl)cccn23)C1] | Example 35b (60 mg, 0.23 mmol) HATU as coupling agent Purified by flash chromatography (0-100% EtOAc in cyclohexane) | 0.911 | 423 |
| 49c | 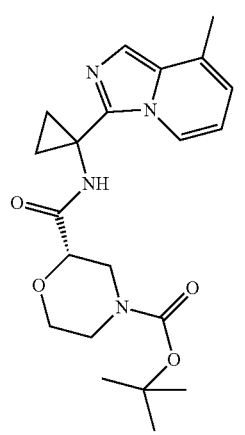 [SMILES: Cc1cccn2c(C3(NC(=O)[C@@H]4CN(C(=O)OC(C)(C)C)CCO4)CC3)ncc12] | Example 35c (48 mg, 0.22 mmol) HATU as coupling agent Purified by flash chromatography (0-100% EtOAc in cyclohexane) | 0.831 | 401 |

| Example | Structure | Reactant(s) Conditions | LC-MS $R_t$ [min], method | MS (ESI+, m/z) $(M + H)^+$ |
|---|---|---|---|---|
| 49d | 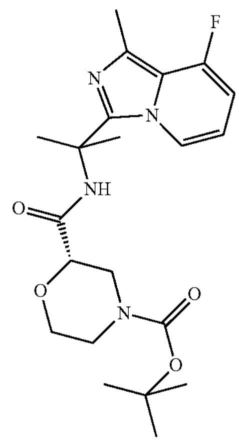 [SMILES: Cc1nc(C(C)(C)NC(=O)[C@@H]2CN(C(=O)OC(C)(C)C)CCO2)n2cccc(F)c12] | Example 35d (30 mg, 0.12 mmol) HATU as coupling agent Purified by flash chromatography (50% EtOAc in cyclohexane) | 1.111 | 421 |
| 49e | 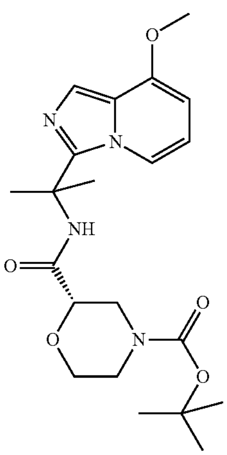 [SMILES: COc1cccn2c(C(C)(C)NC(=O)[C@@H]3CN(C(=O)OC(C)(C)C)CCO3)ncc12] | Example 35e (70 mg, 0.29 mmol) HATU as coupling agent Purified by flash chromatography (0-50% EtOAc in cyclohexane) | 2.4711 | 419 |
| 49f | 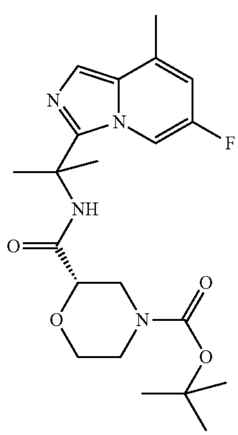 [SMILES: Cc1cc(F)cn2c(C(C)(C)NC(=O)[C@@H]3CN(C(=O)OC(C)(C)C)CCO3)ncc12] | Example 35f (70 mg, 0.29 mmol) HATU as coupling agent Purified by flash chromatography (0-50% EtOAc in cyclohexane) | 1.072 | 421 |

-continued

| Example | Structure | Reactant(s) Conditions | LC-MS R_t [min], method | MS (ESI+, m/z) (M + H)+ |
|---|---|---|---|---|
| 49g | 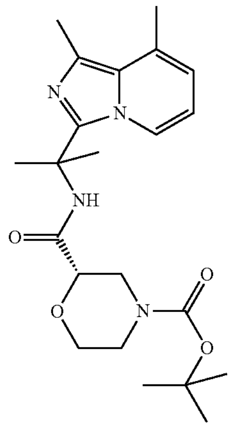 [SMILES: Cc1cccn2c(C(C)(C)NC(=O)[C@@H]3CN(C(=O)OC(C)(C)C)CCO3)nc(C)c12] | Example 35g (79 mg, 0.33 mmol) Purified by flash chromatography (50% EtOAc in cyclohexane) | 1.152 | 417 |
| 49h | 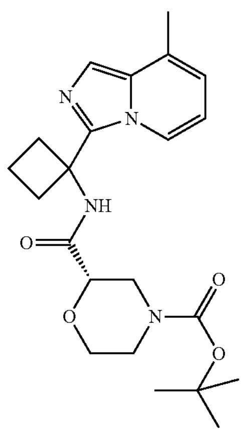 [SMILES: Cc1cccn2c(C3(NC(=O)[C@@H]4CN(C(=O)OC(C)(C)C)CCO4)CCC3)ncc12] | Example 35h (150 mg, 0.63 mmol) Purified by flash chromatography (50% EtOAc in cyclohexane) | 1.122 | 415 |
| 49i | 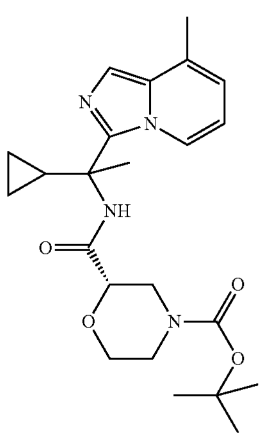 [SMILES: Cc1cccn2c(C(C)(NC(=O)[C@@H]3CN(C(=O)OC(C)(C)C)CCO3)C3CC3)ncc12] | Example 35i (100 mg, 0.40 mmol) HATU as coupling agent Purified by flash chromatography (0-100% EtOAc in cyclohexane) | 1.132 | 429 |

-continued

| Example | Structure | Reactant(s) Conditions | LC-MS R_t [min], method | MS (ESI+, m/z) (M + H)+ |
|---|---|---|---|---|
| 49j | 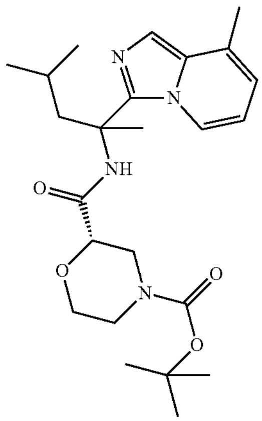 [SMILES: Cc1cccn2c(C(C)(CC(C)C)NC(=O)[C@@H]3CN(C(=O)OC(C)(C)C)CCO3)ncc12] | Example 35j (100 mg, 0.37 mmol) HATU as coupling agent Purified by Preparative TLC (50% EtOAc in cyclohexane) | 1.322 | 445 |
| 49k | 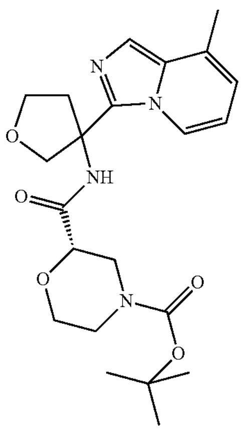 [SMILES: Cc1cccn2c(C3(NC(=O)[C@@H]4CN(C(=O)OC(C)(C)C)CCO4)CCOC3)ncc12] | Example 35k (60 mg, 0.24 mmol) HATU as coupling agent Purified by flash chromatography (80% EtOAc in cyclohexane) | 0.982 | 431 |
| 49l | 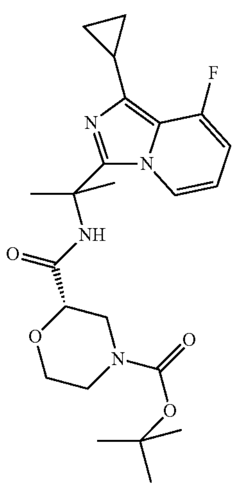 [SMILES: CC(C)(C)OC(=O)N1CCO[C@H](C(=O)NC(C)(C)c2nc(C3CC3)c3c(F)cccn23)C1] | Example 35l (30 mg, 0.11 mmol) HATU as coupling agent Purified by flash chromatography (0-30% EtOAc in cyclohexane) | 1.332 | 447 |

-continued

| Example | Structure | Reactant(s) Conditions | LC-MS R$_t$ [min], method | MS (ESI+, m/z) (M + H)$^+$ |
|---|---|---|---|---|
| 49m | 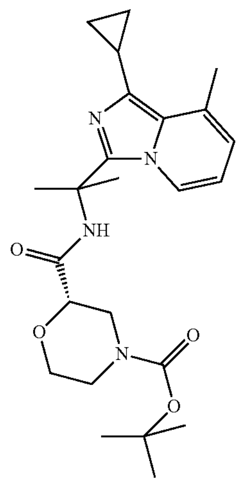 [SMILES: Cc1cccn2c(C(C)(C)NC(=O)[C@@H]3CN(C(=O)OC(C)(C)C)CCO3)nc(C3CC3)c12] | Example 35m (100 mg, 0.38 mmol) HATU as coupling agent Purified by flash chromatography (0-50% EtOAc in cyclohexane) | 1.322 | 443 |
| 49n | 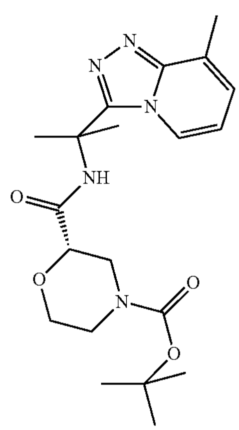 [SMILES: Cc1cccn2c(C(C)(C)NC(=O)[C@@H]3CN(C(=O)OC(C)(C)C)CCO3)nnc12] | Example 40a (30 mg, 0.13 mmol) HATU as coupling agent Purified by flash chromatography (5% MeOH in DCM) | 0.801 | 404 |
| 49o | 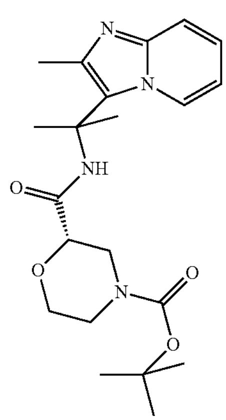 [SMILES: Cc1nc2ccccn2c1C(C)(C)NC(=O)[C@@H]1CN(C(=O)OC(C)(C)C)CCO1] | Example 43a (55 mg, 0.13 mmol) HATU as coupling agent Purified by flash chromatography (0-100% EtOAc in cyclohexane) | 0.771 | 403 |

-continued

| Example | Structure | Reactant(s) Conditions | LC-MS R_t [min], method | MS (ESI+, m/z) (M + H)+ |
|---|---|---|---|---|
| 49p | 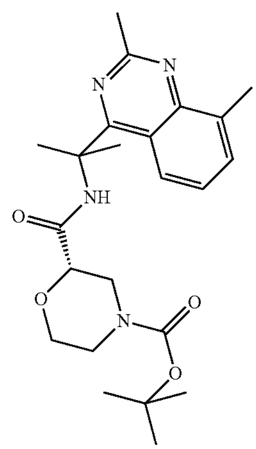 [SMILES: Cc1nc(C(C)(C)NC(=O)[C@@H]2CN(C(=O)OC(C)(C)C)CCO2)c2cccc(C)c2n1] | Example 38a (22 mg, 0.13 mmol) HATU as coupling agent Purified by flash chromatography (0-100% EtOAc in cyclohexane) | 1.322 | 429 |
| 49q | 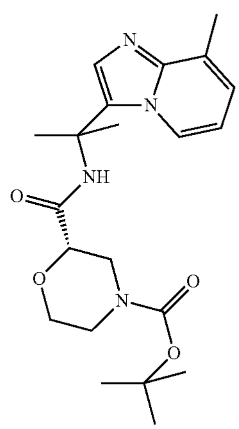 [SMILES: Cc1cccn2c(C(C)(C)NC(=O)[C@@H]3CN(C(=O)OC(C)(C)C)CCO3)cnc12] | Example 44a (50 mg, 0.22 mmol) HATU as coupling agent Purified by flash chromatography (0-100% EtOAc in cyclohexane) | 1.022 | 403 |
| 49r | 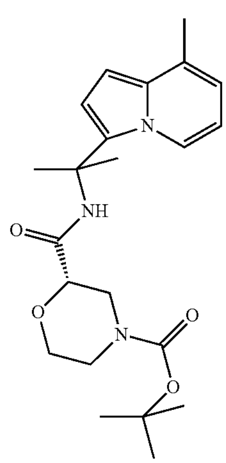 [SMILES: Cc1cccn2c(C(C)(C)NC(=O)[C@@H]3CN(C(=O)OC(C)(C)C)CCO3)ccc12] | Example 48a (70 mg, 0.37 mmol) HATU as coupling agent Purified by flash chromatography (0-50% EtOAc in cyclohexane) | 1.352 | 402 |

The stereoisomers of the example 49i are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 90:10; flow rate: 15 mL/min, temperature: 25° C.; UV Detection: 230 nm Example 49s: stereoisomer 1, unknown absolute stereochemistry at quaternary carbon

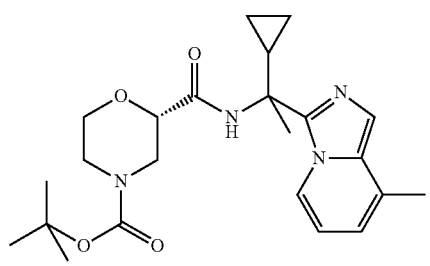

Example 49t: stereoisomer 2 unknown absolute stereochemistry at quaternary carbon

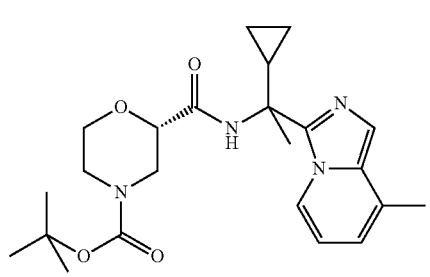

| Example | Chiral HPLC (Method 18) R$_t$ [min] | HPLC-MS (Method 11): R$_t$ [min] | MS (ESI+): m/z |
|---|---|---|---|
| 49s | 23.51 | 2.84 | 429 |
| 49t | 23.51 | 2.84 | 429 |

The stereoisomers of the example 49j are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/IPA 75:25; flow rate: 15 mL/min, temperature: 25° C.; UV Detection: 230 nm Example 49u: stereoisomer 1, unknown absolute stereochemistry at quaternary carbon

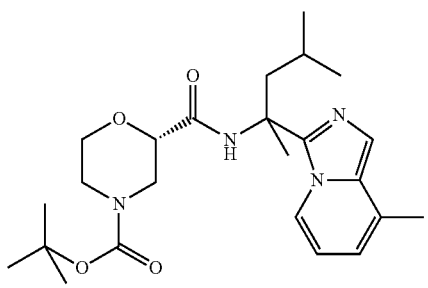

Example 49v: stereoisomer 2 unknown absolute stereochemistry at quaternary carbon

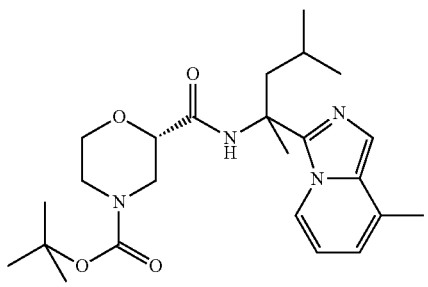

| Example | Chiral HPLC (Method 16) R$_t$ [min] | UPLC-MS (Method 2): R$_t$ [min] | MS (ESI+): m/z |
|---|---|---|---|
| 49u | 5.68 | 1.32 | 445 |
| 49v | 8.24 | 1.31 | 445 |

The stereoisomers of the example 49k are separated by HPLC using a chiral stationary phase.

Method for Separation:

HPLC apparatus type: Waters 600 Pump, 2767 Autosampler, UV Detector 2489; column: Daicel Chiralpak OJ-H, 5.0 µm, 250 mm×20 mm; method: eluent hexane/ethanol 85:15; flow rate: 15 mL/min, temperature: 25° C.; UV Detection: 230 nm Example 49w: stereoisomer 1, unknown abolute stereochemistry at quaternary carbon

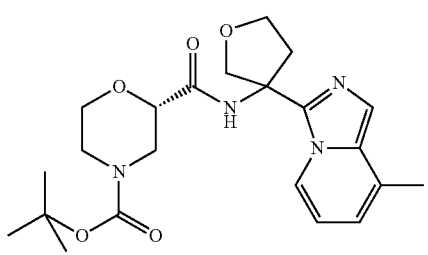

Example 49x: stereoisomer 2 unknown absolute stereochemistry at quaternary carbon

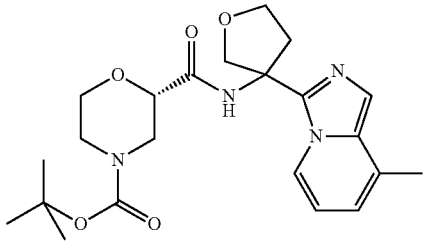

| Example | Chiral HPLC (Method 20) R$_t$ [min] | UPLC-MS (Method 2): R$_t$ [min] | MS (ESI+): m/z |
|---------|---------|---------|---------|
| 49w | 9.47 | 1.00 | 431 |
| 49x | 12.60 | 0.97 | 431 |

Example 50a

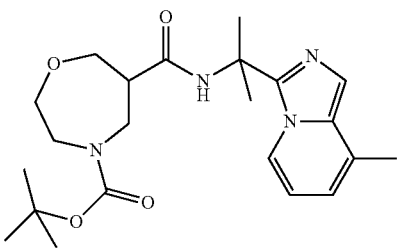 [SMILES: Cc1cccn2c(C(C)(C)NC(=O)C3COCCN(C(=O)OC(C)(C)C)C3)ncc12]

Example 35a (92 mg, 0.41 mmol), (4-(tert-butoxycarbonyl)-1,4-oxazepane-6-carboxylic acid (100 mg, 0.41 mmol), HATU (155 mg, 0.41 mmol) and triethylamine (280 uL, 2.04 mmol) are suspended in dichloromethane (10 mL) and stirred overnight at room temperature. The mixture is diluted with dichloromethane, washed with water and dilute aqueous sodium hydroxide solution, dried and the solvent evaporated. The residue was purified by flash chromatography (0-5% MeOH in DCM) to give the title compound (90 mg)

UPLC-MS (Method 10): R$_t$=2.39 min
MS (ESI+): m/z=417 (M+H)$^+$

The following examples are synthesized in analogy to the preparation of example 50a:

| Example | Structure | Reactant(s) Conditions | HPLC-M or UPLC-MS R$_t$ [min], method | MS (ESI+ or APCI+, m/z) (M + H)$^+$ |
|---------|-----------|---------|---------|---------|
| 50b | 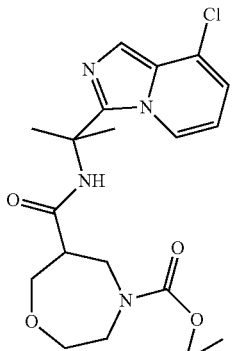 | Example 35b (100 mg, 0.41 mmol) Purified by flash chromatography (0-100% EtOAc in cyclohexane) | 4.207a | 437 |
| 50c | 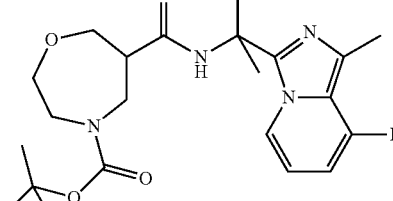 | Example 35d (70 mg, 0.29 mmol) Purified by Preparative RP-HPLC | 1.072 | 435 |
| 50d | 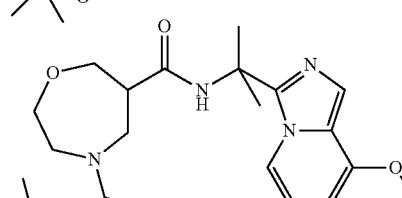 | Example 35e (100 mg, 0.41 mmol) Purified by flash chromatography (0-50% EtOAc in cyclohexane) | 2.3911 | 433 |

-continued

| Example | Structure | Reactant(s) Conditions | HPLC-M or UPLC-MS $R_t$ [min], method | MS (ESI+ or APCI+, m/z) $(M + H)^+$ |
|---|---|---|---|---|
| 50e | 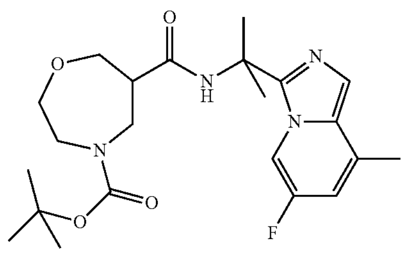 [SMILES: Cc1cc(F)cn2c(C(C)(C)NC(=O)C3COCCN(C(=O)OC(C)(C)C)C3)ncc12] | Example 35f (110 mg, 0.45 mmol) Purified by flash chromatography (0-50% EtOAc in cyclohexane) | 1.534a | 435 |
| 50f | 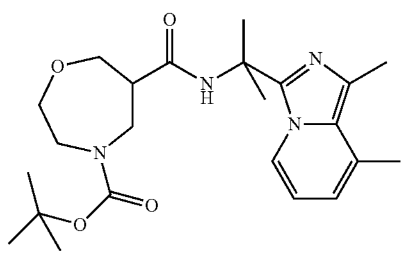 [SMILES: Cc1cccn2c(C(C)(C)NC(=O)C3COCCN(C(=O)OC(C)(C)C)C3)nc(C)c12] | Example 35g (100 mg, 0.42 mmol) Purified by flash chromatography (30-100% EtOAc in cyclohexane) | 1.072 | 431 |
| 50g | 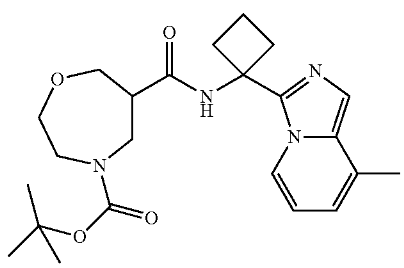 [SMILES: Cc1cccn2c(C3(NC(=O)C4COCCN(C(=O)OC(C)(C)C)C4)CCC3)ncc12] | Example 35h (96 mg, 0.40 mmol) Purified by flash chromatography (EtOAc) | 1.052 | 429 |
| 50h | 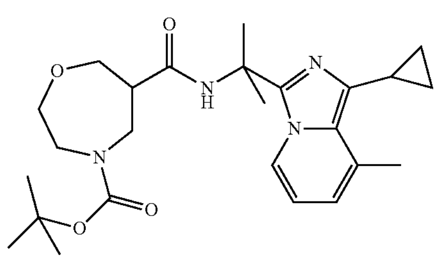 [SMILES: Cc1cccn2c(C(C)(C)NC(=O)C3COCCN(C(=O)OC(C)(C)C)C3)nc(C3CC3)c12] | Example 35n (76 mg, 0.29 mmol) Purified by flash chromatography (0-50% EtOAc in cyclohexane) | 4.867a | 457 |
| 50i | 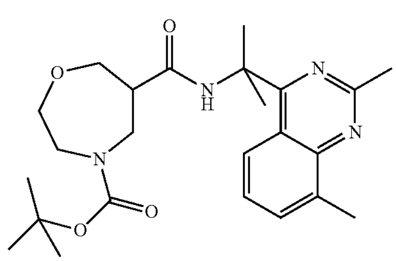 [SMILES: Cc1nc(C(C)(C)NC(=O)C2COCCN(C(=O)OC(C)(C)C)C2)c2cccc(C)c2n1] | Example 38a (119 mg, 0.55 mmol) Purified by preparative RP-HPLC | 1.934a | 443 |

-continued

| Example | Structure | Reactant(s) Conditions | HPLC-M or UPLC-MS R_t [min], method | MS (ESI+ or APCI+, m/z) (M + H)+ |
|---------|-----------|------------------------|-------------------------------------|----------------------------------|
| 50j | 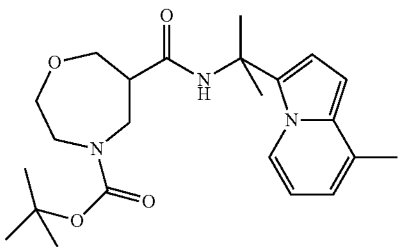 [SMILES: Cc1cccn2c(C(C)(C)NC(=O)C3COCCN(C(=O)OC(C)(C)C)C3)ccc12] | Example 48a (100 mg, 0.53 mmol) Purified by flash chromatography (0-50% EtOAc in cyclohexane) | 1.292 | 416 |

The stereoisomers of the example 50a are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 95:5; flow rate: 15 mL/min, temperature: 25° C.; UV Detection: 230 nm Example 50k: stereoisomer 1, unknown absolute stereochemistry Example 50l: stereoisomer 2 unknown absolute stereochemistry

| Example | Chiral HPLC (Method 21) R_t [min] |
|---------|-----------------------------------|
| 50k | 14.34 |
| 50l | 15.49 |

The stereoisomers of the example 50b are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 92:8; flow rate: 15 mL/min, temperature: 25° C.; UV Detection: 230 nm Example 50m: stereoisomer 1, unknown absolute stereochemistry Example 50n: stereoisomer 2 unknown absolute stereochemistry

| Example | Chiral HPLC (Method 18) R_t [min] |
|---------|-----------------------------------|
| 50m | 14.75 |
| 50n | 15.68 |

The stereoisomers of the example 50c are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 95:5; flow rate: 15 mL/min, temperature: 25° C.; UV Detection: 230 nm Example 50o: stereoisomer 1, unknown absolute stereochemistry

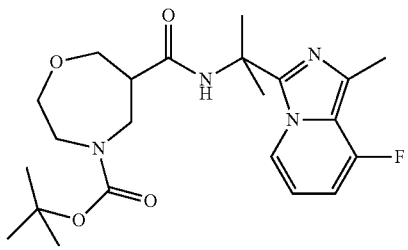

Example 50p: stereoisomer 2 unknown absolute stereochemistry

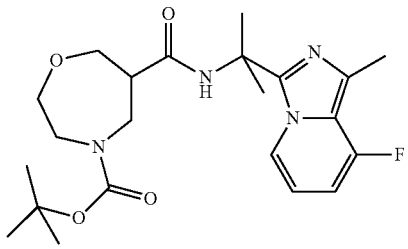

| Example | Chiral HPLC (Method 17) $R_t$ [min] |
|---|---|
| 50o | 4.80 |
| 50p | 5.31 |

The stereoisomers of the example 50d are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/ethanol 80:20; flow rate: 15 mL/min, temperature: 25° C.; UV Detection: 230 nm Example 50q: stereoisomer 1, unknown absolute stereochemistry

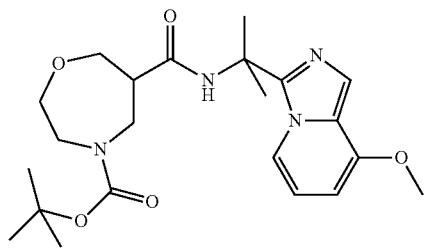

Example 50r: stereoisomer 2 unknown absolute stereochemistry

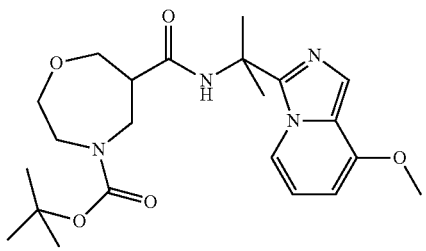

| Example | Chiral HPLC (Method 17) $R_t$ [min] |
|---|---|
| 50q | 16.53 |
| 50r | 19.24 |

The stereoisomers of the example 50f are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/ethanol 92:8; flow rate: 15 mL/min, temperature: 25° C.; UV Detection: 230 nm Example 50s: stereoisomer 1, unknown absolute stereochemistry

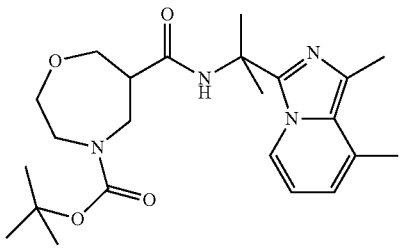

Example 50t: stereoisomer 2 unknown absolute stereochemistry

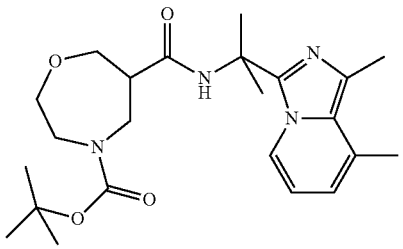

| Example | Chiral HPLC (Method 18) $R_t$ [min] |
|---|---|
| 50s | 5.49 |
| 50t | 6.34 |

The stereoisomers of the example 50g are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/ethanol 80:20; flow rate: 15 mL/min, temperature: 25° C.; UV Detection: 230 nm Example 50u: stereoisomer 1, unknown absolute stereochemistry

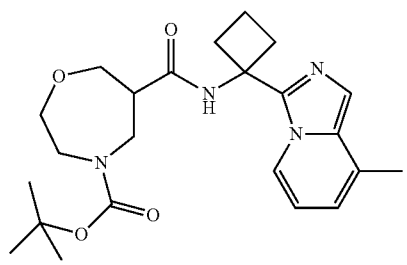

Example 50v: stereoisomer 2 unknown absolute stereochemistry

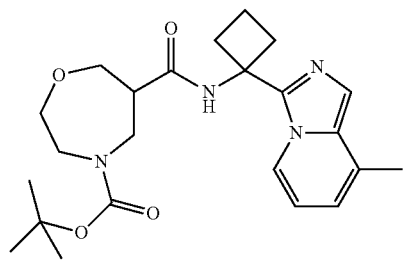

| Example | Chiral HPLC (Method 16) R$_t$ [min] |
|---|---|
| 50u | 4.52 |
| 50v | 5.55 |

The stereoisomers of the example 50g are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/ethanol 80:20; flow rate: 15 mL/min, temperature: 25° C.; UV Detection: 230 nm Example 50u: stereoisomer 1, unknown absolute stereochemistry

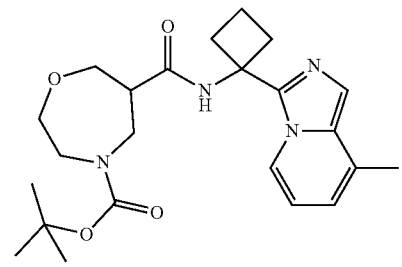

Example 50v: stereoisomer 2 unknown absolute stereochemistry

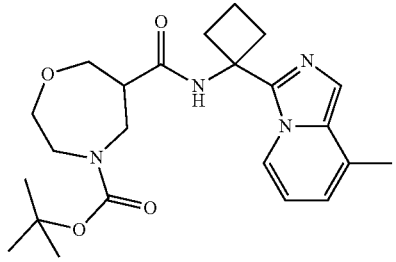

| Example | Chiral HPLC (Method 16) R$_t$ [min] |
|---|---|
| 50u | 4.52 |
| 50v | 5.55 |

The stereoisomers of the example 50i are separated by HPLC using a chiral stationary phase.

Method for Separation:

HPLC apparatus type: Waters 600 Pump, 2767 Autosampler, UV Detector 2489; column: Daicel Chiralpak AD-H, 5.0 µm, 250 mm×20 mm; method: eluent hexane/ethanol 96:4; flow rate: 15 mL/min, temperature: 25° C.; UV Detection: 230 nm Example 50w: stereoisomer 1, unknown absolute stereochemistry

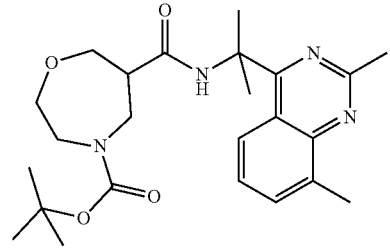

Example 50x: stereoisomer 2 unknown absolute stereochemistry

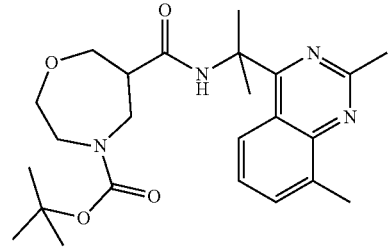

| Example | Chiral HPLC (Method 15) R$_t$ [min] |
|---|---|
| 50w | 6.72 |
| 50x | 7.30 |

The stereoisomers of the example 50j are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 90:10; flow rate: 15 mL/min, temperature: 25° C.; UV Detection: 230 nm Example 50y: stereoisomer 1, unknown absolute stereochemistry

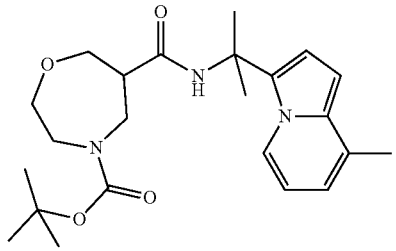

Example 50z: stereoisomer 2 unknown absolute stereochemistry

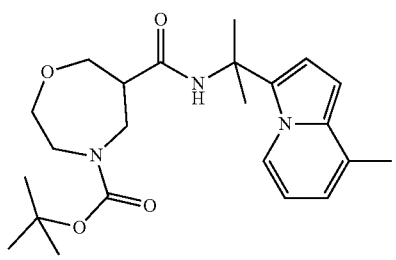

| Example | Chiral HPLC (Method 17) $R_t$ [min] |
|---|---|
| 50y | 4.23 |
| 50z | 4.76 |

The stereoisomers of the example 50h are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 95:5; flow rate: 15 mL/min, temperature: 25° C.; UV Detection: 230 nm Example 50aa: stereoisomer 1, unknown absolute stereochemistry

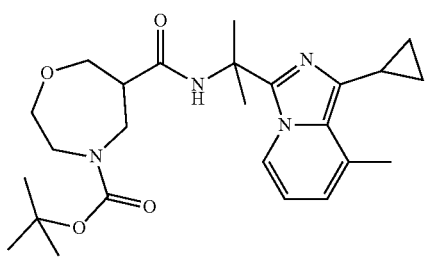

Example 50ab: stereoisomer 2 unknown absolute stereochemistry

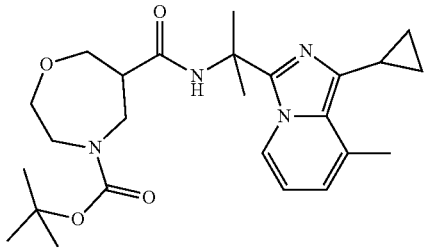

| Example | Chiral HPLC (Method 15) $R_t$ [min] |
|---|---|
| 50aa | 7.18 |
| 50ab | 8.81 |

Example 51a

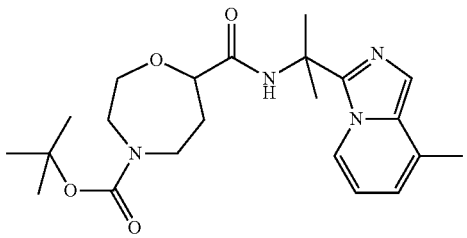 [SMILES: Cc1cccn2c(C(C)(C)NC(=O)C3CCN(C(=O)OC(C)(C)C)CCO3)ncc12]

Example 35a (120 mg, 0.53 mmol), Example 7a (130 mg, 0.53 mmol), HATU (303 mg, 0.80 mmol) and triethylamine (370 uL, 2.66 mmol) are suspended in dichloromethane (10 mL) and stirred overnight at room temperature. The mixture is diluted with dichloromethane, washed with water and dilute aqueous sodium hydroxide solution, dried and the solvent evaporated. The residue was purified by flash chromatography (0-100% EtOAc in cyclohexane) to give the title compound (115 mg)

UPLC-MS (Method 2): $R_t$=1.05 min

MS (ESI+): m/z=417 (M+H)$^+$

The stereoisomers of the example 51a are separated by HPLC using a chiral stationary phase.

Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 88:12; flow rate: 15 mL/min, temperature: 25° C.; UV Detection: 230 nm Example 51b: stereoisomer 1,
unknown absolute stereochemistry Example 51c: stereoisomer 2
unknown absolute stereochemistry

| Example | Chiral HPLC (Method 18) R$_t$ [min] |
|---|---|
| 51b | 14.40 |
| 51c | 15.93 |

Example 52b: stereoisomer 1,
unknown absolute stereochemistry

Example 52c: stereoisomer 2
unknown absolute stereochemistry

| Example | Chiral HPLC (Method 22) R$_t$ [min] |
|---|---|
| 52b | 5.74 |
| 52c | 6.56 |

Example 52a

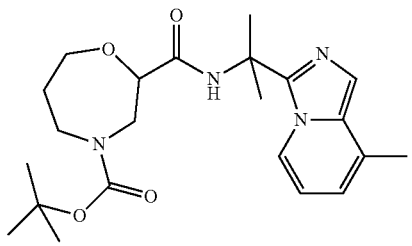 [SMILES: Cc1cccn2c(C(C)(C)NC(=O)C3CN(C(=O)OC(C)(C)C)CCCO3)ncc12]

Example 52d

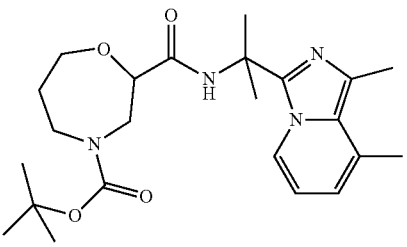 [SMILES: Cc1cccn2c(C(C)(C)NC(=O)C3CN(C(=O)OC(C)(C)C)CCCO3)nc(C)c12]

Example 35a (138 mg, 0.61 mmol), 4-Boc-2-homomorpholinecarboxylic acid (150 mg, 0.61 mmol), HATU (232 mg, 0.61 mmol) and triethylamine (425 uL, 3.05 mmol) are suspended in dichloromethane (10 mL) and stirred overnight at room temperature. The mixture is diluted with dichloromethane, washed with water and dilute aqueous sodium hydroxide solution, dried and the solvent evaporated. The residue was purified by flash chromatography (70% EtOAc in cyclohexane) to give the title compound (250 mg)

UPLC-MS (Method 2): R$_t$=1.08 min

MS (ESI+): m/z=417 (M+H)$^+$

The stereoisomers of the example 52a are separated by HPLC using a chiral stationary phase.
Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 85:15; flow rate: 15 mL/min, temperature: 25° C.; UV Detection: 230 nm Example 35g (70 mg, 0.29 mmol), 4-Boc-2-homomorpholinecarboxylic acid (71 mg, 0.29 mmol), HATU (110 mg, 0.29 mmol) and triethylamine (208 uL, 1.50 mmol) are suspended in dichloromethane (7 mL) and stirred overnight at room temperature. The mixture is diluted with dichloromethane, washed with water and dilute aqueous sodium hydroxide solution, dried and the solvent evaporated. The residue was purified by flash chromatography (70% EtOAc in cyclohexane) to give the title compound (106 mg)

UPLC-MS (Method 2): R$_t$=1.14 min

MS (ESI+): m/z=431 (M+H)$^+$

The stereoisomers of the example 52d are separated by HPLC using a chiral stationary phase.
Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/ethanol 90:10; flow rate: 15 mL/min, temperature: 25° C.; UV Detection: 230 nm Example 52e: stereoisomer 1,
unknown absolute stereochemistry

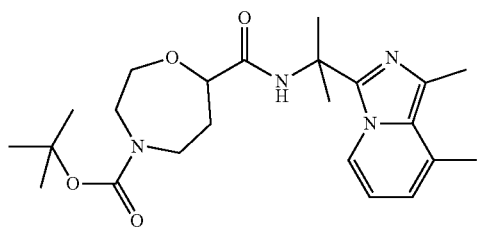

Example 52f: stereoisomer 2
unknown absolute stereochemistry

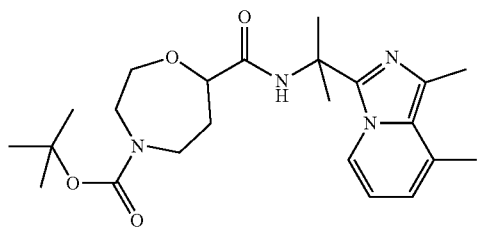

| Example | Chiral HPLC (Method 17) R$_t$ [min] |
|---|---|
| 52e | 5.33 |
| 52f | 6.05 |

EXEMPLARY EMBODIMENTS

Example 1

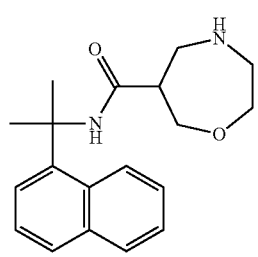

4-tert-butoxycarbonyl-1,4-oxazepane-6-carboxylic acid (2.7 mg, 0.011 mmol) is added to a solution of HATU (8 mg, 0.022 mmol) and DIPEA (6 µl, 0.035 mmol) in DMF (0.200 mL); then 2-(naphthalen-1-yl)propan-2-amine (2 mg, 0.010 mmol) in DMF (0.200 mL) is added and stirring is continued for 18 h at rt. The reaction is filtered on a basic aluminum oxide pad, washed with DMF/MeOH 9:1 (600 µl) and then dried. The residue is diluted with dioxane 0.500 ml and 0.200 mL of 4N HCl solution in dioxane and stirring is continued overnight. Solvent is evaporated to give the title compound (3.5 mg, 100%).

UPLC-MS (Method 4a): R$_t$=1.26
MS (ESI+): m/z=313 (M+H)$^+$

The following examples are synthesized in analogy to the preparation of example 1:

| Example | Structure | Reactants | UPLC-MS R$_t$ [min], method | MS (ESI+, m/z) (M + H)$^+$ |
|---|---|---|---|---|
| 2 | 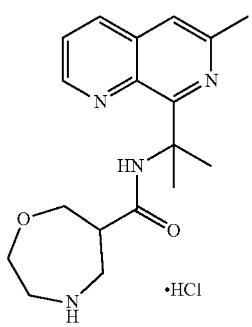 [SMILES: Cc1cc2cccnc2c(C(C)(C)NC(=O)C2CNCCOC2)n1 ; Cl] | 4-tert-butoxycarbonyl-1,4-oxazepane-6-carboxylic acid (2.7 mg, 0.011 mmol); Example 6g (2 mg, 0.010 mmol) | 1.20 4a | 329 |
| 3 | 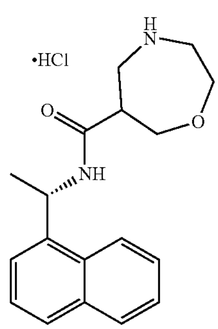 [SMILES: C[C@H](NC(=O)C1CNCCOC1)c1cccc2ccccc12 ; Cl] | 4-tert-butoxycarbonyl-1,4-oxazepane-6-carboxylic acid (2.7 mg, 0.011 mmol); (S)-(−)-1-(1-Naphthyl)ethylamine (1.7 mg, 0.010 mmol) | 1.23 4a | 299 |

| Example | Structure | Reactants | UPLC-MS R$_t$ [min], method | MS (ESI+, m/z) (M + H)$^+$ |
|---|---|---|---|---|
| 4 | 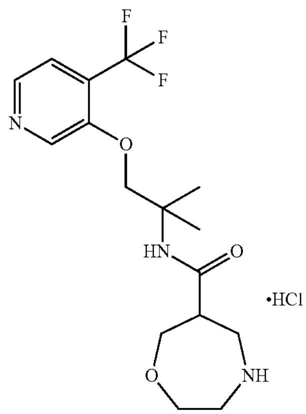 [SMILES: CC(C)(COc1cnccc1C(F)(F)F)NC(=O)C1CNCCOC1 ; Cl] | 4-tert-butoxycarbonyl-1,4-oxazepane-6-carboxylic acid (2.7 mg, 0.011 mmol); Example 2b (2.3 mg, 0.010 mmol) | 1.15 4a | 362 |
| 5 | 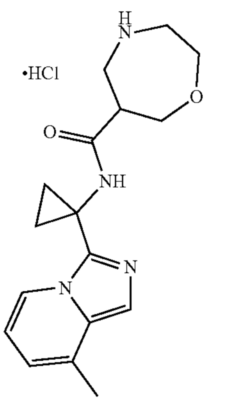 [SMILES: Cc1cccn2c(C3(NC(=O)C4CNCCOC4)CC3)ncc12 ; Cl] | 4-tert-butoxycarbonyl-1,4-oxazepane-6-carboxylic acid (2.7 mg, 0.011 mmol); Example 35c (2.2 mg, 0.010 mmol) | 0.95 4a | 315 |
| 6 | 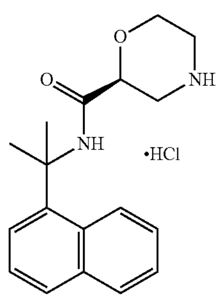 [SMILES: CC(C)(NC(=O)[C@@H]1CNCCO1)c1cccc2ccccc12 ; Cl] | (2S)-4-tert-butoxycarbonylmorpholine-2-carboxylic acid (2.5 mg, 0.011 mmol); 2-(naphthalen-1-yl)propan-2-amine (2 mg, 0.010 mmol) | 1.37 4a | 299 |
| 7 | 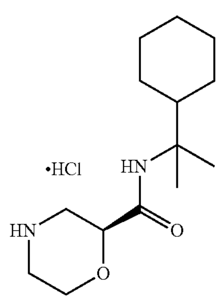 [SMILES: CC(C)(NC(=O)[C@@H]1CNCCO1)C1CCCCC1 ; Cl] | (2S)-4-tert-butoxycarbonyl-morpholine-2-carboxylic acid (2.5 mg, 0.011 mmol); 2-cyclohexylpropan-2-amine hydrochloride (1.8 mg, 0.010 mmol) | 1.54 4a | 255 |

-continued

| Example | Structure | Reactants | UPLC-MS $R_t$ [min], method | MS (ESI+, m/z) (M + H)+ |
|---|---|---|---|---|
| 8 | 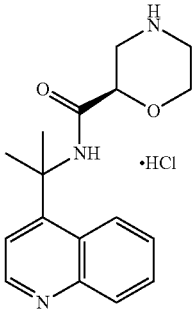 [SMILES: CC(C)(NC(=O)[C@H]1CNCCO1)c1ccnc2ccccc12 ; Cl] | (2R)-4-tert-butoxycarbonyl-morpholine-2-carboxylic acid (2.5 mg, 0.011 mmol); Example 6i (1.9 mg, 0.010 mmol) | 0.93 4a | 300 |
| 9 | 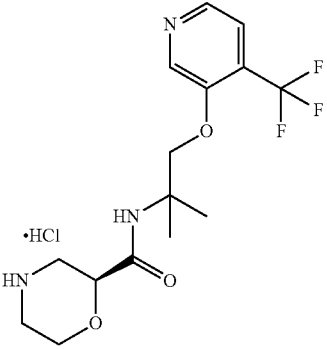 [SMILES: CC(C)(COc1cnccc1C(F)(F)F)NC(=O)[C@@H]1CNCCO1 ; Cl] | (2S)-4-tert-butoxycarbonyl-morpholine-2-carboxylic acid (2.5 mg, 0.011 mmol); Example 2b (2.3 mg, 0.010 mmol) | 1.23 4a | 348 |
| 10 | 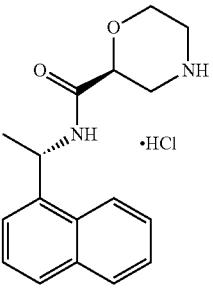 [SMILES: C[C@H](NC(=O)[C@@H]1CNCCO1)c1cccc2ccccc12 ; Cl] | (2S)-4-tert-butoxycarbonylmorpholine-2-carboxylic acid (2.5 mg, 0.011 mmol); (S)-(−)-1-(1-Naphthyl)ethylamine (1.7 mg, 0.010 mmol) | 1.31 4a | 285 |
| 11 | 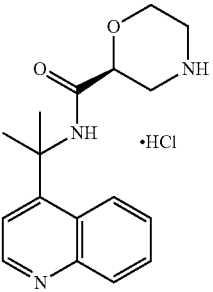 | (2S)-4-tert-butoxycarbonylmorpholine-2-carboxylic acid (2.5 mg, 0.011 mmol); Example 6i (1.9 mg, 0.010 mmol) | 0.93 4a | 300 |

| Example | Structure | Reactants | UPLC-MS $R_t$ [min], method | MS (ESI+, m/z) (M + H)+ |
|---|---|---|---|---|
| 12 | 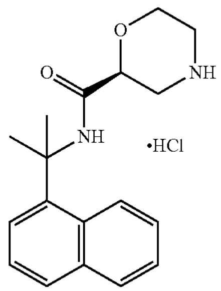 [SMILES: CC(C)(NC(=O)[C@@H]1CNCCO1)c1cccc2ccccc12 ; Cl] | (2R)-4-tert-butoxycarbonylmorpholine-2-carboxylic acid (2.5 mg, 0.011 mmol); 2-(naphthalen-1-yl)propan-2-amine (2 mg, 0.010 mmol) | 1.37 4a | 299 |

Example 13

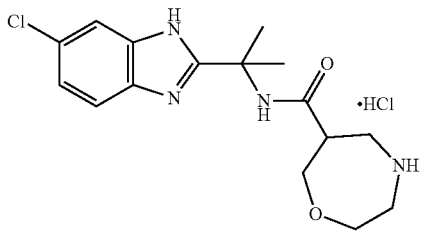 [SMILES: CC(C)(NC(=O)C1CNCCOC1)c1nc2ccc(Cl)cc2[nH]1 ; Cl]

TEA (6 mL, 44.985 mmol) followed by TBTU (5.3 g, 16.511 mmol) are added to 4-chloro-o-phenylenediamine (2.1 g, 15.001 mmol) and α-(Boc-amino)isobutyric acid (3.3 g, 16.247 mmol) in THF (50 mL). After stirring for 3 d at rt, volatiles are evaporated under reduced pressure, the residue taken up in EtOAc, washed with 5% citric acid, 2M NaOH, dried over $Na_2SO_4$, filtered and evaporate under reduce pressure to give a residue that is purified by flash chromatography (eluent 50% EtOAc/cyclohexane) to furnish a mixture of adducts (4.2 g, 85%). Such mixture is heated at 60° C. overnight in acetic acid (35 mL). Volatiles are evaporated under reduced pressure to give a residue that is taken up in EtOAc, washed with 2M NaOH, dried over $MgSO_4$, filtered and evaporate under reduce pressure to give a residue. Such residue is suspended in DCM (25 mL) and treated with TFA (10 mL). Stirring is continued for 2 h. Volatiles are evaporated under reduced pressure and the resulting residue taken up with methyl tert-butyl ether, washed with 0.5 M HCl and evaporated under reduced pressure. The resulting mixture is taken up and evaporated twice with EtOH to give a residue (3.4 g). 2.5 mg of such residue (0.010 mmol) and DIPEA (3 µl, 0.018 mmol) in DMF (0.200 mL) are added to HATU (8 mg, 0.022 mmol), 4-tert-butoxycarbonyl-1,4-oxazepane-6-carboxylic acid (2.7 mg, 0.011 mmol) and DIPEA (3 µl, 0.018 mmol) in DMF (0.200 mL). The reaction is filtered on a basic aluminum oxide pad, washed with DMF/MeOH 9:1 (600 µl) and then dried. The residue is diluted with dioxane 0.500 ml and 0.200 mL of 4N HCl solution in dioxane and stirring is continued overnight. Solvent is evaporated to give the title compound (3.7 mg, 100%).

UPLC-MS (Method 4a): $R_t$=0.98
MS (ESI+): m/z=337 (M+H)+

The following examples are synthesized in analogy to the preparation of example 13:

| Example | Structure | Reactant | UPLC-MS $R_t$ [min], method | MS (ESI+, m/z) (M + H)+ |
|---|---|---|---|---|
| 14 | 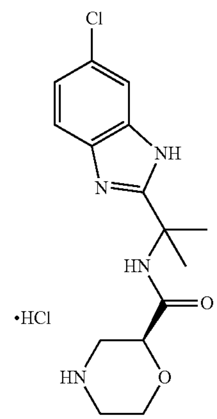 [SMILES: Cl ; CC(C)(NC(=O)[C@@H]1CNCCO1)c1nc2ccc(Cl)cc2[nH]1] | (2S)-4-tert-butoxycarbonyl-morpholine-2-carboxylic acid (2.5 mg, 0.011 mmol); | 1.01 4a | 323 |

Example 15

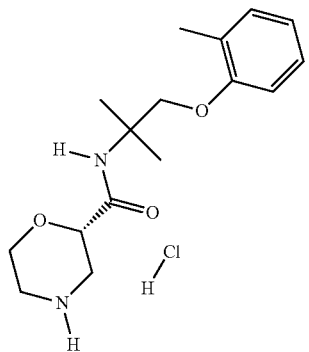

Example 3a (80 mg, 0,204 mmol) is dissolved in MeOH (1 mL) and then hydrogen chloride 2M in ethyl ether (1 mL, 2 mmol) is added dropwise. Stirring is continued for 6 h at rt. Solvents are removed to furnish the title compound (56 mg, 84%).

HPLC-MS (Method 7): $R_t$=6.03 min
MS (APCI+): m/z=293 (M+H)$^+$

Example 16 (Racemic Mixture)

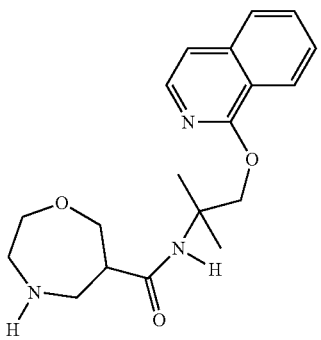 [SMILES: CC(C)(COc1nccc2ccccc12)NC(=O)C1CNCCOC1]

Hydrogen chloride 4M in dioxane (2 mL, 8.0 mmol) is added to example 3b (80 mg, 0.180 mmol) in DCM (2 mL) and stirring is continued for 3 h. The reaction mixture is basified by addition of methanolic ammonia, water and DCM are added, the organic layer is separated, dried by Phase separator cartridge and solvent evaporated affording a residue that is purified by preparative HPLC (stationary phase XTerra C18 OBD 5 μm 30×100 mm. Mobile phase: ACN/H$_2$O+NH$_4$COOH 5 mM). Fractions containing the title compound are combined and ACN is evaporated under reduced pressure. The aqueous layer is extracted with DCM, separated and the DCM is evaporated to furnish the title compound (38 mg, 61%)

HPLC-MS (Method 10): $R_t$=3.38 min
MS (ESI+): m/z=344 (M+H)$^+$

The following examples are synthesized in analogy to the preparation of example 16:

| Example | Structure | Reactant(s) | HPLC-MS $R_t$ [min], method | MS (APCI+, m/z) (M + H)$^+$ |
|---|---|---|---|---|
| 17 (single stereoisomer, unknown absolute stereochemistry) | 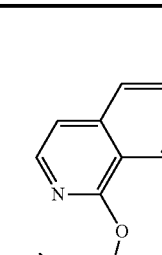 | Example 3c (120 mg, 0.271 mmol) | 3.37 7a | 344 |
| 18 (single stereoisomer, unknown absolute stereochemistry) | 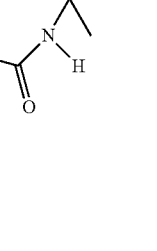 | Example 3d (120 mg, 0.271 mmol) | 3.35 7a | 344 |

Example 19

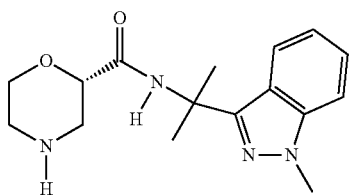 [SMILES: Cn1nc(C(C)(C)NC(=O)[C@@H]2CNCCO2)c2ccccc21]

Example 8a (79 mg, 98% content, 0.192 mmol) is suspended in MeOH/Water 1:1 (1 mL/1 mL) and heated under microwaves irradiation (150° C.) for 35 min. The reaction mixture is loaded on an SCX cartridge. Fractions obtained upon eluting with metabolic ammonia are evaporated under reduced pressure to give the title compound (54 mg, 93%)

HPLC-MS (Method 11): $R_t$=1.85 min

MS (ESI+): m/z=303 (M+H)$^+$

The following examples are synthesized in analogy to the preparation of example 16:

| Example | Structure | Reactant(s) | HPLC-MS $R_t$ [min], method | MS (ESI+ or APCI+, m/z) (M + H)$^+$ |
|---|---|---|---|---|
| 20 (racemic mixture) | 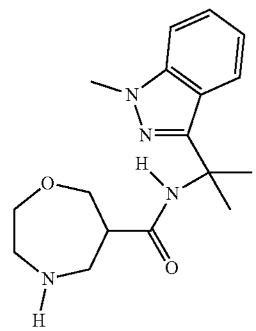 [SMILES: Cn1nc(C(C)(C)NC(=O)C2CNCCOC2)c2ccccc21] | Example 8b (20 mg, 0.048 mmol) | 2.72 7a | 317 |
| 21 (single stereoisomer, unknown absolute stereochemistry) | 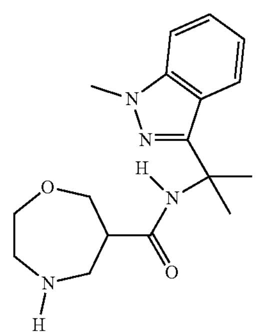 [SMILES: Cn1nc(C(C)(C)NC(=O)C2CNCCOC2)c2ccccc21] | Example 8c (67 mg, 0.161 mmol) | 2.75 7a | 317 |
| 22 (single stereoisomer, unknown absolute stereochemistry) | 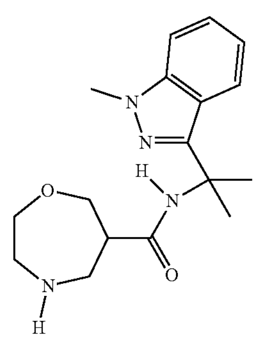 [SMILES: Cn1nc(C(C)(C)NC(=O)C2CNCCOC2)c2ccccc21] | Example 8d (50 mg, 0.120 mmol) | 2.75 7a | 317 |

-continued

| Example | Structure | Reactant(s) | HPLC-MS R$_t$ [min], method | MS (ESI+ or APCI+, m/z) (M + H)+ |
|---|---|---|---|---|
| 23 (racemic mixture) | 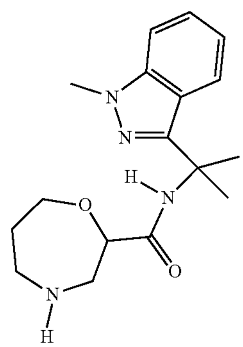 [SMILES: Cn1nc(C(C)(C)NC(=O)C2CNCCCO2)c2ccccc21] | Example 8e (50 mg, 98% content, 0.118 mmol) | 3.00 7a | 317 |
| 24 (single stereoisomer, unknown absolute stereochemistry) | 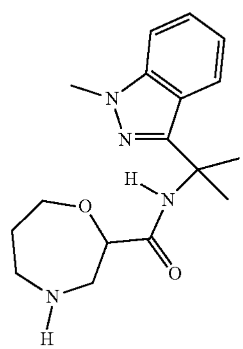 [SMILES: Cn1nc(C(C)(C)NC(=O)C2CNCCCO2)c2ccccc21] | Example 8f (130 mg, 0.312 mmol) | 3.40 7a | 317 |
| 25 (single stereoisomer, unknown absolute stereochemistry) | 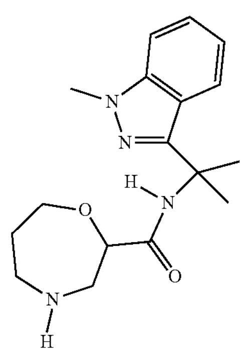 [SMILES: Cn1nc(C(C)(C)NC(=O)C2CNCCCO2)c2ccccc21] | Example 8g (110 mg, 0.264 mmol) | 3.40 7a | 317 |
| 26 (racemic mixture) | 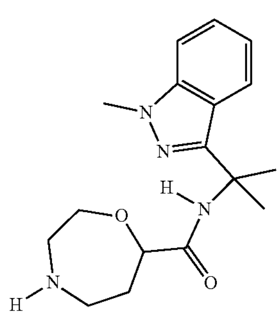 [SMILES: Cn1nc(C(C)(C)NC(=O)C2CCNCCO2)c2ccccc21] | Example 8h (20 mg, 98% content, 0.047 mmol) | 1.98 11 | 317 |

-continued

| Example | Structure | Reactant(s) | HPLC-MS R$_t$ [min], method | MS (ESI+ or APCI+, m/z) (M + H)$^+$ |
|---|---|---|---|---|
| 27 (single stereoisomer, unknown absolute stereochemistry) | 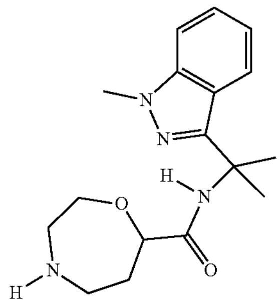 [SMILES: Cn1nc(C(C)(C)NC(=O)C2CCNCCO2)c2ccccc21] | Example 8i (33 mg, 0.078 mmol) | 3.00 7a | 317 |
| 28 (single stereoisomer, unknown absolute stereochemistry) | 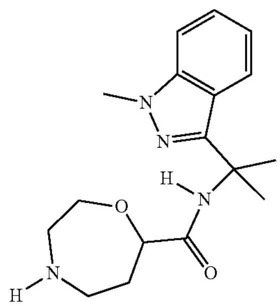 [SMILES: Cn1nc(C(C)(C)NC(=O)C2CCNCCO2)c2ccccc21] | Example 8j (33 mg, 0.079 mmol) | 3.07 7a | 317 |
| 29 | 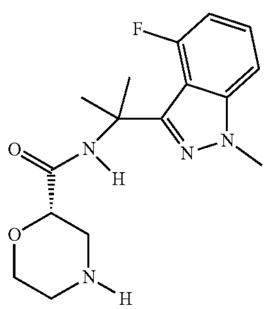 [SMILES: Cn1nc(C(C)(C)NC(=O)[C@@H]2CNCCO2)c2c(F)cccc21] | Example 8k (120 mg, 27% content, 0.077 mmol) | 3.23 7a | 321 |
| 30 | 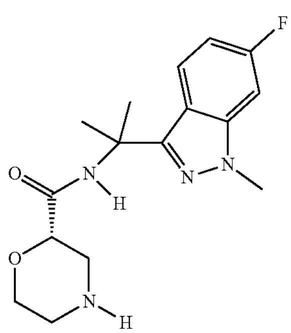 [SMILES: Cn1nc(C(C)(C)NC(=O)[C@@H]2CNCCO2)c2ccc(F)cc21] | Example 8l (100 mg, 40% content, 0.095 mmol) | 3.15 7a | 321 |

| Example | Structure | Reactant(s) | HPLC-MS R$_t$ [min], method | MS (ESI+ or APCI+, m/z) (M + H)$^+$ |
|---|---|---|---|---|
| 31 | 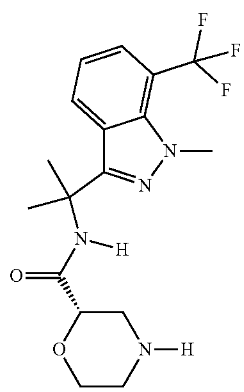 [SMILES: Cn1nc(C(C)(C)NC(=O)[C@@H]2CNCCO2)c2cccc(C(F)(F)F)c21] | Example 8m (210 mg, 60% content, 0.268 mmol) | 2.63 10 | 371 |

Example 32

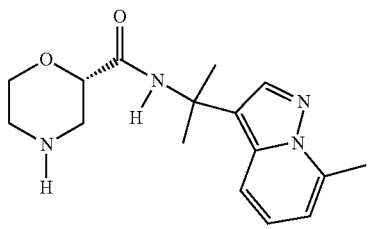 [SMILES: Cc1cccc2c(C(C)(C)NC(=O)[C@@H]3CNCCO3)cnn12]

tert-Butyldimethylsilyl trifluoromethanesulfonate (191 µL, 0.832 mmol) is added to example 8n (154 mg, 95% content, 0,363 mmol) and 2,6-lutidine (127 µL, 1,090 mmol) in DCM (4.4 mL). After 2 h the reaction mixture is washed with saturated ammonium chloride and brine. The organic layer is separated and dried with a Phase separator cartridge and evaporated under vacuum to obtain a residue that is dissolved in THF (4.6 mL) at −30° C. and treated with tetrabutylammonium fluoride (1.0M in THF, 399 µL, 0.399 mmol). After stirring 30 min at −30° C., volatiles are evaporated under reduced pressure and the resulting residue is purified by flash chromatography (eluent 0-10% MeOH+ 1% NH$_4$OH/DCM). Fractions containing the title compound are combined and volatiles are removed under reduced pressure to furnish the title compound (78 mg, 71%).

HPLC-MS (Method 7a): R$_t$=3.18 min
MS (APCI+): m/z=303 (M+H)$^+$

The following examples are synthesized in analogy to the preparation of example 32:

| Example | Structure | Reactant(s) | HPLC-MS R$_t$ [min], method | MS (APCI+, m/z) (M + H)$^+$ |
|---|---|---|---|---|
| 33 (racemic mixture) | 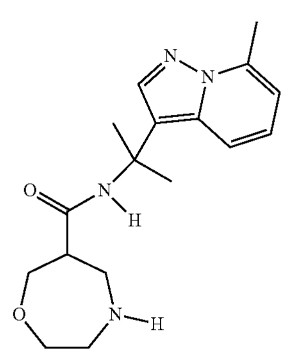 [SMILES: Cc1cccc2c(C(C)(C)NC(=O)C3CNCCOC3)cnn12] | Example 8o (60 mg, 98% content, 0.141 mmol) | 3.05 7a | 317 |

-continued

| Example | Structure | Reactant(s) | HPLC-MS R_t [min], method | MS (APCI+, m/z) (M + H)+ |
|---|---|---|---|---|
| 34 (single stereoisomer, unknown absolute stereochemistry) | 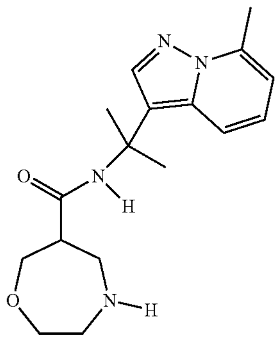 [SMILES: Cc1cccc2c(C(C)(C)NC(=O)C3CNCCOC3)cnn12] | Example 8p (44 mg, 0.105 mmol) | 2.98 7a | 317 |
| 35 (single stereoisomer, unknown absolute stereochemistry) | 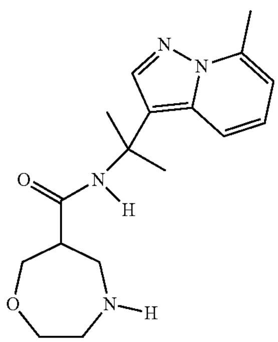 [SMILES: Cc1cccc2c(C(C)(C)NC(=O)C3CNCCOC3)cnn12] | Example 8q (42 mg, 0.101 mmol) | 3.02 7a | 317 |

The following examples are synthesized in analogy to the preparation of example 19:

| Example | Structure | Reactant(s) | HPLC-MS R_t [min], method | MS (APCI+, m/z) (M + H)+ |
|---|---|---|---|---|
| 36 | 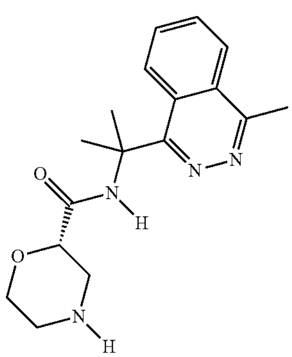 [SMILES: Cc1nnc(C(C)(C)NC(=O)[C@@H]2CNCCO2)c2ccccc12] | Example 8r (35 mg, 0.084 mmol) | 2.73 7a | 315 |
| 37 (racemic mixture) | | Example 8s (10 mg, 0.023 mmol) | 2.48 7a | 329 |

-continued

| Example | Structure | Reactant(s) | HPLC-MS $R_t$ [min], method | MS (APCI+, m/z) (M + H)$^+$ |
|---|---|---|---|---|
| 38 | 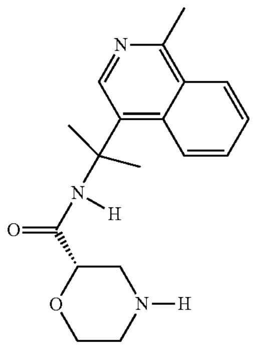 [SMILES: Cc1ncc(C(C)(C)NC(=O)[C@@H]2CNCCO2)c2ccccc12] | Example 8t (60 mg, 95% content, 0.138 mmol) | 3.27 7a | 314 |

| Example | Structure | Reactant(s) | HPLC-MS $R_t$ [min], method | MS (ESI+, m/z) (M + H)$^+$ |
|---|---|---|---|---|
| 39 | 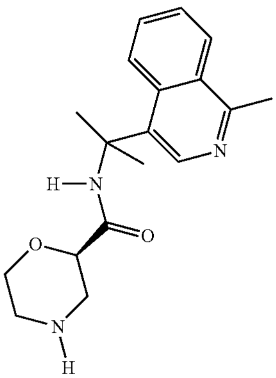 [SMILES: Cc1ncc(C(C)(C)NC(=O)[C@H]2CNCCO2)c2ccccc12] | Example 8u (15 mg, 0.036 mmol) | 1.81 11 | 314 |

The following examples are synthesized in analogy to the preparation of example 16:

The following examples are synthesized in analogy to the preparation of example 19:

| Example | Structure | Reactant(s) | HPLC-MS $R_t$ [min], method | MS (ESI+, m/z) (M + H)$^+$ |
|---|---|---|---|---|
| 40 (racemic mixture) | 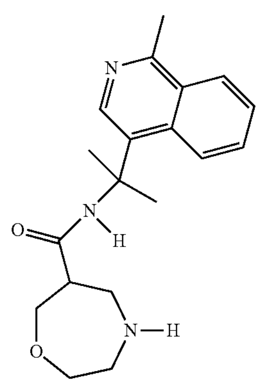 [SMILES: Cc1ncc(C(C)(C)NC(=O)C2CNCCOC2)c2ccccc12] | Example 8v (24 mg, 98% content, 0.055 mmol) | 1.70 11 | 328 |
| 41 (single stereoisomer, unknown absolute stereochemistry) | 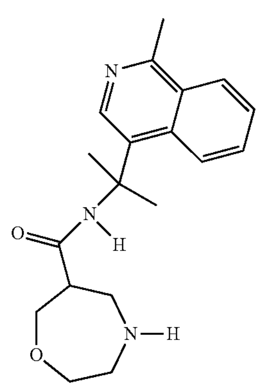 [SMILES: Cc1ncc(C(C)(C)NC(=O)C2CNCCOC2)c2ccccc12] | Example 8w (42 mg, 0.097 mmol) | 0.75-1.55 10 | 328 |

-continued

| Example | Structure | Reactant(s) | HPLC-MS R$_t$ [min], method | MS (ESI+, m/z) (M + H)$^+$ |
|---|---|---|---|---|
| 42 (single stereoisomer, unknown absolute stereochemistry) | 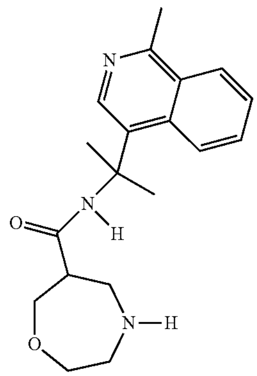 [SMILES: Cc1ncc(C(C)(C)NC(=O)C2CNCCOC2)c2ccccc12] | Example 8y (51 mg, 0.119 mmol) | 0.75-1.57 10 | 328 |
| 43 | 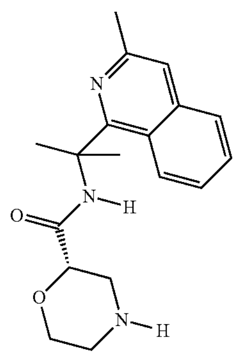 [SMILES: Cc1cc2ccccc2c(C(C)(C)NC(=O)[C@@H]2CNCCO2)n1] | Example 8z (149 mg, 0.359 mmol) | 2.38 11 | 314 |

40

The following examples are synthesized in analogy to the preparation of example 16:

| Example | Structure | Reactant(s) | HPLC-MS R$_t$ [min], method | MS (ESI+ or APCl+, m/z) (M + H)$^+$ |
|---|---|---|---|---|
| 44 (racemic mixture) | 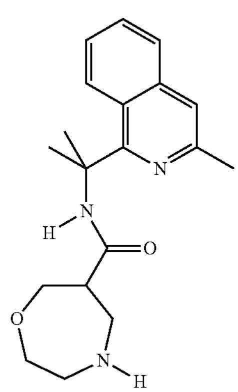 [SMILES: Cc1cc2ccccc2c(C(C)(C)NC(=O)C2CNCCOC2)n1] | Example 8aa (35 mg, 0.082 mmol) | 3.57 7a | 328 |

-continued

| Example | Structure | Reactant(s) | HPLC-MS R$_t$ [min], method | MS (ESI+ or APCI+, m/z) (M + H)$^+$ |
|---|---|---|---|---|
| 45 (single stereoisomer, unknown absolute stereochemistry) | | Example 8ab (80 mg, 0.187 mmol) | 2.25 11 | 328 |
| 46 (single stereoisomer, unknown absolute stereochemistry) | | Example 8ac (70 mg, 0.164 mmol) | 2.22 11 | 328 |
| 47 (racemic mixture) | | Example 8ad (48 mg, 0.112 mmol) | 4.08 7a | 328 |
| 48 (single stereoisomer, unknown absolute stereochemistry) | | Example 8ae (60 mg, 0.140 mmol) | 4.02 7a | 328 |

-continued

| Example | Structure | Reactant(s) | HPLC-MS R$_t$ [min], method | MS (ESI+ or APCI+, m/z) (M + H)$^+$ |
|---|---|---|---|---|
| 49 (single stereoisomer, unknown absolute stereo-chemistry) | 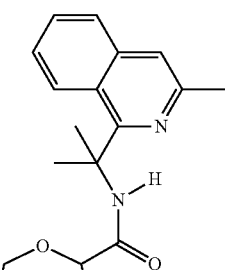 | Example 8af (60 mg, 0.140 mmol) | 4.02 7a | 328 |

The following examples are synthesized in analogy to the preparation of example 19:

| Example | Structure | Reactant(s) | HPLC-MS R$_t$ [min], method | MS (APCI+, m/z) (M + H)$^+$ |
|---|---|---|---|---|
| 50 (racemic mixture) | 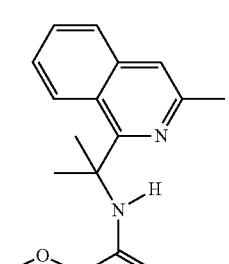 | Example 8ag (15 mg, 95% content, 0.033 mmol) | 3.87 7a | 328 |
| 51 (single stereoisomer, unknown absolute stereo-chemistry) | 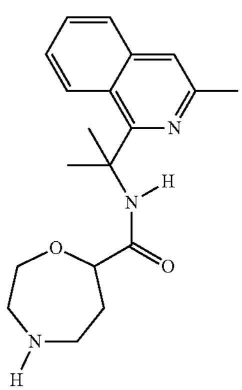 [SMILES: Cc1cc2ccccc2c(C(C)(C)NC(=O)C2CCNCCO2)n1] | Example 8ah (27 mg, 0.062 mmol) | 3.92 7a | 328 |

-continued

| Example | Structure | Reactant(s) | HPLC-MS $R_t$ [min], method | MS (APCl+, m/z) $(M + H)^+$ |
|---|---|---|---|---|
| 52 (single stereoisomer, unknown absolute stereochemistry) | | Example 8ai (20 mg, 0.047 mmol) | 3.93 7a | 328 |

The following examples are synthesized in analogy to the preparation of example 16:

| Example | Structure | Reactant(s) | HPLC-MS $R_t$ [min], method | MS (ESI+ or APCl+, m/z) $(M + H)^+$ |
|---|---|---|---|---|
| 53 | 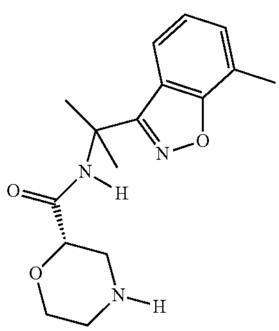 [SMILES: Cc1cccc2c(C(C)(C)NC(=O)[C@@H]3CNCCO3)noc12] | Example 13a (98 mg, 95% content, 0.231 mmol) | 2.05 11 | 304 |
| 54 (racemic mixture) | 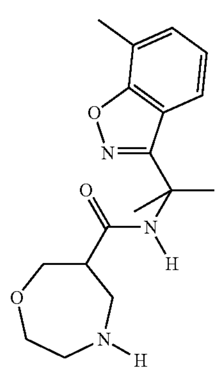 [SMILES: Cc1cccc2c(C(C)(C)NC(=O)C3CNCCOC3)noc12] | Example 13b (70 mg, 95% content, 0.159 mmol) | 1.92 11 | 318 |

| Example | Structure | Reactant(s) | HPLC-MS $R_t$ [min], method | MS (ESI+ or APCI+, m/z) (M + H)+ |
|---|---|---|---|---|
| 55 (single stereoisomer, unknown absolute stereochemistry) | | Example 13c (52 mg, 0.125 mmol) | 3.32 7a | 318 |
| 56 (single stereoisomer, unknown absolute stereochemistry) | | Example 13d (52 mg, 0.123 mmol) | 3.28 7a | 318 |
| 57 | | Example 18a (72 mg, 0.179 mmol) | 3.10 7a | 303 |

Example 58 (Racemic Mixture)

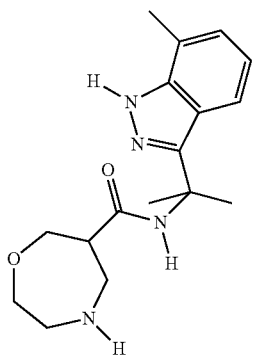 [SMILES: Cc1cccc2c(C(C)(C)NC(=O)C3CNCCOC3)n[nH]c12]

Example 18b (75 mg, 0.137 mmol) is suspended in DCM (1 mL) at 0° C. and TFA (0.5 mL) is added. The mixture is stirred for 30 minutes at RT and the solvent removed under vacuum. The residue is partitioned between DCM and aq. NaHCO$_3$. The aqueous phase is evaporated under reduced pressure and the residue treated with isopropanol. Undissolved material is filtered away, volatiles are evaporated under reduced pressure and the residue loaded onto an SCX cartridge, washed with DCM/MeOH and eluted with 7M ammonia in MeOH. The solvent is removed under vacuum to give a residue that is purified by flash chromatography (eluent DCM/MeOH/NH$_4$OH 100/0/0 to 80/20/0.2). Fractions containing the title compound are combined and volatiles are removed under reduced pressure to furnish the title compound (23 mg, 53%).

HPLC-MS (Method 11): R$_t$=1.65 min
MS (ESI+): m/z=317 [M+H]$^+$

The following examples are synthesized in analogy to the preparation of example 16:

| Example | Structure | Reactant(s) | HPLC-MS R$_t$ [min], method | MS (ESI+ or APCI+, m/z) (M + H)$^+$ |
|---|---|---|---|---|
| 59 (single stereoisomer, unknown absolute stereochemistry) | | Example 23b (25 mg, 0.061 mmol) | 2.85 7a | 317 |
| 60 (single stereoisomer, unknown absolute stereochemistry) | | Example 23c (24 mg, 0.058 mmol) | 2.85 7a | 317 |
| 61 | | Example 29a (160 mg, 0.393 mmol) | 1.96 11 | 308 |

-continued

| Example | Structure | Reactant(s) | HPLC-MS R$_t$ [min], method | MS (ESI+ or APCl+, m/z) (M + H)$^+$ |
|---|---|---|---|---|
| 62 (racemic mixture) | 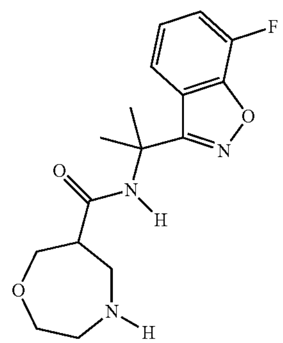 [SMILES: CC(C)(NC(=O)C1CNCCOC1)c1noc2c(F)cccc12] | Example 29b (25 mg, 0.059 mmol) | 3.24 7a | 322 |
| 63 (single stereoisomer, unknown absolute stereochemistry) | | Example 29c (40 mg, 0.095 mmol) | 3.20 7a | 322 |
| 64 (single stereoisomer, unknown absolute stereochemistry) | | Example 29d (50 mg, 0.119 mmol) | 3.15 7a | 322 |
| 65 (racemic mixture) | 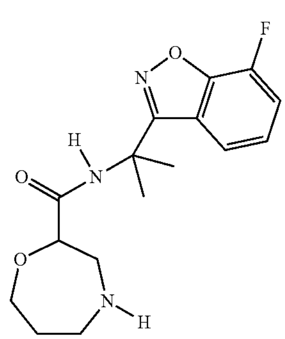 [SMILES: CC(C)(NC(=O)C1CNCCCO1)c1noc2c(F)cccc12] | Example 29e (50 mg, 0.119 mmol) | 3.24 7a | 322 |

-continued

| Example | Structure | Reactant(s) | HPLC-MS R$_t$ [min], method | MS (ESI+ or APCI+, m/z) (M + H)$^+$ |
|---|---|---|---|---|
| 66 (single stereoisomer, unknown absolute stereochemistry) | | Example 29f (30 mg, 0.071 mmol) | 3.22 7a | 322 |
| 67 (single stereoisomer, unknown absolute stereochemistry) | | Example 29g (50 mg, 0.119 mmol) | 3.16 10 | 322 |
| 68 (racemic mixture) | | Example 29h (50 mg, 0.119 mmol) | 3.20 7a | 322 |
| 69 (single stereoisomer, unknown absolute stereochemistry) | | Example 29i (50 mg, 0.119 mmol) | 3.20 7a | 322 |

| Example | Structure | Reactant(s) | HPLC-MS R$_t$ [min], method | MS (ESI+ or APCI+, m/z) (M + H)$^+$ |
|---|---|---|---|---|
| 70 (single stereoisomer, unknown absolute stereo-chemistry) | 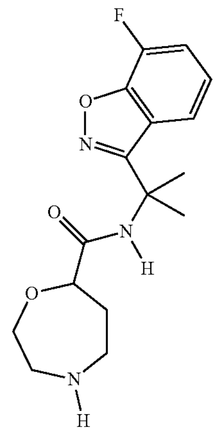 [SMILES: CC(C)(NC(=O)C1CCNCCO1)c1noc2c(F)cccc12] | Example 29j (60 mg, 0.142 mmol) | 3.20 7a | 322 |
| 71 | 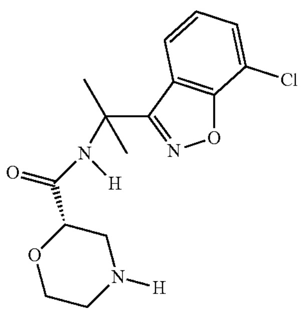 [SMILES: CC(C)(NC(=O)[C@@H]1CNCCO1)c1noc2c(Cl)cccc12] | Example 29k (140 mg, 90% content, 0.297 mmol) | 3.58 7a | 324 |
| 72 (racemic mixture) | 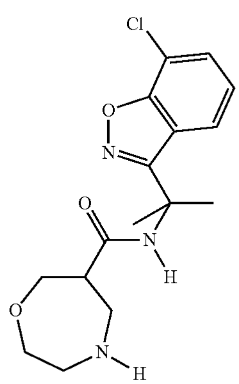 [SMILES: CC(C)(NC(=O)C1CNCCOC1)c1noc2c(Cl)cccc12] | Example 29l (90 mg, 0.206 mmol) | 3.52 7a | 338 |
| 73 (single stereoisomer, unknown absolute stereo-chemistry) | 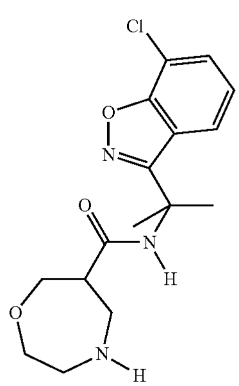 [SMILES: CC(C)(NC(=O)C1CNCCOC1)c1noc2c(Cl)cccc12] | Example 29m (69 mg, 0.157 mmol) | 3.47 7a | 338 |

-continued

| Example | Structure | Reactant(s) | HPLC-MS R<sub>t</sub> [min], method | MS (ESI+ or APCI+, m/z) (M + H)+ |
|---|---|---|---|---|
| 74 (single stereoisomer, unknown absolute stereochemistry) | | Example 29n (71 mg, 0.161 mmol) | 3.47 7a | 338 |
| 75 | 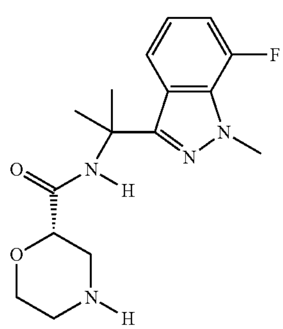 [SMILES: Cn1nc(C(C)(C)NC(=O)[C@@H]2CNCCO2)c2cccc(F)c21] | Example 32a (112 mg, 98% content, 0.261 mmol) | 2.08 11 | 321 |
| 76 (racemic mixture) | 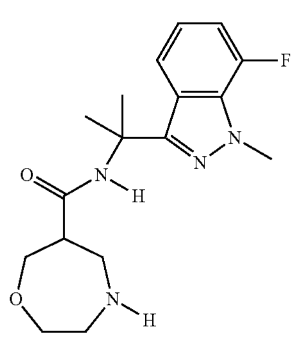 [SMILES: Cn1nc(C(C)(C)NC(=O)C2CNCCOC2)c2cccc(F)c21] | Example 32b (22 mg, 0.051 mmol) | 3.27 7a | 335 |

The enantiomers of the example 76 are separated by HPLC using a chiral stationary phase.
Method for Separation:

HPLC apparatus type: Waters 600 Pump, 2767 Autosampler, UV Detector 2489; column: Daicel Chiralpak AD-H, 5.0 μm, 250 mm×20 mm; method: eluent hexane/IPA 75:25; flow rate: 15 mL/min, temperature: 25° C.; UV Detection: 230 nm

| Example 77: stereoisomer 1, unknown absolute stereochemistry | Example 78: stereoisomer 2, unknown absolute stereochemistry |
|---|---|

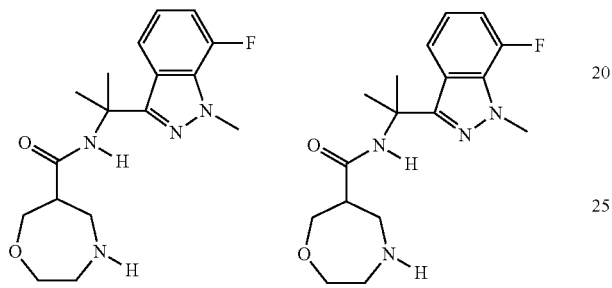

| Example | Chiral HPLC (Method 16) $R_t$ [min] | HPLC-MS (Method-7a): $R_t$ [min] | MS (APCI+): m/z |
|---|---|---|---|
| 77 | 4.73 | 3.22 | 335 |
| 78 | 6.21 | 3.17 | 335 |

The following examples are synthesized in analogy to the preparation of example 19:

| Example | Structure | Reactant(s) | HPLC-MS $R_t$ [min], method | MS (ESI+, m/z) (M + H)+ |
|---|---|---|---|---|
| 79 | 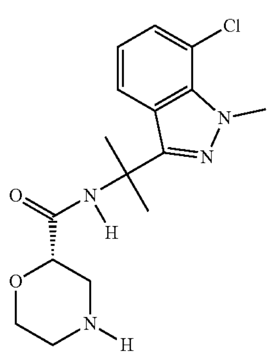 [SMILES: Cn1nc(C(C)(C)NC(=O)[C@@H]2CNCCO2)c2cccc(Cl)c21] | Example 32c (93 mg, 0.213 mmol) | 2.42 11 | 337 |

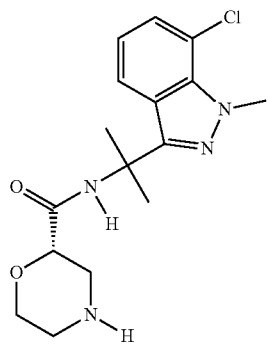

The following examples are synthesized in analogy to the preparation of example 16:

| Example | Structure | Reactant(s) | HPLC-MS R$_t$ [min], method | MS (ESI+, m/z) (M + H)$^+$ |
|---|---|---|---|---|
| 80 (racemic mixture) | | Example 32d (40 mg, 80% content, 0.071 mmol) | 2.20 11 | 351 |
| 81 (single stereoisomer, unknown absolute stereochemistry) | | Example 32e (42 mg, 0.093 mmol) | 2.18 11 | 351 |
| 82 (single stereoisomer, unknown absolute stereochemistry) | | Example 32f (38 mg, 0.084 mmol) | 2.18 11 | 351 |

The following examples are synthesized in analogy to the preparation of example 19:

| Example | Structure | Reactant(s) | HPLC-MS R$_t$ [min], method | MS (ESI+, m/z) (M + H)$^+$ |
|---|---|---|---|---|
| 83 | 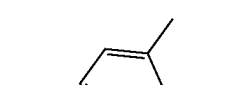 | Example 32g (127 mg, 0.305 mmol) | 2.26 11 | 317 |

The following examples are synthesized in analogy to the preparation of example 16:

| Example | Structure | Reactant(s) | HPLC-MS R$_t$ [min], method | MS (ESI+, or APCl+, m/z) (M + H)$^+$ |
|---|---|---|---|---|
| 84 (racemic mixture) | 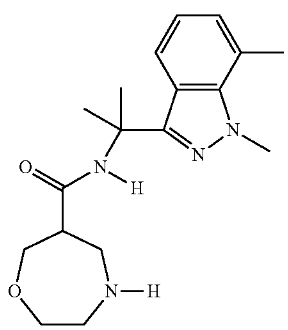 [SMILES: Cc1cccc2c(C(C)(C)NC(=O)C3CNCCOC3)nn(C)c12] | Example 32h (65 mg, 0.151 mmol) | 3.30 7a | 331 |
| 85 (single stereoisomer, unknown absolute stereo-chemistry) | 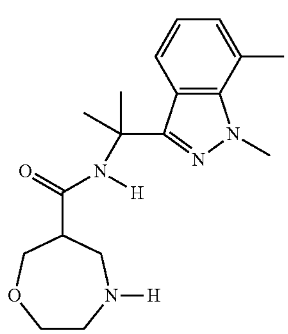 [SMILES: Cc1cccc2c(C(C)(C)NC(=O)C3CNCCOC3)nn(C)c12] | Example 32i (66 mg, 0.153 mmol) | 3.23 7a | 331 |

| Example | Structure | Reactant(s) | HPLC-MS R$_t$ [min], method | MS (ESI+, or APCI+, m/z) (M + H)$^+$ |
|---|---|---|---|---|
| 86 (single stereoisomer, unknown absolute stereochemistry) | | Example 32j (62 mg, 0.144 mmol) | 3.23 7a | 331 |
| 87 | 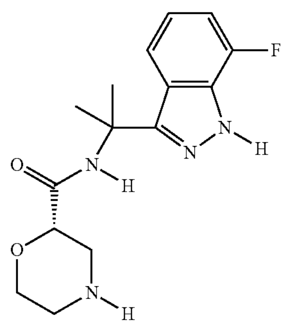 [SMILES: CC(C)(NC(=O)[C@@H]1CNCCO1)c1n[nH]c2c(F)cccc12] | Example 32k (66 mg, 98% content, 0.159 mmol) | 1.68 11 | 307 |
| 88 (racemic mixture) | 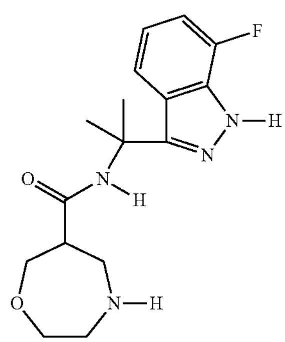 [SMILES: CC(C)(NC(=O)C1CNCCOC1)c1n[nH]c2c(F)cccc12] | Example 32l (17 mg, 82% content, 0.033 mmol) | 1.49 11 | 321 |
| 89 (single stereoisomer, unknown absolute stereochemistry) | | Example 32m (30 mg, 0.071 mmol) | 2.68 7a | 321 |

-continued

| Example | Structure | Reactant(s) | HPLC-MS $R_t$ [min], method | MS (ESI+, or APCI+, m/z) $(M + H)^+$ |
|---|---|---|---|---|
| 90 (single stereoisomer, unknown absolute stereochemistry) | | Example 32n (29 mg, 0.068 mmol) | 2.58 7a | 321 |

The following examples are synthesized in analogy to the preparation of example 19:

| Example | Structure | Reactant(s) | HPLC-MS $R_t$ [min], method | MS (APCI+, m/z) $(M + H)^+$ |
|---|---|---|---|---|
| 91 | 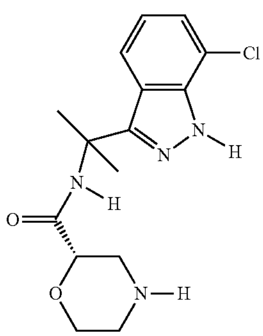 [SMILES: CC(C)(NC(=O)[C@@H]1CNCCO1)c1n[nH]c2c(Cl)cccc12] | Example 32o (71 mg, 0.168 mmol) | 3.15 7a | 323 |
| 92 (racemic mixture) | 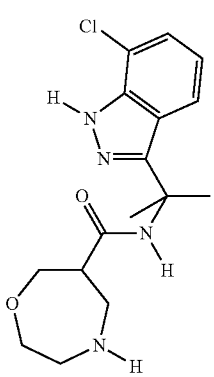 [SMILES: CC(C)(NC(=O)C1CNCCOC1)c1n[nH]c2c(Cl)cccc12] | Example 32p (40 mg, 82% content, 0.075 mmol) | 2.98 7a | 337 |

| Example | Structure | Reactant(s) | HPLC-MS $R_t$ [min], method | MS (APCl+, m/z) (M + H)+ |
|---|---|---|---|---|
| 93 (single stereoisomer, unknown absolute stereochemistry) | | Example 32q (24 mg, 0.055 mmol) | 3.03 7a | 337 |
| 94 (single stereoisomer, unknown absolute stereochemistry) | | Example 32r (22 mg, 0.050 mmol) | 3.00 7a | 337 |

Example 95

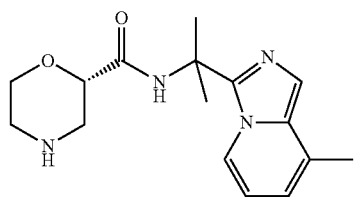 [SMILES: Cc1cccn2c(C(C)(C)NC(=O)[C@@H]3CNCCO3)ncc12]

Example 49a (151 mg, 0.33 mmol) is dissolved in dry methanol (2 mL) and then hydrogen chloride 2M in ethyl ether (1.9 mL, 3.8 mmol) is added. The mixture is stirred until the Boc group has been completely removed and then the solvent is evaporated. The mixture is redissolved in methanol, loaded onto a prewashed SCX cartridge, washed with methanol and eluted with a solution of ammonia in methanol. The solvent is evaporated and the residue dried under vacuum to give the title compound (83 mg, 91%).

HPLC-MS (Method 11): $R_t$=1.70 min

MS (ESI−): m/z=301 (M−H)−

The following examples are synthesized in analogy to the preparation of example 95 using the acids and solvent (if used) described:

| Example | Structure | Reactant, acid, solvent | HPLC-MS $R_t$ [min], method | MS (ESI+/ ESI− or APCl+, m/z) |
|---|---|---|---|---|
| 96 | 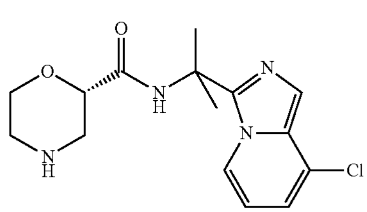 [SMILES: CC(C)(NC(=O)[C@@H]1CNCCO1)c1ncc2c(Cl)cccn12] | Example 49b, (82 mg, 0.19 mmol), TFA (0.3 mL), DCM (3 mL) | 1.74 11 | 321 [M − H]− |

-continued

| Example | Structure | Reactant, acid, solvent | HPLC-MS $R_t$ [min], method | MS (ESI+/ESI− or APCI+, m/z) |
|---|---|---|---|---|
| 97 | 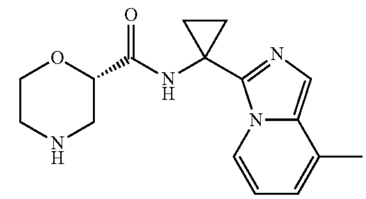 [SMILES: Cc1cccn2c(C3(NC(=O)[C@@H]4CNCCO4)CC3)ncc12] | Example 49c, (70 mg, 0.17 mmol), TFA (2 mL) | 2.76 7a | 301 [M + H]+ |
| 98 | 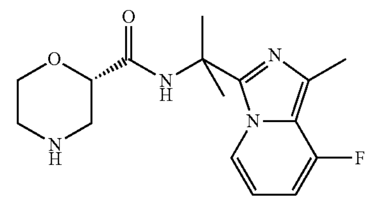 [SMILES: Cc1nc(C(C)(C)NC(=O)[C@@H]2CNCCO2)n2cccc(F)c12] | Example 49d, (40 mg, 0.10 mmol), TFA (1 mL), DCM (3 mL) | 2.97 7a | 321 [M + H]+ |
| 99 | 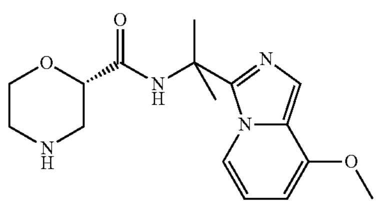 [SMILES: COc1cccn2c(C(C)(C)NC(=O)[C@@H]3CNCCO3)ncc12] | Example 49e, (140 mg, 0.33 mmol), TFA (1 mL), DCM (5 mL) Purified by preparative RP-HPLC | 1.51 11 | 319 [M + H]+ |
| 100 | 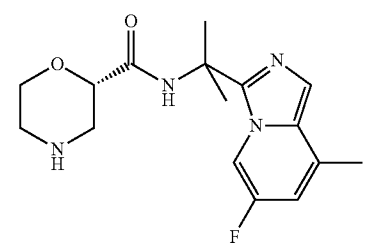 [SMILES: Cc1cc(F)cn2c(C(C)(C)NC(=O)[C@@H]3CNCCO3)ncc12] | Example 49f, (94 mg, 0.22 mmol), TFA (1 mL), DCM (5 mL) | 3.02 7a | 321 [M + H]+ |
| 101 | 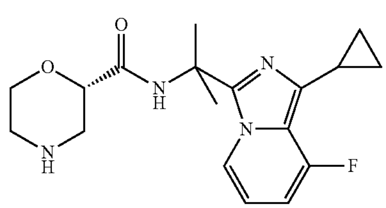 | Example 49g, (128 mg, 0.29 mmol), 2M HCl in diethyl ether (1.55 mL), MeOH (3 mL) | 1.88 11 | 317 [M + H]+ |
| 102 | 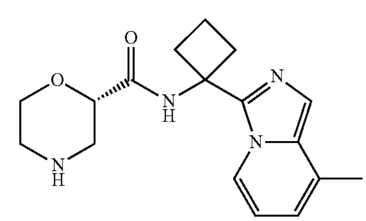 [SMILES: Cc1cccn2c(C3(NC(=O)[C@@H]4CNCCO4)CCC3)ncc12] | Example 49h, (240 mg, 0.52 mmol), 2M HCl in diethyl ether (2.9 mL), MeOH (2 mL) | 2.83 7a | 315 [M + H]+ |
| 103 | 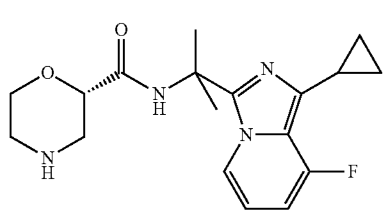 [SMILES: CC(C)(NC(=O)[C@@H]1CNCCO1)c1nc(C2CC2)c2c(F)cccn12] | Example 49l, (40 mg, 0.09 mmol), TFA (2 mL) | 2.43 11 | 347 [M + H]+ |

-continued

| Example | Structure | Reactant, acid, solvent | HPLC-MS R_t [min], method | MS (ESI+/ ESI− or APCl+, m/z) |
|---|---|---|---|---|
| 104 | 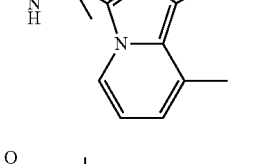 | Example 49m, (100 mg, 0.23 mmol), TFA (1 mL) DCM (5 mL) | 3.71 7a | 343 [M + H]+ |
| 105 | 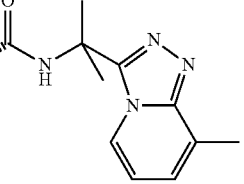 | Example 49n, (40 mg, 0.09 mmol), TFA (1 mL) | 0.30 12 | 304 [M + H]+ |
| 106 | 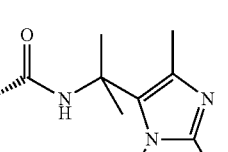 | Example 49o, (40 mg, 0.10 mmol), TFA (2 mL) | 2.02 7a | 303 [M + H]+ |
| 107 | 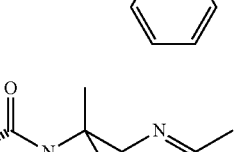 | Example 49p, (35 mg, 0.08 mmol), TFA (2 mL) | 3.32 7a | 319 [M + H]+ |
| 108 | 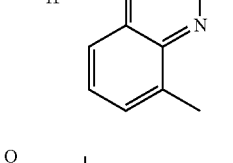 | Example 49q, (120 mg, 60% content, 0.18 mmol), TFA (2 mL) DCM (10 mL) Purified by preparative RP-HPLC | 2.58 7a | 303 [M + H]+ |
| 109 | 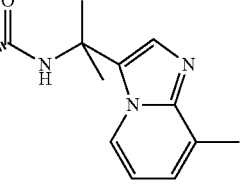 | Example 49r, (100 mg, 0.25 mmol), TFA (1 mL) DCM (5 mL) Purified by preparative RP-HPLC | 3.82 7a | 302 [M + H]+ |
| 110 Single stereo- isomer unknown absolute stereo- chemistry at quaternary carbon | 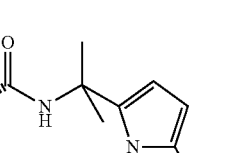 | Example 49s, (60 mg, TFA (1 mL) DCM (5 mL) | 1.85 11 | 329 [M + H]+ |

-continued

| Example | Structure | Reactant, acid, solvent | HPLC-MS $R_t$ [min], method | MS (ESI+/ ESI- or APCI+, m/z) |
|---|---|---|---|---|
| 111 Single stereo-isomer unknown absolute stereo-chemistry at quaternary carbon | 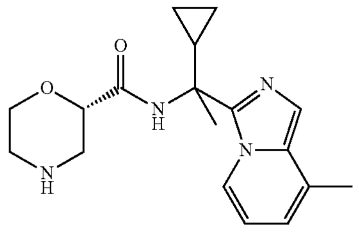 [SMILES: Cc1cccn2c(C(C)(NC(=O)[C@@H]3CNCCO3)C3CC3)ncc12] | Example 49t, (54 mg, TFA (1 mL) DCM (5 mL) | 1.83 11 | 329 [M + H]+ |
| 112 Single stereo-isomer unknown absolute stereo-chemistry at quaternary carbon | 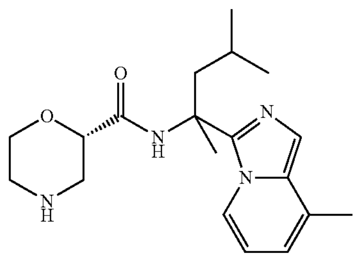 [SMILES: Cc1cccn2c(C(C)(CC(C)C)NC(=O)[C@@H]3CNCCO3)ncc12] | Example 49u, (38 mg, 0.08 mmol), TFA (1 mL) DCM (3 mL) | 2.34 11 | 345 [M + H]+ |
| 113 Single stereo-isomer unknown absolute stereo-chemistry at quaternary carbon | 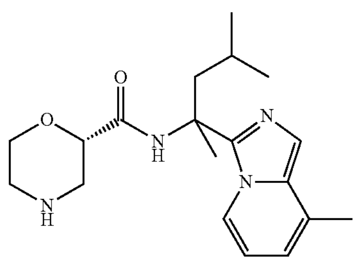 [SMILES: Cc1cccn2c(C(C)(CC(C)C)NC(=O)[C@@H]3CNCCO3)ncc12] | Example 49v, (36 mg, 0.08 mmol), TFA (1 mL) DCM (3 mL) | 2.33 11 | 345 [M + H]+ |
| 114 Single stereo-isomer unknown absolute stereo-chemistry at quaternary carbon | 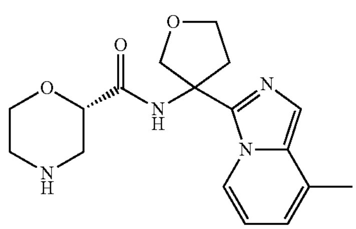 [SMILES: Cc1cccn2c(C3(NC(=O)[C@@H]4CNCCO4)CCOC3)ncc12] | Example 49w, (30 mg, 0.07 mmol), TFA (1 mL) DCM (3 mL) | 2.57 7a | 331 [M + H]+ |
| 115 Single stereo-isomer unknown absolute stereo-chemistry at quaternary carbon | 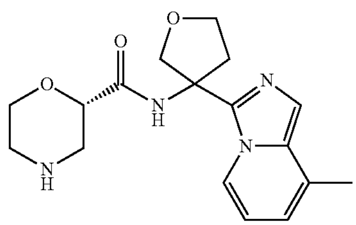 [SMILES: Cc1cccn2c(C3(NC(=O)[C@@H]4CNCCO4)CCOC3)ncc12] | Example 49w, (28 mg, 0.07 mmol), TFA (1 mL) DCM (3 mL) | 2.68 7a | 331 [M + H]+ |
| 116 Racemic mixture | 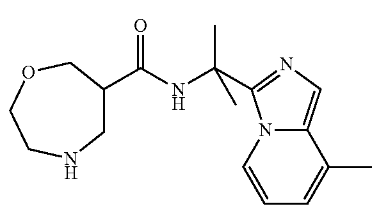 [SMILES: Cc1cccn2c(C(C)(C)NC(=O)C3CNCCOC3)ncc12] | Example 50a, (7 mg, 0.02 mmol), TFA (0.5 mL) DCM (1 mL) | 2.70 7a | 317 [M + H]+ |

-continued

| Example | Structure | Reactant, acid, solvent | HPLC-MS R$_t$ [min], method | MS (ESI+/ ESI− or APCI+, m/z) |
|---|---|---|---|---|
| 117 Single stereo- isomer unknown absolute stereo- chemistry | 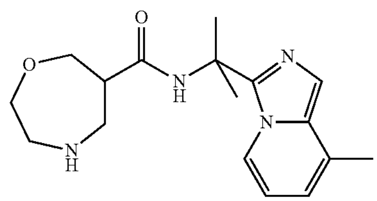 [SMILES: Cc1cccn2c(C(C)(C)NC(=O)C3CNCCOC3)ncc12] | Example 50k, (77 mg, 0.18 mmol), TFA (1 mL) DCM (5 mL) | 2.73 7a | 317 [M + H]$^+$ |
| 118 Single stereo- isomer unknown absolute stereo- chemistry | 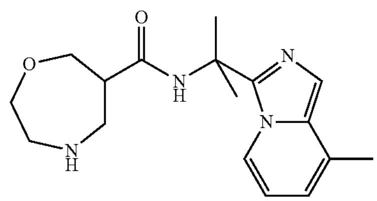 [SMILES: Cc1cccn2c(C(C)(C)NC(=O)C3CNCCOC3)ncc12] | Example 50l, (47 mg, 0.11 mmol), TFA (1 mL) DCM (5 mL) | 2.67 7a | 317 [M + H]$^+$ |
| 119 Single stereo- isomer unknown absolute stereo- chemistry | 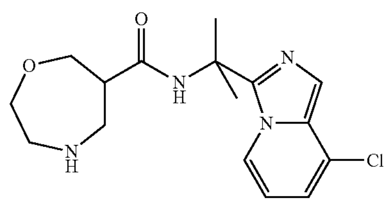 [SMILES: CC(C)(NC(=O)C1CNCCOC1)c1ncc2c(Cl)cccn12] | Example 50m, (35 mg, 0.08 mmol), TFA (1 mL) DCM (5 mL) | 2.09 12a | 337/339 [M + H]$^+$ |
| 120 Single stereo- isomer unknown absolute stereo- chemistry | 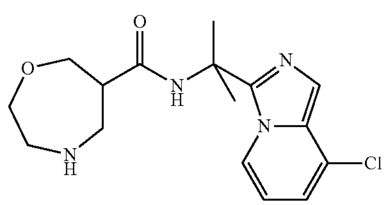 [SMILES: CC(C)(NC(=O)C1CNCCOC1)c1ncc2c(Cl)cccn12] | Example 50l, (30 mg, 0.07 mmol), TFA (1 mL) DCM (5 mL) | 2.09 12a | 337/339 [M + H]$^+$ |
| 121 Single stereo- isomer unknown absolute stereo- chemistry | 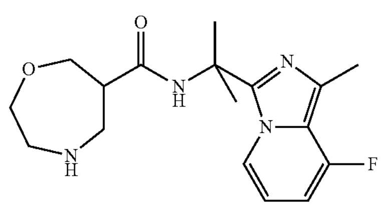 [SMILES: Cc1nc(C(C)(C)NC(=O)C2CNCCOC2)n2cccc(F)c12] | Example 50o, (24 mg, 0.06 mmol), TFA (1 mL) DCM (5 mL) | 1.63 11 | 335 [M + H]$^+$ |
| 122 Single stereo- isomer unknown absolute stereo- chemistry | 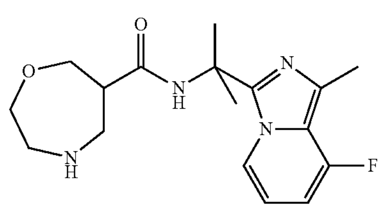 [SMILES: Cc1nc(C(C)(C)NC(=O)C2CNCCOC2)n2cccc(F)c12] | Example 50p, (21 mg, 0.05 mmol), TFA (1 mL) DCM (5 mL) | 1.64 11 | 335 [M + H]$^+$ |
| 123 Racemic mixture | 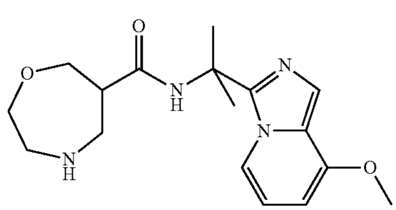 [SMILES: COc1cccn2c(C(C)(C)NC(=O)C3CNCCOC3)ncc12] | Example 50d, (30 mg, 0.07 mmol), TFA (1 mL) DCM (5 mL) | 2.67 7a | 333 [M + H]$^+$ |

-continued

| Example | Structure | Reactant, acid, solvent | HPLC-MS R$_t$ [min], method | MS (ESI+/ ESI− or APCI+, m/z) |
|---|---|---|---|---|
| 124 Single stereo-isomer unknown absolute stereo-chemistry | 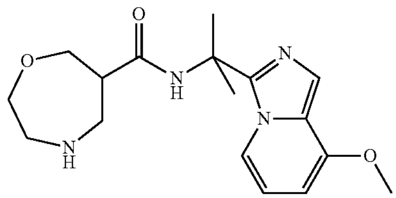 [SMILES: COc1cccn2c(C(C)(C)NC(=O)C3CNCCOC3)ncc12] | Example 50q, (14 mg, 0.03 mmol), TFA (1 mL) DCM (5 mL) | 2.54 7a | 333 [M + H]$^+$ |
| 125 Single stereo-isomer unknown absolute stereo-chemistry | 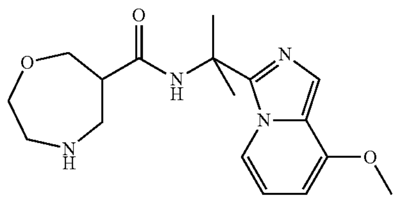 [SMILES: COc1cccn2c(C(C)(C)NC(=O)C3CNCCOC3)ncc12] | Example 50q, (10 mg, 0.02 mmol), TFA (1 mL) DCM (5 mL) | 2.54 7a | 333 [M + H]$^+$ |
| 126 Single stereo-isomer unknown absolute stereo-chemistry | 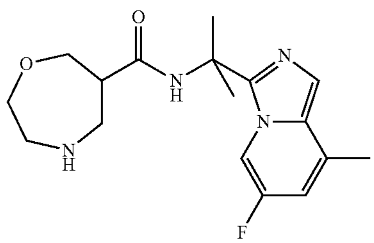 [SMILES: Cc1cc(F)cn2c(C(C)(C)NC(=O)C3CNCCOC3)ncc12] | Example 50e, (40 mg, 0.08 mmol), TFA (1 mL), DCM (5 mL) Separation by chiral HPLC (Chiralpak AD-H, hexane/IPA 75/25) | 2.98 7a Chiral HPLC method 16 5.37 | 333 [M + H]$^+$ |
| 127 Single stereo-isomer unknown absolute stereo-chemistry | 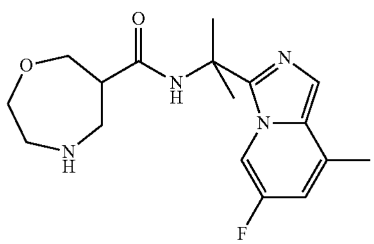 [SMILES: Cc1cc(F)cn2c(C(C)(C)NC(=O)C3CNCCOC3)ncc12] | Example 50e, (40 mg, 0.08 mmol), TFA (1 mL), DCM (5 mL) Separation by chiral HPLC (Chiralpak AD-H, hexane/IPA 75/25) | 2.93 7a Chiral HPLC method 16 10.49 | 333 [M + H]$^+$ |
| 128 Racemic mixture | 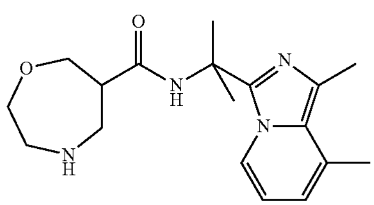 [SMILES: Cc1cccn2c(C(C)(C)NC(=O)C3CNCCOC3)nc(C)c12] | Example 50f, (53 mg, 0.12 mmol), TFA (1 mL) DCM (3 mL) | 1.72 11 | 331 [M + H]$^+$ |
| 129 Single stereo-isomer unknown absolute stereo-chemistry | 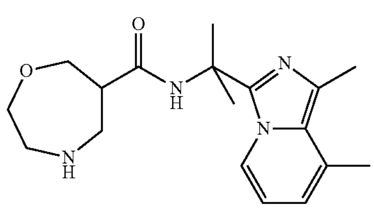 [SMILES: Cc1cccn2c(C(C)(C)NC(=O)C3CNCCOC3)nc(C)c12] | Example 50s, (39 mg, 0.09 mmol), TFA (1 mL) DCM (3 mL) | 2.15 12a | 331 [M + H]$^+$ |
| 130 Single stereo-isomer unknown absolute stereo-chemistry | 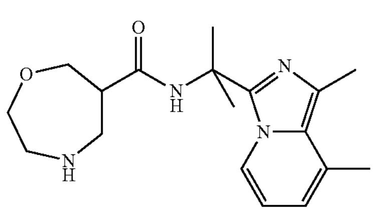 [SMILES: Cc1cccn2c(C(C)(C)NC(=O)C3CNCCOC3)nc(C)c12] | Example 50t, (30 mg, 0.07 mmol), TFA (1 mL) DCM (3 mL) | 2.15 12a | 331 [M + H]$^+$ |

-continued

| Example | Structure | Reactant, acid, solvent | HPLC-MS $R_t$ [min], method | MS (ESI+/ESI− or APCI+, m/z) |
|---|---|---|---|---|
| 131 Single stereo-isomer unknown absolute stereo-chemistry | 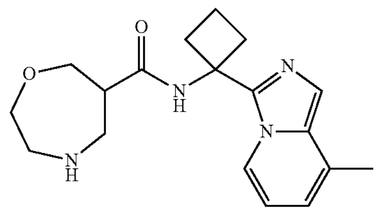 [SMILES: Cc1cccn2c(C3(NC(=O)C4CNCCOC4)CCC3)ncc12] | Example 50u, (54 mg, 0.13 mmol), TFA (1 mL) DCM (3 mL) | 2.16 12a | 329 [M + H]+ |
| 132 Single stereo-isomer unknown absolute stereo-chemistry | 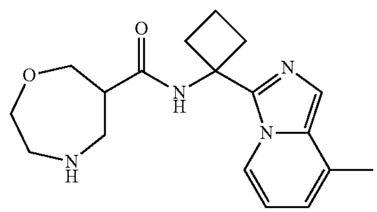 [SMILES: Cc1cccn2c(C3(NC(=O)C4CNCCOC4)CCC3)ncc12] | Example 50v, (52 mg, 0.12 mmol), TFA (1 mL) DCM (3 mL) | 2.13 12a | 329 [M + H]+ |
| 133 Racemic mixture | 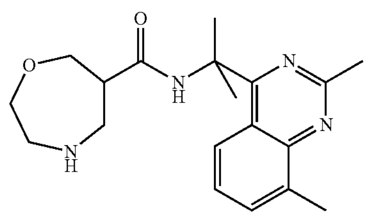 [SMILES: Cc1nc(C(C)(C)NC(=O)C2CNCCOC2)c2cccc(C)c2n1] | Example 50i, (29 mg, 0.07 mmol), TFA (1 mL) DCM (5 mL) | 3.40 7a | 343 [M + H]+ |
| 134 Single stereo-isomer unknown absolute stereo-chemistry | 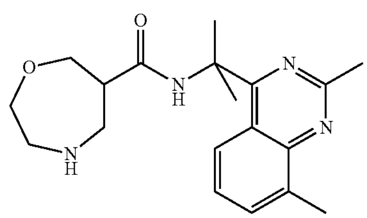 [SMILES: Cc1nc(C(C)(C)NC(=O)C2CNCCOC2)c2cccc(C)c2n1] | Example 50w, (50 mg, 0.11 mmol), TFA (1 mL) DCM (5 mL) Purified by flash chromatography (10% MeOH in DCM) | 3.52 7a | 343 [M + H]+ |
| 135 Racemic mixture | 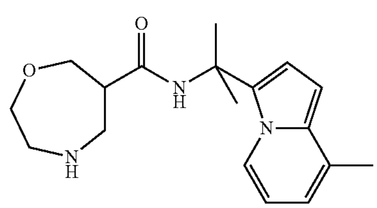 [SMILES: Cc1cccn2c(C(C)(C)NC(=O)C3CNCCOC3)ccc12] | Example 50j, (7 mg, 0.02 mmol), TFA (1 mL) DCM (5 mL) | 3.67 7a | 316 [M + H]+ |
| 136 Single stereo-isomer unknown absolute stereo-chemistry | 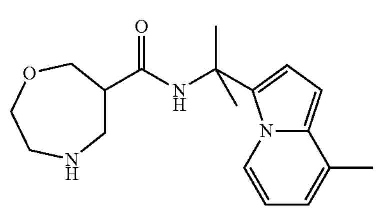 [SMILES: Cc1cccn2c(C(C)(C)NC(=O)C3CNCCOC3)ccc12] | Example 50y, (37 mg, 0.09 mmol), TFA (1 mL) DCM (5 mL) | 3.42 12a | 316 [M + H]+ |
| 137 Single stereo-isomer unknown absolute stereo-chemistry | 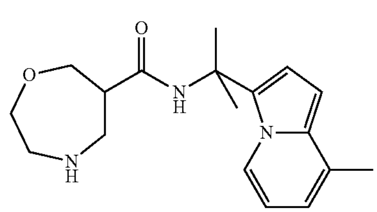 [SMILES: Cc1cccn2c(C(C)(C)NC(=O)C3CNCCOC3)ccc12] | Example 50z, (32 mg, 0.08 mmol), TFA (1 mL) DCM (5 mL) | 3.40 12a | 316 [M + H]+ |

-continued

| Example | Structure | Reactant, acid, solvent | HPLC-MS $R_t$ [min], method | MS (ESI+/ ESI- or APCI+, m/z) |
|---|---|---|---|---|
| 138 Racemic mixture | | Example 50h, (6 mg, 0.01 mmol), TFA (1 mL) DCM (5 mL) | 3.72 7a | 357 [M + H]$^+$ |
| 139 Single stereoisomer unknown absolute stereochemistry | | Example 50aa, (20 mg, 0.04 mmol), TFA (1 mL) DCM (5 mL) | 3.73 7a | 357 [M + H]$^+$ |
| 140 Single stereoisomer unknown absolute stereochemistry | | Example 50ab, (19 mg, 0.07 mmol), TFA (1 mL) DCM (5 mL) | 3.72 7a | 357 [M + H]$^+$ |
| 141 Racemic mixture | | Example 51a, (35 mg, 0.08 mmol), TFA (1 mL) DCM (5 mL) | 1.72 11 | 317 [M + H]$^+$ |
| 142 Single stereoisomer unknown absolute stereochemistry | | Example 51b, (35 mg, 0.08 mmol), TFA (1 mL) DCM (5 mL) | 1.63 11 | 317 [M + H]$^+$ |
| 143 Single stereoisomer unknown absolute stereochemistry | | Example 51c, (37 mg, 0.09 mmol), TFA (1 mL) DCM (5 mL) | 1.61 11 | 317 [M + H]$^+$ |
| 144 Racemic mixture | | Example 52a, (52 mg, 0.12 mmol), TFA (1 mL) DCM (3 mL) | 2.75 7a | 317 [M + H]$^+$ |

| Example | Structure | Reactant, acid, solvent | HPLC-MS $R_t$ [min], method | MS (ESI+/ ESI− or APCI+, m/z) |
|---|---|---|---|---|
| 145 Single stereo- isomer unknown absolute stereo- chemistry | 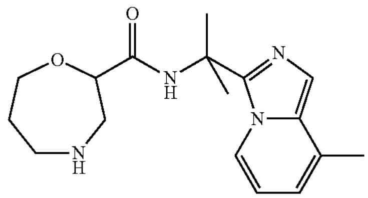 [SMILES: Cc1cccn2c(C(C)(C)NC(=O)C3CNCCCO3)ncc12] | Example 52b, (74 mg, 0.18 mmol), TFA (1 mL) DCM (3 mL) | 2.75 7a | 317 [M + H]+ |
| 146 Single stereo- isomer unknown absolute stereo- chemistry | 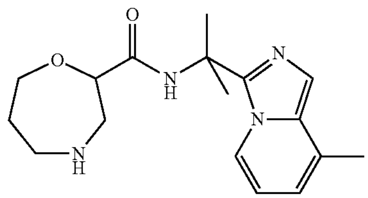 [SMILES: Cc1cccn2c(C(C)(C)NC(=O)C3CNCCCO3)ncc12] | Example 52c, (86 mg, 0.21 mmol), TFA (1 mL) DCM (3 mL) | 2.68 7a | 317 [M + H]+ |
| 147 Racemic mixture | 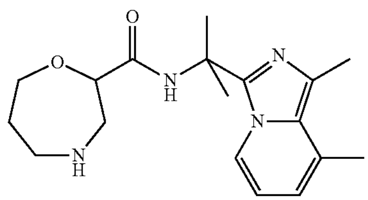 [SMILES: Cc1cccn2c(C(C)(C)NC(=O)C3CNCCCO3)nc(C)c12] | Example 52d, (32 mg, 0.07 mmol), TFA (1 mL) DCM (3 mL) | 1.93 11 | 331 [M + H]+ |
| 148 Single stereo- isomer unknown absolute stereo- chemistry | 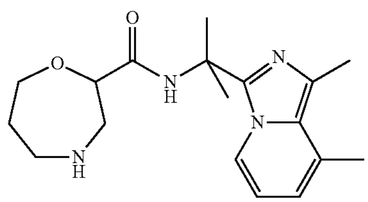 [SMILES: Cc1cccn2c(C(C)(C)NC(=O)C3CNCCCO3)nc(C)c12] | Example 52e, (22 mg, 0.05 mmol), TFA (1 mL) DCM (3 mL) | 1.93 11 | 331 [M + H]+ |
| 149 Single stereo- isomer unknown absolute stereo- chemistry | 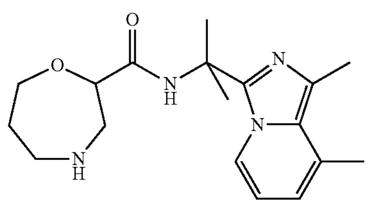 [SMILES: Cc1cccn2c(C(C)(C)NC(=O)C3CNCCCO3)nc(C)c12] | Example 52f, (24 mg, 0.06 mmol), TFA (1 mL) DCM (3 mL) | 1.92 11 | 331 [M + H]+ |

Camp Assay

Method Description for cAMP Assay with Human Somatostatin 4 Receptor

The activation of the SSTR4 receptor (Gi coupled) causes an inhibition of intracellular cAMP after stimulation with Forskolin, which can be quantifiable by use of a suitable assay Kit and an adequate plate reader. This technique is used to characterize pharmacological effects of the SSTR4 receptor agonists by use of hSSTR4 expressing H4 cells.

Description

Compounds are dissolved and diluted in DMSO. The final test solution contains 1% DMSO. The cAMP standard (Lance cAMP 384 Kit; PerkinElmer, Cat# AD0264) is prepared in assay buffer (HBSS with 0.1% BSA, 5 mM HEPES, 0.5 M IBMX, pH 7.4) containing 1% DMSO and the cAMP standard curve is included at least on one plate. Cells are centrifuged and suspended in assay buffer (incl. 1:100 diluted Alexa antibody).

For the assay 5 μl of a cell suspension (approximately 5000 cells/well)—incl. Alexa antibody (diluted 1:100) are added into a 384 well MTP microtitre plate excepting one row or column (depending on the plate layout), which is reserved for the standard curve. Then 2 μl of compound sample is added as concentration response curve (e.g. 1e-5 M to 6e-10 M), usually in triplicates. Each assay contains incubations with vehicle controls instead of compound as controls for non-inhibited cAMP generation (100% CTL; 'high values') and incubations with 1 μM Somatosatin as controls for full inhibition and background (0% CTL; 'low values'). After approximately 10-15 min incubation time 3 μl Forskolin (dissolved in DMSO, final conc. 15 μM) is added. Then the plates are shaken briefly and incubated for 60 min at room temperature. After 60 min 10 μl of the detection mix is added into all wells followed by an additional incubation period of 1 h. The plates are read in a suitable plate reader.

The analysis of the data is based on the "ratio" of the time-resolved fluorescence measurements of donor and acceptor fluorophore (Ex: 320 nm; Em1: 665 nm; Em2: 615 nm; ratio 665/615). From this ratio, cAMP concentrations are calculated from standard curve and the EC50 is estimated by least square curve fit program.

Radioligand Binding Assays

Method description for binding assays with human Somatostatin receptors by use of CHO cell membranes expressing recombinant human SSTR1 or human SSTR2 or human SSTR3 or human SSTR4 or human SSTR5

Receptor binding assays refer to a technique in which labeled receptor ligands are used to detect binding to a receptor. In competition experiments test compounds, which are not labeled, compete with the binding side of a labeled ligand. The displacement of the labeled ligand by the test compound leads to a decreased signal.

Procedure:

For the binding experiments 200 μL of membrane homogenate from one of the following protein amounts is used: hSSTR1 (40 μg/well); hSSTR2 (25 μg/well); hSSTR3 (1.5 μg/well); hSSTR4 (0.5 μg/well); hSSTR5 (25 μg/well). The homogenate is incubated with 0.05 nM of radioligand ([3-125I-Tyr]-Somatostatin-(1-14)) in addition to increasing concentrations of a test compound or vehicle (100% binding) in a total volume of 250 μL using a Hepes buffer (10 mM, EDTA 1 mM, $MgCl_2$ 5 mM, pH7.6, BSA 0.5%, Bacitracin 0.003%, DMSO 1%) for 180 min at room temperature. The incubation is terminated by filtration with ice cold NaCl 0.9% through polyethyleneimine treated (0.3%) GF/B glass fiber filters using a cell harvester. The protein-bound radioactivity is measured in a suitable reader. The non-specific binding is defined as radioactivity bound in the presence of 1 μM Somatostatin-14 during the incubation period.

The analysis of the concentration-binding curves is performed by computer-assisted nonlinear least square curve fitting method using the model of one receptor binding site.

Metabolic Stability

The metabolic stability of the compounds according to the invention may be investigated as follows:

The metabolic degradation of the test compound is assayed at 37° C. with pooled human liver microsomes. The final incubation volume of 100 μl per time point contains TRIS buffer pH 7.6 at room temperature (0.1 M), magnesium chloride (5 mM), microsomal protein (1 mg/mL) and the test compound at a final concentration of 1 μM. Following a short preincubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life is determined by the slope of the semi-logarithmic plot of the concentration-time profile.

Biological Activity

The agnostic activity of the above described examples is demonstrated by the data in Table 2. The EC50 values were obtained with the aid of the above described cAMP ASSAY.

TABLE 2

Agonistic activity of compounds of the present invention.

| Example | SSTR4 agonism EC50 [nM] |
|---|---|
| 1 | 4.7 |
| 2 | 90.1 |
| 3 | 18.0 |
| 4 | 271.5 |
| 5 | 20.4 |
| 6 | 4.9 |
| 7 | 2420.0 |
| 8 | 257.5 |
| 9 | 189.5 |
| 10 | 51.2 |
| 11 | 26.3 |
| 12 | 36.0 |
| 13 | 355.5 |
| 14 | 796.5 |
| 15 | 244.0 |
| 16 | 393.0 |
| 17 | 30000.0 |
| 18 | 209.0 |
| 19 | 13.3 |
| 20 | 3.9 |
| 21 | 3.2 |
| 22 | 192.0 |
| 23 | 36.5 |
| 24 | 36.2 |
| 25 | 1000.0 |
| 26 | 61.3 |
| 27 | 55.8 |
| 28 | 48.4 |
| 29 | 21.6 |
| 30 | 13.1 |
| 31 | 52.7 |
| 32 | 10.9 |
| 33 | 7.7 |
| 34 | 5.7 |
| 35 | 2865.0 |
| 36 | 25.4 |
| 37 | 11.7 |
| 38 | 1.3 |
| 39 | 179.8 |
| 40 | 0.8 |
| 41 | 0.7 |
| 42 | 415.0 |
| 43 | 6.6 |
| 44 | 7.0 |
| 45 | 795.0 |
| 46 | 3.4 |
| 47 | 25.9 |
| 48 | 18.9 |
| 49 | 988.5 |
| 50 | 104.9 |
| 51 | 42.9 |
| 52 | 48.9 |
| 53 | 13.6 |
| 54 | 8.2 |
| 55 | 2.9 |
| 56 | 737.5 |
| 57 | 2.4 |
| 58 | 4.1 |
| 59 | 1070.0 |
| 60 | 1.3 |
| 61 | 146.8 |
| 62 | 65.7 |
| 63 | 42.0 |
| 64 | 1855.0 |
| 65 | 997.8 |
| 66 | 624.5 |
| 67 | 23000.0 |
| 68 | 628.5 |
| 69 | 434.5 |
| 70 | 544.5 |
| 71 | 35.1 |
| 72 | 17.3 |
| 73 | 8.4 |
| 74 | 1186.7 |
| 75 | 18.0 |
| 76 | 10.0 |
| 77 | 5.1 |

TABLE 2-continued

Agonistic activity of compounds of the present invention.

| Example | SSTR4 agonism EC50 [nM] |
|---|---|
| 78 | 430.0 |
| 79 | 2.2 |
| 80 | 4.8 |
| 81 | 152.5 |
| 82 | 3.0 |
| 83 | 4.1 |
| 84 | 4.5 |
| 85 | 2.0 |
| 86 | 1000.0 |
| 87 | 13.4 |
| 88 | 11.1 |
| 89 | 3.1 |
| 90 | 670.0 |
| 91 | 3.4 |
| 92 | 2.5 |
| 93 | 1.4 |
| 94 | 31.0 |
| 95 | 4.5 |
| 96 | 13.0 |
| 97 | 40.8 |
| 98 | 85.3 |
| 99 | 43.4 |
| 100 | 103.0 |
| 101 | 6.5 |
| 102 | 31.0 |
| 103 | 60.7 |
| 104 | 73.5 |
| 105 | 596.3 |
| 106 | 229.7 |
| 107 | 51.1 |
| 108 | 58.1 |
| 109 | 3.7 |
| 110 | 1000.0 |
| 111 | 289.8 |
| 112 | 5500.0 |
| 113 | 380.3 |
| 114 | 1000.0 |
| 115 | 294.5 |
| 116 | 9.3 |
| 117 | 2.6 |
| 118 | 86.8 |
| 119 | 73.9 |
| 120 | 5.9 |
| 121 | 11.1 |
| 122 | 1000.0 |
| 123 | 32.4 |
| 124 | 1000.0 |
| 125 | 16.4 |
| 126 | 46.0 |
| 127 | 1000.0 |
| 128 | 5.0 |
| 129 | 5.3 |
| 130 | 466.0 |
| 131 | 19.0 |
| 132 | 10000.0 |
| 133 | 55.3 |
| 134 | 98.1 |
| 135 | 8.5 |
| 136 | 3.7 |
| 137 | 1430.0 |
| 138 | 59.7 |
| 139 | 22.2 |
| 140 | 1000.0 |
| 141 | 90.2 |
| 142 | 90.5 |
| 143 | 77.6 |
| 144 | 71.8 |
| 145 | 29.1 |
| 146 | 1000.0 |
| 147 | 185.0 |
| 148 | 93.0 |
| 149 | 1000.0 |

Selectivity

Selectivity data was obtained with the aid of the above described radioligand binding assays.

TABLE 3

Selectivity of compounds of the present invention for SSTR4 over other SSTRs.

| Ex | SSTR4 binding Ki [nM] | SSTR1 binding Ki [nM] | SSTR2 binding Ki [nM] | SSTR3 binding Ki [nM] | SSTR5 binding Ki [nM] |
|---|---|---|---|---|---|
| 19 | 194 | 9010 | 9630 | 8710 | 9860 |
| 21 | 89.2 | 9450 | 9600 | 8620 | 9750 |
| 24 | 522.5 | 9450 | 9600 | 8620 | 9750 |
| 95 | 218 | 9480 | 9630 | 8690 | 9770 |

Stability

Stability data was obtained with the above described experimental procedure.

TABLE 4

Stability of compounds of the present invention in human liver microsomes.

| Example | Half-life $t_{1/2}$ [min] |
|---|---|
| 19 | >130 |
| 20 | >130 |
| 21 | >130 |
| 23 | >130 |
| 24 | >130 |
| 26 | >130 |
| 27 | >130 |
| 28 | >130 |
| 30 | >130 |
| 34 | >130 |
| 37 | >130 |
| 38 | >130 |
| 41 | >130 |
| 43 | 110 |
| 44 | >130 |
| 46 | >130 |
| 48 | >130 |
| 55 | >130 |
| 57 | >130 |
| 60 | >130 |
| 73 | >130 |
| 77 | >130 |
| 79 | 100 |
| 82 | >130 |
| 83 | >130 |
| 85 | >130 |
| 89 | >130 |
| 91 | >130 |
| 93 | >130 |
| 95 | >130 |
| 96 | >130 |
| 101 | >130 |
| 109 | 84 |
| 116 | >130 |
| 117 | >130 |
| 120 | >130 |
| 128 | >130 |
| 136 | >130 |
| 145 | >130 |

What is claimed is:

1. A compound of formula (I)

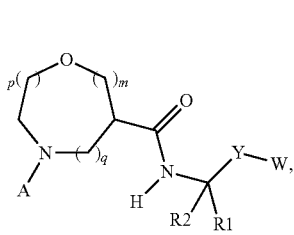

or a pharmaceutically acceptable salt thereof, wherein
m=0, p=1, q=1 or;
m=1, p=1, q=1 or;
m=0, p=2, q=1 or;
m=0, p=1, q=2;
A is selected from the group consisting of
H and $C_{1-6}$-alkyl;
$R^1$ and $R^2$ are independently selected from the group consisting of
$C_{1-6}$-alkyl and $C_{3-6}$-cycloalkyl, or wherein $R^1$ and $R^2$ together form a 2- to 5-membered alkylene-bridge incorporating 0 to 2 heteroatoms independently selected from the group consisting of N, O or S, wherein the $C_{1-6}$-alkyl, the $C_{3-6}$-cycloalkyl or the alkylene-bridge is optionally substituted with halogens;
W is selected from the group consisting of a
monocyclic aryl, monocyclic heteroaryl, monocyclic heterocyclyl and monocyclic cycloalkyl,
wherein each of these ring systems is optionally substituted with one or more $R^3$, and wherein the heteroaryl comprises up to 4 heteroatoms and one or two 5- or 6-membered ring(s);
$R^3$ is independently selected from the group consisting of
$C_{1-6}$ alkyl, $C_{3-8}$-cycloalkyl, $C_{1-6}$-alkyl-O—, benzyl, halogen, HO—, NC—, mono- or bicyclic heteroaryl, and 5- or 6-membered monocyclic heterocyclyl containing one heteroatom selected from the group consisting of N, O or $S(O)_r$, wherein the heteroaryl contains up to 4 heteroatoms and one or two 5- or 6-membered ring(s), and r is 0, 1 or 2,
wherein the $C_{1-6}$-alkyl, $C_{3-8}$-cycloalkyl, $C_{1-6}$-alkyl-O—, benzyl, heteroaryl and the heterocyclyl are optionally substituted with halogens, HO—, acetyl, $C_{1-6}$-alkyl-O—, oxo, $R^4$—$S(O)_2$—, with $R^4$ being aryl, $C_{3-6}$-cycloalkyl and/or $C_{1-6}$-alkyl; and
Y is —$CH_2O$—.

2. The compound according to claim 1, or a pharmaceutically acceptable salt thereof, wherein A is H.

3. The compound according to claim 1, or a pharmaceutically acceptable salt thereof, wherein
W is selected from the group consisting of a
monocyclic aryl, a monocyclic heteroaryl and a monocyclic heterocyclyl, wherein each of these ring systems is optionally substituted with one or more $R^3$, and wherein the heteroaryl comprises up to 4 heteroatoms and one or two 5- or 6-membered ring(s).

4. The compound according to claim 1, or a pharmaceutically acceptable salt thereof, wherein W is selected from the group consisting of

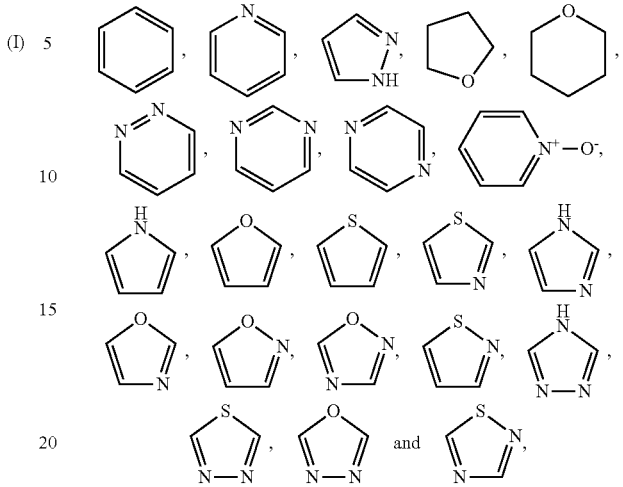

wherein each of these ring systems is optionally substituted with one or more $R^3$.

5. The compound according to claim 1, or a pharmaceutically acceptable salt thereof, wherein
W is selected from the group consisting of

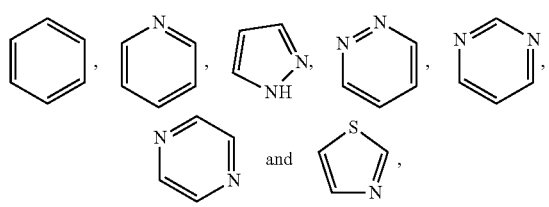

wherein each of these ring systems is optionally substituted with one to three $R^3$.

6. The compound according to claim 1, or a pharmaceutically acceptable salt thereof, wherein
m is 0, p is 1 and q is 1, or
m is 1, p is 1 and q is 1.

7. The compound according to claim 1, or a pharmaceutically acceptable salt thereof, wherein
$R^3$ is selected from the group consisting of
$C_{1-3}$-alkyl, $C_{3-6}$-cycloalkyl, $C_{1-3}$-alkyl-O—, halogen, NC—,
wherein, in case $R^3$ is connected to N-atoms of W, $R^3$ is selected from the group
consisting of $C_{1-3}$-alkyl and $C_{3-6}$-cycloalkyl,
wherein the $C_{1-3}$-alkyl, $C_{3-6}$-cycloalkyl, and the $C_{1-3}$-alkyl-O-substituents are optionally substituted with halogens.

8. The compound according to claim 1, or a pharmaceutically acceptable salt thereof, wherein
$R^3$ is selected from the group consisting of $H_3C$—, F— and $F_3C$—,
wherein, $R^3$ is $H_3C$— when $R^3$ is connected to N-atoms of W.

9. The compound according to claim 1, or a pharmaceutically acceptable salt thereof, wherein $R^1$ and $R^2$ are both $H_3C$—.

10. A compound selected from the group consisting of:

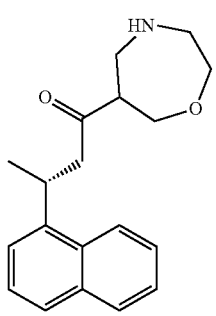
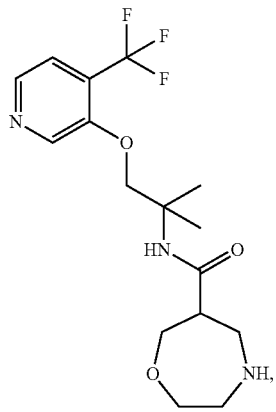
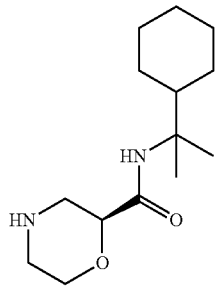
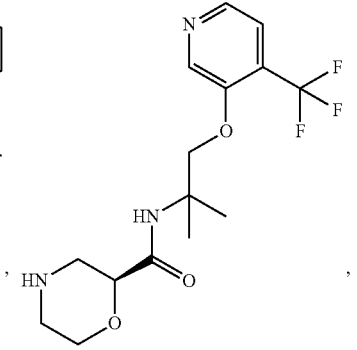
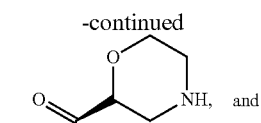
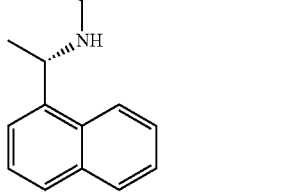
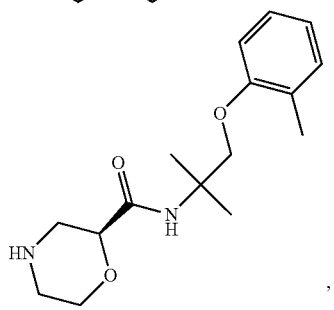

or a pharmaceutically acceptable salt thereof.

11. A pharmaceutical composition comprising a compound according to claim 1, or a pharmaceutically acceptable salt thereof, together with one or more pharmaceutically acceptable carriers.

12. A method for the treatment of pain comprising administering to a human a therapeutically effective amount of a compound according to claim 1, or a pharmaceutically acceptable salt thereof, wherein the pain is selected from the group consisting of acute pain, neuropathic peripheral pain, chronic pain and osteoarthritis.

* * * * *